US011787861B2

(12) United States Patent
Chen et al.

(10) Patent No.: US 11,787,861 B2
(45) Date of Patent: Oct. 17, 2023

(54) ANTI-CD200R1 ANTIBODIES AND METHODS OF USE THEREOF

(71) Applicant: 23andMe, Inc., Sunnyvale, CA (US)

(72) Inventors: Yu Chen, Foster City, CA (US); Jilean Beth Fenaux, San Mateo, CA (US); Germaine Fuh-Kelly, Pacifica, CA (US); Yao-Ming Huang, San Mateo, CA (US); Wei-Jen Chung, El Granada, CA (US); Erik Edward Karrer, Los Altos, CA (US); Cecilia Lay, Brisbane, CA (US); Steven J. Pitts, San Francisco, CA (US); Louise Scharf, Redwood City, CA (US)

(73) Assignee: 23andMe, Inc., Sunnyvale, CA (US)

( * ) Notice: Subject to any disclaimer, the term of this patent is extended or adjusted under 35 U.S.C. 154(b) by 13 days.

(21) Appl. No.: 17/333,963

(22) Filed: May 28, 2021

(65) Prior Publication Data
US 2021/0371521 A1 Dec. 2, 2021

Related U.S. Application Data

(60) Provisional application No. 63/032,508, filed on May 29, 2020.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *A61K 2039/505* (2013.01); *C07K 2317/34* (2013.01); *C07K 2317/76* (2013.01); *C07K 2317/92* (2013.01)

(58) Field of Classification Search
CPC ............ C07K 16/2803; C07K 2317/34; C07K 2317/76; C07K 2317/92; A61P 35/00; A61K 2039/505
See application file for complete search history.

(56) References Cited

U.S. PATENT DOCUMENTS

2010/0178296 A1 7/2010 Presta et al.
2017/0355756 A1* 12/2017 Julien ................... A61P 25/00

FOREIGN PATENT DOCUMENTS

| EP | 2341143 A | 7/2011 | |
|----|-----------|--------|---|
| WO | WO-2007042573 A2 * | 4/2007 | ............... A61P 1/04 |
| WO | 2009121162 A | 10/2009 | |
| WO | 2015057906 A | 4/2015 | |

OTHER PUBLICATIONS

Almagro JC, Fransson J. Humanization of antibodies. Front Biosci. Jan. 1, 2008;13:1619-33. (Year: 2008).*
Chen et al. Enhancement and destruction of antibody function by somatic mutation: unequal occurrence is controlled by V gene combinatorial associations.EMBO J. Jun. 15, 1995; 14(12): 2784-94. (Year: 1995).*
Kussie et al. A single engineered amino acid substitution changes antibody fine specificity.J Immunol. Jan. 1, 1994;152(1):146-52. (Year: 1994).*
Koenig et al. Mutational landscape of antibody variable domains reveals a switch modulating the interdomain conformational dynamics and antigen binding.PNAS Jan. 24, 2017 114(4)E486-E495;firstpublished Jan. 5, 2017. (Year: 2017).*
Edwards et al. The remarkable flexibility of the human antibody repertoire;isolation of over one thousand different antibodies to a single protein,BLyS. J Mol Biol Nov. 14, 2003;334(1):103-18. (Year: 2003).*
Akkaya et al., "Dissection of Agonistic and Blocking Effects of CD200 Receptor Antibodies," PLOS ONE, vol. 8, No. 5, May 14, 2013, p. e63325, XP055647634, DOI: 10.1371/journal.pone.0063325.
Gorczynski, "CD200:CD200R-mediated regulation of immunity." ISRN Immunology, vol. 2012; Article ID 682168, 18 pages doi:10.5402/2012/682168.
Rygiel T P, Meyaard L. "CD200R signaling in tumor tolerance and inflammation: a tricky balance." Curr Opin Immunol. 2012; 24(2):233-8.
McWhirter et al. "Antibodies selected from combinatorial libraries block a tumor antigen that plays a key role in immunomodulation." Proc Natl Acad Sci USA. 2006; 103(4):1041-6.
Mahadevan et al., "Phase I study of samalizumab in chronic lymphocytic leukemia and multiple myeloma: blockade of the immune checkpoint CD200," J. Immunotherapy Cancer 7, 227 (2019).
Achyut et al., "Canonical NFκB signaling in myeloid cells is required for the glioblastoma growth," Scientific Reports 7: 13754; published online: Oct. 23, 2017; DOI:10.1038/s41598-017-14079-4.
Akkaya et al., "Heterogeneity in the CD200R paired receptor family," Immunogenetics (2010) 62:15-22, DOI 10.1007/s00251-009-0415-6.
Alapat et al., "Diagnostic Usefulness and Prognostic Impact of CD200 Expression in Lymphoid Malignancies and Plasma Cell Myeloma," Am J Clin Pathol. Jan. 2012 ; 137(1): 93-100. doi:10.1309/AJCP59UORCYZEVQO.
Ambarus et al., "Systematic validation of specific phenotypic markers for in vitro polarized human macrophages," Journal of Immunological Methods 375 (2012) 196-206; doi:10.1016/j.jim.2011.10.013.

(Continued)

*Primary Examiner* — Aurora M Fontainhas
*Assistant Examiner* — Jennifer A Benavides
(74) *Attorney, Agent, or Firm* — FISHERBROYLES LLP; Adam K. Whiting

(57) ABSTRACT

The present disclosure provides binding proteins, such as antibodies and antigen-binding fragments, which specifically bind to human CD200R1 receptor protein (hu-CD200R1) and are capable of decreasing, inhibiting, and/or fully-blocking immune regulatory effects mediated by hu-CD200R1. The present disclosure also provides methods of using the antibodies (and compositions thereof) to treat diseases and conditions responsive to decreasing, inhibiting and/or blocking immune regulatory function or activity mediated by CD200 binding to CD200R1.

30 Claims, 41 Drawing Sheets

Specification includes a Sequence Listing.

(56) References Cited

OTHER PUBLICATIONS

Bensch et al., "89Zr-atezolizumab imaging as a non-invasive approach to assess clinical response to PD-L1 blockade in cancer," Nature Medicine, vol. 24: 1852-1858. (Dec. 2018); https://doi.org/10.1038/s41591-018-0255-8.
Betts et al., "Linear pharmacokinetic parameters for monoclonal antibodies are similar within a species and across different pharmacological targets: A comparison between human, cynomolgus monkey and hFcRn Tg32 transgenic mouse using a population-modeling approach," MABS 2018, vol. 10, No. 5, 751-764; https://doi.org/10.1080/19420862.2018.1462429.
Caserta et al., "Chronic Infection Drives Expression of the Inhibitory Receptor CD200R, and Its Ligand CD200, by Mouse and Human CD4 T Cells," PLoS ONE, vol. 7, Issue 4, e35466 (Apr. 2012).
Cassetta et al., "Human tumor-associated macrophage and monocyte transcriptional landscapes reveal cancer-specific reprogramming, biomarkers, and therapeutic targets." Cancer Cell 35 588-602.e510. (2019).
Cerignoli et al., "In vitro immunotherapy potency assays using real-time cell analysis," PLOS ONE | https://doi.org/10.1371/journal.pone 0193498, Mar. 2, 2018.
Chen et al., "Role of a distal enhancer in the transcriptional responsiveness of the human CD200 gene to interferon-gamma and tumor necrosis factor-alpha," Molecular Immunology 46 (2009) 1951-1963; doi:10.1016/j.molimm.2009.03.015.
Choueiry et al., "CD200 promotes immunosuppression in the pancreatic tumor microenvironment," J. Immunother. Cancer 2020;8:e000189. doi:10.1136/jitc-2019-000189.
Czarnowicki et al., "Circulating CLA+ T cells in atopic dermatitis and their possible role as peripheral biomarkers," Allergy 72 (2017) 366-372; DOI:10.1111/all.13080.
Deng et al., "Projecting human pharmacokinetics of therapeutic antibodies from nonclinical data," mAbs, 3:1, 61-66 (2011); DOI: 10.4161/mabs.3.1.13799.
Dirks et al., "Population Pharmacokinetics of Therapeutic Monoclonal Antibodies," Clin. Pharmacokinet. 2010; 49 (10). 633-659.
"ICH guideline S6 (R1)—Preclinical safety evaluation of biotechnology-derived pharmaceuticals" Jun. 2011 EMA/CHMP/ICH/731268/1998, Committee for medicinal products for human use (CHMP).
US Food and Drug Administration, "Guidance for Industry—Estimating the Maximum Safe Starting Dose in Initial Clinical Trials for Therapeutics in Adult Healthy Volunteers," Jul. 2005, Pharmacology and Toxicology.
US Food and Drug Administration, "International Conference on Harmonisation; Addendum to International Conference on Harmonisation Guidance on S6 Preclinical Safety Evaluation of Biotechnology-Derived Pharmaceuticals; Availability," Federal Register /vol. 77, No. 97 / Friday, May 18, 2012 /Notices.
US Food and Drug Administration, "Nonclinical Safety Evaluation of the Immunotoxic Potential of Drugs and Biologies," Feb. 2020.
Foster-Cuevas et al., "Human Herpesvirus 8 K14 Protein Mimics CD200 in Down-Regulating Macrophage Activation through CD200 Receptor," Journal of Virology, Jul. 2004, vol. 78, No. 14, p. 7667-7676; DOI: 10.1128/JVI.78.14.7667-7676.2004.
Ginos et al., "Identification of a Gene Expression Signature Associated with Recurrent Disease in Squamous Cell Carcinoma of the Head and Neck," Cancer Research 64, 55-63, Jan. 1, 2004.
Gorczinsky et al., "Breast cancer cell CD200 expression regulates immune response to EMT6 tumor cells in mice," Breast Cancer Res Treat (2010) 123:405-415; DOI 10.1007/s10549-009-0667-8.
Gordon et al., "Identification of Novel Candidate Oncogenes and Tumor Suppressors in Malignant Pleural Mesothelioma Using Large-Scale Transcriptional Profiling," American Journal of Pathology, vol. 166, No. 6, Jun. 2005.
Hagemann et al., "'Re-educating' tumor-associated macrophages by targeting NF-KB," J. Exp. Med. vol. 205 No. 6 1261-1268; www.jem.org/cgi/doi/10.1084/jem.20080108.
Hatherley et al., "The CD200 and CD200 receptor cell surface proteins interact through their N-terminal immunoglobulin-like domains," Eur. J. Immunol. 2004. 34: 1688-1694.
Hatherley et al., "Structures of CD200/CD200 Receptor Family and Implications for Topology, Regulation, and Evolution," Structure 21, 820-832, May 7, 2013.
Hayakawa et al., "CD200 increases alternatively activated macrophages through cAMP-response element binding protein—C/EBP-beta signaling," Journal of Neurochemistry, 136: 900-906 (2016).
Jacobsen et al., "Engineering an IgG Scaffold Lacking Effector Function with Optimized Developability," The Journal of Biological Chemistry vol. 292, No. 5, pp. 1865-1875, Feb. 3, 2017.
Jenkins et al., "Mechanisms of resistance to immune checkpoint inhibitors," British Journal of Cancer (2018) 118, 9-16; doi: 10.1038/bjc.2017.434.
Klein et al., "Gene Expression Profiling of B Cell Chronic Lymphocytic Leukemia Reveals a Homogeneous Phenotype Related to Memory B Cells," J. Exp. Med., vol. 194, No. 11, Dec. 3, 2001 1625-1638; www.jem.org/cgi/content/full/194/11/1625.
Koning et al., "Expression of the Inhibitory CD200 Receptor Is Associated with Alternative Macrophage Activation," J Innate Immun 2010;2:195-200; DOI: 10.1159/000252803.
Korkola et al., "Down-Regulation of Stem Cell Genes, Including Those in a 200-kb Gene Cluster at 12p13.31, Is Associated with In vivo Differentiation of Human Male Germ Cell Tumors," Cancer Res 2006; 66: (2). Jan. 15, 2006.
Kretz-Rommel et al., "CD200 Expression on Tumor Cells Suppresses Antitumor Immunity: New Approaches to Cancer Immunotherapy," J Immunol 2007; 178:5595-5605; doi: 10.4049/jimmunol.178.9.5595.
Kyi et al., "Immune checkpoint inhibitor combinations in solid tumors: opportunities and challenges," Immunotherapy (2016) 8(7), 821-837.
Lau et al., "Tumour and host cell PD-L1 is required to mediate suppression of anti-tumour immunity in mice," Nature Communications, 8:14572; Published Feb. 21, 2017; DOI: 10.1038/ncomms14572.
Lauzon et al., "Lung CD200 Receptor Activation Abrogates Airway Hyperresponsiveness in Experimental Asthma," American Journal of Respiratory Cell and Molecular Biology vol. 53 No. 2 | Aug. 2015.
Leabman et al., "Effects of altered FcγR binding on antibody pharmacokinetics in cynomolgus monkeys," mAbs, 5:6, 896-903, DOI: 10.4161/mabs.26436.
Lenburg et al., "Previously unidentified changes in renal cell carcinoma gene expression identified by parametric analysis of microarray data," BMC Cancer 2003, 3:31. Published: Nov. 27, 2003.
Li et al., "c-Rel is a myeloid checkpoint for cancer immunotherapy," Nature Cancer, vol. 1, 507-517; May 2020.
Love et al., "CD200 Expression in Neuroendocrine Neoplasms," Am J Clin Pathol 2017;148:236-242. DOI: 10.1093/AJCPIAQX071.
Mahadevan et al., "Phase I study of samalizumab in chronic lymphocytic leukemia and multiple myeloma: blockade of the immune checkpoint CD200," Journal for ImmunoTherapy of Cancer (2019) 7:227; doi.org/10.1186/s40425-019-0710-1.
Markowitz et al., "Immune reprogramming via PD-1 inhibition enhances early-stage lung cancer survival," JCI Insight. 2018; 3(13):e96836. https://doi.org/10.1172/jci.insight.96836.
McWhirter et al., "Antibodies selected from combinatorial libraries block a tumor antigen that plays a key role in immunomodulation," PNAS, vol. 103, No. 4, 1041-1046. Jan. 24, 2006.
Mihrshahi et al., "Essential Roles for Dok2 and RasGAP in CD200 Receptor-Mediated Regulation of Human Myeloid Cells," J Immunol 2009; 183:4879-4886; Prepublished online Sep. 28, 2009.
Mihrshahi et al., "Downstream of Tyrosine Kinase 1 and 2 Play Opposing Roles in CD200 Receptor Signaling," J Immunol 2010; 185:7216-7222; Prepublished online Nov. 15, 2010; doi: 10.4049/jimmunol.1002858.
Misstear et al., "Suppression of Antigen-Specific T Cell Responses by the Kaposi's Sarcoma-Associated Herpesvirus Viral OX2 Protein and Its Cellular Orthologue, CD200," Journal of Virology, vol. 86, No. 11, p. 6246-6257 (Jun. 2012).

(56) References Cited

OTHER PUBLICATIONS

Moreaux et al., "CD200 is a new prognostic factor in multiple myeloma," Blood, vol. 108, No. 13:4194-4197 (Dec. 15, 2006).

Moreaux et al., "CD200: A putative therapeutic target in cancer," Biochemical and Biophysical Research Communications 366 (2008) 117-122.

Mukhopadhyay et al., "Immune Inhibitory Ligand CD200 Induction by TLRs and NLRs Limits Macrophage Activation to Protect the Host from Meningococcal Septicemia," Cell Host & Microbe 8, 236-247, Sep. 16, 2010.

Rexin et al., "The Immune Checkpoint Molecule CD200 Is Associated with Tumor Grading and Metastasis in Bladder Cancer," Anticancer Research 38: 2749-2754 (2018); doi:10.21873/anticanres.12517.

Rijkers et al., "The inhibitory CD200R is differentially expressed on human and mouse T and B lymphocytes," Molecular Immunology 45 (2008) 1126-1135.

Saber et al., "An FDA oncology analysis of immune activating products and first-in-human dose selection," Regulatory Toxicology and Pharmacology 81 (2016) 448-456. dx.doi.org/10.1016/j.yrtph.2016.10.002.

Salek et al., "CD200R1 regulates eosinophilia during pulmonary fungal infection in mice," Eur. J. Immunol. 2019. 49: 1380-1390. DOI: 10.1002/eji.201847861.

Schoenfeld et al., "Acquired Resistance to Immune Checkpoint Inhibitors," Cancer Cell 37: 443-455 (Apr. 13, 2020). DOI: 10.1016/j.ccell.2020.03.017.

Shields et al., "High Resolution Mapping of the Binding Site on Human IgG1 for FcgRI, FcgRII, FcgRIII, and FcRn and Design of IgG1 Variants with Improved Binding to the FcgR," The Journal of Biological Chemistry, vol. 276, No. 9, Issue of Mar. 2, pp. 6591-6604, 2001. DOI 10.1074/jbc.M009483200.

Shiratori et al., "Down-Regulation of Basophil Function by Human CD200 and Human Herpesvirus-8 CD200," J Immunol 2005; 175:4441-4449; doi: 10.4049/jimmunol.175.7.4441.

Siva et al., "Immune modulation by melanoma and ovarian tumor cells through expression of the immunosuppressive molecule CD200," Cancer Immunol Immunother (2008) 57:987-996. DOI 10.1007/s00262-007-0429-6.

Snelgrove et al., "A critical function for CD200 in lung immune homeostasis and the severity of influenza infection," Nature Immunology, vol. 9, No. 9, pp. 1074-1083. (Sep. 2008).

Sun et al., "CD200R, a co-inhibitory receptor on immune cells, predicts the prognosis of human hepatocellular carcinoma," Immunology Letters 178 (2016) 105-113. DOI: 10.1016/j.imlet.2016.08.009.

Thommen et al., "A transcriptionally and functionally distinct PD-1+ CD8+ T cell pool with predictive potential in nonsmall-cell lung cancer treated with PD-1 blockade," Nature Medicine, vol. 24: 994-1004 (Jul. 2018).

Tonks et al., "CD200 as a prognostic factor in acute myeloid leukaemia," Leukemia (2007) 21, 566-568. doi:10.1038/sj.leu.2404559; published online Jan. 25, 2007.

VanMeer et al., "Immunogenicity of mAbs in non-human primates during nonclinical safety assessment," mAbs 5:5, 810-816; Sep./Oct. 2013.

Wang et al., "Siglec-15 as an immune suppressor and potential target for normalization cancer immunotherapy," Nature Medicine, vol. 25: 656-666. (Apr. 2019).

Wright et al., "Lymphoid/Neuronal Cell Surface OX2 Glycoprotein Recognizes a Novel Receptor on Macrophages Implicated in the Control of Their Function," Immunity, vol. 13, 233-242 (Aug. 2000).

Wright et al., "The unusual distribution of the neuronal/lymphoid cell surface CD200 (OX2) glycoprotein is conserved in humans," Immunology 102:173-179 (2001).

Wright et al., "Characterization of the CD200 Receptor Family in Mice and Humans and Their Interactions with CD200," J Immunol 171:3034-3046 (2003).

Zhang et al., "Molecular Mechanisms of CD200 Inhibition of Mast Cell Activation," J Immunol 173:6786-6793 (2004).

Zheng et al., "Landscape of Infiltrating T Cells in Liver Cancer Revealed by Single-Cell Sequencing," Cell 169, 1342-1356. Jun. 15, 2017.

Zou et al., "Application of cDNA microarrays to generate a molecular taxonomy capable of distinguishing between colon cancer and normal colon," Oncogene (2002) 21, 4855-4862.

PCT International Search Report and Written Opinion of the International Search Authority for PCT application No. PCT/US2021/034852, dated Nov. 9, 2021.

\* cited by examiner

FIG. 1A

VL domain sequences

```
OX108-LC   1  DIVLTQSPASLAVSLGQRATISCRASKSVSTSGYSYMHWYQQKPGQPPKLLIYLASNLES   56
22.1-LC    1  DIVLTQSPASLAVSLGQRATISCRASKSVSTSGYSYMHWYQQKPGQPPKLLIYLASNLES   56
10F6-LC    1  DIVLTQSPPSLAVSLGQRATMSCRASESVDISGNSFMHWFQQKAGQPPKLLIYRASNLES   56
9B8-LC     1  QIVLTQSPALTSASPGEKVTMTCSASSSV---SYMYWFQQKPRSSPKPWIYTSKLAS     56
5D1-LC     1  DVQITQSPSYLAASPGETITINCRASKSIS---KYLAWYQEKPGKTNKFLIYSGSTLQS   56
10A2-LC    1  DVQITQSPSYLAASPGETITINCRASKSIS---KYLAWYQEKPGKTNKLLIYSGSTLQS   56
1F3-LC     1  DVQMIQSPSSLSASLGDKVTMTCQASHTIN-LNWFQQKPGKAPKLLIYGTSNLED       56
11E4-LC    1  DVQMIQSPSSLSASLGDKVTMTCQASHTIN-LNWFQQKPGKAPKLLIYGTSNLED       56

OX108-LC  57  GVPARFSGSGSGTDFTLNIHPVEEEDAATYYCQHSRE LPLTFGAGTKVEIK        107
22.1-LC   57  GVPVRFSGSGSGTDFTLNIHPVEEEDAATYYCQHNRE LPLTFGAGTKLELK        107
10F6-LC   57  GIPARFSGSGSRIDFTLTINPLEADDVATYYCQSHEDPPLTFGGGTKLEMK         107
9B8-LC    57  GVPARFSGSGSGTSYSLTISSMEAEDAATYYCQMSSYPLTFGAGTKLELK          107
5D1-LC    57  GIPSRFSGSGSGTDFTLTISSLEPEDFAMYYCQQYNEYPWTFGGGTKLEIK         107
10A2-LC   57  GIPSRFSGSGSGTDFTLTISSLEPEDFAMYYCQQYNEYPWTFGGGTKLEIK         107
1F3-LC    57  GVPPRFSGSGYGTDFTLTISSLEDEDMATYFCQHYLPMTFGGGTKLEIK           107
11E4-LC   57  GVPPRFSGSGYGTDFTLTISSLEDEDMATYFCQHYLPWTFGGGTKLEIK           107
```

FIG. 1B

VH domain sequences

```
OX108-HC   1  EVKLQQSGPELVKPGASVKMSCKASGYTFTSYVMHWVKQKPGQGLEWIGYINPYNDGTNYNE      61
22.1-HC    1  EVQLQQSGPELVKPGASVKMSCKASGYTFSYVMEWVKQKPGQGLEWIGYINPYNDGTKYNE      61
10F6-HC    1  QVQLKESGPGLVAPSQSLSITCTVSGFSLTNYAVSWVRQPPKGLEWLGVMWAG-EGTNYNS      61
9B8-HC     1  EVQLQQSGTVLVRPGASVKLSCTASGFNIKDDYMHWVKQRPEQGLEWIGRIDPANDNTKYAP     61
5D1-HC     1  EVQLQQSGAELVRPGASVKLSCTASGFNIKDDYMHWVKQRPEQGLEWIGRIDPENGNTKYDP     61
10A2-HC    1  EVQLQQSGAEFVRPGASVRLSCTTSGFYIKDDYIHWVKQRPEQGLEWIGRIDPANGNTKYAP     61
1F3-HC     1  EVQLQQSGAEFVRPGASVRLSCTTSGFYIKDDYIHWVKQRPEQGLEWIGRIDPANGNTKYAP     61
11E4-HC    1  EVQLQQSGTVLARPGASVKMSCEASGYTFTSWMHWVKQSPGQGLEWVGALYPGNSDTNYNQ     61

OX108-HC   62 KFKGKATLTSDKSSSTAYMELSSLTSEDSAVYYCAREDIYGSR------WGYWGQGTTLTVSS  113
22.1-HC    62 KFKGKATLTSDKSSSTAYMELSSLTSEDSAVYYCAREDIYGSR------EYYWGQGTLVTVSS  113
10F6-HC    62 VFKSRLTISKDNSKSQVFLKMNSLQTDDTARYYCAREPITGY------MDIWGQGTSVTVSS  113
9B8-HC     62 KFQDRATITADTSSNTAYLQLSSLTSEDTAVYYCIRVEGTGIY-----FDYWGQGTTLTVSS  113
5D1-HC     62 KFQDKATITADTSSNTAYLQFSSLTSEDTAVYYCTRQIGIRFWFAIDYWGQGTSVTVSS    113
10A2-HC    62 KFQDKATITADTSSRLTSEDTAVYYCARDIGIRFMYSDYWGQGTSVTVSS            113
1F3-HC     62 KFQDKATITADTSSNTAYLQLNSLTSEDTAVYYCTRQIGIRFNYAMDYWGQGTSVTVSS    113
11E4-HC    62 KFKGKAKLTAVTSASTAYMELSSLTNEDSAVYYCTTA--------V-----GSYWGQGTLVTVSA  113
```

FIG. 2

VH domain sequence

```
Human germline  1 QVQLQESGPGLVKPSETLSLTCTVSGFSLTNYAVSWVRQPPGKGLEWLGVMWAGGGTNYN  60
Murine 10F6     1 .....K.......A..QS.I........................................  60
Humanized 10F6  1 E...Q........K..ET..L.......................................  60

Human germline 61 SVFKSRLTISKDNSKNQVSLKLSSVTAADTAVYYCARERPLTGVMDYWGQGTLVTVSS  113
Murine 10F6    61 ........S..F..MN.LQTD...R.................S......          113
Humanized 10F6 61 ........N..S..LS.VTAA...V.................L......          113
```

VL domain sequence

```
Human germline  1 DIVLTQSPDSLAVSLGERATINCRASESVDYSGNSFMHWFQQKPGQPPKLLIYRASNLES  60
Murine 10F6     1 ..........P.......Q...MS.............A......................  60
Humanized 10F6  1 ..........D.......E..IN..............P......................  60

Human germline 61 GIPDRFSGSGSRTDFTLTISSLQAEDVAVYYCHQSNEDPPTFGGGTKVEIK 107
Murine 10F6    61 ...A..............NP.E.D...T...........L.M.         107
Humanized 10F6 61 ...D..............SS.Q.E..V............V.I.         107
```

FIG. 5A
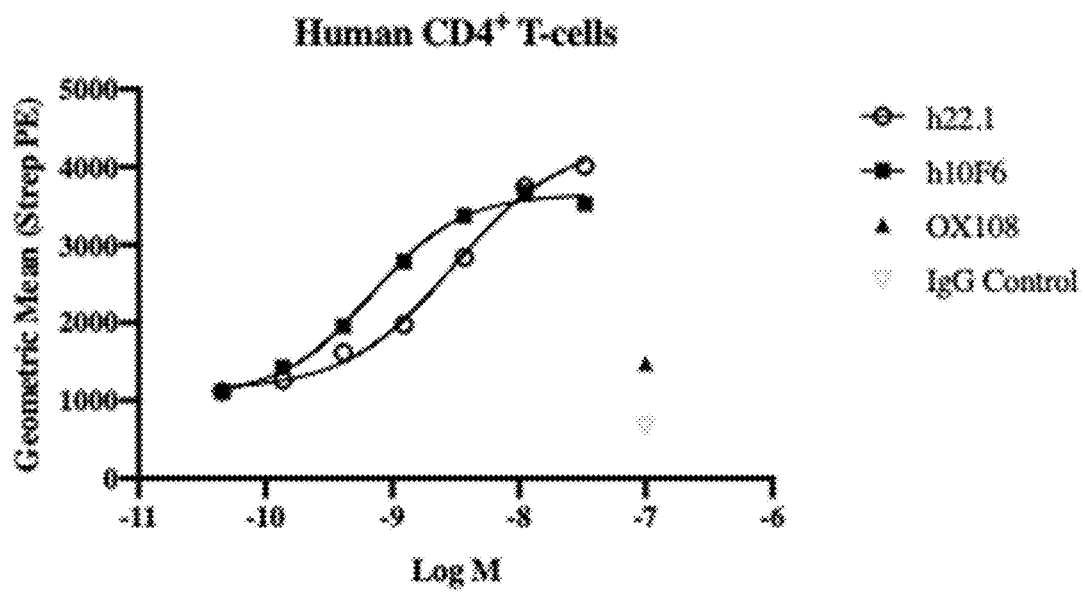
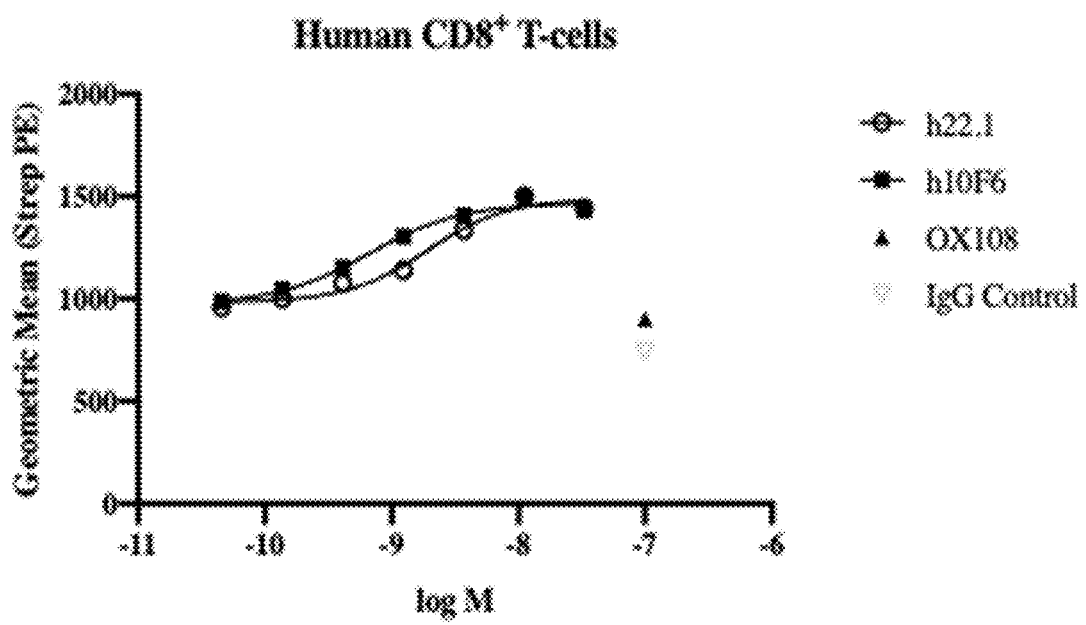

FIG. 5B
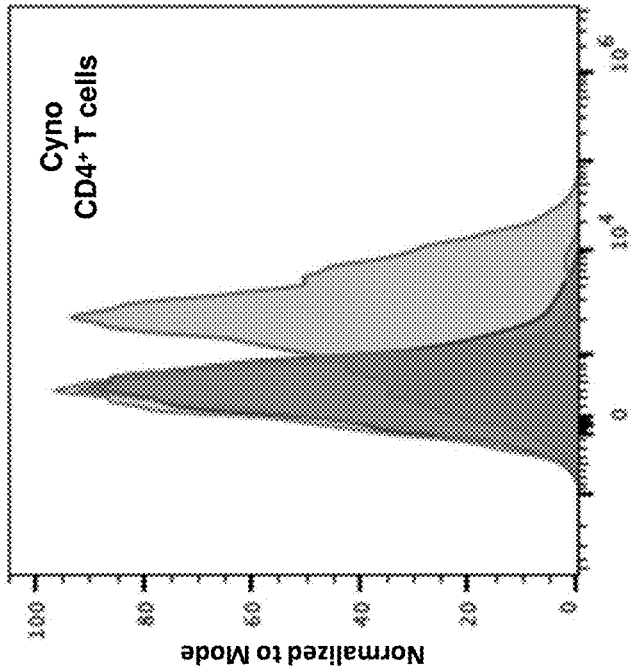
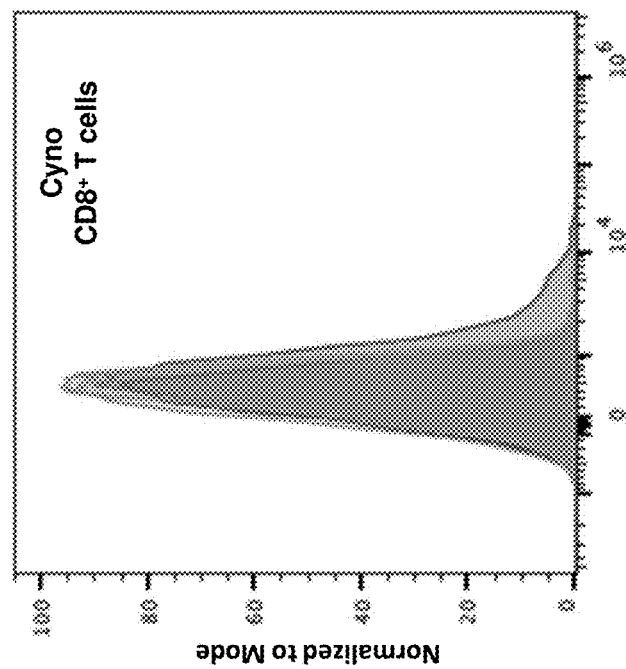

FIG. 11
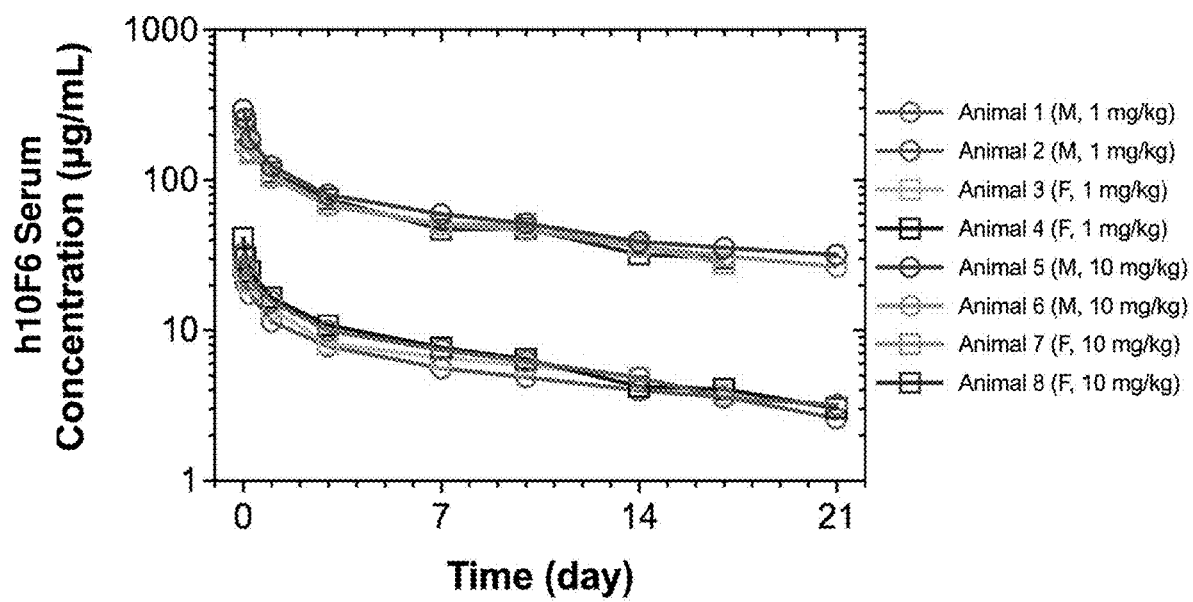
mAb=22.1
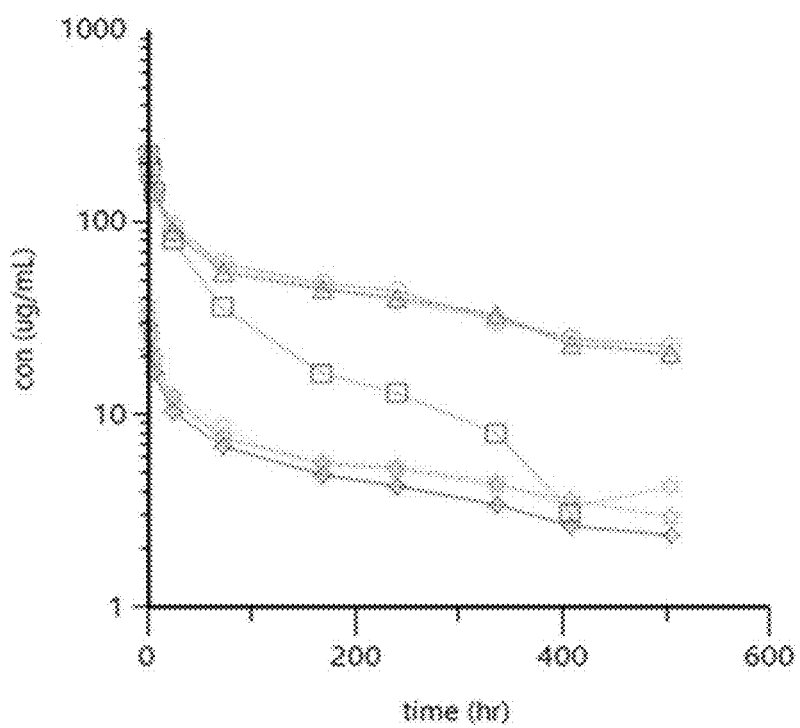

ANTI-CD200R1 ANTIBODIES AND METHODS OF USE THEREOF

CROSS-REFERENCE TO RELATED APPLICATION

This application claims priority benefit to U.S. Provisional Application No. 63/032,508, filed May 29, 2020, which is hereby incorporated by reference herein.

FIELD

The present disclosure relates generally to binding proteins, such as antibodies and antigen-binding fragments, which bind to the CD200R1 receptor protein and methods of using such binding proteins.

REFERENCE TO SEQUENCE LISTING

The official copy of the Sequence Listing is submitted concurrently with the specification as an ASCII formatted text file via EFS-Web, with a file name of "09402-007PV1_SeqList_ST25.txt", a creation date of Apr. 11, 2023, and a size of 84,261 bytes. The Sequence Listing filed via EFS-Web is part of the specification and is incorporated in its entirety by reference herein.

BACKGROUND

Cell surface transmembrane glycoprotein CD200 receptor 1 (referred to herein as "CD200R1" and also known in the art as CD200 receptor 1, CD200R, HCRTR2, OX2R, and MOX2R) is a human protein expressed on the surface of myeloid cells and CD4+ T cells. CD200R1 is a cell surface glycoprotein containing two immunoglobulin-like domains. CD200R and its binding partner, CD200, are both highly conserved type I paired membrane glycoproteins, consisting of two immunoglobulin (Ig)-like domains (V and C) that belong to the Ig protein superfamily. CD200R is expressed mainly on subsets of T cells and myeloid lineage cells. CD200, however, is expressed more widely on a variety of human cells including neurons, epithelial cells, endothelial cells, fibroblasts, and lymphoid cells. CD200R1 acts to regulate expression of pro-inflammatory molecules such as tumor necrosis factor (TNF-α), and interferons. The binding of CD200R to its ligand CD200 has been found to signal an immunosuppressive activity including inhibiting T-cell immune response and natural killer (NK) cell cytotoxic activity, promoting macrophage secretion of indoleamine-2,3 dioxygenase (IDO), and triggering regulatory T cell (Treg) expansion (see e.g., Gorczynski, "CD200:CD200R-mediated regulation of immunity." ISRN Immunol. 2012; 2012). CD200 is understood to have an immune checkpoint function on dendritic cells and lymphoid effector cells, modulating activation inflammatory immune responses and contributing to the maintenance of self-tolerance (see e.g., Rygiel T P, Meyaard L. "CD200R signaling in tumor tolerance and inflammation: a tricky balance." Curr Opin Immunol. 2012; 24(2):233-8). CD200 is overexpressed in a wide variety of solid and hematological tumor cell types, including chronic lymphocytic leukemia (CLL) multiple myeloma (MM), acute myeloid leukemia (AML) and others (see e.g., McWhirter et al. "Antibodies selected from combinatorial libraries block a tumor antigen that plays a key role in immunomodulation." Proc Natl Acad Sci USA. 2006; 103 (4):1041-6). A finding of decreased anti-tumor cytotoxic T cell (CTL) response correlated with aggressive tumor progression, and reduced patient survival has been associated with the overexpression of CD200 on tumor cells and correlated. Accordingly, CD200 has been targeted for cancer immunotherapy including the development of a humanized antibody, Samalizumab, that specifically binds to CD200 and blocks its ligation to the CD200R1, and which is in clinical trials for reduction of tumor burden in patients with advanced chronic lymphocytic leukemia (CLL) (see e.g., Mahadevan et al., "Phase I study of samalizumab in chronic lymphocytic leukemia and multiple myeloma: blockade of the immune checkpoint CD200," J. Immunotherapy Cancer 7, 227 (2019)).

SUMMARY

The present disclosure provides antibodies that specifically bind human CD200R1 with high affinity. The antibodies are capable of decreasing, inhibiting, and/or fully-blocking immune regulatory effects mediated by CD200R1. The present disclosure also provides compositions for and methods of treating diseases and conditions responsive to decreasing, inhibiting and/or blocking immune regulatory function or activity mediated by CD200R1.

In at least one embodiment, the present disclosure provides an anti-CD200R1 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:

(a) HVR-L1 comprises an amino acid sequence selected from RASESVDYSGNSFMH (SEQ ID NO: 11), SASSSVSYMY (SEQ ID NO: 19), RASKSISKYLA (SEQ ID NO: 27), RASKSISKYLA (SEQ ID NO: 35), QASHTINLN (SEQ ID NO: 43), QASHTINLN (SEQ ID NO: 51), RASKSVSTSGYSYMH (SEQ ID NO: 59), and RASESVDYSGNSFMH (SEQ ID NO: 77);

(b) HVR-L2 comprises an amino acid sequence selected from RASNLES (SEQ ID NO: 12), LTSKLAS (SEQ ID NO: 20), SGSTLQS (SEQ ID NO: 28), SGSTLQS (SEQ ID NO: 36), GTSNLED (SEQ ID NO: 44), GTSNLED (SEQ ID NO: 52), LASNLES (SEQ ID NO: 60), and RASNLES (SEQ ID NO: 78);

(c) HVR-L3 comprises an amino acid sequence selected from HQSNEDPPT (SEQ ID NO: 13), QQWSSYPLT (SEQ ID NO: 21), QQYNEYPWT (SEQ ID NO: 29), QQYNEYPWT (SEQ ID NO: 37), LQHTYLPWT (SEQ ID NO: 45), LQHTYLPWT (SEQ ID NO: 53), QHNRELLT (SEQ ID NO: 61), and HQSNWDPPT (SEQ ID NO: 79);

(d) HVR-H1 comprises an amino acid sequence selected from TNYAVS (SEQ ID NO: 15), KDDYMH (SEQ ID NO: 23), KDDYMH (SEQ ID NO: 31), KDDYIH (SEQ ID NO: 39), KDDYIH (SEQ ID NO: 47), TSYWMH (SEQ ID NO: 55), TSYVMF (SEQ ID NO: 63), TNYRVS (SEQ ID NO: 81), and TNYWVS (SEQ ID NO: 85);

(e) HVR-H2 comprises an amino acid sequence selected from VMWAGGGTNYNS (SEQ ID NO: 16), RIDPANDNTKYAP (SEQ ID NO: 24), RIDPENGNTKYGP (SEQ ID NO: 32), RIDPANGNTKYAP (SEQ ID NO: 40), RIDPANGNTKYAP (SEQ ID NO: 48), AIYPGNSDTNYNQ (SEQ ID NO: 56), YINPYNDDTKYNE (SEQ ID NO: 64), VMYAGGGTNYNS (SEQ ID NO: 82), and TMWAGGGTNYNS (SEQ ID NO: 86);

(f) HVR-H3 comprises an amino acid sequence selected from ARERPLTGVMDY (SEQ ID NO: 17), TRVEGRTGTYFDY (SEQ ID NO: 25), TRQLGLRRVWYALDY (SEQ ID NO: 33), ARQLGLRRTWYSLDY (SEQ ID NO: 41), TRQLGLRRTWYAMDY (SEQ ID NO: 49), TTAVGSY (SEQ ID NO: 57), AREDYYGSRFVYW (SEQ ID NO: 65), ARERPLTGVMDN (SEQ ID NO: 83), and ARERPLTGPMDY (SEQ ID NO: 87).

In at least one embodiment of the anti-CD200R1 antibody of the present disclosure, the antibody comprises:
(a) HVR-L1 of SEQ ID NO: 11, HVR-L2 of SEQ ID NO: 12, and HVR-L3 of SEQ ID NO: 13; and/or HVR-H1 of SEQ ID NO: 15, HVR-H2 of SEQ ID NO: 16, and HVR-H3 of SEQ ID NO: 17;
(b) HVR-L1 of SEQ ID NO: 19, HVR-L2 of SEQ ID NO: 20, and HVR-L3 of SEQ ID NO: 21; and/or HVR-H1 of SEQ ID NO: 23, HVR-H2 of SEQ ID NO: 24, and HVR-H3 of SEQ ID NO: 25;
(c) HVR-L1 of SEQ ID NO: 27, HVR-L2 of SEQ ID NO: 28, and HVR-L3 of SEQ ID NO: 29; and/or HVR-H1 of SEQ ID NO: 31, HVR-H2 of SEQ ID NO: 32, and HVR-H3 of SEQ ID NO: 33;
(d) HVR-L1 of SEQ ID NO: 35, HVR-L2 of SEQ ID NO: 36, and HVR-L3 of SEQ ID NO: 37; and/or HVR-H1 of SEQ ID NO: 39, HVR-H2 of SEQ ID NO: 40, and HVR-H3 of SEQ ID NO: 41;
(e) HVR-L1 of SEQ ID NO: 43, HVR-L2 of SEQ ID NO: 44, and HVR-L3 of SEQ ID NO: 45; and/or HVR-H1 of SEQ ID NO: 47, HVR-H2 of SEQ ID NO: 48, and HVR-H3 of SEQ ID NO: 49;
(f) HVR-L1 of SEQ ID NO: 51, HVR-L2 of SEQ ID NO: 52, and HVR-L3 of SEQ ID NO: 53; and/or HVR-H1 of SEQ ID NO: 55, HVR-H2 of SEQ ID NO: 56, and HVR-H3 of SEQ ID NO: 57;
(g) HVR-L1 of SEQ ID NO: 59, HVR-L2 of SEQ ID NO: 60, and HVR-L3 of SEQ ID NO: 61; and/or HVR-H1 of SEQ ID NO: 63, HVR-H2 of SEQ ID NO: 64, and HVR-H3 of SEQ ID NO: 65;
(h) HVR-L1 of SEQ ID NO: 77, HVR-L2 of SEQ ID NO: 78, and HVR-L3 of SEQ ID NO: 79; and/or HVR-H1 of SEQ ID NO: 81, HVR-H2 of SEQ ID NO: 82, and HVR-H3 of SEQ ID NO: 83;
(i) HVR-L1 of SEQ ID NO: 11, HVR-L2 of SEQ ID NO: 12, and HVR-L3 of SEQ ID NO: 13; and/or HVR-H1 of SEQ ID NO: 85, HVR-H2 of SEQ ID NO: 86, and HVR-H3 of SEQ ID NO: 87;
(j) HVR-L1 of SEQ ID NO: 11, HVR-L2 of SEQ ID NO: 12, and HVR-L3 of SEQ ID NO: 13; and/or HVR-H1 of SEQ ID NO: 81, HVR-H2 of SEQ ID NO: 82, and HVR-H3 of SEQ ID NO: 83; or
(k) HVR-L1 of SEQ ID NO: 77, HVR-L2 of SEQ ID NO: 78, and HVR-L3 of SEQ ID NO: 79; and/or HVR-H1 of SEQ ID NO: 85, HVR-H2 of SEQ ID NO: 86, and HVR-H3 of SEQ ID NO: 87.

In at least one embodiment of the anti-CD200R1 antibody of the present disclosure, the antibody comprises a light chain variable domain (VL) amino acid sequence having at least 90% identity to a sequence selected from SEQ ID NO: 10, 18, 26, 34, 42, 50, 58, 66, or 76; and/or a heavy chain variable domain (VH) amino acid sequence having at least 90% identity to a sequence selected from SEQ ID NO: 14, 22, 30, 38, 46, 54, 62, 67, 80, or 84.

In at least one embodiment of the anti-CD200R1 antibody of the present disclosure, the antibody comprises:
(a) a light chain variable domain (VL) amino acid sequence having at least 90% identity to SEQ ID NO: 10, and/or a heavy chain variable domain (VH) amino acid sequence having at least 90% identity to SEQ ID NO: 14;
(b) a light chain variable domain (VL) amino acid sequence having at least 90% identity to SEQ ID NO: 18, and/or a heavy chain variable domain (VH) amino acid sequence having at least 90% identity to SEQ ID NO: 22;
(c) a light chain variable domain (VL) amino acid sequence having at least 90% identity to SEQ ID NO: 26, and/or a heavy chain variable domain (VH) amino acid sequence having at least 90% identity to SEQ ID NO: 30;
(d) a light chain variable domain (VL) amino acid sequence having at least 90% identity to SEQ ID NO: 34, and/or a heavy chain variable domain (VH) amino acid sequence having at least 90% identity to SEQ ID NO: 38;
(e) a light chain variable domain (VL) amino acid sequence having at least 90% identity to SEQ ID NO: 42, and/or a heavy chain variable domain (VH) amino acid sequence having at least 90% identity to SEQ ID NO: 46;
(f) a light chain variable domain (VL) amino acid sequence having at least 90% identity to SEQ ID NO: 50, and/or a heavy chain variable domain (VH) amino acid sequence having at least 90% identity to SEQ ID NO: 54;
(g) a light chain variable domain (VL) amino acid sequence having at least 90% identity to SEQ ID NO: 58, and/or a heavy chain variable domain (VH) amino acid sequence having at least 90% identity to SEQ ID NO: 62;
(h) a light chain variable domain (VL) amino acid sequence having at least 90% identity to SEQ ID NO: 66, and/or a heavy chain variable domain (VH) amino acid sequence having at least 90% identity to SEQ ID NO: 67;
(i) a light chain variable domain (VL) amino acid sequence having at least 90% identity to SEQ ID NO: 76, and/or a heavy chain variable domain (VH) amino acid sequence having at least 90% identity to SEQ ID NO: 80;
(j) a light chain variable domain (VL) amino acid sequence having at least 90% identity to SEQ ID NO: 66, and/or a heavy chain variable domain (VH) amino acid sequence having at least 90% identity to SEQ ID NO: 84;
(k) the antibody comprises a light chain variable domain (VL) amino acid sequence having at least 90% identity to SEQ ID NO: 66, and/or a heavy chain variable domain (VH) amino acid sequence having at least 90% identity to SEQ ID NO: 80; or
(l) the antibody comprises a light chain variable domain (VL) amino acid sequence having at least 90% identity to SEQ ID NO: 76, and/or a heavy chain variable domain (VH) amino acid sequence having at least 90% identity to SEQ ID NO: 84.

In at least one embodiment of the anti-CD200R1 antibody of the present disclosure, the antibody comprises a light chain (LC) amino acid sequence having at least 90% identity to a sequence selected from SEQ ID NO: 68, 71, and 74; and/or a heavy chain (HC) amino acid sequence having at least 90% identity to a sequence selected from SEQ ID NO: 69, 70, 72, 73, 75, 88, and 89.

In at least one embodiment of the anti-CD200R1 antibody of the present disclosure, the antibody comprises:

(a) a light chain (LC) amino acid sequence having at least 90% identity SEQ ID NO: 68; and/or a heavy chain (HC) amino acid sequence having at least 90% identity to SEQ ID NO: 69;
(b) a light chain (LC) amino acid sequence having at least 90% identity SEQ ID NO: 68; and/or a heavy chain (HC) amino acid sequence having at least 90% identity to SEQ ID NO: 70;
(c) a light chain (LC) amino acid sequence having at least 90% identity SEQ ID NO: 71; and/or a heavy chain (HC) amino acid sequence having at least 90% identity to SEQ ID NO: 88;
(d) a light chain (LC) amino acid sequence having at least 90% identity to SEQ ID NO: 71; and/or a heavy chain (HC) amino acid sequence having at least 90% identity to SEQ ID NO: 72;
(e) a light chain (LC) amino acid sequence having at least 90% identity SEQ ID NO: 68; and/or a heavy chain (HC) amino acid sequence having at least 90% identity to SEQ ID NO: 89;
(f) a light chain (LC) amino acid sequence having at least 90% identity SEQ ID NO: 68; and/or a heavy chain (HC) amino acid sequence having at least 90% identity to SEQ ID NO: 73;
(g) a light chain (LC) amino acid sequence having at least 90% identity SEQ ID NO: 68; and/or a heavy chain (HC) amino acid sequence having at least 90% identity to SEQ ID NO: 88;
(h) a light chain (LC) amino acid sequence having at least 90% identity SEQ ID NO: 71; and/or a heavy chain (HC) amino acid sequence having at least 90% identity to SEQ ID NO: 89; or
(i) a light chain (LC) amino acid sequence having at least 90% identity to SEQ ID NO: 74; and/or a heavy chain (HC) amino acid sequence having at least 90% identity to SEQ ID NO: 75.

In at least one embodiment of the anti-CD200R1 antibody of the present disclosure, the antibody is characterized by one or more of the following properties:
(a) binds to hu-CD200R1 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD200R1 polypeptide of SEQ ID NO: 1, 2, 3, and/or 4;
(b) binds to hu-CD200R1-iso4 and hu-CD200R1-iso1 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD200R1-iso4 polypeptide of SEQ ID NO: 1 and/or 2, and a hu-CD200R1-iso1 polypeptide of SEQ ID NO: 3 and/or 4;
(c) binds to hu-CD200R1-iso4-Alt and hu-CD200R1-iso4-Ref with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD200R1-iso4-Alt polypeptide of SEQ ID NO: 1, and a hu-CD200R1-iso4-Ref polypeptide of SEQ ID NO: 2;
(d) binds to hu-CD200R1-iso4-Alt, hu-CD200R1-iso4-Ref, hu-CD200R1-iso1-Alt, and hu-CD200R1-iso1-Ref with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD200R1-iso4-Alt polypeptide of SEQ ID NO: 1, hu-CD200R1-iso4-Ref polypeptide of SEQ ID NO: 2, hu-CD200R1-iso1-Alt polypeptide of SEQ ID NO: 3, and a hu-CD200R1-iso1-Ref polypeptide of SEQ ID NO: 4;
(e) binds to cyno-CD200R1 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a cyno-CD200R1 polypeptide of SEQ ID NO: 5;
(f) binds to hu-CD200R1 and to cyno-CD200R1 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD200R1 polypeptide of SEQ ID NO: 1, 2, 3, and/or 4, and a cyno-CD200R1 polypeptide of SEQ ID NO: 5;
(g) blocks hu-CD200-Fc binding to hu-CD200R1-iso4-Alt (SEQ ID NO: 1), hu-CD200R1-iso4-Ref (SEQ ID NO: 2), hu-CD200R1-iso1-Alt (SEQ ID NO: 3), and hu-CD200R1-iso1-Ref (SEQ ID NO: 4) measured by ELISA with an $IC_{50}$ of 10 nM or less, 7 nM or less, 5 nM or less, 2 nM or less, or 1 nM or less;
(h) blocks hu-CD200-Fc binding to hu-CD200R1 expressed on a cell with an $IC_{50}$ of 2.5 nM or less, 1 nM or less, or 0.5 nM or less; optionally, wherein the cell is a U937 cell stably expressing hu-CD200R1;
(i) binds to human T-cells with an $EC_{50}$ of 2.5 nM or less, 1 nM or less, or 0.5 nM or less; optionally, wherein the human T-cells are CD4+ T-cells or CD8+ T-cells;
(j) increases IFNγ production from human tumor cells by at least 1.2-fold, 1.5-fold, 2-fold, or more, with an antibody concentration of 100 nM or less, 50 nM or less, or 10 nM or less; optionally, wherein the tumor cell type is selected from colorectal, endometrial, lung, melanoma, ovarian, pancreatic, or prostate;
(k) increases IFNγ and/or IL-2 production from hu-CD200-Fc coated human T cells relative to IgG control by at least 1.2-fold, 1.5-fold, 2-fold, or more;
(l) increases activation of human CD4+ T-cells or human Cd8+ T-cells by at least 1.5-fold, at least 2-fold, at least 2.5-fold, at least 3-fold or more;
(m) does not agonize CD200R1 signaling;
(n) blocks induction of pDok2 activity in U937 monocytic cell lines treated with soluble hu-CD200-Fc; and/or
(o) blocks NFkβ transcription induced by hu-CD200 binding hu-CD200R1 expressing cell-lines; optionally, wherein the cell lines are a CD200R1-expressing K562 reporter cells and CD200-expressing 293T cells.

In some embodiments, the therapeutically effective amount is at least about 1 mg/kg, at least about 2 mg/kg, at least about 10 mg/kg, at least about 20 mg/kg. In some embodiments, the therapeutically effective amount is at least about 0.3 mg, at least about 1.0 mg, at least about 3.0 mg, at least about 10 mg, at least about 30 mg, at least about 100 mg, at least about 300 mg, or at least about 900 mg. In some embodiments, the therapeutically effective amount is at least about 10 mg/kg, at least about 20 mg/kg, or at least about 100 mg/kg. In some embodiments, there are no significant off-target effects of the anti-CD200R1 antibody of the present disclosure at the therapeutically effective amount. In some embodiments, there are no significant off-target effects of the anti-CD200R1 antibody of the present disclosure at a dose of not more than 10 mg/kg. In some embodiments, there are no significant off-target effects of the anti-CD200R1 antibody of the present disclosure at a dose of not more than 20 mg/kg.

The present disclosure also provides embodiments of the anti-CD200R1 antibody, wherein: (i) the antibody is a monoclonal antibody; (ii) the antibody is a human, humanized, or chimeric antibody; (iii) the antibody is a full length antibody of class IgG, optionally, wherein the class IgG antibody has an isotype selected from IgG1, IgG2, IgG3, IgG4, and IgG4 S228P and IgG4 S228P/L235E; (iv) the antibody is an Fc region variant, optionally an Fc region variant that alters effector function (e.g., a variant resulting in an effectorless antibody), or an Fc region variant that alters antibody half-life, or an Fc region variant that alters both effector function and antibody half-life, including in all instances where the Fc region may or may not contain a c-terminal lysine; (v) the antibody is an antibody fragment, optionally selected from the group consisting of F(ab')$_2$, Fab', Fab, Fv, single domain antibody (VHH), and scFv; (vi) the antibody is an immunoconjugate, optionally, wherein the immunoconjugate comprises a therapeutic agent for treatment of a CD200R1-mediated disease or condition; (vii) the antibody is a multispecific antibody, optionally a bispecific antibody; and (viii) the antibody is a synthetic antibody, wherein the HVRs are grafted onto a scaffold or framework other than an immunoglobulin scaffold or framework; optionally, a scaffold selected from an alternative protein scaffold and an artificial polymer scaffold.

In other embodiments, the present disclosure provides isolated nucleic acids encoding the anti-CD200R1 antibodies disclosed herein.

In some embodiments, the present disclosure also provides a host cell comprising a nucleic acid encoding an anti-CD200R1 antibody as disclosed herein.

The disclosure also provides a method of producing an anti-CD200R1 antibody, wherein the method comprises culturing a host cell comprising a nucleic acid (or vector) encoding an anti-CD200R1 antibody so that an antibody is produced.

In some embodiments, the disclosure provides a pharmaceutical composition comprising an anti-CD200R1 antibody as disclosed herein and a pharmaceutically acceptable carrier. In some embodiments, the pharmaceutical composition further comprises a therapeutic agent for treatment of a CD200R1-mediated disease or condition. In some embodiments, the anti-CD200R1 antibody is the sole active agent of the pharmaceutical composition. In some embodiments, the pharmaceutical composition comprises the anti-CD200R1 antibody and an additional active agent, such as but not limited to a checkpoint inhibitor, such as e.g., a second antibody comprising a specificity for an antigen that is an immune checkpoint molecule; optionally, wherein the immune checkpoint molecule is selected from PD-1, PDL-1TIGIT, LAG3, PVRIG, KIR, TIM-3, CRTAM, CTLA-4, BTLA, CD96, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD73, CD83, CD39, TRAIL, CD226, VEGF, and VISTA.

In some embodiments, the present disclosure provides a method of treating a CD200R1-mediated disease in a subject, comprising administering to the subject a therapeutically effective amount of an anti-CD200R1 antibody as disclosed herein, or a therapeutically effective amount of a pharmaceutical formulation of an anti-CD200R1 antibody as disclosed herein. In some embodiments, the anti-CD200R1 antibody is the sole active agent administered to the subject to treat the CD200R1-mediated condition. In some embodiments, the subject is administered more than one active agents, including e.g., 2 or more, 3 or more, 4 or more, or 5 or more active agents effective to treat the subject for the CD200R1-mediated condition. In some embodiments, the more than one active agents administered to the subject include the anti-CD200R1 antibody and at least one additional active agent, such as a checkpoint inhibitor e.g., an antibody comprising a specificity for an antigen that is an immune checkpoint molecule.

In some embodiments, the present disclosure provides a method of treating a disease mediated by binding of CD200 to CD200R1 expressed on cells in a subject, comprising administering to the subject a therapeutically effective amount of an anti-CD200R1 antibody as disclosed herein, or a therapeutically effective amount of a pharmaceutical formulation of an anti-CD200R1 antibody as disclosed herein. In some embodiments, the anti-CD200R1 antibody is the sole active agent administered to the subject to treat the subject for the disease mediated by binding of CD200 to CD200R1 expressed on cells in the subject. In some embodiments, the subject is administered a plurality of active agents effective to treat the subject, including e.g., where the plurality of active agents include the anti-CD200R1 antibody and an additional active agent, such as but not limited to e.g., a checkpoint inhibitor such as e.g., a second antibody comprising a specificity for an antigen that is an immune checkpoint molecule. In at least one embodiment, the anti-CD200R1 antibodies bind to hu-CD200R1 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to any one or more of the four hu-CD200R1 isoforms of SEQ ID NO: 1, 2, 3, and/or 4.

In some embodiments of the uses and methods of treatment disclosed herein, the CD200R1-mediated diseases and conditions, or the diseases mediated by CD200 that can be treated with the anti-CD200R1 antibodies of the present disclosure, or pharmaceutical compositions thereof, include cancer. In some embodiments, the cancer is selected from adrenal gland cancer, bladder cancer, sarcomas, microsatellite instability-high (MSI-H) cancer (including solid MSI-cancer), TMB (tumor mutational burden)-high tumor, mismatch repair deficient (dMMR) cancer, brain cancer, breast cancer, cervical cancer, colorectal cancer, EGJ adenocarcinoma, esophageal cancer, gall bladder cancer, gastric cancer (e.g. gastrointestinal carcinoid (GI carcinoid)), head and neck cancer, heart cancer, hepatocellular carcinoma, kidney cancer, liver cancer, melanoma, mesothelioma (e.g. pleural mesothelioma), non-small cell lung cancer, ovarian cancer, epithelial ovarian cancer, endometrial cancer, pediatric solid cancers, pancreatic cancer, prostate cancer, spleen cancer, small cell lung cancer, testicular cancer, thyroid cancer (e.g. medullary thyroid cancer or follicular thyroid cancer), blood cancers (e.g. diffuse large B cell lymphoma (DLBCL), leukemias, lymphomas, myelomas), renal cell carcinoma, clear cell renal carcinoma, neuroendocrine tumors (e.g. malignant pheochromocytoma and paraganglioma), and uterine cancer. In some embodiments, the cancer is selected from lung cancer (e.g. small cell lung cancer), skin cancer (e.g., melanoma), pancreatic cancer, endometrial cancer, prostate cancer, colorectal cancer, ovarian cancer, mesothelioma, and bladder cancer.

BRIEF DESCRIPTION OF THE FIGURES

FIG. 1A and FIG. 1B depict alignments of VL domain and VH domain sequences from selected anti-CD200R1 antibodies of the present disclosure and a commercial antibody, OX108. HVRs are highlighted in grey and positions are numbered based on Kabat numbering.

FIG. 2 depicts alignments of the VL domain and VH domain sequences of the murine anti-CD200R1 antibody, 10F6, to the closest human germline sequences, and the sequences of the humanized version of 10F6. Positions numbered based on Kabat numbering.

FIG. 5A and FIG. 5B depict plots of assay results showing the binding of the anti-CD200R1 antibodies h10F6 and h22.1 to human or cyno T cells

FIG. 8C depicts calculated IFNg release with treatment of 10 µg/mL fixed CD200R1 antibody relative to isotype control (labeled here as Iso IgG E−) 4, 5, and 6 days post-MLR

FIG. 10A: IgG form of antibodies; FIG. 10B: Fab form of antibodies.

FIG. 11 depicts plots of data from pharmacokinetic studies in rats of the anti-CD200R1 antibodies, h10F6 and h22.1, carried out as described in Example 7.

DETAILED DESCRIPTION

Figure 3:
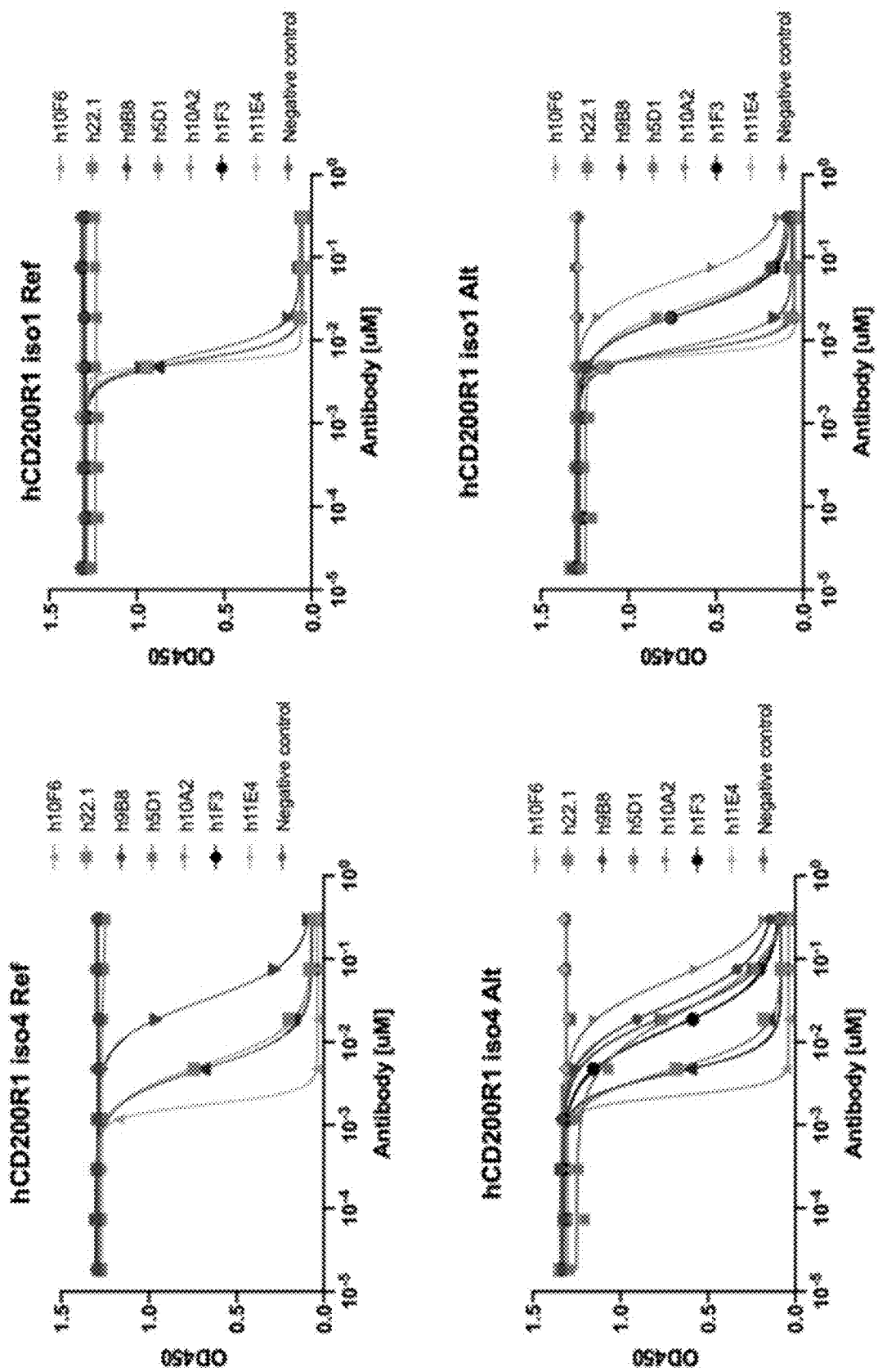
FIG. 3 depicts plots of ELISA results for blocking of hu-CD200-Fc binding to hu-CD200R1 (isoform 1 or 4 and haplotype Ref or Alt) by selected anti-CD200R1 antibodies of the present disclosure. 1 µg/mL hu-CD200-Fc was coated in the plate. A serial dilution of antibody in solution with hu-CD200R1 (0.1 µg/mL or 0.4 µg/mL) was incubated with plate-bound hu-CD200-Fc. Streptavidin poly-HRP antibody (Thermo-Fisher) was used for detection.

The present disclosure provides antibodies, including humanized antibodies, that specifically bind CD200R1 with high affinity and thereby inhibit, decrease, and/or fully block the function of CD200R1 as a cell surface receptor involved in immune regulation, particularly the function of CD200R1 as an inhibitor of lymphocyte (e.g., T cell and NK cell) activation. Accordingly, it is contemplated that any of the compositions or formulations comprising an anti-CD200R1 antibody of the present disclosure can be used as therapeutics for treatment of diseases mediated by the function of CD200R1 or its target ligand. CD200, such as cancers and viral infections. Further, it is contemplated that the anti-CD200R1 antibody of the present disclosure can be used as a therapeutic in combination with other therapeutics, such as antibodies that target immune checkpoint molecules including, but not limited to, PD1, TIGIT, LAG3, PVRIG, KIR, TIM-3, and CRTAM. Among the therapeutics contemplated by the present disclosure is a bispecific antibody comprising the anti-CD200R1 binding specificity of an antibody of the present disclosure and another binding specificity of an antibody to an immune checkpoint molecule such as PD1, TIGIT, LAG3, PVRIG, KIR, TIM-3, and CRTAM.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., *Molecular Cloning-A Laboratory Manual* (2nd Ed.), Vols. 1-3, Cold Spring Harbor Laboratory, Cold Spring Harbor, N.Y., 1989 (hereinafter "Sambrook"); *Current Protocols in Molecular Biology*, F. M. Ausubel et al., eds., Current Protocols, a joint venture between Greene Publishing Associates, Inc. and John Wiley & Sons, Inc. (supplemented through 2011) (hereinafter "Ausubel"); *Antibody Engineering*, Vols. 1 and 2, R. Kontermann and S. Dubel, eds., Springer-Verlag, Berlin and Heidelberg (2010); *Monoclonal Antibodies: Methods and Protocols*, V. Ossipow and N. Fischer, eds., 2nd Ed., Humana Press (2014); *Therapeutic Antibodies: From Bench to Clinic.* Z. An, ed., J. Wiley & Sons, Hoboken, N.J. (2009); and *Phage Display*. Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for the purpose of describing particular embodiments only and is not intended to be limiting. For purposes of interpreting this disclosure, the following description of terms will apply and, where appropriate, a term used in the singular form will also include the plural form and vice versa.

"CD200R1" as used herein, refers to the cell surface transmembrane glycoprotein CD200 receptor 1, and encompasses the CD200R1 proteins of human, cynomolgus monkey (herein referred to in some cases as "cyno"), rhesus monkey, and their various isoforms. Amino acid sequences of various exemplary CD200R1 proteins and isoforms are known in the art and are provided in Table 2 below and the attached Sequence Listing.

"CD200R1 mediated condition" or "CD200R1 mediated disease," as used herein, encompasses any medical condition associated with the specific binding of CD200R1 to a ligand (e.g., CD200). For example, specific binding of CD200 expressed on cell surfaces to other cells expressing the CD200R1 receptor can affect the binding of CD200 expressing cells to other immune regulatory molecules, which can alters activation of lymphocytes (e.g., T cells). Accordingly, CD200R1 mediated diseases can include, but are not limited to, any disease or condition mediated by and/or responsive to antagonists or inhibitors of binding between CD200R1 or CD200 expressing cells, and/or any disease or condition responsive to inhibition of immune checkpoint inhibitors, including but not limited to cancers. Specific exemplary cancers are provided elsewhere herein.

"Immune checkpoint molecule," as used herein, refers to a molecule that functions to regulate an immune system pathway and thereby prevent it from attacking cells unnecessarily. Many immune checkpoint molecules, both inhibitory and co-stimulatory, are targets for immunotherapy (e.g., with blocking antibodies to block immune inhibition or with agonists to promote immune stimulation) in the treatment of cancer and viral infections. Exemplary immune checkpoint molecules targeted for cancer immunotherapy include, but are not limited to, PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD73, CD83, CD39, TRAIL, CD226, and VISTA.

"Antibody," as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, multispecific (or heteroconjugate) antibodies (e.g., bispecific antibodies), monovalent antibodies (e.g., single-arm antibodies), multivalent antibodies, antigen-binding fragments (e.g., Fab', F(ab')$_2$, Fab, Fv, rIgG, and scFv fragments), antibody fusions, and synthetic antibodies (or antibody mimetics).

"Anti-CD200R1 antibody" or "antibody that binds CD200R1" refers to an antibody that binds CD200R1 with sufficient affinity such that the antibody is useful as a diagnostic and/or therapeutic agent in targeting CD200R1. In some embodiments, the extent of binding of an anti-CD200R1 specific antibody to an unrelated, non-CD200R1 antigen is less than about 20%, less than about 15%, less than about 10%, or less than about 5% of the binding of the antibody to CD200R1 as measured, e.g., by a radioimmunoassay (RIA) or surface plasmon resonance (SPR). In some embodiments, an antibody that binds to CD200R1 has a dissociation constant ($K_D$) of <1 µM, <100 nM, <10 nM, <1 nM, <0.1 nM, <0.01 nM, or <1 pM (e.g., $10^{-8}$ M or less, e.g., from $10^{-8}$ M to $10^{-13}$ M, e.g., from $10^{-9}$ M to $10^{-13}$ M).

"Full-length antibody," "intact antibody," or "whole antibody" are used herein interchangeably to refer to an antibody having a structure substantially similar to a native antibody structure or having heavy chains that contain an Fc region as defined herein.

"Antibody fragment" refers to a portion of a full-length antibody which is capable of binding the same antigen as the full-length antibody. Examples of antibody fragments include, but are not limited to, Fv, Fab, Fab', Fab'-SH, F(ab')$_2$; diabodies; linear antibodies; monovalent, or single-armed antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

"Variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs) (see, e.g., Kindt et al., Kuby Immunology, 6$^{th}$ ed., W.H. Freeman and Co., page 91). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (see, e.g., Portolano et al., J. Immunol. 150: 880-887 (1993); Clarkson et al., Nature 352:624-628 (1991)).

"Hypervariable region" or "HVR," as used herein, refers to each of the regions of an antibody variable domain which are hypervariable in sequence and/or form structurally defined loops ("hypervariable loops"). Generally, native antibodies comprise four chains with six HVRs; three in the heavy chain variable domain, $V_H$ (HVR-H1, HVR-H2, HVR-H3), and three in the light chain variable domain, $V_L$ (HVR-L1, HVR-L2, HVR-L3). The HVRs generally comprise amino acid residues from the hypervariable loops and/or from the "complementarity determining regions" (CDRs). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted in the table 1 below.

TABLE 1

CD200R1, CD200, and associated sequences

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B[1] | H26-H35B[1] | H26-H32[1] | H30-H35B[1] |
|  | H31-H35[2] | H26-H35[2] | H26-H32[2] | H30-H35[2] |
| H2 | H50-H65 | H50-H58 | H53-H55 | H47-H58 |
| H3 | H95-H102 | H95-H102 | H96-H101 | H93-H101 |

[1]Kabat numbering
[2]Chothia numbering

Unless otherwise indicated, HVR residues and other residues in the variable domain (e.g., FR residues) are numbered herein according to Kabat et al., supra.

Hypervariable regions, as used herein, may include extended or alternative hypervariable regions as follows: 24-36 or 24-34 (L1), 46-56 or 50-56 (L2) and 89-97 or 89-96 (L3) in the $V_L$ domain and 26-35 or 30-35 (H1), 50-61, 50-65 or 49-65 (H2) and 93-102, 94-102, or 95-102 (H3) in the $V_H$ domain. The variable domain residues are numbered according to Kabat et al., supra, for each of these definitions.

"Complementarity determining region," or "CDR," as used herein, refers to the regions within the HVRs of the variable domain which have the highest sequence variability and/or are involved in antigen recognition. Generally, native antibodies comprise four chains with six CDRs; three in the heavy chain variable domains, $V_H$ (H1, H2, H3), and three in the light chain variable domains, $V_L$ (L1, L2, L3). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35 of H1, 50-61 of H2, and 95-102 of H3. (Numbering according to Kabat et al., supra).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

"Native antibody" refers to a naturally occurring immunoglobulin molecule. For example, native IgG antibodies are heterotetrameric glycoproteins of about 150,000 Daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially all of at least one, and typically two, variable domains, in which all or substantially all of the HVRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In some embodiments, for the $V_L$, the subgroup is subgroup kappa I as in Kabat et al., supra. In some embodiments, for the $V_H$, the subgroup is subgroup III as in Kabat et al., supra.

"Acceptor human framework" as used herein is a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence. However, the C-terminal lysine (Lys447) of the Fc sequence may or may not be present. The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcR, as used herein, also includes the neonatal receptor, FcRn, which is responsible for the transfer of maternal IgGs to the fetus (Guyer et al, J. Immunol. 1 17:587 (1976) and Kim et al, J. Immunol. 24:249 (1994)) and regulation of homeostasis of immunoglobulins. FcRs are reviewed, for example, in Ravetch and Kinet, Annu. Rev. Immunol 9:457-92 (1991); Capel et al, Immunomethods 4:25-34 (1994); and de Haas et al, J. Lab. Clin. Med. 126:330-41 (1995).

"Multivalent antibody," as used herein, is an antibody comprising three or more antigen binding sites. The multivalent antibody is preferably engineered to have the three or more antigen binding sites and is generally not a native sequence IgM or IgA antibody.

"Multispecific antibody" is an antibody having at least two different binding sites, each site with a different binding specificity. A multispecific antibody can be a full length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

"Fab fragment' refers to an antibody fragment that contains a variable and constant domain of the light chain and a variable domain and the first constant domain (CH1) of the heavy chain. "F(ab')$_2$ fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically the antigen binding arm is a complex of immunoglobulin polypeptide sequences, e.g., HVR and/or variable domain sequences of an immunoglobulin light and heavy chain.

"Single-chain Fv" or "scFv" refer to antibody fragments comprising the $V_H$ and $V_L$ domains of an antibody, wherein these domains are present in a single polypeptide chain. Generally, an Fv polypeptide further comprises a polypeptide linker between the $V_H$ and $V_L$ domains which enables the scFv to form the desired antigen binding structure.

"Diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites.

"Linear antibodies" refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

"Naked antibody" refers to an antibody that is not conjugated to a heterologous moiety (e.g., a cytotoxic moiety) or radiolabel.

"Affinity" refers to the strength of the sum total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1 \times 10^{-7}$ M. In some embodiments, an antibody may have a secondary affinity for an antigen other than the antigen to which it binds specifically, where "secondary affinity" will generally refer to binding of an antibody to a secondary antigen with an affinity value of more than about 10 nM as described elsewhere herein. Where an antibody may have a secondary affinity for a secondary antigen, such an antibody will nevertheless bind specifically to the primary antigen.

"Affinity matured" antibody refers to an antibody with one or more alterations in one or more HVRs, compared to a parent antibody which does not possess such alterations, such alterations resulting in an improvement in the affinity of the antibody for antigen.

"Functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., J. Chromatogr. B 848:79-87.

"Substantially similar" or "substantially the same," as used herein, refers to a sufficiently high degree of similarity between two numeric values (for example, one associated with a test antibody and the other associated with a reference antibody), such that one of skill in the art would consider the difference between the two values to be of little or no biological and/or statistical significance within the context of the biological characteristic measured by said values (e.g., $K_D$ values).

"Substantially different," as used herein, refers to a sufficiently high degree of difference between two numeric values (generally one associated with a molecule and the other associated with a reference molecule) such that one of skill in the art would consider the difference between the two values to be of statistical significance within the context of the biological characteristic measured by said values (e.g., $K_D$ values).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat" or "treating" refers to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-CD200R1 antibody to a subject to delay development or slow progression of a disease or condition mediated by CD200R1 or disease or condition in which CD200R1 may play a role in the pathogenesis and/or progression.

"Pharmaceutical formulation" refers to a preparation in a form that allows the biological activity of the active ingredient(s) to be effective, and which contain no additional components which are toxic to the subjects to which the formulation is administered. A pharmaceutical formulation may include one or more active agents. For example, a pharmaceutical formulation may include an anti-CD200R1 antibody as the sole active agent of the formulation or may include an anti-CD200R1 antibody and one or more additional active agents, such as e.g., an immune checkpoint inhibitor.

By "sole active agent", as used herein, is meant that the agent referred to is the only agent present in the formulation, or used in the therapy, that provides, or would be expected to provide, the relevant pharmacological effect to treat the subject for the condition, consistent with the description of "treatment" as provided herein. A pharmaceutical formulation comprising a sole active agent does not exclude the presence of one or more non-active agents, such as e.g., a pharmaceutically acceptable carrier, in the formulation. A "non-active agent" is an agent that would not be expected to provide, or otherwise significantly contribute to, the relevant pharmacological effect intended to treat the subject for the condition.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a CD200R1 mediated disease or condition, the therapeutically effective amount of the therapeutic agent is an amount that reduces, prevents, inhibits, and/or relieves to some extent one or more of the symptoms associated with the disease, disorder, or condition. For cancer therapy, efficacy in vivo can, for example, be measured by assessing the growth of a primary tumor, occurrence and/or growth of secondary tumor(s), occurrence and/or number of metastases, duration, severity, and/or recurrence of symptoms, the response rate (RR), duration of response, and/or quality of life.

"Concurrently," as used herein, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a mammal, including but not limited to, domesticated animals (e.g., cows, sheep, cats, dogs, and horses), primates (e.g., humans and non-human primates such as monkeys), rabbits, and rodents (e.g., mice and rats).

Detailed Description of Various Embodiments

I. CD200R1

Human CD200R1 ("hu-CD200R1") is a transmembrane glycoprotein that is expressed on the surface of cells, notably, myeloid cells and T cells. The hu-CD200R1 Uniprot sequence Q8TD46-1 encodes a 325 amino acid isoform referred to as isoform 1. The hu-CD200R1 Uniprot sequence Q8TD46-4 encodes a 348 amino acid isoform referred to in as isoform 1. The predominantly observed hu-CD200R1 isoform in human populations, however, is a 348 amino acid sequence variant of UniProt sequence Q8TD46-4 isoform 4 with a E335Q substitution. This variant of isoform 4 (Q8TD46-4+E335Q) represents one of two major haplotypes that account for >99/6 of all individuals observed in the 1000 Genomes project (https://www.intenationalgenome.org/). This haplotype (referred to herein as "Alt") is the most frequently observed in individuals of European ancestry with a frequency of 0.54. The other major haplotype (referred to herein as "Ref") is observed in individuals of European ancestry with a frequency of 0.46 and corresponds with the human genome reference sequence. The Alt haplotype has the extracellular domain (ECD, amino acids 1-266) of the Q8TD46-4 sequence, and the intracellular domain (ICD, amino acids 291-348) of the Q8TD46-4 sequence with the E335Q substitution. The Ref haplotype has the extracellular domain (ECD, amino acids 1-266) of Q8TD46-4 sequence with three substitutions, R112K, P144T and Q200H, and the intracellular domain (ICD, amino acids 291-348) of the Q8TD46-4 sequence.

A 240 amino acid segment of the hu-CD200R1-iso4 Alt and Ref haplotype ECD sequences (positions 27-266) are set forth herein as SEQ ID NO: 1 and 2, respectively, in Table 2 below. A 215 amino acid segment of hu-CD200R1-iso1 Alt and Ref haplotype ECD sequences (positions 29-243) are set forth herein as SEQ ID NO: 3 and 4, respectively, in Table 2 below.

Recombinantly prepared segments of cyno-CD200R1 and rhesus CD200R1, analogous to hu-CD200R1 isoform 4 are set forth as SEQ ID NO: 5 and 6, respectively, in Table 2 below.

The hu-CD200R1 receptor target ligand, hu-CD200 protein can be found at Uniprot P41217 and is set forth herein as SEQ ID NO: 7. The corresponding cyno-CD200R1 CD200 proteins are also provided herein as SEQ ID NO: 8. All CD200 polypeptides are a C-terminal fusion with effectorless human IgG Fc as SEQ ID NO: 9.

Table 2 below provides a summary description of the sequences of the various CD200R1 and CD200 polypeptides of the present disclosure, and their sequence identifiers. The sequences also are included in the accompanying Sequence Listing.

TABLE 2

CD200R1, CD200, and associated sequences

| Name | Sequence | SEQ ID NO: |
|---|---|---|
| hu-CD200R1-iso4-Alt ECD | AAQPNNSLMLQTSKENHALASSSLC MDEKQITQNYSKVLAEVNTSWPVKM ATNAVLCCPPIALRNLIIITWEIIL RGQPSCTKAYRKETNETKETNCTDE RITWVSRPDQNSDLQIRPVAITHDG YYRCIMVTPDGNFHRGYHLQVLVTP EVTLFQNRNRTAVCKAVAGKPAAQI SWIPEGDCATKQEYWSNGTVTVKST CHWEVHNVSTVTCHVSHLTGNKSLY IELLPVPGAKKSAKL | 1 |
| hu-CD200R1-iso4-Ref ECD | AAQPNNSLMLQTSKENHALASSSLC MDEKQITQNYSKVLAEVNTSWPVKM ATNAVLCCPPIALRNLIIITWEIIL RGQPSCTKAYKKETNETKETNCTDE RITWVSRPDQNSDLQIRTVAITHDG YYRCIMVTPDGNFHRGYHLQVLVTP EVTLFQNRNRTAVCKAVAGKPAAHI SWIPEGDCATKQEYWSNGTVTVKST CHWEVHNVSTVTCHVSHLTGNKSLY IELLPVPGAKKSAKL | 2 |
| hu-CD200R1-iso1-Alt ECD | MDEKQITQNYSKVLAEVNTSWPVKM ATNAVLCCPPIALRNLIIITWEIIL RGQPSCTKAYRKETNETKETNCTDE RITWVSRPDQNSDLQIRPVAITHDG YYRCIMVTPDGNFHRGYHLQVLVTP EVTLFQNRNRTAVCKAVAGKPAAQI SWIPEGDCATKQEYWSNGTVTVKST CHWEVHNVSTVTCHVSHLTGNKSLY IELLPVPGAKKSAKL | 3 |
| hu-CD200R1-iso1-Ref ECD | MDEKQITQNYSKVLAEVNTSWPVKM ATNAVLCCPPIALRNLIIITWEIIL RGQPSCTKAYKKETNETKETNCTDE RITWVSRPDQNSDLQIRTVAITHDG YYRCIMVTPDGNFHRGYHLQVLVTP EVTLFQNRNRTAVCKAVAGKPAAHI SWIPEGDCATKQEYWSNGTVTVKST CHWEVHNVSTVTCHVSHLTGNKSLY IELLPVPGAKKSAKL | 4 |
| cyno-CD200R1 ECD (UniProt G7NZT0; positions 27-267) | AAQSNNSLMLQTSKENHTLASNSLC MDEKQITQNHSKVLAEVNISWPVQM ARNAVLCCPPIEFRNLIVITWEIIL RGQPSCTKTYRKDTNETKETNCTDE RITWVSTPDQNSDLQIHPVAITHDG YYRCIMATPDGNFHRGYHLQVLVTP EVTLFESRNRTAVCKAVAGKPAAQI SWIPAGDCAPTEQEYWGNGTVTVKS TCHWEGHNVSTVTCHVSHLTGNKSL YIELLPVPGAKKSAKL | 5 |

TABLE 2-continued

CD200R1, CD200, and associated sequences

| Name | Sequence | SEQ ID NO: |
|---|---|---|
| rhesus-CD200R1 ECD (UniProt F7EF72; positions 27-267) | AAQSNNSLMLQTSKENHTLASNSLC MDEKQITQNHSKVLAEVNISWPVQM ARNAVLCCPPIEFRNLIVITWEIIL RGQPSCTKSYRKETNETKETNCTDE RITWVSTPDQNSDLQIYPVAITHDG YYRCIMATPDGNFHRGYHLQVLVTP EVTLFESRNRTAVCKAVAGKPAAQI SWIPAGDCAPTEQEYWGNGTVTVKS TCHWEGHNVSTVTCHVSHLTGNKSL YIELLPVPGAKKSAKL | 6 |
| hu-CD200 (Uniprot: P41217) | MERLVIRMPFSHLSTYSLVWVMAAV VLCTAQVQVVTQDEREQLYTPASLK CSLQNAQEALIVTWQKKKAVSPENM VTFSENHGVVIQPAYKDKINITQLG LQNSTITFWNITLEDEGCYMCLFNT FGFGKISGTACLTVYVQPIVSLHYK FSEDHLNITCSATARPAPMVFWKVP RSGIENSTVTLSHPNGTTSVTSILH IKDPKNQVGKEVICQVLHLGTVTDF KQTVNKG | 7 |
| cyno-CD200 (Uniprot: A0A2K5TQS2) | MERLVIRMPFCHLSTYSLVWGMAAV VLCAAQVQVVTQDEREQLYTPASLR CSLQNAQEVLIVTWQKKKAVSPENM VTFSENHGVVIQPAYKDKINITQLG LQNTTITFWNITLEDEGCYMCLFNT FGSGKISGTACLTVYVQPIVSLHYK YSEDHLNITCSATARPAPMIFWKVP RSGFENSTVTQSHPNGTTSVTSILH VKDPKNQVGKEVICQVLHLGTVTDF KQTFDKG | 8 |
| human IgG Fc N297G | GGSGSGTCPPCPAPELLGGPSVFLF PPKPKDTLMISRTPEVTCVVVDVSH EDPEVKFNWYVDGVEVHNAKTKPRE EQYGSTYRVVSVLTVLHQDWLNGKE YKCKVSNKALPAPIEKTISKAKGQP REPQVYTLPPSRDELTKNQVSLTCL VKGFYPSDIAVEWESNGQPENNYKT TPPVLDSDGSFFLYSKLTVDKSRWQ QGNVFSCSVMHEALHNHYTQKSLSL SPG | 9 |

II. Anti-CD200R1 Antibodies

In some embodiments, the present disclosure provides structures of anti-CD200R1 antibodies in terms of the amino acid and encoding nucleotide sequences of the various well-known immunoglobulin features (e.g., HVRs, FRs, $V_H$, $V_L$ domains, and full-length heavy and light chains). Table 3 below provides a summary description of anti-CD200R1 antibody sequences of the present disclosure, and their sequence identifiers. The sequences are included in the accompanying Sequence Listing.

TABLE 3

Anti-CD200R1 antibody sequences

| Description | Sequence | SEQ ID NO: |
|---|---|---|
| 10F6 (mAb1)-VL | DIVLTQSPPSLAVSLGQRATMSCRASESVDYSGNSFMHWFQQKAGQPPKL LIYRASNLESGIPARFSGSGSRTDFTLTINPLEADDVATYYCHQSNEDPP TFGGGTKLEMK | 10 |
| 10F6-HVR-L1 h10F6-HVR-L1 h10F6.V2-HVR-L1 h10F6.V3-HVR-L1 (VL positions 24-34) | RASESVDYSGNSFMH | 11 |
| 10F6-HVR-L2 h10F6-HVR-L2 h10F6.V2-HVR-L2 h10F6.V3-HVR-L2 (VL positions 50-56) | RASNLES | 12 |
| 10F6-HVR-L3 h10F6-HVR-L3 h10F6.V2-HVR-L3 h10F6.V3-HVR-L3 (VL positions 89-97) | IIQSNEDFFT | 13 |
| 10F6-VH | QVQLKESGPGLVAPSQSLSITCTVSGFSLTNYAVSWVRQPPGKGLEWLGV MWAGGGTNYNSVFKSRLTISKDNSKSQVFLKMNSLQTDDTARYYCARERP LTGVMDYWGQGTSVTVSS | 14 |
| 10F6-HVR-H1 h10F6-HVR-H1 (VH positions 30-35) | TNYAVS | 15 |

TABLE 3-continued

Anti-CD200R1 antibody sequences

| Description | Sequence | SEQ ID NO: |
|---|---|---|
| 10F6-HVR-H2 h10F6-HVR-H2 (VH positions 50-61) | VMWAGGGTNYNS | 16 |
| 10F6-HVR-H3 h10F6-HVR-H3 (VH positions 93-102) | ARERPLTGVMDY | 17 |
| 9B8-VL | QIVLTQSPALTSASPGEKVTMTC<u>SASSSVSYMY</u>WFQQKPRSSPKPWIY<u>LTSKLAS</u>GVPARFSGSGSGTSYSLTISSMEAEDAATYYC<u>QQWSSYPLT</u>FGAGTKLELK | 18 |
| 9B8-HVR-L1 (VL positions 24-34) | SASSSVSYMY | 19 |
| 9B8-HVR-L2 (VL positions 50-56) | LTSKLAS | 20 |
| 9B8-HVR-L3 (VL positions 89-97) | QQWSSYPLT | 21 |
| 9B8-VH | EVQLQQSGTVLVRPGASVKLSCTASGFNI<u>KDDYMH</u>WVKQRPEQGLEWIG<u>RIDPANDNTKYAP</u>KFQDRATITADTSSNTAYLQLSSLTSEDTAVYYC<u>TRVEGRTGTYFDY</u>WGQGTTLTVSS | 22 |
| 9B8-HVR-H1 (VH positions 30-35) | KDDYMH | 23 |
| 9B8-HVR-H2 (VH positions 50-61) | RIDPANDNTKYAP | 24 |
| 9B8-HVR-H3 (VH positions 93-102) | TRVEGRTGTYFDY | 25 |
| 5D1-VL | DVQITQSPSYLAASPGETITINC<u>RASKSISKYLA</u>WYQEKPGKTNKFLIY<u>SGSTLQS</u>GIPSRFSGSGSGTDFTLTISSLEPEDFAMYYC<u>QQYNEYPWT</u>FGGGTKLEIK | 26 |
| 5D1-HVR-L1 (VL positions 24-34) | RASKSISKYLA | 27 |
| 5D1-HVR-L2 (VL positions 50-56) | SGSTLQS | 28 |
| 5D1-HVR-L3 (VL positions 89-97) | QQYNEYPWT | 29 |
| 5D1-VH | EVQLQQSGAELVRPGASVKLSCTASGFNI<u>KDDYMH</u>WVKQRPEQGLEWIG<u>RIDPENGNTKYGP</u>KFQDKATITADTSSNTAYLQFSSLTSEDTAVYYC<u>TRQLGLRRVWYALDY</u>WGQGTSVTVSS | 30 |
| 5D1-HVR-H1 (VH positions 30-35) | KDDYMH | 31 |
| 5D1-HVR-H2 (VH positions 50-61) | RIDPENGNTKYGP | 32 |
| 5D1-HVR-H3 (VH positions 93-102) | TRQLGLRRVWYALDY | 33 |
| 10A2-VL | DVQITQSPSYLAASPGETITINC<u>RASKSISKYLA</u>WYQEKPGKTNKLLIY<u>SGSTLQS</u>GIPSRFSGSGSGTDFTLTISSLEPEDFAMYYC<u>QQYNEYPWT</u>FGGGTKLEIK | 34 |

TABLE 3-continued

Anti-CD200R1 antibody sequences

| Description | Sequence | SEQ ID NO: |
| --- | --- | --- |
| 10A2-HVR-L1 (VL positions 24-34) | RASKSISKYLA | 35 |
| 10A2-HVR-L2 (VL positions 50-56) | SGSTLQS | 36 |
| 10A2-HVR-L3 (VL positions 89-97) | QQYNEYPWT | 37 |
| 10A2-VI3 | EVQLQQSGAEFVRPGASVKLSCTTSGFYI<u>KDDYIH</u>WVKQRPEQGLEWIG<u>R IDPANGNTKYAP</u>KFQDKATITADTSSNTAYLQLSRLTSEDTAVYYC<u>ARQL GLRRTWYSLDY</u>WGQGTSVTVSS | 38 |
| 10A2-HVR-H1 (VH positions 30-35) | KDDYIH | 39 |
| 10A2-HVR-H2 (VH positions 50-61) | RIDPANGNTKYAP | 40 |
| I0A2-HVR-H3 (VH positions 93-102) | ARQLGLRRTWYSLDY | 41 |
| 1F3-VL | DVQMIQSPSSLSASLGDKVTMTC<u>QASHTINLN</u>WFQQKPGKAPKLLIY<u>GTS NLED</u>GVPPRFSGSGYGTDFTLTISSLEDEDMATYFC<u>LQHTYLPWT</u>FGGGT KLEIK | 42 |
| 1F3-HVR-L2 (VL positions 24-34) | QASHTINLN | 43 |
| 1F3-HVR-L2 (VL positions 50-56) | GTSNLED | 44 |
| 1F3-HVR-L3 (VL positions 89-97) | LQHTYLPWT | 45 |
| 1F3-VH | EVQLQQSGAEFVRPGASVRLSCTTSGFYI<u>KDDYIH</u>WVKQRPEQGLEWIG<u>R IDPANGNTKYAP</u>KFQDKATITADTSSNTAYLQLNSLTSEDTAVYYC<u>TRQL GLRRTWYAMDY</u>WGQGTSVTVSS | 46 |
| 1F3-HVR-H1 (VH positions 30-35) | KDDYIH | 47 |
| 1F3-HVR-H2 (VH positions 50-61) | RIDPANGNTKYAP | 48 |
| 1F3-HVR-H3 (VH positions 93-102) | TRQLGLRRTWYAMDY | 49 |
| 11E4-VL | DVQMIQSPSSLSASLGDKVTMTC<u>QASHTINLN</u>WFQQKPGKAPKLLIY<u>GTS NLED</u>GVPPRFSGSGYGTDFTLTISSLEDEDMATYFC<u>LQHTYLPWT</u>FGGGT KLEIK | 50 |
| 11E4-HVR-L2 (VL positions 24-34) | QASHTINLN | 51 |
| 11E4-HVR-L2 (VL positions 50-56) | GTSNLED | 52 |

TABLE 3-continued

Anti-CD200R1 antibody sequences

| Description | Sequence | SEQ ID NO: |
|---|---|---|
| 11E4-HVR-L3 (VL positions 89-97) | LQHTYLPWT | 53 |
| 11E4-VH | EVQLQQSGTVLARPGASVKMSCEASGYTF<u>TSYWMH</u>WVKQSPGQGLEWVGA<br><u>IYPGNSDTNYNQ</u>KFKGKAKLTAVTSASTAYMELSSLTNEDSAVYYC<u>TTAV</u><br><u>GSY</u>WGQGTLVTVSA | 54 |
| 11E4-HVR-H1 (VH positions 30-35) | TSYWMH | 55 |
| 11E4-HVR-H2 (VH positions 50-61) | AIYPGNSDTNYNQ | 56 |
| 11E4-HVR-H3 (VH positions 93-102) | TTAVGSY | 57 |
| 22.1-VL | DIVLTQSPASLAVSLGQRATISC<u>RASKSVSTSGYSYMH</u>WYQQKPGQPPKL<br>LIY<u>LASNLES</u>GVPVRFSGSGSGTDFTLNIHPVEEEDAATYYC<u>QHNRELLT</u><br>FGAGTKLELK | 58 |
| 22.1-HVR-L2 (VL positions 24-34) | RASKSVSTSGYSYMH | 59 |
| 22.1-HVR-L2 (VL positions 50-56) | LASNLES | 60 |
| 22.1-HVR-L3 (VL positions 89-97) | QHNRELLT | 61 |
| 22.1-VH | EVQLQQSGPELVKPGASVKMSCKASGYTF<u>TSYVMF</u>WVKQKPGQGLEWIG<u>Y</u><br><u>INPYNDDTKYNE</u>KFKGKATLTSDKSSSTAYMELSSLTSEDSAVYYC<u>ARED</u><br><u>YYGSRFVYW</u>GQGTLVTVSS | 62 |
| 22.1-HVR-H1 (VH positions 30-35) | TSYVMF | 63 |
| 22.1-HVR-H2 (VH positions 50-61) | YINPYNDDTKYNE | 64 |
| 22.1-HVR-H3 (VH positions 93-102) | AREDYYGSRFVYW | 65 |
| h10F6-VL h10F6.V2-VL h10F6.V3-VL | DIVLTQSPDSLAVSLGERATINC<u>RASESVDYSGNSFMH</u>WFQQKPGQPPKL<br>LIY<u>RASNLES</u>GIPDRFSGSGSRTDFTLTISSLQAEDVAVYYC<u>HQSNEDPP</u><br><u>T</u>FGGGTKVEIK | 66 |
| h10F6-VH | EVQLQESGPGLVKPSETLSLTCTVSGFSL<u>TNYAVS</u>WVRQPPGKGLEWLG<u>V</u><br><u>MWAGGGTNYNS</u>VFKSRLTISKDNSKNQVSLKLSSVTAADTAVYYC<u>ARERP</u><br><u>LTGVMDY</u>WGQGTLVTVSS | 67 |
| h10F6-LC h10F6.V2-LC h10F6.V3-LC | MGWSCIILFLVATATGVHSDIVLTQSPDSLAVSLGERATINCRASESVDY<br>SGNSFMHWFQQKPGQPPKLLIYRASNLESGIPDRFSGSGSRTDFTLTISS<br>LQAEDVAVYYCHQSNEDPPTFGGGTKVEIKRTVAAPSVFIFPPSDEQLKS<br>GTASVVCLLNNFYPREAKVQWKVDNALQSGNSQESVTEQDSKDSTYSLSS<br>TLTLSKADYEKHKVYACEVTHQGLSSPVTKSFNRGEC | 68 |
| h10F6-HC | MGWSCIILFLVATATGVHSEVQLQESGPGLVKPSETLSLTCTVSGFSLTN<br>YAVSWVRQPPGKGLEWLGVMWAGGGTNYNSVFKSRLTISKDNSKNQVSLK<br>LSSVTAADTAVYYCARERPLTGVMDYWGQGTLVTVSSASTKGPSVFPLAP<br>SSKSTSGGTAAGCLVKDYFPEPVTVSWNSGALTSGVHTFPAVLQSSGLYS<br>LSSVVTVPSSSLGTQTYICNVNHKPSNTKVDKKVEPKSCDKTHTCPPCPA<br>PELLGGPSVFLFPPKPKDTLMISRTPEVTCVVVDVSHEDPEVKFNWYVDG<br>VEVHNAKTKPREEQYGSTYRVVSVLTVLHQDWLNGKEYKCKVSNKALPAP | 69 |

TABLE 3-continued

Anti-CD200R1 antibody sequences

| Description | Sequence | SEQ ID NO: |
|---|---|---|
| | IEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEA LHNHYTQKSLSLSPG | |
| h10F6-C-Lys-HC | MGWSCIILFLVATATGVHSEVQLQESGPGLVKPSETLSLTCTVSGFSLTN YAVSWVRQPPGKGLEWLGVMWAGGGTNYNSVFKSRLTISKDNSKNQVSLK LSSVTAADTAVYYCARERPLTGVMDYWGQGTLVTVSSASTKGPSVFPLAP SSKSTSGGTAAGCLVKDYFPEPVTVSWNSGALTSGVHTFPAVLQSSGLYS LSSVVTVPSSSLGTQTYICNVNHKPSNTKVDKKVEPKSCDKTHTCPPCPA PELLGGPSVFLFPPKPKDTLMISRTPEVTCVVVDVSHEDPEVKFNWYVDG VEVHNAKTKPREEQYGSTYRVVSVLTVLHQDWLNGKEYKCKVSNKALPAP IEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEA LHNHYTQKSLSLSPGK | 70 |
| h10F6.V1-LC h10F6.V4-LC | MGWSCIILFLVATATGVHSDIVLTQSPDSLAVSLGERATINCRASESVDY SGNSFMHWFQQKPGQPPKLLIYRASNLESGIPDRFSGSGSRTDFTLTISS LQAEDVAVYYCHQSNWDPPTFGGGTKVEIKRTVAAPSVFIFPPSDEQLKS GTASVVCLLNNFYPREAKVQWKVDNALQSGNSQESVTEQDSKDSTYSLSS TLTLSKADYEKHKVYACEVTHQGLSSPVTKSFNRGEC | 71 |
| h10F6.V1-C-Lys-HC h10F6.V3-C-Lys-HC | MGWSCIILFLVATATGVHSEVQLQESGPGLVKPSETLSLTCTVSGFSLTN YRVSWVRQPPGKGLEWLGVMYAGGGTNYNSVFKSRLTISKDNSKNQVSLK LSSVTAADTAVYYCARERPLTGVMDNWGQGTLVTVSSASTKGPSVFPLAP SSKSTSGGTAAGCLVKDYFPEPVTVSWNSGALTSGVHTFPAVLQSSGLYS LSSWTVPSSSLGTQTYICNVNHKPSNTKVDKKVEPKSCDKTHTCPPCPA PELLGGPSVFLFPPKPKDTLMISRTPEVTCVVVDVSHEDPEVKFNWYVDG VEVHNAKTKPREEQYGSTYRWSVLTVLHQDWLNGKEYKCKVSNKALPAP IEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEA LHNHYTQKSLSLSPGK | 72 |
| h10F6.V2-C-Lys-HC h10F6.V4-C-Lys-HC | MGWSCIILFLVATATGVHSEVQLQESGPGLVKPSETLSLTCTVSGFSLTN YWVSWVRQPPGKGLEWLGTMWAGGGTNYNSVFKSRLTISKDNSKNQVSLK LSSVTAADTAVYYCARERPLTGPMDYWGQGTLVTVSSASTKGPSVFPLAP SSKSTSGGTAAGCLVKDYFPEPVTVSWNSGALTSGVHTFPAVLQSSGLYS LSSVVTVPSSSLGTQTYICNVNHKPSNTKVDKKVEPKSCDKTHTCPPCPA PELLGGPSVFLFPPKPKDTLMISRTPEVTCVVVDVSHEDPEVKFNWYVDG VEVHNAKTKPREEQYGSTYRVVSVLTVLHQDWLNGKEYKCKVSNKALPAP IEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEA LHNHYTQKSLSLSPGK | 73 |
| h22.1-FL-LC | MGWSCIILFLVATATGVHSDIQLTQSPSSLSASVGDRVTITCRASKSVST SGYSYMHWYQQKPGKPPKLLIYLASNLESGVPSRFSGSGSGTDFTLTISS LQPEDFATYYCQHNRELLTFGGGTKVEIKRTVAAPSVFIFPPSDEQLKSG TASVVCLLNNFYPREAKVQWKVDNALQSGNSQESVTEQDSKDSTYSLSST LTLSKADYEKHKVYACEVTHQGLSSPVTKSFNRGEC | 74 |
| h22.1-FL-HC | MGWSCIILFLVATATGVHSEVQLVQSGAEVKKPGASVKVSCKASGYTFTS YVMFWVRQAPGQRLEWIGYINPYNDDTKYNEKFKGRATLTSDKSASTAYM ELSSLRSEDTAVYYCAREDYYGSRFVYWGQGTLVTVSSASTKGPSVFPLA PSSKSTSGGTAALGCLVKDYFPEPVTVSWNSGALTSGVHTFPAVLQSSGL YSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYV DGVEVHNAKTKPREEQYGSTYRVVSVLTVLHQDWLNGKEYKCKVSNKALP APIEKTISKAKGQPREPQVYTLPPSRDELTKNQVSLTCLVKGFYPSDIAV EWESNGQPENNYKTTPPVLDSDGSFFLYSKLTVDKSRWQQGNVFSCSVMH EALHNHYTQKSLSLSPG | 75 |
| h10F6.V1-VL h10F6.V4-VL | DIVLTQSPDSLAVSLGERATINC<u>RASESVDYSGNSFMH</u>WFQQKPGQPPKL LIY<u>RASNLES</u>GIPDRFSGSGSRTDFTLTISSLQAEDVAVYYC<u>HQSNWDPP T</u>FGGGTKVEIK | 76 |
| h10F6.V1-HVR-L1 h10F6-HVR-L1 h10F6.V4-HVR-L1 (VL positions 24-34) | RASESVDYSGNSFMH | 77 |
| h10F6.V1-HVR-L2 h10F6-HVR-L2 h10F6.V4-HVR-L2 (VL positions 50-56) | RASNLES | 78 |

TABLE 3-continued

Anti-CD200R1 antibody sequences

| Description | Sequence | SEQ ID NO: |
|---|---|---|
| h10F6.V1-HVR-L3<br>h10F6.V4-HVR-L3<br>(VL positions 89-97) | HQSNWDPPT | 79 |
| h10F6.V1-VH<br>h10F6.V3-VH | EVQLQESGPGLVKPSETLSLTCTVSGFSLTNYRVSWVRQPPGKGLEWLGV<br>MYAGGGTNYNSVFKSRLTISKDNSKNQVSLKLSSVTAADTAVYYCARERP<br>LTGVMDNWGQGTLVTVSS | 80 |
| h10F6.V1-HVR-H1<br>h10F6.V3-HVR-H1<br>(VH positions 30-35) | TNYRVS | 81 |
| h10F6.V1-HVR-H2<br>h10F6.V3-HVR-H2<br>(VH positions 50-61) | VMYAGGGTNYNS | 82 |
| h10F6.V1-HVR-H3<br>h10F6.V3-HVR-H3<br>(VL positions 93-102) | ARERPLTGVMDN | 83 |
| h10F6.V2-VH<br>h10F6.V4-VH | EVQLQESGPGLVKPSETLSLTCTVSGFSLTNYWVSWVRQPPGKGLEWLGT<br>MWAGGGTNYNSVFKSRLTISKDNSKNQVSLKLSSVTAADTAVYYCARERP<br>LTGPMDYWGQGTLVTVSS | 84 |
| h10F6.V2-HVR-H1<br>h10F6.V4-HVR-H1<br>(VH positions 30-35) | TNYWVS | 85 |
| h10F6.V2-HVR-H2<br>h10F6.V4-HVR-H2<br>(VH positions 50-61) | TMWAGGGTNYNS | 86 |
| h10F6.V2-HVR-H3<br>h10F6.V4-HVR-H3<br>(VH positions 93-102) | ARERPLTGPMDY | 87 |
| h10F6.V1-HC<br>h10F6.V3-HC | MGWSCIILFLVATATGVHSEVQLQESGPGLVKPSETLSLTCTVSGFSL<br>TNYRVSWVRQPPGKGLEWLGVMYAGGGTNYNSVFKSRLTISKDNSKNQ<br>VSLKLSSVTAADTAVYYCARERPLTGVMDNWGQGTLVTVSSASTKGPS<br>VFPLAPSSKSTSGGTAAGCLVKDYFPEPVTVSWNSGALTSGVHTFPAV<br>LQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHE<br>DPEVKFNWYVDGVEVHNAKTKPREEQYGSTYRVVSVLTVLHQDWLNGK<br>EYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVD<br>KSRWQQGNVFSCSVMHEALHNHYTQKSLSLSPG | 88 |
| h10F6.V2-HC<br>h10F6.V4-HC | MGWSCIILFLVATATGVHSEVQLQESGPGLVKPSETLSLTCTVSGFSL<br>TNYWVSWVRQPPGKGLEWLGTMWAGGGTNYNSVFKSRLTISKDNSKNQ<br>VSLKLSSVTAADTAVYYCARERPLTGPMDYWGQGTLVTVSSASTKGPS<br>VFPLAPSSKSTSGGTAAGCLVKDYFPEPVTVSWNSGALTSGVHTFPAV<br>LQSSGLYSLSSVVTVPSSSLGTQTYICNVNHKPSNTKVDKKVEPKSCD<br>KTHTCPPCPAPELLGGPSVFLFPPKPKDTLMISRTPEVTCVVVDVSHE<br>DPEVKFNWYVDGVEVHNAKTKPREEQYGSTYRVVSVLTVLHQDWLNGK<br>EYKCKVSNKALPAPIEKTISKAKGQPREPQVYTLPPSRDELTKNQVSL<br>TCLVKGFYPSDIAVEWESNGQPENNYKTTPPVLDSDGSFFLYSKLTVD<br>KSRWQQGNVFSCSVMHEALHNHYTQKSLSLSPG | 89 |

1. Binding Affinity, Blocking, and Cell-Signaling Inhibition of Anti-CD200R1 Antibodies In some embodiments, the anti-CD200R1 antibodies provided herein have an equilibrium dissociation constant ($K_D$) for binding to CD200R1 of <100 nM, <10 nM, <1 nM, <0.1 nM, <0.01 nM, or <0.001 nM (e.g., $10^{-8}$ M or less, from $10^{-8}$ M to $10^{-13}$ M, e.g., from $10^{-9}$ M to $10^{-13}$ M).

In some embodiments, the binding affinity is measured by equilibrium dissociation constant ($K_D$) to a hu-CD200R1 isoform/haplotype polypeptide of SEQ ID NO: 1, 2, 3, and/or 4. In some embodiments, the anti-CD200R1 is capable of binding with an affinity of an equilibrium dissociation constant ($K_D$) for binding to CD200R1 of <100 nM, <10 nM, <1 nM, <0.1 nM, <0.01 nM, or <0.001 nM (e.g., $10^{-8}$ M or less, from $10^{-8}$ M to $10^{-31}$ M, e.g., from $10^{-9}$ M to $10^{-13}$ M) to all four hu-CD200R1 isoform/haplotype polypeptides of SEQ ID NO: 1, 2, 3, and 4. In at least one embodiment, the anti-CD200R1 is capable of binding with comparable (e.g., within 20%) or equivalent affinity in the range of $10^{-13}$ M or less to the hu-CD200R1 polypeptides of SEQ ID NO: 1 and 2.

In at least one embodiment, the anti-CD200R1 antibody is characterized by binding to hu-CD200R1-iso4 and hu-CD200R1-iso1 with a binding affinity of $1 \times 10^{-8}$ M or less, $1 \times 10^{-9}$ M or less, $1 \times 10^{-10}$ M or less, or $1 \times 10^{-11}$ M or less. In some embodiments, wherein the binding affinity is measured by equilibrium dissociation constant ($K_D$) to a hu-CD200R1-iso4 polypeptide of SEQ ID NO: 1 and/or 2, and a hu-CD200R1-iso1 polypeptide of SEQ ID NO: 3 and/or 4.

In at least one embodiment, the anti-CD200R1 antibody is characterized by binding to hu-CD200R1-iso4-Alt and hu-CD200R1-iso4-Ref with a binding affinity of $1 \times 10^{-8}$ M or less, $1 \times 10^{-9}$ M or less, $1 \times 10^{-10}$ M or less, or $1 \times 10^{-11}$ M or less. In some embodiments, wherein the binding affinity is measured by equilibrium dissociation constant ($K_D$) to a hu-CD200R1-iso4-Alt polypeptide of SEQ ID NO: 1, and a hu-CD200R1-iso4-Ref polypeptide of SEQ ID NO: 2.

It is contemplated that the various anti-CD200R1 antibodies generated as disclosed herein include antibodies capable of high-affinity binding to cyno-CD200R1, and/or to both hu-CD200R1 and cyno-CD200R1. More specifically, in some embodiments, the anti-CD200R1 antibodies of the present disclosure bind to cyno-CD200R1 with a binding affinity of $1 \times 10^{-8}$ M or less, $1 \times 10^{-8}$ M or less, $1 \times 10^{-10}$ M or less, or $1 \times 10^{-11}$ M or less. In some embodiments, the binding affinity is measured as the equilibrium dissociation constant ($K_D$) for binding to the hu-CD200R1 polypeptide of SEQ ID NO: 5. In some embodiments, the anti-CD200R1 antibodies of the present disclosure bind to cyno-CD200R1 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to the cyno-CD200R1 polypeptide of SEQ ID NO: 5. In some embodiments, the anti-CD200R1 antibodies of the present disclosure bind to both hu-CD200R1 and cy-CD200R1 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to a hu-CD200R1 polypeptide of SEQ ID NO: 1, 2, 3, or 4, and a cyno-CD200R1 polypeptide of SEQ ID NO: 5.

Generally, binding affinity of a ligand to its receptor can be determined using any of a variety of assays and expressed in terms of a variety of quantitative values. Specific CD200R1 binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in WO2005/012359), immunoprecipitation assays, fluorescent immunoassays, protein A immunoassays, flow cytometric and fluorescence activated cell sorting (FACS) assays, and the like.

Accordingly, in some embodiments, the binding affinity is expressed as $K_D$ values and reflects intrinsic binding affinity (e.g., with minimized avidity effects). The anti-CD200R1 antibodies of the present disclosure exhibit strong binding affinities for the extracellular domains of the four distinct CD200R1 isoform/haplotype combinations that are predominant in humans: hu-CD200R1-iso4-Alt (SEQ ID NO: 1); hu-CD200R1-iso4-Ref (SEQ ID NO: 2); hu-CD200R1-iso1-Alt (SEQ ID NO: 3); and hu-CD200R1-iso1-Ref (SEQ ID NO: 4). The extracellular domains of these four isoforms four hu-CD200R1 polypeptides of SEQ ID NOs: 1-4, exhibit $K_D$ values of between 10 nM and 1 pM. Accordingly, anti-CD200R1 antibodies of the present disclosure may compete with antibodies having lower affinity for the same or overlapping epitopes of CD200R1.

In some embodiments, the anti-CD200R1 antibodies provided herein decrease, inhibit, and/or fully-block binding of CD200 to CD200R1, and thereby block immune regulation and/or immune signaling mediated by CD200R1, including the activation of T cells. The ability of the antibodies to inhibit these immune regulatory and/or immune signaling pathways mediated by CD200R1-expressing cells binding to CD200-expressing cells can be assayed in vitro using known cell-based assays including the various cell-based assays described in the Examples of the present disclosure. Accordingly, in some embodiments, the CD200R1 antibodies of the present disclosure are characterized by one or more of following functional properties based on the ability to decrease, inhibit, and/or fully-block cellular signaling pathways mediated by CD200R1 binding to CD200.

In at least one embodiment, the CD200R1 antibody of the present disclosure blocks hu-CD200-Fc binding to hu-CD200R1-iso4-Alt (SEQ ID NO: 1), hu-CD200R1-iso4-Ref (SEQ ID NO: 2), hu-CD200R1-iso1-Alt (SEQ ID NO: 3), and hu-CD200R1-iso1-Ref (SEQ ID NO: 4) measured by ELISA with an $IC_{50}$ of 10 nM or less, 7 nM or less, 5 nM or less, 2 nM or less, or 1 nM or less.

In at least one embodiment, the CD200R1 antibody of the present disclosure blocks hu-CD200-Fc binding to hu-CD200R1 expressed on a cell with an $IC_{50}$ of 2.5 nM or less, 1 nM or less, or 0.5 nM or less; optionally, wherein the cell is a U937 cell stably expressing hu-CD200R1.

In at least one embodiment, the CD200R1 antibody of the present disclosure blocks CD200 binding to CD200R1 expressed on a human T cell with an antibody ICs concentration of 10 nM or less, 5 nM or less, 1 nM or less, or 0.1 nM or less; optionally, wherein the cell is a CD8+ T-cell or a CD4+ T-cell.

In at least one embodiment, the CD200R1 antibody of the present disclosure binds to human T-cells with an $EC_{50}$ of 2.5 nM or less, 1 nM or less, or 0.5 nM or less; optionally, wherein the human T-cells are CD4+ T-cells or CD8+ T-cells.

In at least one embodiment, the CD200R1 antibody of the present disclosure increases IFNγ production from human tumor cells by at least 1.2-fold, 1.5-fold, 2-fold, or more, with an antibody concentration of 100 nM or less, 50 nM or less, or 10 nM or less; optionally, wherein the tumor cell type is selected from colorectal, endometrial, lung, melanoma, ovarian, pancreatic, or prostate.

In at least one embodiment, the CD200R1 antibody increases IFNγ and/or IL-2 production from CD200-Fc coated human T cells relative to IgG control by at least 1.2-fold, 1.5-fold, 2-fold, or more.

In at least one embodiment, the CD200R1 antibody increases activation of CD4+ T-cells and/or Cd8+ T-cells by at least 1.5-fold, at least 2-fold, at least 2.5-fold, at least 3-fold or more.

In at least one embodiment, the CD200R1 antibody blocks NFkβ transcription induced by binding between CD200 and CD200R1 expressing cell-lines; optionally, wherein the cell lines are a CD200R1-expressing K562 reporter cells and CD200-expressing 293T cells.

In at least one embodiment, the CD200R1 antibodies of the present disclosure are capable of blocking CD200R1-mediated cell-signaling and not act as an agonist of CD200R1 activity, or otherwise inadvertently agonize CD200R1 signaling. One experimental measure of induction of CD200R1 agonist activity is the induction of pDok2 activity in cells treated with CD200. Accordingly, in at least one embodiment, the anti-CD200R1 antibody of the present disclosure blocks induction of pDok2 activity in U937 monocytic cell lines treated with soluble CD200-Fc.

2. Antibody Fragments

In some embodiments, the anti-CD200R1 antibody of the present disclosure can be an antibody fragment. Antibody fragments useful with the binding determinants the present disclosure include, but are not limited to, Fab, Fab', Fab'-SH, F(ab')$_2$, Fv, scFv fragments, monovalent, single domain antibody, one-armed or single-arm antibody, and other fragments described herein and known in the art. Accordingly, in some embodiments of the anti-CD200R1 antibodies of the present disclosure, the antibody is an antibody fragment selected from the group consisting of F(ab')$_2$, Fab', Fab, Fv, single domain antibody (VHH), single-arm antibody, and scFv.

For a review of various antibody fragments, see e.g., Hudson et al. Nat. Med. 9: 129-134 (2003). For a review of scFv fragments, see, e.g., Pluckthun, in The Pharmacology of Monoclonal Antibodies, vol. 113. Rosenburg and Moore eds., (Springer-Verlag, New York), pp. 269-315 (1994); see also WO93/16185; and U.S. Pat. Nos. 5,571,894 and 5,587,458. For a description of Fab and F(ab')$_2$ fragments comprising salvage receptor binding epitope residues and having increased in vivo half-life, see U.S. Pat. No. 5,869,046. Other monovalent antibody forms are described in, e.g., WO2007/048037, WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., Nat. Med. 9: 129-134 (2003); and Hollinger et al., Proc. Natl. Acad. Sci. USA 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In some embodiments, the anti-CD200R1 antibody of the present disclosure can be a chimeric antibody. (See e.g., chimeric antibodies as described in U.S. Pat. No. 4,816,567; and Morrison et al., Proc. Natl. Acad. Sci. USA, 81:6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched: antibody in which the class or subclass has been changed from that of the parent antibody. It is contemplated that chimeric antibodies can include antigen-binding fragments thereof.

In some embodiments, the anti-CD200R1 antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which HVRs, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc. Nat'l Acad. Sci. USA 86: 10029-10033 (1989); U.S. Pat. Nos. 5,821,337, 7,527,791, 6,982,321, and 7,087,409; Kashmiri et al., Methods 36:25-34 (2005) (describing SDR (a-HVR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol, 151:2623 (1993)); human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem. 271:2261 1-22618 (1996)).

4. Human Antibodies

In some embodiments, the anti-CD200R1 antibody of the present disclosure can be a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., XENOMOUSE™ technology in U.S. Pat. Nos. 6,075,181 and 6,150,584; HUMAB® technology in U.S. Pat. No. 5,770,429; K-M MOUSE® technology in U.S. Pat. No. 7,041,870; and VELOCIMOUSE® technology in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor J. Immunol, 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

In some embodiments, the anti-CD200R1 antibody of the present disclosure may be isolated by screening combinatorial libraries for antibodies with the desired activity or activities. For example, a variety of methods are known in the art for generating phage display libraries and screening such libraries for antibodies possessing the desired binding characteristics. The use of phage display for preparation of affinity matured variants of the humanized version of the anti-CD200R1 antibody of the present disclosure are described in the Examples disclosed herein. Other methods for producing such library-derived antibodies can be found in e.g., Hoogenboom et al., Methods in Molecular Biology 178: 1-37 (O'Brien et al., ed., Human Press, Totowa, N.J. 2001); McCafferty et al., Nature 348:552-554; Clackson et al., Nature 352: 624-628 (1991); Marks et al., J. Mol. Biol. 222: 581-597 (1992); Marks and Bradbury, m Methods in Molecular Biology 248: 161-175 (Lo, ed., Human Press. Totowa, N.J. 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 1 19-132(2004).

6. Multispecific Antibodies

In some embodiments, the anti-CD200R1 antibody of the present disclosure is a multispecific antibody, e.g., a bispecific antibody. In some embodiments, the multispecific antibody is a monoclonal antibody having at least two different binding sites, each with a binding specificity for a different antigen, at least one of which specifically binds CD200R1.

In some embodiments, the multispecific antibody is a bispecific antibody comprising a specificity for CD200R1 and a specificity for another antigen that mediates immune regulation, immune signaling, and/or is expressed on a cancer or tumor cell. In some embodiments of the bispecific antibody, the other specificity is for an antigen that is an immune checkpoint molecule selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD73, CD83, CD39, TRAIL, CD226, and VISTA. In some embodiments, the anti-CD200R1 bispecific antibody, the other antigen for which the antibody has specificity is selected from PD1, TIGIT, LAG3, PVRIG, KIR, TIM-3, and CRTAM.

In some embodiments, at least one of binding sites specifically binds a cytotoxic agent. In exemplary embodiments, an anti-CD200R1 antibody of the present disclosure is a bispecific antibody and can be used to localize a cytotoxic agent to cells which express CD200R1.

Techniques for making multispecific antibodies include, but are not limited to, recombinant co-expression of two immunoglobulin heavy chain-light chain pairs having different specificities (see e.g., Milstein and Cuello. Nature 305: 537 (1983), WO 93/08829, and Traunecker et al., EMBOJ. 10: 3655 (1991)). "Knob-in-hole" engineering can also be used to generate bispecific antibodies useful with the anti-CD200R1 antibodies of the present disclosure. Techniques for knob-in-hole engineering are known in the art and described in e.g., U.S. Pat. No. 5,731,168.

Multispecific antibodies can also be made by engineering "electrostatic steering" effects that favor formation of Fc-heterodimeric antibody molecules rather than homodimers (WO 2009/089004A1); cross-linking two or more antibodies or fragments (see, e.g., U.S. Pat. No. 4,676,980, and Brennan et al., Science. 229: 81 (1985)); using leucine zippers to produce bispecific antibodies (see. e.g., Kostelny et al., J. Immunol, 148(5): 1547-1553 (1992)); using "diabody" technology for making bispecific antibody fragments (see, e.g., Hollinger et al., Proc. Natl. Acad. Sci. USA, 90:6444-6448 (1993)); using single-chain Fv (scFv) dimers (see. e.g. Gruber et al., J. Immunol, 152:5368 (1994)); or tri-specific antibodies (see e.g., Tutt et al., J. Immunol. 147: 60 (1991).

7. Antibody Variants

In some embodiments, variants of the anti-CD200R1 antibody of the present disclosure are also contemplated. For example, antibodies with improved binding affinity and/or other biological properties of the antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of CD200R1 antigen binding.

A. Substitution, Insertion, and Deletion Variants

In some embodiments, anti-CD200R1 antibody variants having one or more amino acid substitutions in addition to those described herein are provided. Sites for mutagenesis can include the HVRs and FRs. Typical "conservative" amino acid substitutions and/or substitutions based on common side-chain class or properties are well-known in the art and can be used in the embodiments of the present disclosure. The present disclosure also contemplates variants based on non-conservative amino acid substitutions in which a member of one of amino acid side chain class is exchanged for an amino acid from another class.

Amino acid side chains are typically grouped according to the following classes or common properties: (1) hydrophobic: Met, Ala, Val, Leu, Ile, Norleucine; (2) neutral hydrophilic: Cys, Ser, Thr, Asn, Gln; (3) acidic: Asp, Glu; (4)

basic: His, Lys, Arg; (5) chain orientation influencing: Gly, Pro; and (6) aromatic: Trp, Tyr, Phe.

Techniques are well-known in the art for amino acid substitution into an antibody and subsequent screening for desired function, e.g., retained/improved antigen binding, decreased immunogenicity, or improved ADCC or CDC.

Amino acid substitution variants can include substituting one or more hypervariable region residues of a parent antibody (e.g., a humanized or human antibody). Generally, the resulting variant(s) selected for further study will have modifications in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described in the Examples herein. Briefly, one or more HVR residues are mutated and the variant antibodies displayed on phage and screened for a particular biological activity (e.g., binding affinity).

A useful method for identifying residues or regions of an antibody that may be targeted for mutagenesis is "alanine scanning mutagenesis" (see e.g., Cunningham and Wells (1989) Science, 244: 1081-1085). In this method, a residue or group of target residues (e.g., charged residues such as Arg, Asp. His. Lys. and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively. or additionally, a crystal structure of an antigen-antibody complex to identify contact points between the antibody and antigen can be determined. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Substitutions can be made in HVRs to improve antibody affinity. Such alterations may be made in "hotspots," i.e., residues encoded by codons that undergo mutation at high frequency during the somatic maturation process (see, e.g., Chowdhury, Methods Mol. Biol. 207: 179-196 (2008)) with the resulting variant $V_H$ or $V_L$ being tested for binding affinity. In some embodiments, affinity maturation can be carried out by constructing and reselecting from secondary libraries (see e.g., in Hoogenboom et al., Methods in Molecular Biology 178: 1-37 (O'Brien et al., ed., Human Press, Totowa, N.J., (2001).) Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots." In some embodiments of the variant $V_H$ and $V_L$ sequences provided above, each HVR either is unaltered, or contains no more than one, two or three amino acid substitutions.

B. Glycosylation Variants

In some embodiments, the anti-CD200R1 antibody of the present disclosure is altered to increase or decrease the extent to which the antibody is glycosylated. Addition or deletion of glycosylation sites to an antibody can be carried out by altering the amino acid sequence such that one or more glycosylation sites can be created or removed.

In embodiments where the antibody comprises an Fc region, the carbohydrate attached to the Fc region can be altered. Typically, native antibodies produced by mammalian cells comprise a branched, biantennary oligosaccharide attached by an N-linkage to the asparagine at about position 297 ("N297") of the CH2 domain of the Fc region (see, e.g., Wright et al. TIBTECH 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the biantennary oligosaccharide structure. In some embodiments, the modifications of the oligosaccharide of an Fc region of an antibody can create a variant with certain improved properties.

In some embodiments, the anti-CD200R1 antibody of the present disclosure can be a variant of a parent antibody, wherein the variant comprises a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain at N297, relative to the sum of all glyco-structures attached to Asn 297 (e.g., complex, hybrid and high mannose structures) as measured by MALDI-TOF mass spectrometry (see e.g., WO 2008/077546). N297 refers to the asparagine residue located at about position 297 in the Fc region (Eu numbering of Fc region residues); however, N297 may also be located about 3 amino acids upstream or downstream of position 297, i.e., between positions 294 and 300, due to minor sequence variations in antibodies.

In some embodiments, the fucosylation variants can have improved ADCC function. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704: US2004/0110282; US2004/0109865; WO2000/61739; WO2001/29246; WO2003/085119; WO2003/084570; WO2005/035586; WO2005/035778; WO2005/053742; WO2002/031140: Okazaki et al. J. Mol. Biol. 336: 1239-1249 (2004); Yamane-Ohnuki et al. Biotech. Bioeng. 87: 614 (2004).

Cell lines useful for producing defucosylated antibodies include Led 3 CHO cells deficient in protein fucosylation (see e.g., Ripka et al. Arch. Biochem. Biophys. 249:533-545 (1986); US2003/0157108, and WO2004/056312), and knockout cell lines, such as alpha-1,6-fucosyltransferase gene. FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

C. Fc Region Variants

In some embodiments, an anti-CD200R1 antibody of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-CD200R1 antibodies of the present disclosure are described below.

In some embodiments, the anti-CD200R1 antibody can be an Fc region variant which has altered effector function. In some embodiments, the antibody with altered effector function can possess some (but not all of) the effector functions, decreased effector function, or none of the effector functions (e.g., effectorless) of the parent antibody. Effectorless Fc region variants can be be more desirable for certain applications where effector function (such as ADCC) is unnecessary or deleterious, and/or in vivo half-life of the antibody is important.

Fc region variant antibodies with reduced effector function, or which are effectorless, can include an amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581). In some embodiments, the anti-CD200R1 antibodies of the present disclosure are effectorless Fc region variants. In some embodiments, the effectorless Fc region variants of the anti-CD200R1 antibodies comprise one or more amino acid substitutions selected from N297G (see e.g., Shields, R. et al., "High Resolution Mapping of the Binding Site on Human IgG1 for FcγRI, FcγRII, FcγRIII and FcRn and Design of IgG1 Variants with Improved Binding to the FcγR*", Journal of Biological Chemistry, 276(9): 6591-6604 (2001)); N297A (see e.g., Friend. P. J. et al., "Phase I Study of an Engineered Aglycosylated Humanized CD3 Antibody in Renal Transplant Rejection", Transplantation. 68(11): 1632-7 (1999)); P331S/K322A (see e.g., Tawara, T. et al., "Complement Activation Plays a Key Role in Antibody-induced Infusion Toxicity in Monkeys and Rats", J Immunol, 180(4): 2294-8 (2008)); S228P/L235E (see e.g., Newman, R. et al., "Modification of the Fc Region of a Primatized IgG Antibody to Human CD4 Retains Its Ability to Modulate CD4 Receptors but Does Not Deplete CD4(+) T Cells iN Chimpanzees", Clin Immunol. 98(2): 164-74 (2001); or L234A/L235A/P329G (also referred to as "LALAPG") (see e.g., Schlothauer, T. et al., "Novel human IgG1 and IgG4 Fc-engineered antibodies with completely abolished immune effector functions", Protein Eng. Des. Sel., 29(10): 457-466 (2016); Lo, M. et al., "Effector-attenuating Substitutions That Maintain Antibody Stability and Reduce Toxicity in Mice", Journal of Biological Chemistry, 292(9): 3900-3908 (2017). In other embodiments, the effectorless Fc region variants of the anti-CD200R1 antibodies comprise the amino acid substitutions L234A/L235A ("LALA") (Woodle. E. Steve et al., Transplantation, 68(5): 608-616 (1999)).

Accordingly, in some embodiments, the effectorless Fc region variants of the anti-CD200R1 antibodies comprise one or more amino acid substitutions selected from N297A or N297G. In some embodiments, the effectorless Fc region variants of the anti-CD200R1 antibodies comprise the pair of amino acid substitutions P331S/K322A. In other embodiments, the effectorless Fc region variants of the anti-CD200R1 antibodies comprise the amino acid substitutions L234A/L235A (LALA) or L234A/L235A/P329G (LA-LAPG). In some embodiments, wherein the anti-CD200R1 is of isotype IgG2 or IgG4, the anti-CD200R1 antibody comprises the amino acid substitutions S228P and/or L235E.

Fc region variants having improved or diminished binding to FcRs are disclosed in e.g., U.S. Pat. No. 6,737,056: WO 2004/056312; and Shields et al., J. Biol. Chem. 9(2): 6591-6604 (2001). Fc region variants having improved ADCC can comprise one or more amino acid substitutions at e.g., positions 298, 333, and/or 334 of the Fc region (based on EU numbering). Fc region variants having altered (i.e., either improved or diminished) C1q binding and/or Complement Dependent Cytotoxicity (CDC), as described in e.g., U.S. Pat. No. 6,194,551. WO99/51642, and Idusogie et al., J. Immunol. 164: 4178-4184 (2000). Fc region variants with increased half-lives and improved binding to the neonatal Fc receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E) described in e.g., U.S. Pat. No. 7,658,921B2 (Dall'Acqua et al.). Other examples of Fc region variants can be found in e.g., U.S. Pat. Nos. 5,648,260 and 5,624,821; and WO94/29351.

Generally, in vitro and/or in vivo cytotoxicity assays can be carried out to confirm the reduction/depletion of CDC and/or ADCC activities in an Fc region variant. For example, Fc receptor (FcR) binding assays can be conducted to ensure that the antibody lacks FcγR binding (hence likely lacking ADCC activity) but retains FcRn binding ability. The primary cells for mediating ADCC. NK cells express FcγRIII only, whereas monocytes express FcγRI, FcγRII, and FcγRIII. Non-limiting examples of in vitro assays to assess ADCC activity of a molecule of interest is described in U.S. Pat. No. 5,500,362 (see, e.g. Hellstrom, et al., Proc. Nat'l Acad. Sci. USA 83:7059-7063 (1986)) and Hellstrom, et al., Proc. Nat'l Acad. Sci. USA 82: 1499-1502 (1985): 5,821.337 (see Bruggemann, M. et al., J. Exp. Med. 166: 1351-1361 (1987)). Alternatively, non-radioactive assay methods may be employed (see, for example, ACTI™ nonradioactive cytotoxicity assay for flow cytometry (CellTechnology, Inc. Mountain View, Calif.; and Cyto-Tox96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO2006/029879 and WO2005/100402. To assess complement activation, a CDC assay may be performed (see, e.g., Gazzano-Santoro et al., J. Immunol. Methods 202: 163 (1996); Cragg, M. S. et al., Blood 101: 1045-1052 (2003); and Cragg, M. S.

and M. J. Glennie, SW 103:2738-2743 (2004)). FcRn binding and in vivo clearance/half-life determinations can be performed using methods known in the art (see, e.g., Petkova, et al., Intl. Immunol. 18(12): 1759-1769 (2006)).

D. Cysteine Engineered Antibody Variants

In some embodiments, it is contemplated that the anti-CD200R1 antibody described herein can be substituted at specific non-HVR positions with cysteine residues so as to create reactive thiol groups. Such engineered "thioMAbs" can be used to conjugate the antibody to e.g., drug moieties or linker-drug moieties and thereby create immunoconjugates, as described elsewhere herein. Cysteine engineered antibodies can be generated as described in e.g., U.S. Pat. No. 7,521,541. In some embodiments, any one or more of the following antibody residues can be substituted with cysteine: V205 (Kabat numbering) of the light chain; A118 (EU numbering) of the heavy chain; and S400 (EU numbering) of the heavy chain Fc region.

E. Antibody Derivatives

In some embodiments, the anti-CD200R1 antibody of the present disclosure may be further modified (i.e., derivatized) with non-proteinaceous moieties. Non-proteinaceous moieties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1, 3-dioxolane, poly-1, 3, 6-trioxane, ethylene/maleic anhydride copolymer, poly-amino acid homo-polymers or random co-polymers, and dextran or poly(n-vinyl pyrrolidone)polyethylene glycol, propropylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody, e.g., whether the antibody derivative will be used in a therapy under defined conditions.

8. Immunoconjugates

In some embodiments, the anti-CD200R1 antibody of the present disclosure can also be an immunoconjugate, wherein the immunoconjugate comprises an anti-CD200R1 antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes.

In some embodiments, the immunoconjugate is an antibody-drug conjugate (ADC) in which an anti-CD200R1 antibody, as described herein, is conjugated to one or more drugs.

In some embodiments, an immunoconjugate of the present disclosure comprises an anti-CD200R1 antibody as described herein conjugated to a drug or therapeutic agent for the treatment of a CD200R1-mediated disease or condition.

In some embodiments, an anti-CD200R1 antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate of the present disclosure comprises an anti-CD200R1 antibody as described herein conjugated to a radioactive isotope (i.e., a radioconjugate). A variety of radioactive isotopes are available for the production of such radioconjugates. Examples include, but are not limited to, $^{61}$Cu $^{89}$Zr, $^{211}$At, $^{123}$I, $^{90}$Y, $^{186}$Re, $^{188}$Re, $^{153}$Sm, $^{212}$Bi, $^{32}$P, $^{212}$Pb, and radioactive isotopes of Lu. In some embodiments, a radioactive isotope can be or comprise $^{18}$F, FDG. In some embodiments, the immunoconjugate may comprise a radioisotope for scintigraphic detection, or a spin label for NMR detection or MRI. Suitable radioisotopes or spin labels can include, as $^{123}$I, $^{131}$I, $^{111}$In, $^{13}$C, $^{19}$F, $^{15}$N, $^{17}$O, various isotopes of Gd, Mn, and Fe.

Immunoconjugates of an anti-CD200R1 antibody and a cytotoxic agent, can be made using a variety of well-known bifunctional reagents and chemistries suitable for conjugating to proteins. Such reagents include but are not limited to: N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene).

Reagents for preparing immunoconjugates of the present disclosure can also include commercially available "cross-linking" reagents such as: BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) (see e.g., Pierce Biotechnology, Inc., Rockford, Ill., U.S.A).

9. Synthetic Antibodies

In some embodiments, the anti-CD200R1 antibody of the present disclosure can be a synthetic antibody comprising a set of CDRs or HVRs from an anti-CD200R1 immunoglobulin (e.g., HVR-L1, etc.) grafted onto a scaffold or framework other than an immunoglobulin scaffold or framework, such as an alternative protein scaffold, or an artificial polymer scaffold.

Exemplary alternative protein scaffolds contemplated for preparation of synthetic antibodies of the present disclosure can include, but are not limited to: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDZ domains, TEM-1 beta-lactamase, thioredoxin, staphylococcal nuclease, PHD-fmger domains, CL-2, BPTI, APPI, HPSTI, ecotin, LACI-D1, LDT1, MTI-II, scorpion toxins, insect defensin-A peptide, EETI-II, Min-23, CBD, PBP, cytochrome b-562, Ldl receptor domains, gamma-crystallin, ubiquitin, transferrin, and/or C-type lectin-like domains.

Exemplary artificial polymer (non-protein) scaffolds useful for synthetic antibodies are described in e.g., Fiedler et al., (2014) "Non-Antibody Scaffolds as Alternative Therapeutic Agents," in Handbook of Therapeutic Antibodies (eds S. Dübel and J. M. Reichert), Wiley-VCH Verlag GmbH & Co.; Gebauer et al., Curr. Opin. Chem. Biol, 13:245-255 (2009); Binz et al, Nat. Biotech., 23(10): 1257-1268 (2005).

IV. Recombinant Methods and Compositions

The anti-CD200R1 antibody of the present disclosure can be produced using recombinant methods and materials well-known in the art of antibody production. In some embodiments, the present disclosure provides an isolated nucleic acid encoding an anti-CD200R1 antibody. The nucleic acid can encode an amino acid sequence comprising the $V_L$ and/or an amino acid sequence comprising the $V_H$ of the antibody (e.g., the light and/or heavy chains of the antibody). In some embodiments, one or more vectors (e.g., expression vectors) comprising nucleic acid sequences encoding an anti-CD200R1 antibody of the present disclosure are provided. In some embodiments, a host cell comprising nucleic acid sequences encoding an anti-CD200R1 antibody of the present disclosure are provided. In one embodiment, the host cell has been transformed with a vector comprising a nucleic acid that encodes an amino acid sequence comprising the $V_L$ of the antibody and an amino acid sequence comprising the $V_H$ of the antibody. In another embodiment, the host cell has been transformed with a first vector comprising a nucleic acid that encodes an amino acid sequence comprising the $V_L$ of the antibody and a second vector comprising a nucleic acid that encodes an amino acid sequence comprising the $V_H$ of the antibody.

In some embodiments of the recombinant methods, the host cell used is a eukaryotic cell, such as a Chinese Hamster Ovary (CHO) cell, or a lymphoid cell (e.g., Y0, NS0, Sp20). In at least one embodiment, a method of making an anti-CD200R1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-CD200R1 antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, Nat. Biotech. 22: 1409-1414 (2004), and Li et al., Nat. Biotech. 24:210-215 (2006)).

Suitable host cells for the expression of glycosylated anti-CD200R1 antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (see, e.g., U.S. Pat. Nos. 5,959,177, 6,040,498, 6,420,548, and 7,125,978.

Examples of mammalian host cell lines useful for the production of the anti-CD200R1 antibodies of the present disclosure include Chinese hamster ovary (CHO) cells, including DHFR-CHO cells (see e.g., Urlaub et al., Proc. Natl. Acad. Sci. USA 77:4216 (1980)); myeloma cell lines such as Y0, NS0 and Sp2/0; monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse Sertoli cells (TM4 cells as described. e.g., in Mather, Biol. Reprod. 23:243-251 (1980)); monkey kidney cells (CVI); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells (see e.g., in Mather et al., Annals N Y. Acad. Sci. 383:44-68 (1982) and U.S. Pat. No. 6,235,498); Medical Research Council 5 (MRC 5) cells (such as e.g., those available from ATCC and also referred to as CCL-171); and Foreskin 4 (FS-4) cells (see e.g., in Vilcek et al. Ann. N. Y. Acad. Sci. 284:703-710 (1977), Gardner & Vilcek. J. Gen. Virol. 44:161-168 (1979), and Pang et al. Proc. Natl. Acad. Sci. U.S.A. 77:5341-5345 (1980)). For a general review of useful mammalian host cell lines suitable for antibody production, see, e.g., Yazaki and Wu, Methods in Molecular Biology, Vol. 248 (B. K. C. Lo, ed., Humana Press, Totowa, N.J.). pp. 255-268 (2003).

V. Pharmaceutical Compositions and Formulations of Anti-CD200R1 Antibodies

The present disclosure also provides pharmaceutical compositions and pharmaceutical formulations comprising an anti-CD200R1 antibody. In some embodiments, the present disclosure provides a pharmaceutical formulation comprising an anti-CD200R1 antibody as described herein and a pharmaceutically acceptable carrier. In some embodiments, the anti-CD200R1 antibody is the sole active agent of the pharmaceutical composition. Such pharmaceutical formulations can be prepared by mixing an anti-CD200R1 antibody, having the desired degree of purity, with one or more pharmaceutically acceptable carriers. Typically, such antibody formulations can be prepared as an aqueous solution (see e.g., U.S. Pat. No. 6,171,586, and WO2006/044908) or as a lyophilized formulation (see e.g., U.S. Pat. No. 6,267, 958).

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) poly peptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

It is also contemplated that the formulations disclosed herein may contain active ingredients in addition to the anti-CD200R1, as necessary for the particular indication being treated in the subject to whom the formulation is administered. Preferably, any additional active ingredient has activity complementary to that of the anti-CD200R1 antibody activity and the activities do not adversely affect each other.

In some embodiments, the pharmaceutical composition comprises the anti-CD200R1 antibody and an additional active agent such as, but not limited to, a checkpoint inhibitor. Checkpoint inhibitors useful in such embodiments include, but are not limited to, a second antibody comprising a specificity for an antigen that is an immune checkpoint molecule. In some embodiments, the second antibody comprises a specificity for an immune checkpoint molecule selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA.

In at least one embodiment, the pharmaceutical composition comprises an anti-CD200R1 antibody and an additional active agent, wherein the additional active agent is an antibody comprising a specificity for an immune checkpoint molecule selected from PD1, TIGIT, LAG3, PVRIG, KIR, TIM-3, and CRTAM.

In at least one embodiment, the pharmaceutical composition comprising an anti-CD200R1 antibody and an additional active agent, wherein the additional active agent is an antibody comprising a specificity for the immune checkpoint molecule PD1. Exemplary antibodies comprising a specificity for PD1 that are useful in the pharmaceutical composition embodiments disclosed herein include, but are not limited to, dostarlimab, pembrolizumab, nivolumab, and pidilizumab.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

IV. Uses and Methods of Treatment

It is contemplated that any of the compositions or formulations comprising an anti-CD200R1 antibody of the present disclosure can be used for any methods or uses, such as in therapeutic methods that utilize their ability to specifically bind to CD200R1 and thereby inhibit, decrease, and/or fully block the function of CD200R1 as a cell surface receptor involved in immune regulation or signaling, particularly the function of CD200R1 in negatively regulating (or inhibiting) T cell or NK cell activation.

The cell surface glycoprotein CD200 is the natural binding target of CD200R1. CD200, however, is expressed more widely on a variety of human cells including neurons, epithelial cells, endothelial cells, fibroblasts, and lymphoid cells, and the binding of CD200R1 to its ligand CD200 has been found to signal an immunosuppressive activities. Accordingly, it is contemplated that the anti-CD200R1 antibodies can be used in therapeutic methods that involve inhibiting, decreasing, and/or fully blocking the specific binding of CD200R1 to CD200.

There are a range of diseases, disorders, and conditions that can potentially be treated by inhibiting, decreasing, and/or fully blocking the immune regulatory and/or immune signaling activity of CD200R1, particularly, the immune inhibitory effect of CD200R1 on lymphocyte activation. The range of diseases, disorders, and conditions include, but are not limited to, cancers.

For example, agents that block the immune inhibitory effects of certain proteins (e.g., PD1) are currently under development to treat a wide range of cancers including adrenal gland cancer, bladder cancer, sarcomas, microsatellite instability-high (MSI-H) cancer (including solid MSI-cancer), TMB (tumor mutational burden)-high tumor, mismatch repair deficient (dMMR) cancer, brain cancer, breast cancer, cervical cancer, colorectal cancer, EGJ adenocarcinoma, esophageal cancer, gall bladder cancer, gastric cancer (e.g. gastrointestinal carcinoid (GI carcinoid)), head and neck cancer, heart cancer, hepatocellular carcinoma, kidney cancer, liver cancer, melanoma, mesothelioma (e.g. pleural mesothelioma), non-small cell lung cancer, ovarian cancer, epithelial ovarian cancer, endometrial cancer, pediatric solid cancers, pancreatic cancer, prostate cancer, spleen cancer, small cell lung cancer, testicular cancer, thyroid cancer (e.g. medullary thyroid cancer or follicular thyroid cancer), blood cancers (e.g. diffuse large B cell lymphoma (DLBCL), leukemias, lymphomas, myelomas), renal cell carcinoma, clear cell renal carcinoma, neuroendocrine tumors (e.g. malignant pheochromocytoma and paraganglioma), and uterine cancer. In some embodiments, the cancer is selected from lung cancer (e.g. small cell lung cancer), skin cancer (e.g., melanoma), pancreatic cancer, endometrial cancer, prostate cancer, colorectal cancer, ovarian cancer, mesothelioma, and bladder cancer. Accordingly, it is contemplated that any of the compositions or formulations comprising an anti-CD200R1 antibody of the present disclosure can be used for a method or use for the treatment of any of the above-listed cancers. In some embodiments, the cancer is selected from lung cancer (e.g. small cell lung cancer), skin cancer (e.g., melanoma), pancreatic cancer, endometrial cancer, prostate cancer, colorectal cancer, ovarian cancer, mesothelioma and bladder cancer. In some embodiments, the present disclosure provides a method of treating cancer in a subject, the method comprising administering to the subject in need thereof a therapeutically effective amount of an anti-CD200R1 antibody of the present disclosure or administering to a subject a therapeutically effective amount of a pharmaceutical composition comprising an anti-CD200R1 antibody of the present disclosure and a pharmaceutically acceptable carrier.

As disclosed herein, including in the Examples below, the anti-CD200R1 antibodies of the present disclosure have the ability to decrease, inhibit, and/or block CD200R1 binding to CD200, and thereby alter immunosuppressive signaling pathways. Accordingly, in some embodiments, the present disclosure provides a method of treating a CD200R1-mediated disease or condition in a subject, the method comprising administering to the subject a therapeutically effective amount of an anti-CD200R1 antibody of the present disclosure or administering to a subject in need thereof a therapeutically effective amount of a pharmaceutical composition comprising an anti-CD200R1 antibody of the present disclosure and a pharmaceutically acceptable carrier. Similarly, in some embodiments, the present disclosure provides a method of treating a disease mediated by binding to CD200 expressed on cells in a subject, the method comprising administering to the subject, the method comprising administering to the subject a therapeutically effective amount of an anti-CD200R1 antibody of the present disclosure or administering to a subject in need thereof a therapeutically effective amount of a pharmaceutical composition comprising an anti-CD200R1 antibody of the present disclosure and a pharmaceutically acceptable carrier.

A therapeutically effective amount of a pharmaceutical composition can comprise at least about 1 mg/kg of an anti-CD200R1 antibody or at least about 10 mg/kg of an anti-CD200R1 antibody. A therapeutically effective amount of a pharmaceutical composition can comprise at least about 2 mg/kg of an anti-CD200R1 antibody or at least about 20 mg/kg of an anti-CD200R1 antibody. A therapeutically effective amount of a pharmaceutical composition can comprise at least about 0.3 mg of an anti-CD200R1 antibody, at least about 1.0 mg of an anti-CD200R1 antibody, at least about 3.0 mg of an anti-CD200R1 antibody, at least about 10 mg of an anti-CD200R1 antibody, at least about 30 mg of an anti-CD200R1 antibody, at least about 100 mg of an anti-CD200R1 antibody, at least about 300 mg of an anti-CD200R1 antibody, at least about 900 mg of an anti-CD200R1 antibody, or at least about 1400 mg of an anti-CD200R1 antibody. A therapeutically effective amount of a pharmaceutical composition can comprise at least about 10 mg/kg of an anti-CD200R1 antibody, at least about 20 mg/kg of an anti-CD200R1 antibody, or at least about 100 mg/kg of an anti-CD200R1 antibody. In some embodiments, a therapeutically effective amount of a pharmaceutical composition can comprise an amount of an anti-CD200R1 antibody residing in a range between any two foregoing values.

In some embodiments, the therapeutically effective amount of a pharmaceutical composition can elicit no significant off-target effects. For example, in some cases there can be no significant off-target effects of an anti-CD200R1 antibody at a dose of not more than 10 mg/kg. As another example, in some cases there can be no significant off-target effects of an anti-CD200R1 antibody at a dose of not more than 20 mg/kg, or at a dose of not more than 100 mg/kg In some embodiments, off target effects can include non-specific binding (e.g., as measured by BV ELISA) or cross-reactivity in human tissue. In some pharmaceutical compositions, there can be no significant off-target effects of an anti-CD200R1 antibody at another therapeutically effective amount provided herein, or within a range of any two provided therapeutically effective amounts provided herein.

Administration of the anti-CD200R1 antibody, composition, or pharmaceutical formulation in accordance with the method of treatment provides an antibody-induced therapeutic effect that protects the subject from and/or treats the progression of a CD200R1-mediated disease in a subject. In some embodiments, the method of treatment can further comprise administration of one or more additional therapeutic agents or treatments known to those of skill in the art to prevent and/or treat the CD200R1-mediated disease or condition. Such methods comprising administration of one or more additional agents can encompass combined administration (where two or more therapeutic agents are included in the same or separate formulations), and separate administration. In which case, administration of the antibody composition or formulation can occur prior to, simultaneously, and/or following, administration of the additional therapeutic agent.

In some embodiments of the methods of treatment of the present disclosure, the anti-CD200R1 antibody or pharmaceutical formulation comprising an anti-CD200R1 antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion.

In some embodiments, a pharmaceutical formulation of the anti-CD200R1 antibody is formulated such that the antibody is protected from inactivation in the gut. Accordingly, the method of treatments can comprise oral administration of the formulation.

In some embodiments, use of the compositions or formulations comprising an anti-CD200R1 antibody of the present disclosure as a medicament are also provided. Additionally, in some embodiments, the present disclosure also provides for the use of a composition or a formulation comprising an anti-CD200R1 antibody in the manufacture or preparation of a medicament, particularly a medicament for treating, preventing or inhibiting a CD200R1-mediated disease. In a further embodiment, the medicament is for use in a method for treating, preventing or inhibiting a CD200R1-mediated disease comprising administering to an individual having a CD200R1-mediated disease an effective amount of the medicament. In certain embodiments, the medicament further comprises an effective amount of at least one additional therapeutic agent, or treatment. Exemplary additional therapeutic agents or treatments that can be used in such medicaments can include but are not limited to an antibody comprising a specificity for an immune checkpoint molecule such as PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD73, CD83, CD39, TRAIL, CD226, and VISTA. In at least one embodiment, the additional therapeutic agent or treatment present in a medicament of the present disclosure is an antibody comprising a specificity for the immune checkpoint molecule PD1, including but not limited to an antibody selected from dostarlimab, pembrolizumab, nivolumab, and pidilizumab.

In a further embodiment, the medicament is for use in treating, inhibiting or preventing a CD200R1-mediated disease in a subject comprising administering to the subject an amount effective of the medicament to treat, inhibit or prevent the CD200R1-mediated disease.

For the prevention or treatment of a CD200R1-mediated disease or condition, the appropriate dosage of the anti-CD200R1 antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-CD200R1 antibody included in the compositions and formulations described herein, can be suitably administered to the patient at one time, or over a series of treatments. Various dosing schedules including but not limited to single or multiple administrations over various time-points, bolus administration, and pulse infusion are contemplated herein.

Depending on the type and severity of the disease, about 1 μg/kg to 20 mg/kg of anti-CD200R1 antibody in a formulation of the present disclosure is an initial candidate dosage for administration to a human subject, whether, for example, by one or more separate administrations, or by continuous infusion. Generally, the administered dosage of the antibody can be in the range from about 0.05 mg/kg to about 20 mg/kg. In some embodiments, one or more doses of about 0.5 mg/kg, 2.0 mg/kg, 4.0 mg/kg 10 mg/kg, 20 mg/kg, or a range between any two foregoing values (or any combination thereof) may be administered to a human subject. In some embodiments, a dose administered to a human subject can be greater than about 20 mg/kg.

In some embodiments, a therapeutically effective amount can be administered to a subject, such as a human subject. A therapeutically effective amount can be at least about 1 mg/kg, at least about 10 mg/kg, at least about a dose between about 1 mg/kg and about 10 mg/kg. A therapeutically effective amount can be at least about 2 mg/kg, at least about 20 mg/kg, or at least about a dose between about 2 mg/kg and about 20 mg/kg. A therapeutically effective amount can be at least about 0.3 mg, at least about 1.0 mg, at least about 3.0 mg, at least about 10 mg, at least about 30 mg, at least about 100 mg, at least about 300 mg, at least about 900 mg, at least about 1400 mg/kg, or at least about a dose residing in a range between any two foregoing values. A therapeutically effective amount can be at least about 10 mg/kg, at least about 20 mg/kg, at least about 100 mg/kg, or at least about a dose residing in a range between any two foregoing values.

Dosage administration can be maintained over several days or longer, depending on the condition of the subject, for example, administration can continue until the CD200R1-mediated disease is sufficiently treated, as determined by methods known in the art. In some embodiments, an initial higher loading dose may be administered, followed by one or more lower doses (e.g., one or more maintenance doses). However, other dosage regimens may be useful. The progress of the therapeutic effect of dosage administration can be monitored by conventional techniques and assays.

Accordingly, in some embodiments of the methods of the present disclosure, the administration of the anti-CD200R1 antibody comprises a daily dosage from about 1 mg/kg to about 100 mg/kg. In some embodiments, the dosage of anti-CD200R1 antibody comprises a daily dosage of at least about 1 mg/kg, at least about 5 mg/kg, at least about 10 mg/kg, at least about 20 mg/kg, or at least about 30 mg/kg.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Generation of CD200R1 Polypeptides

This example illustrates the preparation of the various CD200R1 polypeptide constructs used as antigens in eliciting and screening the anti-CD200R1 antibodies of the present disclosure.

A. CD200R1 Production

The Extracellular Domains of Four Hu-CD200R1 Isoforms, Hu-CD200R1-Iso4-Alt (SEQ ID NO: 1), hu-CD200R1-iso4-Ref (SEQ ID NO: 2), hu-CD200R1-iso1-Alt (SEQ ID NO: 3), hu-CD200R1-iso1-Ref (SEQ ID NO: 4), and the analogous extracellular domain segments for cynomolgus monkey CD200R1 (SEQ ID NO: 5), and rhesus monkey CD200R1 (SEQ ID NO: 6), were cloned into mammalian expression vectors with CMV promoter for expression. The constructs contain a C-terminal purification tag, GGGSGLNDIFEAQKIEWHEGSGGHHHHHHHH (SEQ ID NO: 90) and an N-terminal mouse IgG1 heavy chain secretory signal, MGWSCIILFLVATATGVHS (SEQ ID NO: 91). The recombinant CD200R1 polypeptides were expressed using the Expi293 system (Thermo Fisher Scientific, Waltham, Mass., USA) with standard instruction. Supernatant media was clarified by centrifugation at 300 g and subsequently filtered with 0.22 micron filter. The recombinant CD200R1 was purified from the filtered media by immobilized metal affinity chromatography with a Histrap FF column (GE Healthcare, Chicago, Ill., USA) connected to an Akta purifier system (GE Healthcare). The eluate of the Histrap column was further purified by size-exclusion chromatography in 1×PBS buffer with Superdex 200 connected to an Akta purifier system (GE Healthcare). The major fraction of purified protein was concentrated and filtered by a 0.22 micron filter.

B. CD200 Production

The extracellular domain of the human CD200 (SEQ ID NO: 7), and cynomolgus CD200 (SEQ ID NO: 8) were cloned into a mammalian expression vectors with CMV promoter for expression. The constructs contain N-terminal mouse IgG1 heavy chain secretory signal (SEQ ID NO: 91) and a C-terminal human IgG fragment crystallizable (Fc) region with N297G mutation (SEQ ID NO: 9). CD200-Fc polypeptides were expressed using the Expi293 system (ThermoFisher) with standard instruction. Supernatant media was clarified by centrifugation at 300 g and subsequently filtered with 0.22 micron filter. Recombinant CD200-Fc was purified from the filtered media by affinity chromatography with a MabSelect SuRe column (GE Healthcare) connected to the Akta purifier system (GE Healthcare). Purified CD200-Fc was eluted from MabSelect SuRe with 100 mM sodium citrate, pH 3.0 and neutralized by 100 mM Tris pH8.8 immediately. The eluate of MabSelect SuRe was further purified by size-exclusion chromatography in 1×PBS buffer with Superdex 200 connected to an Akta purifier system (GE Healthcare). The major fraction of purified protein was concentrated and filtered by a 0.22 micron filter.

Example 2: Generation of Anti-CD200R1 Antibodies Using Hybridoma Methods, Screening and Characterization This example illustrates the methods using mouse hybridoma technology to generate anti-CD200R1 antibodies, and methods to screen and select antibodies for further characterization.

A. Immunization Campaign

Immunizations of BalbC (for 22.1) or Swiss Webster mice (for 10F6) were carried out with recombinant extracellular domains of hu-CD200R1-iso4-Alt polypeptide (SEQ ID NO: 1) and hu-CD200R1-iso4-Ref haplotype polypeptide (SEQ ID NO: 2), which were produced in-house. The Sigma adjuvant system (Millipore Sigma St. Louis, Mo.) was used for all immunizations. Titers were determined by ELISA as described below. Mice selected based on their titers were given a final pre-fusion boost without adjuvant. One day later, spleens were harvested and processed according to standard protocols. Splenocytes were fused with myeloma cells P3X63Ag8.653 cells (American Type Culture Collection CRL 1580) using PEG and following standard protocols and plated into 96-well plates at approximately 50,000 myeloma cells/well using standard techniques to maximize clonality of the resulting colonies. Parental hybridomas were selected using a selection medium supplemented with AH (Azaserine+Hypoxanthine).

B. ELISA Screening of Hybridoma Supernatants

After 12-14 days of culture, supernatants were collected and subjected to primary screening by ELISA with 96 well plates coated with human CD200R1. 96-well MAXISORP® flat bottom plates (ThermoScientific, catalogue number 439454) were coated overnight at 4° C. with 50 pg/well of protein at a concentration of 1 µg/mL in coating buffer (0.05 M carbonate buffer, pH 9.6 or phosphate buffered saline, PBS). After removing the coating solution, unspecific binding was blocked by addition of 200 µL of assay/blocking solution containing 1% bovine serum albumin (BSA) in phosphate buffered saline (PBS) pH 7.4 (ELISA diluent) and incubation at room temperature for one hour.

C. Hybridoma Sequencing

Monoclonal anti-CD200R1 hybridoma hits were grown to a density of 1-3×10⁵ in standard hybridoma medium (DMEM/F12, 10% FBS, 1% Glutamax, 1% pen/strep) for 7-10 days in a T75 flask with >80% viability. 1-3 million cells from cultures were pelleted in a 15 ml falcon tube at 300 g for 5 min. Pelleted cells were washed by resuspending cells in 5 ml ice cold PBS. PBS was removed and cells were resuspended in 1 ml of TRIZOL reagent (Life technologies). The lysate was passed through a 1 ml syringe with a 20G1 gauge needle (BD 305175) 20 times to ensure lysis of the cells. TRIZOL/cell suspension was immediately frozen on dry ice and stored at −80 C until processing.

Total RNA was isolated from the lysate using Direct-zol RNA Miniprep Plus kit (Zymo Research) and 5 ug of total RNA was used to generate 5'-RACE-ready hybridoma cDNA using SMARTer RACE 5' kit (Takara). To amplify heavy chain and light chain specific gene fragments from the cDNA the following primers were used in conjunction with universal primer provided in the kit in 5'-RACE PCR reactions:

(a) mouse $V_H$ family specific variable region primers

```
                                     (SEQ ID NO: 92)
           TCTTGTCCACCTTGGTGCTGCTGGCCGG, (SEQ ID NO: 93)
           TTTGTCCACCGTGGTGCTGCTGGCTGGT;
```

(b) mouse Vkappa family specific variable region primer:

```
                                     (SEQ ID NO: 94)
           GATCAGTCCAACTGTTCAGGACGCC;
``` or (c) mouse Vlambda family specific variable region primers:

```
                                     (SEQ ID NO: 95)
           ACACTCAGCACGGGACAAACTCTTCTCCACAGT, (SEQ ID NO: 96)
           ACACTCTGCAGGAGACAGACTCTTTTCCACAGT, (SEQ ID NO: 97)
           ACACTCAGCACGGGACAAACTCTTCTCCACATG.
```

PCR products were purified and cloned into pRACE using an In-Fusion cloning kit (Takara) and both strands were sequenced using Sanger Sequencer with M13 forward and M13 reverse primers. The VL domain, $V_H$ domain, and hypervariable region (HVR) sequences of the seven anti-CD200R1 hybridomas (10F6, 9B8, 5D1, 10A2, 1F3, 11E4, 22.1) are summarized in Table 2. Alignment of the sequences of 10F6, 9B8, 5D1, 10A2, 1F3, 11E4, 22.1 and a commercial antibody, OX108, are provided for the VL domains in FIG. 1A and the VH domains in FIG. 1B.

D. Humanization of 10F6 and 22.1

The light chain variable region (VL) and heavy chain variable region ($V_H$) sequences of the murine 10F6 antibody were aligned against human germline antibody sequences, and the human germline kappa light chain (Gene ID: IGKJ4.02) and the human germline heavy chain (Gene ID: IGHJ4.03) were identified as the closest human frameworks (alignment shown FIG. 2). The complementarity-determining regions (CDRs) of murine 10F6 light chain and heavy chain were grafted into the identified closest human frameworks respectively to generate humanized antibody clone. In this process, positions 24-34 in CDR-L1, 50-56 in CDR-L2 and 89-97 in CDR-L3 of murine 10F6 VL were grafted to the human kappa light chain framework acceptor, and positions 31-35 in CDR-H1, 50-61 in CDR-H2, and 93-102 in CDR-H3 of murine 10F6 VH were grafted to the human heavy chain framework acceptor. The resulting VH domain, VL domain, and HVR sequences of the humanized version of 10F6, "h10F6" are summarized in Table 3. The full-length heavy and light chain sequences of h10F6 are also provided in Table 3. The 22.1 antibody was humanized similarly to provide the h22.1 antibody. The relevant sequences of h22.1 are also summarized in Table 3.

E. Expression and Purification of h10F6 and h22.1

The heavy and light chain variable domains of humanized 10F6 (h10F6) and humanized 22.1 were synthesized and cloned into pRK plasmid. The expression of recombinant humanized 10F6 IgG and 22.1 IgG was performed using Expi293F expression system (Life Technologies) in accordance with the instruction provided. The ratio of the plasmids for the heavy chain and the light chain was kept at 1 to 1 for the transfection reaction and the transfected cells were cultured for 6 days before harvest. Recombinant IgG molecule was purified with the following protocols. Supernatant media was clarified by centrifugation at 300 g for 10 min to remove cells and by filtration with 0.22 micron filter. Clarified supernatant media was mixed with POROS Mab-Capture A resin (Thermo Scientific) equilibrated with PBS buffer and incubated with gentle rotation for 1.5 hrs at room temperature. After incubation, the slurry was loaded into a column and the resin was washed with 20 column volume of PBS buffer containing 0.5M NaCl then eluted with 3 column volumes of 0.1M acetic acid, 0.15M NaCl. The eluent was quickly neutralized to pH5.2 with 1M MOPS, pH7.0 and buffer exchanged to PBS buffer with PD-10 column (GE Healthcare).

Example 3: Binding Affinity, Epitope Mapping, and Blocking Ability of Anti-CD200R1 Antibodies This example illustrates studies of binding and epitope characteristics of anti-CD200R1 antibodies prepared in Examples 1 and 2.

A. CD20.R1 Binding Affinity Measurements

To determine binding affinities of the humanized anti-CD200R1, h10F6, to various human CD200R1 isoforms (Iso1 and Iso4, alternative or reference haplotype) and to cyno CD200R1, SPR measurements were carried out using a BIACORE™ 8K instrument. Briefly, a 1:4 dilution of Biotin CAPture Reagent (GE) into HBS-EP buffer (0.01 M HEPES pH 7.4, 0.15 M NaCl, 3 mM EDTA, 0.005% Surfactant P20) was applied to the chip at 2 µL/min flow rate. For kinetics measurements, 3 nM biotinylated human CD200R1. Next, 3-fold serial dilutions of the antibody, h10F6 in HBS-P buffer (0.01M HEPES pH 7.4, 0.15M NaCl, 0.005% surfactant P20) from low (0.27 nM) to high (200 nM) were injected (flow rate: 30 µL/min) at 37° C. The sensorgram was recorded and subject to reference and buffer subtraction before evaluating by BIACORE 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) was calculated as the ratio of $k_{off}/k_{on}$. The binding affinity of h10F6 to cyno-CD200R1 was determined with the same protocol, using 6 nM biotinylated cyno-CD200R1. The binding affinity data for h10F6 to the various hu-CD200R1 isoforms is summarized below in Table 4.

TABLE 4

Binding affinities of h10F6 and OX108 to four different hu-CD200R1 isoforms

| clone | Kon (1/Ms) | Koff (1/s) | KD (M) | Kon (1/Ms) | Koff (1/s) | KD (M) |
|---|---|---|---|---|---|---|
| | hu-CD200R1-iso4-Ref | | | hu-CD200R1-iso1-Ref | | |
| h22.1 | 5.98E+05 | 1.15E−03 | 1.92E−09 | 3.02E+06 | 1.51E−03 | 5.01E−10 |
| h11E4 | 1.90E+05 | 1.21E−04 | 6.39E−10 | 2.03E+05 | 1.13E−04 | 5.58E−10 |
| h10A2 | 9.34E+05 | 1.41E−01 | 1.50E−07 | 1.13E+05 | 2.52E−02 | 2.24E−07 |
| h10F6 | 7.17E+05 | 6.05E−05 | 8.43E−11 | 1.37E+06 | 7.47E−05 | 5.47E−11 |
| h1F3 | 7.27E+05 | 1.96E−01 | 2.69E−07 | 2.02E+05 | 3.97E−02 | 1.97E−07 |
| h5D1 | 6.69E+05 | 1.80E−01 | 2.70E−07 | 3.36E+05 | 2.35E−02 | 7.02E−08 |
| h9B8 | 8.83E+02 | 6.09E−03 | 6.89E−06 | 3.56E+04 | 1.06E−02 | 2.97E−07 |
| OX108 | 2.40E+05 | 3.89E−03 | 1.62E−08 | 3.43E+06 | 7.65E−03 | 2.23E−09 |
| | hu-CD200R1-iso4-Alt | | | hu-CD200R1-iso1-Alt | | |
| h22.1 | 6.04E+05 | 1.16E−03 | 1.92E−09 | 3.11E+06 | 1.66E−03 | 5.35E−10 |
| h11E4 | 1.73E+05 | 1.55E−04 | 8.94E−10 | 1.93E+05 | 1.71E−04 | 8.85E−10 |
| h10A2 | 6.79E+05 | 5.16E−03 | 7.61E−09 | 3.71E+05 | 4.33E−03 | 1.17E−08 |
| h10F6 | 7.57E+05 | 6.91E−05 | 9.13E−11 | 1.40E+06 | 9.79E−05 | 7.00E−11 |
| h1F3 | 2.19E+05 | 9.59E−04 | 4.37E−09 | 1.65E+05 | 8.78E−04 | 5.32E−09 |
| h5D1 | 6.02E+05 | 4.69E−03 | 7.80E−09 | 3.33E+05 | 4.02E−03 | 1.21E−08 |
| h9B8 | 8.65E+05 | 1.21E−02 | 1.40E−08 | 3.72E+05 | 9.48E−03 | 2.55E−08 |
| OX108 | 2.57E+05 | 3.86E−03 | 3.86E−03 | 3.86E+06 | 8.24E−03 | 2.13E−09 |

Results: As shown in Table 4, h10F6 has an affinity for binding to hu-CD200R1 that is between 100-fold to 1000-fold greater than the commercially available antibody, OX108. The affinity is dependent on the particular hu-CD200R1 isoform and haplotype used in the binding assay. As the long CD200R1 isoform 4 (iso4) is the predominant form (isoform 4 is predicted to be in 86% and isoform 1 is predicted to be in 14% of healthy individuals from prediction analysis performed using a method for genome-guided prediction and quantification of splice events from RNA-seq data from healthy and diseased samples from ALS, T1D, sepsis and multiple sclerosis patients before and after interferon-beta treatment (see e.g., Linsley P. S., et al., PLoS One, 9(10): e109760 (2014)), with the reference and alternate haplotype frequencies essentially split among the population (Ref 46% and Alt 54%), an anti-CD200R1 therapeutic should bind with high affinity to both the reference and alternate haplotypes of the predominant isoform 4 in order to accommodate patient heterogeneity and allow treatment of the broadest population. h10F6 binds isoform 4 alt and isoform 4 ref with 1000-fold greater affinity than OX108. In contrast, OX108 binds to the less common isoform 1 with 10-fold greater affinity compared to its binding affinity for the predominant isoform 4, which makes it less suitable as a therapeutic. The affinity of h10F6 to the cyno-CD200R1 is >1000 nM.

B. Hu-CD200R1 Blocking Measured by ELISA h10F6, and 6 other humanized anti-CD200R1 antibodies (h22.1, h9B8, h5D1, h10A2, h1F3, and h11E4) were assayed for blocking of hu-CD200R1 by ELISA as follows. 96-well MAXISORP® flat bottom plates (Thermofisher, Cat #439454) were coated overnight at 4° C. with 1 pg/mL human CD200-Fc in PBS. After removing the coating solution, unspecific binding was blocked with PBS containing 1% bovine serum albumin (BSA) and incubation at room temperature for one hour. Plates were then washed five times in PBS with 0.05% TWEEN®-20 (wash buffer). During the blocking period, 60 µl/well of 0.1 nM or 0.4 nM biotinylated human CD200R1 with serial dilution of the antibodies 60 ul/well (starting at 0.3 uM, 1:4 dilution) for one hour at room temperature with PBS containing 0.5% BSA and 0.05% Tween 20 (ELISA buffer) in NUNC F plate (Thermofisher, Cat #269620). Then transferred the antigen-antibody mix solution 100 ul/well into huCD200-Fc coated wells at room temperature for 15 min. Plates were then washed with wash buffer and added 50 µl/well Streptavidin poly-HRP (Thermofisher, Cat #21140) diluted 1:5000 in ELISA buffer at room temperature for 1 h. The plates were washed with wash buffer and developed for 15 minutes by addition of 50 µL/well of tetramethylbenzidine (TMB) microwell peroxidase substrate (VWR, Cat #95059-156). Enzymatic color development was stopped with 50 µL/well of TMB stop solution (VWR, Cat #95059-200). Plates were analyzed with a SpectraMax i3X plate reader (Molecular Devices) at 450 nm.

Results: Plots depicting the ELISA blocking data for h10F6, h22.1, h9B8, h5D1, h10A2, h1F3, h11E4, against various isoforms of hu-CD200R1 are shown in FIG. 3. As shown by the plots, the humanized anti-CD200R1, h10F6 is a better blocker the hu-CD200:hu-CD200R1 interaction than the other anti-CD200R1 antibodies tested.

The blocking $IC_{50}$ represents the concentration of h10F6 that inhibits 50% of biotinylated hu-CD200R1 binding to coated hu-CD200-Fc. As shown by the $IC_{50}$ values summarized in Table 5, h10F6 blocks the hu-CD200:hu-CD200R1 interaction with an $IC_{50}$ between 1.7 nM to 6.6 nM, dependent on the particular hu-CD200R1 isoform and haplotype used in the blocking assay.

TABLE 5

CD200 blocking $IC_{50}$ of h10F6 to hu-CD200R1

| | hu-CD200:hu-CD200R1 Blocking $IC_{50}$ (nM) | | | |
|---|---|---|---|---|
| Antibody | hu-CD200R1-Iso4-Ref | hu-CD200R1-Iso1-Ref | hu-CD200R1-Iso4-Alt | hu-CD200R1-Iso1-Alt |
| h10F6 | 1.77 | 5.26 | 2.24 | 6.62 |
| h22.1 | 5.32 | 5.86 | 4.59 | 7.45 |
| h9B8 | NonBlocker | NonBlocker | 27.91 | 21.1 |
| h5D1 | NonBlocker | NonBlocker | 23.66 | 25.5 |
| h10A2 | NonBlocker | NonBlocker | 56.51 | 55.0 |
| h1F3 | NonBlocker | NonBlocker | 14.79 | 21.4 |
| h11E4 | NonBlocker | NonBlocker | NonBlocker | NonBlocker |

C. Epitope Binning Analysis

Epitope binning experiments were carried out on six humanized anti-CD200R1 antibodies h10F6, h9B8, h5D1, h10A2, h1F3, h11E4, and h22.1, prepared as described in Example 2. Epitope binning measurements were performed with an OctetRed96 by capturing biotinylated Human CD200R1 on SAV Octet sensors (ForteBio), binding antibody 1, and subsequently probing with antibody 2. If antibody 2 was capable of binding antibody 1-bound CD200R1 then the two antibodies were assigned to different bins. If antibody 2 was unable to bind antibody 1-bound CD200R1 then the two antibodies were assigned to the same epitope bin.

Results: Results of the epitope binning experiments are summarized in Table 6. The six anti-CD200R1 antibodies measured were determined by epitope binning to recognize 3 distinct epitopes on CD200R1. h10F6 and h22.1 were determined to bind an overlapping CD200-blocking epitopes on CD200R1. The antibodies h9B8, h10A2, h5D1 and h1F3 share an epitope bin, while h11E4 binds a distinct epitope on CD200R.

TABLE 6

Epitope binning of anti-CD200R1 antibodies.

| Antibody | h9B8 | h5D1 | h10F6 | h10A2 | h11E4 | h1F3 | h22.1 |
|---|---|---|---|---|---|---|---|
| h9B8 | − | − | + | − | + | − | + |
| h5D1 | − | − | + | − | + | − | + |
| h10F6 | + | + | − | + | + | + | − |
| h10A2 | − | − | + | − | + | − | + |
| h11E4 | + | + | + | + | − | + | + |
| h1F3 | − | − | + | − | + | − | + |
| h22.1 | + | + | − | + | + | + | − |

D. Cell-Based Assay of Hu-CD200R1 Blocking by Antibodies

Blocking activity of the humanized anti-CD200R1 antibodies was tested in a cell based assay as follows. U937 cells stably expressing hu-CD200R1 (UNQ #Q8TD46) were incubated with human TruStain FcX (Biolegend, catalog #422302) for 10 min at 4 C before adding the anti-CD200R1 antibody for 20 min at 4 C. Cells were washed, and then incubated with 55 nM huCD200-Fc-Flag for 20 min at 4 C. Cells were washed, and then huCD200-Fc-Flag binding was detected by incubation with anti-Flag-PE clone LS (Biolegend Catalog #637310) for 20 min at 4 C. Cell binding was analyzed by flow cytometry with a CytoFLEX (Beckman Coulter). Binding curves were calculated based on the mean fluorescence intensity (MFI).

Figure 4:
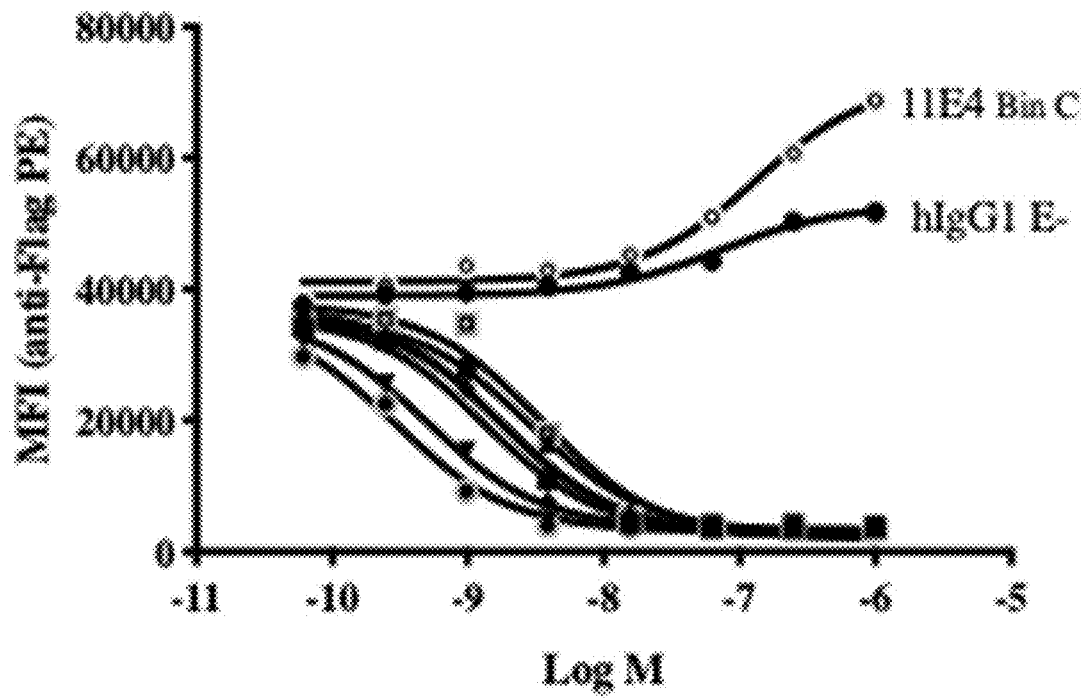
FIG. 4 depicts plots of assay results showing the ability of the anti-CD200R1 antibodies of the present disclosure to block binding of hu-CD200-Fc to cells expressing CD200R1.

Results: As shown in FIG. 4, the BinA antibody, h10F6 exhibits 10-fold and 6-fold stronger blocking of hu-CD200R1 (i.e., lower $IC_{50}$ values) than the two other BinA antibodies, OX108, and h22.1. The four humanized BinB antibodies h9B8, h5D1, h10A2, and h1F3 have varying levels of CD200R1 blocking activity weaker than h10F6, while the lone Bin C humanized clone h11E4 does not block CD200Fc binding.

E. Binding of h10F6 and h22.1 to Human and Cynomolgus T Cells

The ability of the humanized anti-CD200R1 antibodies to bind to endogenous antigens was measured using human Pan T cells isolated from healthy donor (StemCell Technologies, catalog #70500.2) and cynomolgus monkey peripheral blood mononuclear cells (WorldWide Primates). For human, T cells were isolated using Pan T cell isolation kit (Miltenyi Biotec Catalog #130-095-535). Cells were incubated with human TruStain FcX (Biolegend, catalog #422302) for 10 min at 4 C, followed by incubation with a biotin labeled anti-CD200R1 antibody (h10F6 or h22.1) or an isotype control for 20 min at 4 C. Cells were washed and the anti-CD200R1 binding was detected using a streptavidin-PE (BD Biosciences). Human immune cell types were labeled with anti-CD4 clone OKT4 and anti-CD8 clone RPA-T8 (Biolegend). Cyno immune cells were labeled with anti-CD3 clone10D12, anti-CD4 clone M-T466, and anti-CD8 clone BW135/80 (Miltenyi Biotec). Cell binding was analyzed by flow cytometry with a CytoFLEX (Beckman Coulter). Binding curves were calculated based on the geometric mean fluorescence intensity.

Results: As shown in FIG. 5A, h10F6 has higher affinity to human T cells than h22.1 and OX108; however, as shown in FIG. 5B, neither h10F6 or OX108 display cross-reactivity with cynomolgus T cells.

Example 4: In Vitro and In Vivo Functional Assays of Anti-CD200R1 Antibodies

This example illustrates in vitro cell-based assays and in vivo studies used to characterize the functional activity of the anti-CD200R1 antibodies of the present disclosure.

A. Immune Activation of PBMCs from Tumor Patients by Anti-CD200R1 Antibodies

Functional activity of anti-CD200R1 antibodies was tested on primary peripheral blood mononuclear cells (PBMCs). PBMCs from nine tumor patients were purchased from Discovery Life Sciences (Los Osos, Calif.). $2-4\times10^4$ cells were seeded per well in triplicates in a 384 well plate with 100 nM of the selected anti-CD200R1 antibodies. Cells were then stimulated with 0.1 ng/mL Staphylococcal enterotoxin B (SEB) (Toxin Technology Catalog #BT202) and cultured for three days at 37 C. IFNγ levels of the supernatant were determined by ELISA using the kit commercially available from ThermoScientific. Average of biological triplicates were normalized to isotype control and a multiple T test performed to determine significant differences.

Figure 6:
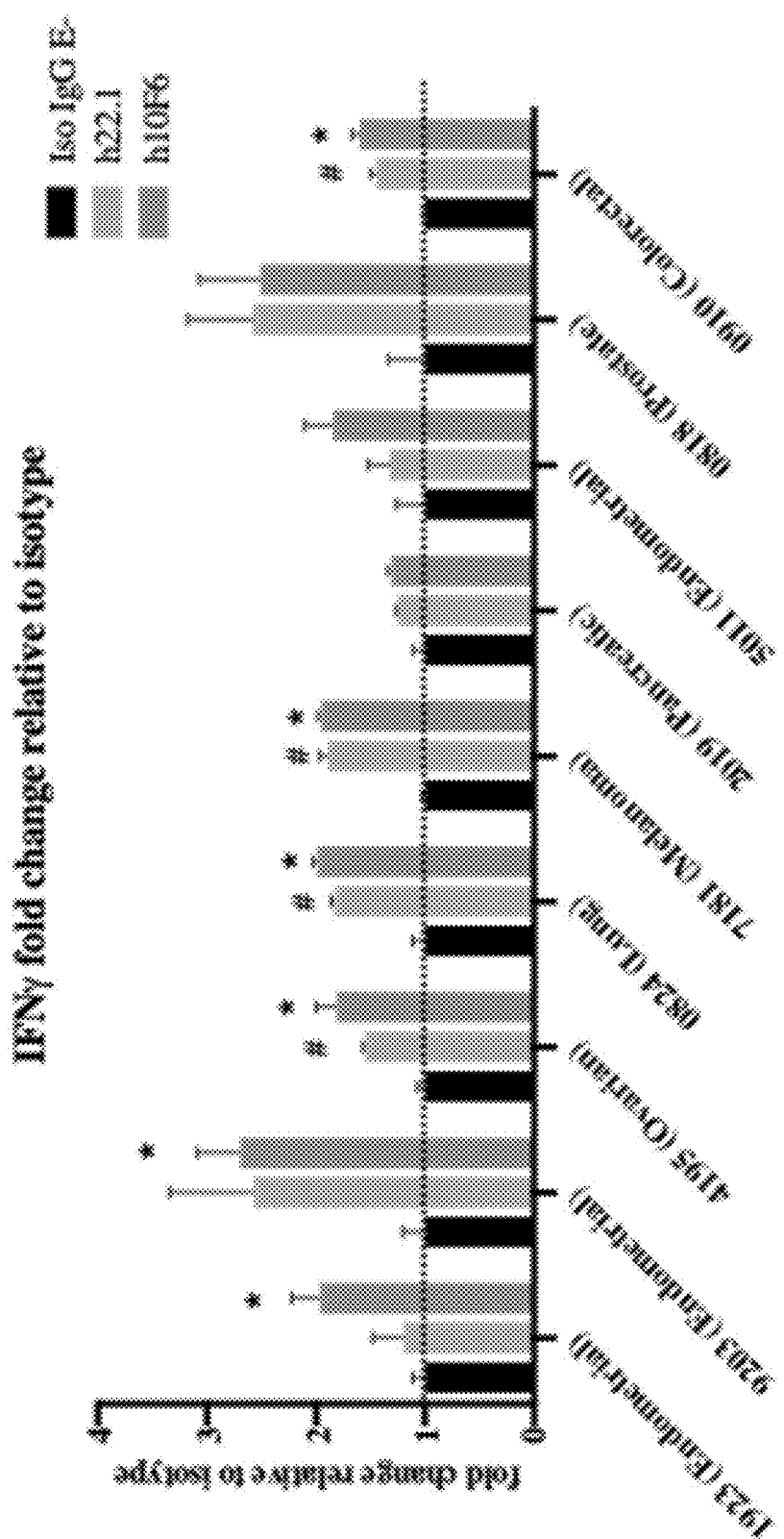
FIG. 6 depicts plots of data showing that treatment with anti-CD200R1 blocking antibodies resulted in immune activation (increased IFNγ secretion) of primary PBMC samples collected from 9 cancer patients. PBMCs were treated with 100 nM of the anti-CD200R1 antibodies, h22.1 or h10F6, or an effectorless isotype control, and assay was carried out as described in Example 5.

Results: As shown in FIG. 6, the humanized anti-CD200R1 antibodies, h10F6 and h22.1, increased the production of IFNγ in samples derived from patients having various cancer types. Specifically, FIG. 6 shows the fold change of IFNγ production, normalized to isotype control, in samples treated with 100 nM of h10F6 or h22.1. Six of the 9 tumor patients' cells had a statistically significant increase of IFNγ production when treated with h10F6. Four of the 9 patients had a significant treatment effect when treated with h22.1.

B: Primary Human Pan-T Cell Assay

Functional activity of anti-CD200R1 antibodies in rescuing IFNγ secretion was measured in the presence of plate-bound CD200-Fc. Primary human Pan-T cells isolated from healthy PBMC donors (Stem Cell, catalog #70500.2) were chronically stimulated with 2 μg/mL PHA (Sigma, catalog #11082132001) and 4 ng/mL human IL-2 (Roche, catalog #24951700) for 7 days in complete media. Cells were then harvested and primed with 40 ng/mL human IL-4 (Pepro-tech, catalog #200-04) for 24 hrs. Prior to plating cells, plates were coated overnight at 4° C. with 1 pg/mL anti-CD3 clone OKT3 (Biolegend, catalog #317326) and 15 pg/mL human CD200Fc or Isotype control diluted in PBS (Corning, cat #21-040-CM). Cells were harvested, washed and plated with anti-CD200R1 antibodies for 24 hrs. Cell supernatant was harvested and cytokines, human IFNγ (Invitrogen, Catalog #88-7025-88) and human IL-2 (Invitrogen, coated 88-7316-88), secretion were measured by ELISA.

Figure 7A:
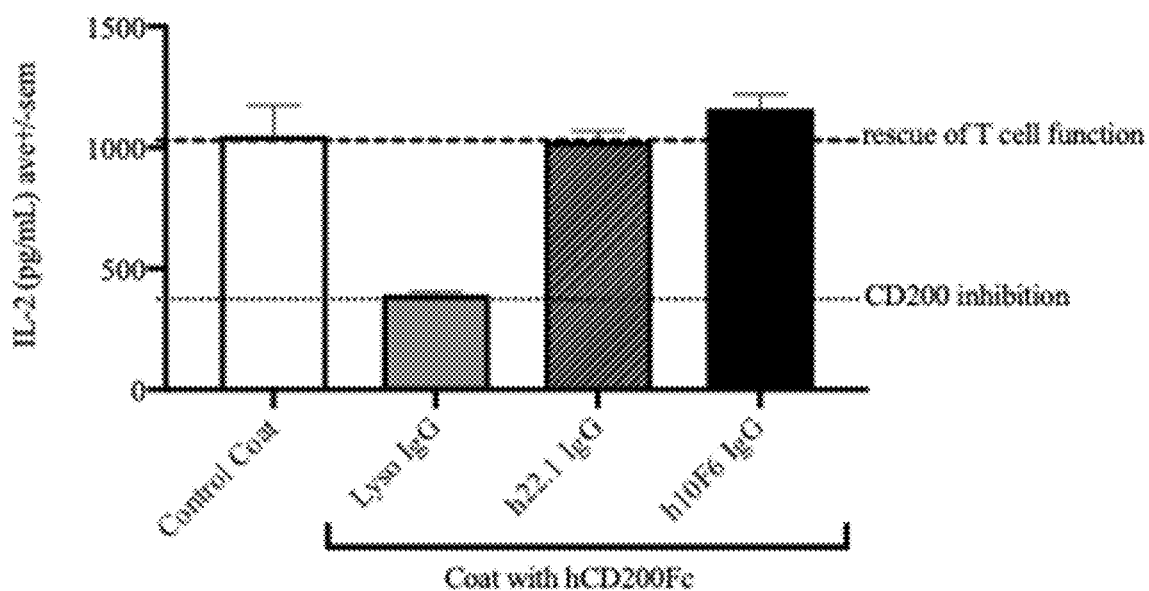
FIG. 7A, FIG. 7B, FIG. 7C, and FIG. 7D depict plots showing that soluble anti-CD200R1 antibodies, h10F6 and h22.1, can rescue IL-2 and IFNγ secretion suppressed by CD200-Fc in pan T-cells from healthy donors relative to an isotype control (Lyso IgG). Antibodies were tested using 100 nM fixed or top-dose response concentrations. Error bars shown are representative of the standard deviation or standard error mean from triplicate samples. Plate bound humanized CD200-Fc ligand inhibits pan T-cell function. IL-2 and IFNγ levels were measured by ELISA as described in Example 5.
Figure 7B:
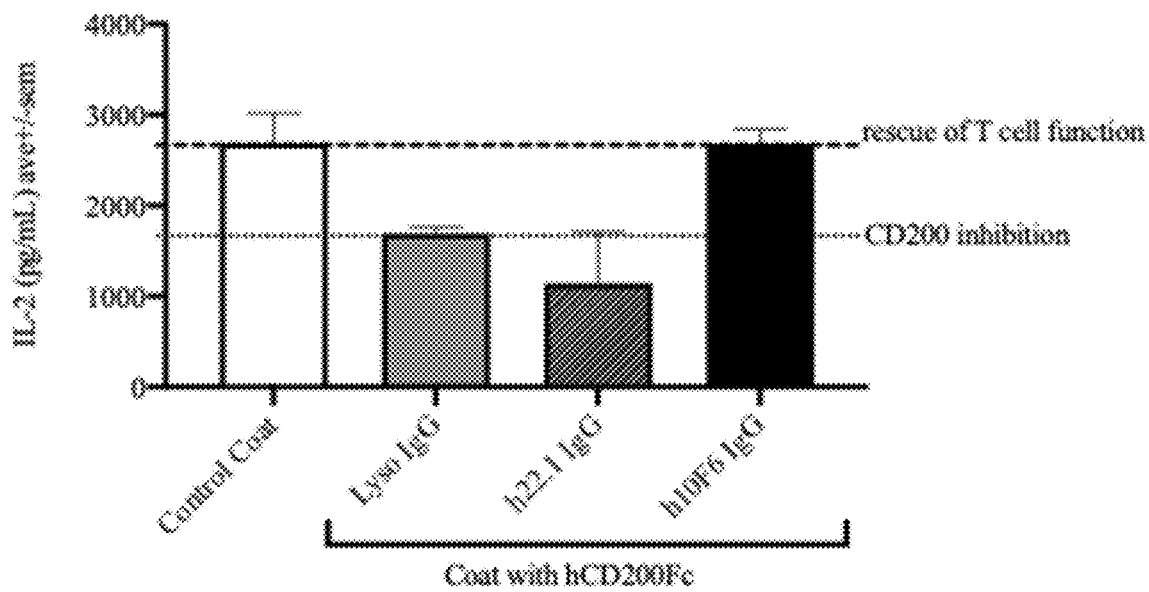
Figure 7C:
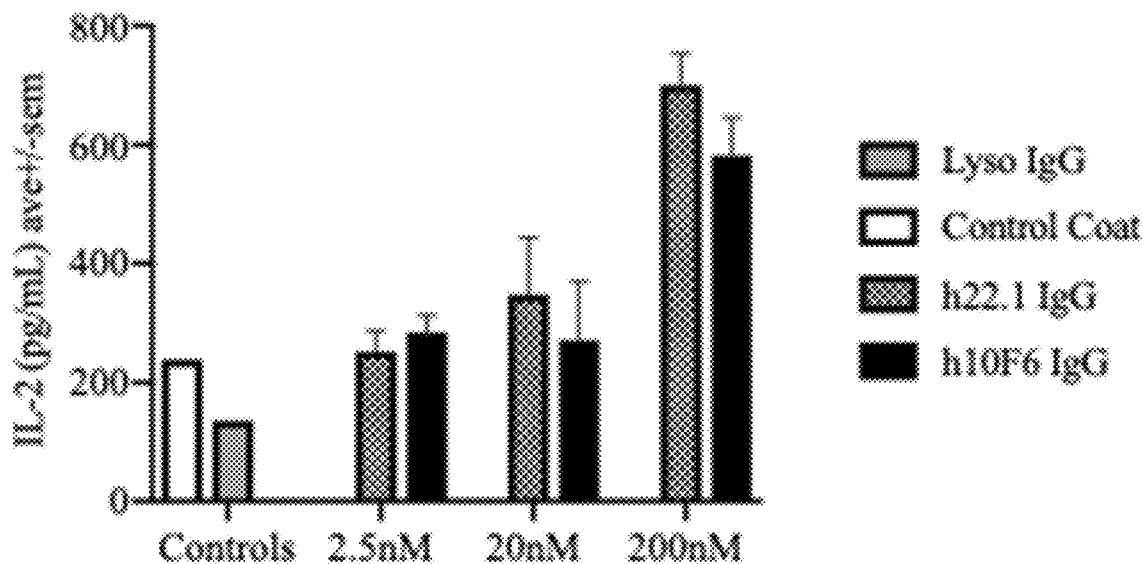
Figure 7D:
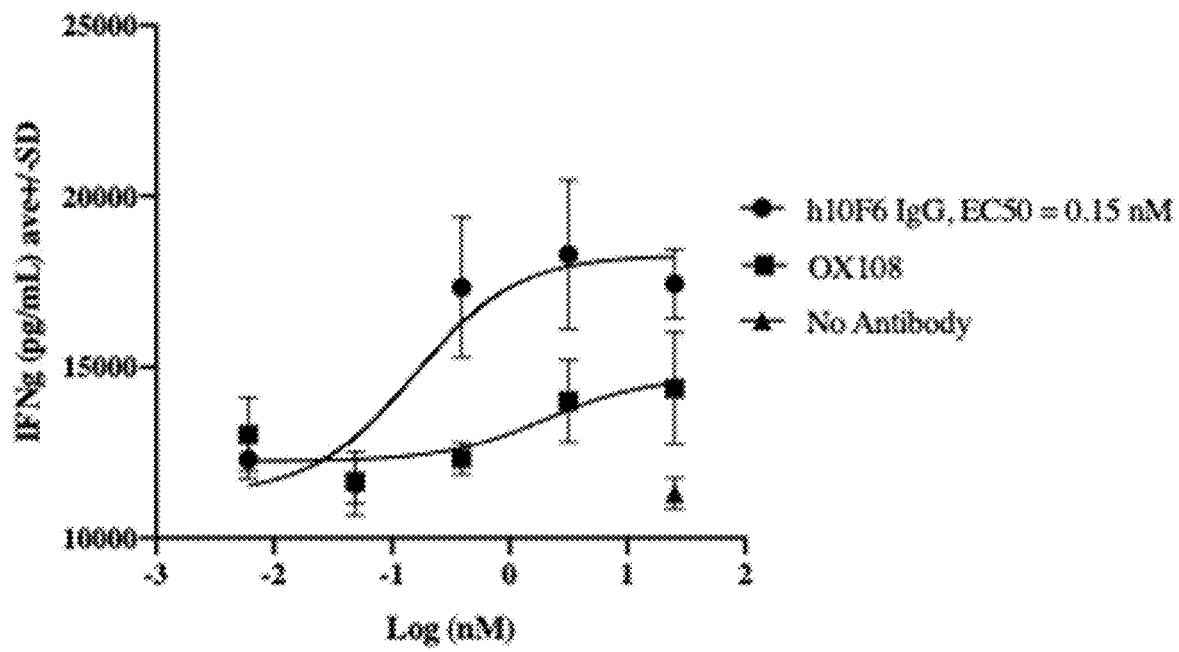

Results: As shown in FIG. 7A and FIG. 7B, treatment with the h10F6 IgG shows functional rescue of IL-2 secretion in two different healthy donors (Donor 203 and Donor 538), whereas rescue by treatment with h22.1 is only seen in one donor. As shown in FIG. 7C and FIG. 7D, treatment with h10F6 also showed better efficacy in dose-dependent responses than the isotype control in IL-2 secretion (FIG. 7C) and better efficacy than the commercial antibody, OX108 in IFNγ secretion (FIG. 7D).

D. Primary Human Mixed Lymphocyte Reaction Assay

Functional activity of humanized anti-CD200R1 antibodies was measured using Pan-T cells and polarized dendritic cells in an allogeneic mixed lymphocyte reaction assay. PBMCs were prepared from healthy donor leukopaks from Stemcell Technologies, Cat #70500.1 by centrifugation and red blood cell lysis using ACK Lysis buffer (Gibco, Cat #A10492-01). Monocytes were isolated from PBMCs using a pan monocyte isolation kit (Miltenyi, Cat #130-096-537). Pan-T cells were isolated using Miltenyi's Pan-T Cell isolation kit (Miltenyi, Cat #130-096-535). Monocytes were then plated at 1 million/mL in complete media with 20 ng/mL GM-CSF (Fisher Scientific, catalog #215GM010) and IL-4 (Fisher Scientific, catalog #204IL010) for 7 days. Dendritic cells were then further polarized into immunogenic DCs using 100 ng/mL LPS (Sigma, catalog #L-4391) and 50 ng/mL TNFα (Fisher Scientific, catalog #210TA020CF) or tolerized DCs using 20 ng/mL IL-10 (Fisher Scientific, catalog #217IL010) and 20 ng/mL IFNa-2b (Fisher Scientific, catalog #111051) for 3 days. After polarization, Pan-T cells and mature DCs were mixed together at a 1:20 panT:DC cell ratio with 10 pg/mL anti-CD200R1 antibody or isotype control in complete media. MLR supernatants and cells were harvested on days 4, 5, and 6 to assess the activation of T cells. Cytokine secretion was measured using IFNγ Human Luminex Procartaplex kits (ThermoFisher, catalog #EPX01A-10228-901). To assess T cell activation, cells were incubated with human TruStain FcX (Biolegend, catalog #422302) for 10 min at 4 C followed by extracellular stains anti-CD3 Clone UCHT1, anti-CD4 Clone OKT4, anti-CD8 clone RPA-T8, anti-CD86 clone BU63, anti-CD11c clone BU15. In addition, activation markers added to measure T-Cell activation were anti-CD69 clone FN50, anti-CD25 clone BC96, and anti-HLA-DR clone L243. Cells were stained for 20 min at 4° C. and washed to prepare for intracellular staining. Foxp3/Transcription Factor Staining Buffer Set (Thermofisher Scientific, catalog #00-5523-00) was used to fix and permeabilize the cells for intracellular staining with anti-Ki67 clone B56 for 45 min at 4 C. After intracellular staining, cells were washed again and resuspended in PBS+2% FBS. Expression was analyzed by flow cytometry with a CytoFLEX (Beckman Coulter).

Figure 8A:
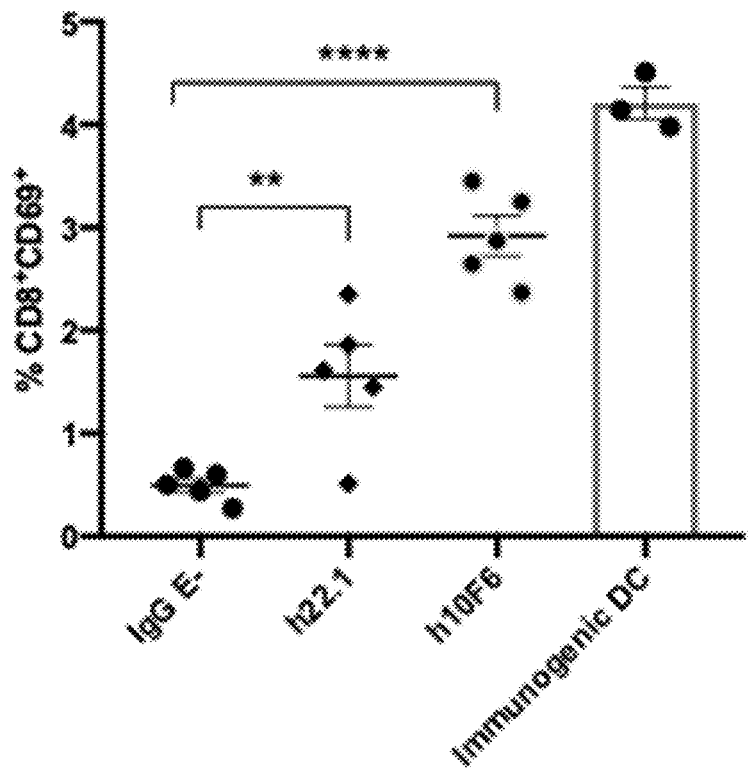
FIG. 8A, FIG. 8B, and FIG. 8C depict plots showing how treatment of T-cells with anti-CD200R1 antibodies, h10F6 and h22.1 the surface expression results in Tolerogenic Dendritic Cell suppression on T-cells or activation by Immunogenic Dendritic Cells. Expression of an early T-cell activation marker CD69 on CD8+ T cells (see FIG. 8A) and proliferation marker Ki67 on CD4+ T cells (see FIG. 8B) with fixed CD200R1 antibodies at 10 µg/mL are compared to isotype control (labeled as IgG E).
Figure 8B:
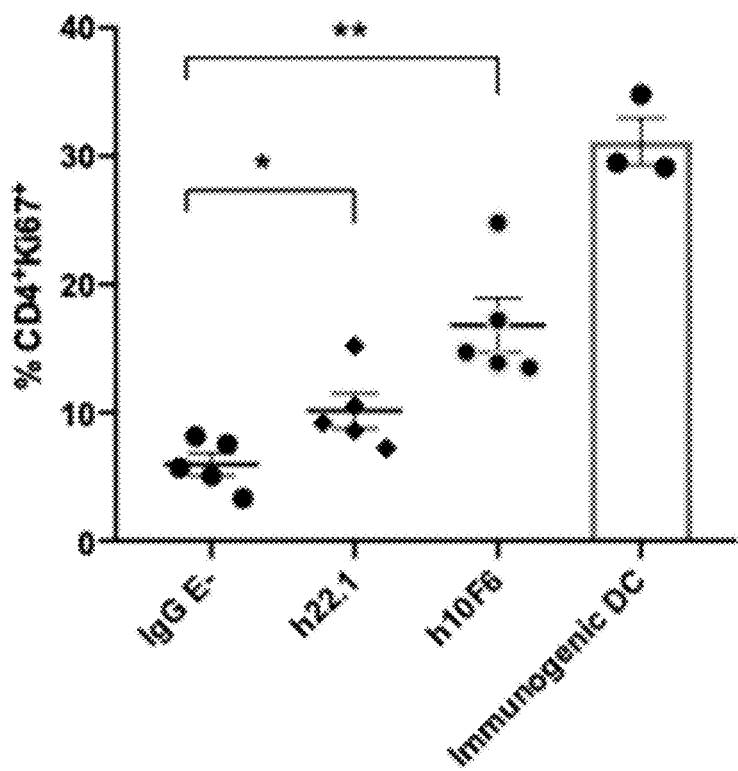
Figure 8C:
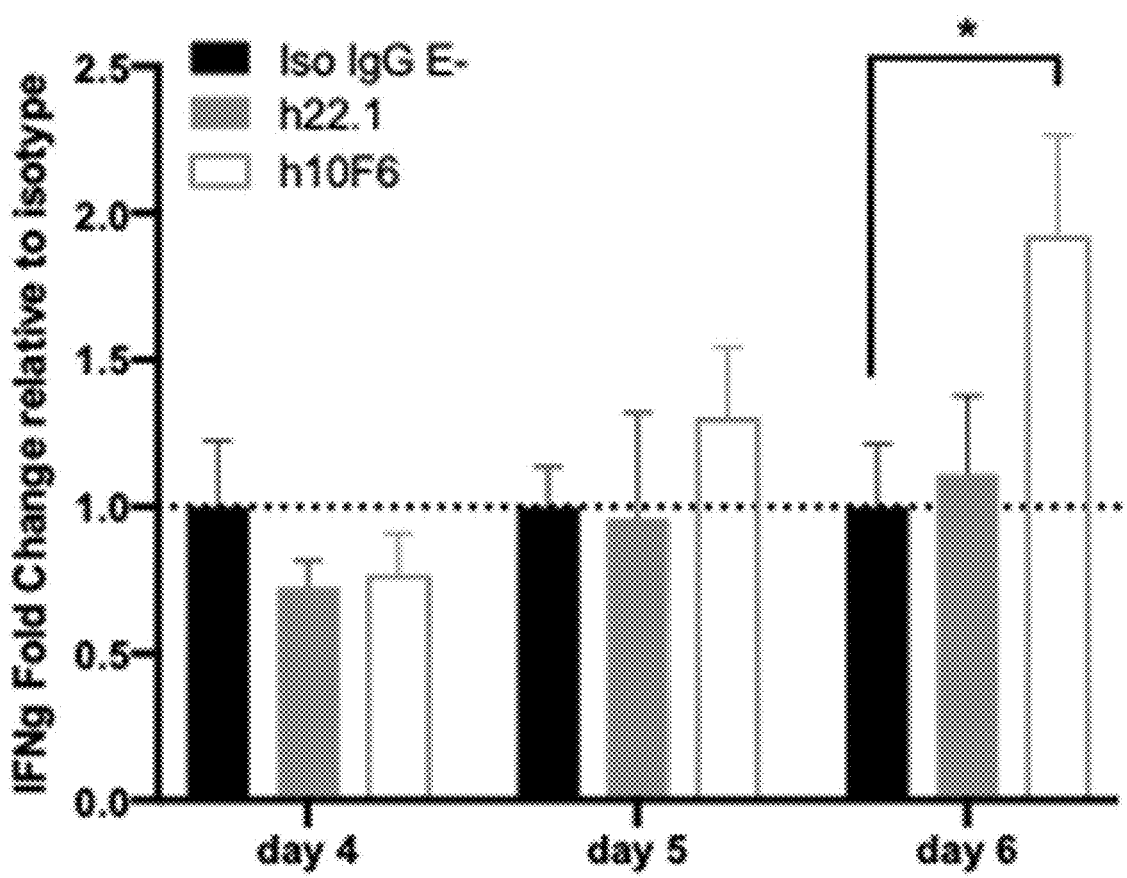

Results: As shown in FIG. 8A, FIG. 8B, and FIG. 8C, treatment with the humanized anti-CD200R antibody, h10F6 increases activation in CD8 T cells (FIG. 8A), proliferation in CD4 T cells (FIG. 8B), and IFNγ secretion (FIG. 8C) greater than h22.1 IgG and significantly beyond isotype control.

E. Phosoho-Dok2 Induction Assay of Anti-CD200R1 Antibodies

Upon engagement with CD200, CD200R1 inhibitory signaling is initiated via the recruitment of Dok2 kinase to the phosphotyrosine binding recognition motif of CD200R1 (see e.g., Mihrshahi 2009, and Mihrshahi 2010). Agonism activity of the humanized anti-CD200R1 antibodies, h10F6 and h22.1, was evaluated by the induction of phospho-Dok2 in both U937 monocytic cell line (ATCC #CRL-1593.2) and U937 stably expressing hu-CD200R1 cell lines. Once serum starved for 18 hr, parental or CD200R1 over-expressing cells were treated with various concentrations of soluble humanized anti-CD200R1 or an isotype control or CD200-Fc for 60 min. Cells were lysed in 1×SDS+protease and phosphatase inhibitors. Lysates were separated on NuPAGE 4-12% Bis-Tris MES SDS (BioRad) in non-reducing conditions. Western blots were performed using anti-pDok2 Y351 (Cell Signaling Technology Catalog #3911S) and anti-Dok2 (Santa Cruz Biotechnology Catalog #sc-17830).

Figure 9:
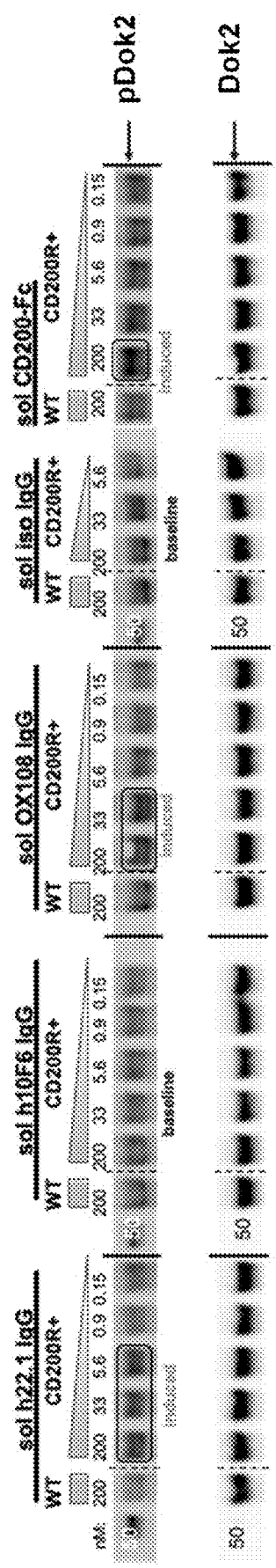
FIG. 9 depicts the pDok2 levels induced after 30 min treatment with soluble humanized 22.1 (indicated as sol 22.1 IgG in the figure), humanized 10F6 (sol 10F6 IgG), OX108 (sol OX108 IgG), CD200-Fc (sol CD200Fc), and isotype control IgG (sol Iso IgG). U937 stably expressing CD200R1 is indicated as "CD200R+" in the figure and were treated with a 6 fold dilution starting at 200 nM. Parental cells were treated with the highest dose, 200 nM, and is indicated as "WT" in the figure. The top row displays pDok2 and the bottom row displays total Dok2.

Results: As shown in FIG. 9, compared to the wildtype (WT) U937 cell line, pDok2 is induced when treated with the 200 nM highest dose of soluble CD200-Fc, 33 nM of OX108, and as low as 5.6 nM of h22.1. In contrast, treatment with h10F6 failed to induce pDok2 compared to WT suggesting that h10F6 lacks CD200R1 agonistic characteristics. The ability of h10F6 to block CD200R1 binding of CD200 while not inadvertently agonizing CD200R1 signaling (as measured by pDok2 expression), greatly enhances the therapeutic capability of h10F6 relative to h22.1 and OX108, both of which exhibit inadvertent CD200R1 agonistic activity.

F Antagonist Activity Against K562-CD200R1 Assayed NFKb-Luc Reporter Cell Line

CD200 was previously reported to induce NFkB transcription when co-culturing CD200 with CD200R1 expressing cell lines (see e.g., Wang, et al., Nat. Med., 25: 656-666 (2019)). A K562 monocytic cell line (ATCC CCL-243) was engineered with stable expression of CD200R1 and a NFkB luciferase reporter in order to measure the antagonistic activity of the humanized anti-CD200R1 antibodies, h10F6 and h22.1. Both bivalent and monovalent Fab formats of the anti-CD200R1 clones, h22.1 and h10F6, were added at varying concentrations to a co-culture of K562 reporter cells and 293T stably expressing CD200 (UNQ #P41217) for 6 hours at 37 C. Cultures were supplemented with 20 ng/mL of TNFα (RnD Systems Catalog #210-TA).

Figure 10A:
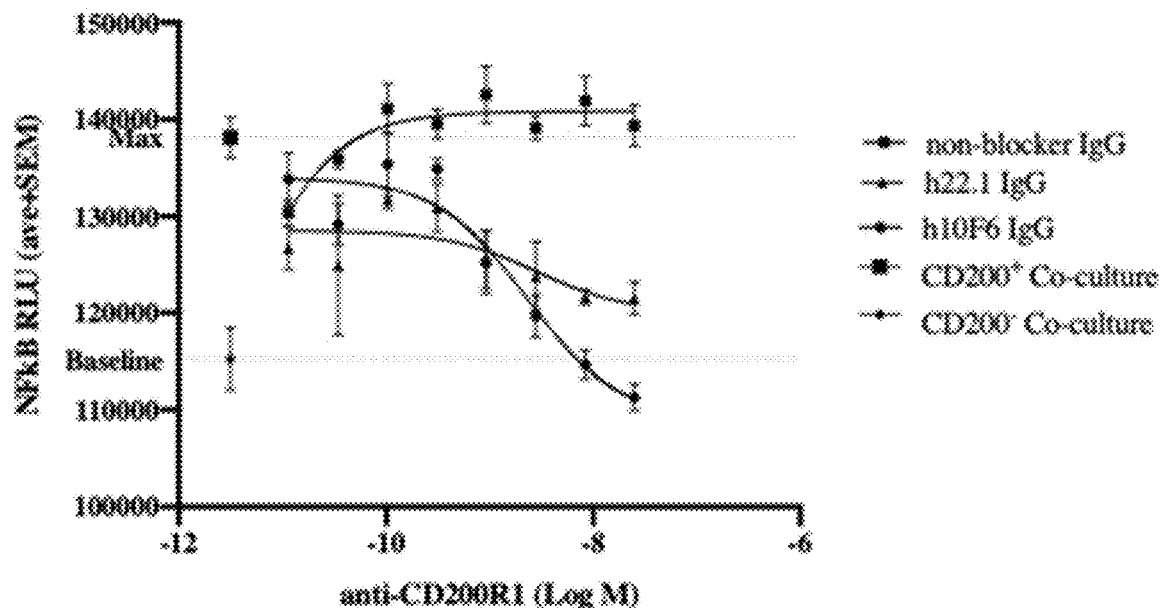
FIG. 10A and FIG. 10B depict plots of data showing the antagonism of soluble anti-CD200R1 antibodies h10F6 and h22.1 against K562-CD200R1 co-cultured with a CD200 expressing cells.
Figure 10B:
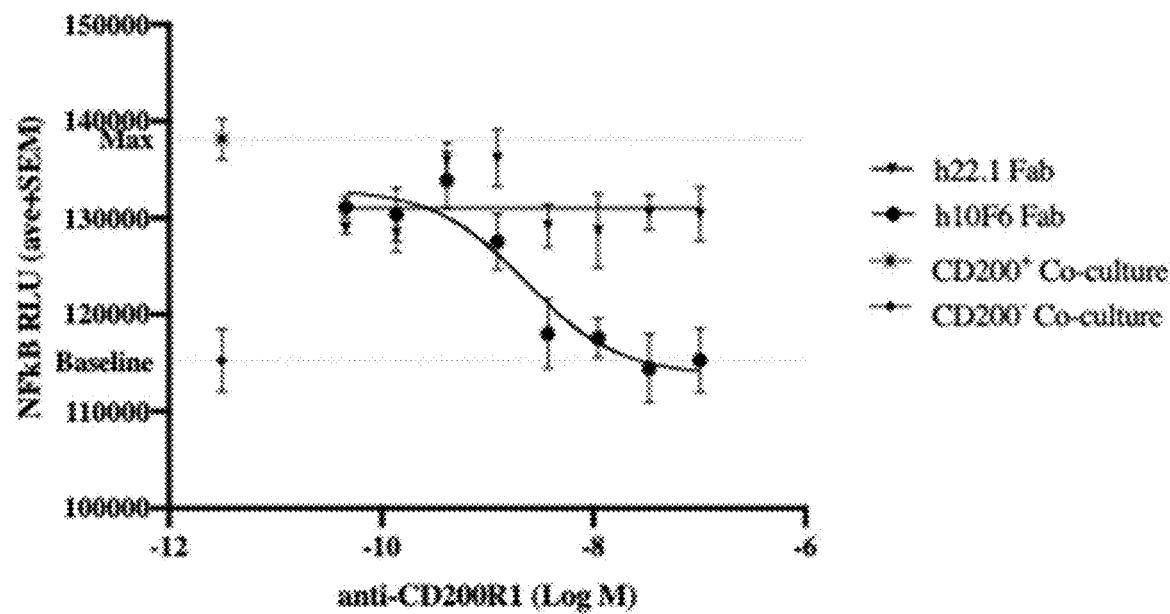

Results: As shown in FIG. 10A and FIG. 10B, NFkB transcription is induced by CD200$^+$ expressing cells compared to CD200$^-$ expressing cells. After adding blocking antibodies to the co-cultures, differences in antagonistic function between h10F6 and h22.1 become apparent. Both bivalent (FIG. 10A) and monovalent h10F6 (FIG. 10B) can block CD200 driven NFkB transcription to baseline level. CD200$^+$ co-culture with h22.1 IgG, however, only partially blocks NFkB induction, and the monovalent h22.1 Fab has no effect.

Example 5: Affinity Maturation of Humanized Anti-CD200R1 Antibody h10F6

This example illustrates phage library construction and panning techniques used for affinity maturation of the humanized anti-CD200R1 antibody h10F6 for improved binding to both hu-CD200R1 and cyno-CD200R1.

A. h10F6 Affinity Maturation NNK Library Construction and Panning

To identify affinity matured variant sequences of the anti-CD200R1 antibody clone h10F6, phage libraries were constructed in Fab-amber format for monovalent Fab phage display with heavy chain and light chain residues randomized using the NNK degenerate codon that encodes for all 20 amino acids with 32 codons (Brenner et al., 1992). Libraries were designed to allow one NNK mutation in each of the three light chain or heavy chain HVRs. Synthesized mutagenesis oligonucleotides were then used to construct heavy chain and light chain libraries using Kunkel mutagenesis (Kunkel et al., 1987). The resultant library DNA was electroporated into E. coli XL 1 cells, yielding approximately $6.5 \times 10^8$ to $4.3 \times 10^9$ transformants.

Phage libraries were incubated in SUPERBLOCK™ PBS buffer (Pierce) and 0.05% TWEEN® 20 for 30 min and then applied on hu-CD200R1 (iso4, Alt and Ref haplotypes) and cyno-CD200R1 coated plate for first round panning. In the subsequent two to three rounds, phage libraries were incubated with decreasing concentration of biotinylated hu-CD200R1 or cyno-CD200R1 antigen. The eluted phage was infected with log-phase XL-1 and plated on LB carbenicillin plate at 37° C. overnight for further affinity screening.

To extract sequences from affinity maturation libraries using NGS, phagemid double stranded DNA was isolated from E. coli XL-1 cells carrying phagemids from the initial phage library (unsorted libraries) and from the first and second rounds of solution selection (sorted libraries). Purified DNA was used as the template to generate amplicons of $V_H$ and VL regions using Illumina 16s library preparation protocol. Sequencing adapters and dual-index barcodes were added using Illumina Nextera XT Index Kit. In preparation for sequencing on Illumina MiSeq, adapter-ligated amplicons were subjected to standard Illumina library denaturing and sample loading protocol using MiSeq Reagent Kit v3 (600 cycles). Paired-end sequencing was performed to cover the entire length of the amplicon with insert size of 200 bp to 300 bp.

Paired-end sequencing data were first assembled using paired-end assembler PANDAseq (Masella et al., 2012) to obtain complete amplicons. Quality control (QC) was then performed on identified amplicons, where each amplicon was checked for no insertion or deletion of sequences and no stop codons, each CDR sequence was allowed to carry only up to one NNK mutation and no non-NNK mutation. Position weight matrices were generated by calculating the frequency of all mutations of every randomized position. Enrichment ratios for each mutation were calculated by dividing the frequency of a given mutation at a given position in the sorted sample with the frequency of the very same mutation in the unsorted sample, as described previously (Koenig et al., 2015).

Results: The enriched HVR mutations that support increased binding of the resulting h10F6 variant to both hu-CD200R1 and cyno-CD200R1 are summarized in Table 7.

TABLE 7 h10F6 mutation in VH and VL domains supporting increased hu-CD200R1 and cyno-CD200R1 binding affinity

| VH Position | Preferred amino acids VH Domain | VL Position | Preferred amino acids VL Domain |
|---|---|---|---|
| T30 | E, D, K, S, A, H, N, R, V, Y | G30C | N, D |
| N31 | D, E, K, G | N30D | E, A, S, D, V, Q, T, K |
| Y32 | N, T, S | S31 | — |
| A33 | G, S, P, A, N, T, R, W | F32 | M, H, Y, S, N |
| V34 | I, V, M, L, T, E | R50 | N, G, Q, D |
| S35 | A, G, T, S, N, C | A51 | G |
| V50 | T, S, E, A, N, D | S52 | N, K, D, E, H, T, Q |
| M51 | A, S, V, T, E, I | N53 | E |
| W52 | H, N, S, R, Y | L54 | R, K |
| A53 | S, T, V, A, G | E55 | A |
| G54 | N, E, S, D, K | H89 | G, A, M, S |
| G55 | — | Q90 | — |
| G56 | E, D, K, N | S91 | — |
| T57 | A, V, S | N92 | A, M, F, Y |
| N58 | S, D, A, M | E93 | G, W |
| Y59 | I, V, E, T | D94 | — |
| N60 | D | P95 | — |
| S61 | E, D, K, N, G, T | P96 | — |
| A93 | V, T, I | | |
| R94 | A | | |
| E95 | T, S, N, Q, A, M | | |
| R96 | I, V, K, M, L | | |
| P97 | G, N, S, M, V, A | | |
| L98 | G, M, A, K, R, N | | |
| T99 | S, E, N, G | | |
| G100 | — | | |
| V100A | E, A, T, I, P | | |
| M100B | L | | |
| D101 | E | | |
| Y102 | V, I, K, E, N | | |

Example 6: Characterization of Purified Affinity-Improved Variants of h10F6

This example illustrates hu-CD200R1 and cyno-CD200R1 binding affinity and blocking by selected h10F6 variants, h10F6.V1, h10F6.V2, h10F6.V3, and h10F6.V4, prepared by affinity maturation as described in Example 6.

A. Biacore Binding h10F6 variants were synthesized for cloning into a mammalian expression construct to generate IgG1 proteins. The LC and HC sequences of the variant IgG1 proteins are summarized in Table 3. The h10F6.V1 has LC of SEQ ID NO: 71 and HC of SEQ ID NO: 88. h10F6.V2 has a LC of SEQ ID NO: 68 (same as h10F6 and h10F6.V3) and a HC of SEQ ID NO: 89 (same as h10F6.V4. h10F6.V3 has a LC of SEQ ID NO: 68 (same as h10F6 and h10F6.V2), and a HC of SEQ ID NO: 88 (same h10F6.V1). h10F6.V4 has a LC of SEQ ID NO: 71 (same as h10F6.V1) and a HC of SEQ ID NO: 89 (same as h10F6.V2).

Plasmids encoding the heavy or light chain were expressed and purified as described in Example 2. To determine the binding kinetics of selected h10F6 affinity improved variants binding to hu-CD200R1-iso4 (Alt and Ref haplotypes) and cyno-CD200R1, SPR measurement with a BIACORE™ 8K instrument was performed as in Example 3.A. Briefly, h10F6 variants were diluted at 0.5 pg/mL in HBS-P buffer (0.01 M HEPES pH 7.4, 0.15 M NaCl, 0.005% Surfactant P20) and applied to the Protein A chip at 30 μL/min flow rate for 60 sec in flow cell 2 (FC2). Then flow 3-fold serial dilutions of human or cyno-CD200R1 in HBS-P buffer (0.01M HEPES pH 7.4, 0.15M NaCl, 0.005% surfactant P20) from 300 nM were injected (flow rate: 30 μL/min) at 37° C. to both flow cell 1 (FC1) and flow cell 2 (FC2). The sensorgram was recorded and subject to reference and buffer subtraction before evaluation by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant (KD) was calculated as the ratio of $k_{off}/k_{on}$, summarized in Table 8.

determined representing the concentration of the anti-CD200R1 variant IgG1 that inhibits 50% of the biotinylated hu-CD200R1 or the biotinylated cyno-CD200R1 binding to coated hu-CD200-Fc or cyno-CD200-Fc.

Results: As summarized in Table 9, the four h10F6 variants exhibited cross-reactive blocking activity with h10F6.V1 exhibiting the strongest blocking of both hu-CD200R1 and cyno-CD200R1.

TABLE 9

CD200:CD200R1 blocking $IC_{50}$ of h10F6 variants.

| Variants | CD200:CD200R1 $IC_{50}$ (nM) | |
|---|---|---|
| | hu-CD200R1-iso4 Ref | cyno-CD200R1 |
| h10F6.V1 | 0.58 | 2.44 |
| h10F6.V2 | 4.79 | 4.25 |
| h10F6.V3 | 0.56 | 11.39 |
| h10F6.V4 | 10.91 | 2.15 |

Example 7: Rat Pharmacokinetic Study of Anti-CD200R1 Antibodies

This Example illustrates an in vivo pharmacokinetic (PK) study in rats of the humanized anti-CD200R1 antibodies h10F6 and h22.1.

Materials and methods: the humanized anti-CD200R1 antibodies h10F6 and h22.1 were intravenously dosed in Sprague-Dawley rats. A single dose of 10 mg/kg or 1 mg/kg was given to 2 male and 2 female rats per dosing group. Blood collections were taken 5 min, 2 h, 6 h, 24 h, 3 days, 7 days, 10 days, 14 days, 17 days and 21 days post injection. Anti-CD200R1 levels in serum were quantified using a generic ELISA method capturing human IgG antibodies with sheep anti human IgG1 and detection with biotin labeled goat anti-human IgG (H+L) and streptavidin-HRP. Noncompartmental analysis was used to calculate the PK parameters with time range from 3-21 days.

As shown in FIG. 11, the pharmacokinetics exemplifies that of a non-targeted mediated depletion profile. The half-

TABLE 8

Binding affinity of h10F6 variants to human hu-CD200R1 and cyno-CD200R1

| | hu-CD200R1-iso4-Alt | | | hu-CD200R1-iso4-Ref | | | cyno-CD200R1 | | |
|---|---|---|---|---|---|---|---|---|---|
| Variants | Kon (1/Ms) | Koff (1/s) | KD (M) | Kon (1/Ms) | Koff (1/s) | KD (M) | Kon (1/Ms) | Koff (1/s) | KD (M) |
| h10F6.V1 | 1.44E+06 | 1.17E−03 | 8.14E−10 | 1.35E+06 | 9.64E−04 | 7.16E−10 | 4.36E+05 | 4.57E−03 | 1.05E−08 |
| h10F6.V2 | 6.35E+05 | 4.25E−03 | 6.68E−09 | 6.07E+05 | 3.67E−03 | 6.04E−09 | 2.16E+05 | 3.51E−03 | 1.63E−08 |
| h10F6.V3 | 2.04E+06 | 1.91E−03 | 9.35E−10 | 1.88E+06 | 1.53E−03 | 8.17E−10 | 3.22E+05 | 1.95E−02 | 6.07E−08 |
| h10F6.V4 | 3.88E+05 | 3.87E−03 | 9.99E−09 | 3.77E+05 | 3.36E−03 | 8.93E−09 | 1.93E+05 | 1.13E−03 | 5.87E−09 |

Results: As shown by the binding affinity values summarized in Table 8, four variants, h10F6.V1, h10F6.V2, h10F6.V3, and h10F6.V4, were identified as exhibiting are binding cross-reactivity to the hu-CD200R1 and cyno-CD200R1.

B. Blocking Assay

The four h10F6 variants, h10F6.V1, h10F6.V2, h10F6.V3, and h10F6.V4, were assayed for performance in a human CD200:CD200R1 blocking ELISA assay carried out as described in Example 3.B. Blocking $IC_{50}$ values were life of h10F6 ranges from 11.4 to 14.8 days in 1 mg/kg and 10 mg/kg dosing groups, respectively. The half-life of h22.1 is approximately 12 days in both dosage groups. One animal in the 10 mg/kg h22.1 group had a faster clearance profile compared to other 3 rats in the same group and was omitted from the analysis.

Mean PK parameters of h10F6 in rats are summarized in Table 10 below. Following a single IV bolus injection of 1 or 10 mg/kg to Sprague-Dawley rats, the h10F6 serum concentration declined in a biphasic manner. The PK of h10F6 was dose proportional and similar in males and females. The mean terminal half-life of h22.1 in Sprague-Dawley rats was 11.4 and 14.8 days for a dose of 1 mg/kg and 10 mg/kg, respectively.

TABLE 10

PK Parameters of h10F6 Following Single-dose IV Administration in Rats

Mean PK Parameters (N = 4; 2M/2F)

| Dose of h10F6 | $T_{1/2}$ (day) | CL (mL/kg) (day) | $V_{ss}$ (mL/kg) | $C_{max}$ (μg/mL) | $AUC_{last}$ (day * μg/mL) | $AUC_{inf}$ (day * μg/mL) | $AUC_{extra}$ (%) |
|---|---|---|---|---|---|---|---|
| 1 mg/kg | 11.4 | 5.35 | 82.5 | 32.0 | 139.5 | 188.2 | 26.0 |
| CV (%) | 11.9 | 9.4 | 17.7 | 21.9 | 11.6 | 8.6 | 13.1 |
| 10 mg/kg | 14.8 | 6.17 | 113 | 258 | 1068 | 1705 | 35.5 |
| CV (%) | 48.0 | 24.1 | 15.2 | 9.3 | 12.1 | 27.7 | 26.0 |

Example 8: Single-Dose Pharmacokinetics of h10F6 in Monkeys

A single-dose PK study of h10F6 was performed in cynomolgus monkeys, a nonbinding species, to characterize its PK properties and tolerability.

Figure 12:
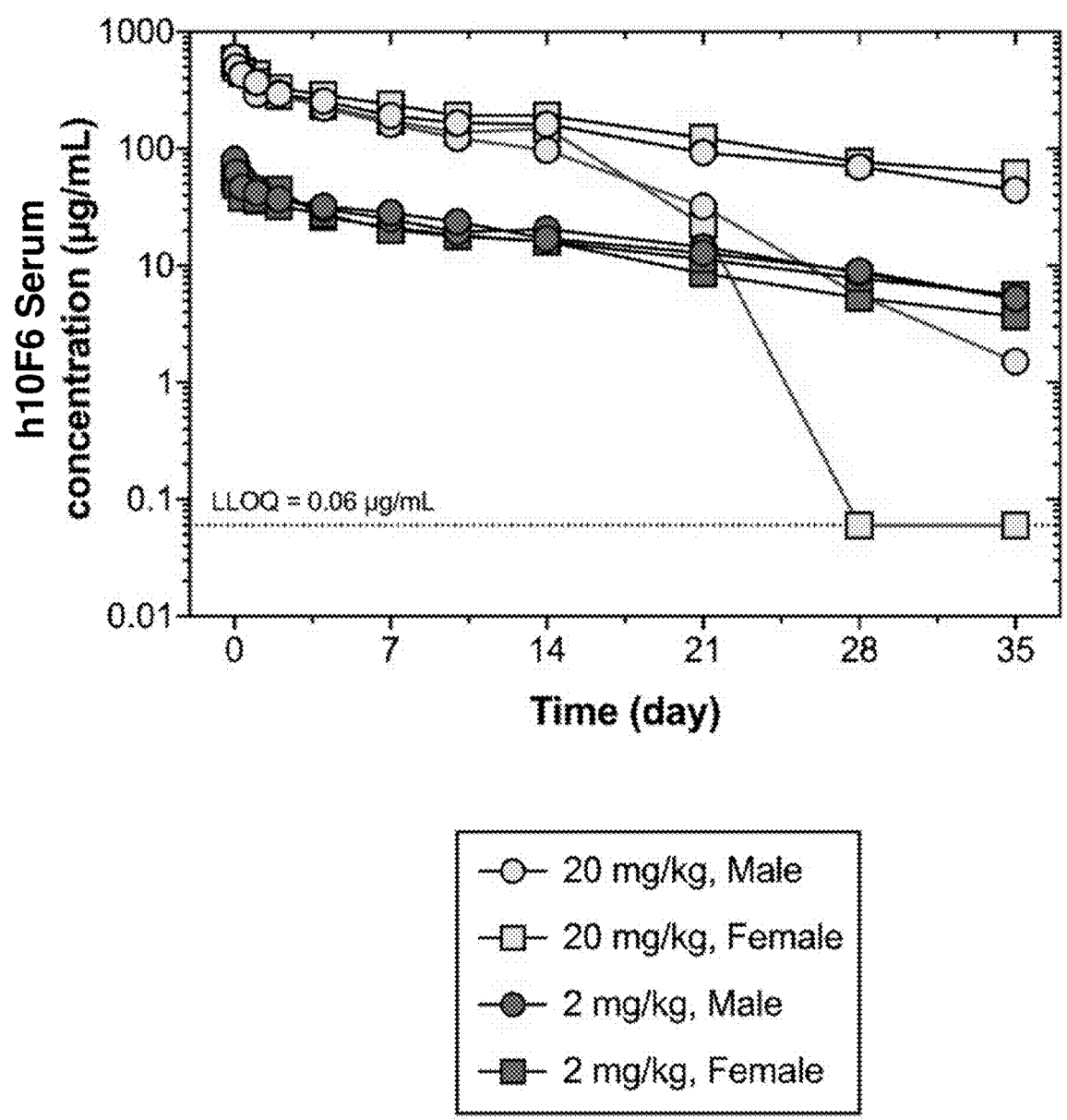
FIG. 12 depicts the serum concentrations of h10F6 for two male and two female monkeys over time after either a 2 mg/kg dose or 20 mg/kg dose of h10F6.

Naïve cynomolgus monkeys (N=8, 4M/4F) were administered h10F6 by single IV bolus injection at 2 and 20 mg/kg, respectively (2M/2F per group). The concentration of h10F6 in serum, clinical chemistry parameters, hematology parameters, and general health and appearance of the monkeys were monitored for 35 days post-dose. Blood samples for PK analysis were collected predose and at 15 min, 2 hours, 8 hours, and 1, 2, 4, 7, 10, 14, 21, 28, and 35 days post-dose. Samples for clinical pathology were collected predose and on Day 1 and Day 35 post-dose. The concentration of h10F6 in monkey serum samples was determined using an ELISA that was developed and qualified to measure the concentration of h10F6 with a lower limit of quantification (LLOQ) of 0.06 sg/mL. The concentration-time PK profiles of h10F6 in monkeys are shown in FIG. 12.

Mean PK parameters of h10F6 in monkeys are summarized in Table 11 below. Following a single IV bolus injection of 2 or 20 mg/kg h10F6 to cynomolgus monkeys, h10F6 serum concentrations declined in a biphasic manner. The mean terminal half-life (T½) of h10F6 was 11.5 and 13.3 days for the 2 mg/kg and 20 mg/kg groups, respectively. The PK of h10F6 was dose proportional and no sex differences were observed over the studied dose range of 2 to 20 mg/kg. Two of the 8 monkeys (one male and one female in the 20 mg/kg group) showed a sharp decrease in serum concentration of h10F6 between Day 14 and Day 21. This finding was attributed to the possible formation of antidrug antibodies (ADAs). As such, PK parameters that were suspected to have been impacted by ADAs were excluded from h10F6 summary data and a partial AUC (AUC0-14D) was included in the PK analysis. Exclusion of data from two animals with suspected ADA from the summary mean data did not impact the conclusions for h10F6 dose proportionality or sex differences.

10F6 had linear PK in monkeys, similar PK in males and females, and the mean values for clearance and estimated volume of distribution at steady-state were consistent with values that are typical for humanized IgG with linear PK in monkeys (Betts, et al., 2018). As expected for a non-binding species, the PK profile of h10F6 suggests that linear, non-saturable, non-specific clearance mechanisms are the predominant elimination pathway of h10F6 in monkeys. h10F6 was well tolerated through Day 35 based on clinical observations and an assessment of serum chemistry and hematology parameters.

TABLE 11

PK Parameters of h10F6 Following Single-dose IV Administration to Monkeys

Mean PK Parameters (N = 4 is 2M/2F; N = 2 is 1M/1F)

| Dose of h10F6 | $C_{max}$ (μg/mL) | $AUC_{0-14D}$ (%) | $AUC_{last}$ (day * μg/mL) | $T_{1/2}$ (day) | CL (mL/kg/day) | $V_{ss}$ (mL/kg) |
|---|---|---|---|---|---|---|
| 2 mg/kg | 69.0 | 371 | 582 | 11.5 | 3.04 | 50.8 |
| CV (%) | 19.6 | 9.5 | 11.1 | 15.7 | 15.7 | 14.0 |
| N | 4 | 4 | 4 | 4 | 4 | 4 |
| 20 mg/kg | 588 | 3100 | 5470 | 13.3 | 13.3 | 57.7 |
| CV (%) | 4.9 | 13.9 | ND | ND | ND | ND |
| N | 4 | 4 | 2 | 2 | 2 | 2 |

Example 9: Pharmacokinetics of h10F6 in Humans

The PK of h10F6 was assessed in single dose studies ranging from 2 to 20 mg/kg in cynomolgus monkey and 1 to 10 mg/kg in Sprague-Dawley rats. h10F6 exposure was approximately dose proportional, and no differences were observed between males and females. The PK profiles do not suggest evidence of target mediated disposition or ADA effects, with the exception of 2 monkeys dosed at 20 mg/kg which had a PK profile suggestive of ADA formation. These results support that allometric methods can be appropriate to predict the human PK of h10F6.

Human PK parameters such as clearance and volume of distribution were calculated from nonclinical data in monkeys, as shown in Table 12 below. Briefly, h10F6 serum concentrations in monkeys declined after administration in a biphasic manner. Therefore, concentration-time data from N=8 monkeys dosed 2 or 20 mg/kg h10F6, with ADA-suspected data excluded, were simultaneously fit to a two-compartment model. The monkey PK parameters from this model were scaled allometrically to derive human PK parameters, based on an assumption that volume of distribution terms (V1 and V2) scale with allometric exponent=1, and that clearance terms (CL and Q) scale with exponent=0.85 (Deng, et al., 2011). Body weights of 2.4 kg (mean body weight of monkeys in single dose PK study, h10F6-VIV-01) and 70 kg were adopted for monkey and human weights, respectively. The scaled human PK parameters for a 70-kg person fall within the typical range for humanized IgG monoclonal antibodies.

Because h10F6 is specific to CD200R1 from humans, target-mediated drug disposition could not be assessed preclinically. However, toxicokinetic (TK) data from the GLP h10F6.V1 hazard identification study can be assessed for TMDD, and findings from this study can be used to inform or potentially refine the h10F6 human PK prediction if TMDD is found to be a dominant clearance pathway of h10F6.V1 in monkeys. Based on these PK parameters, the h10F6 elimination half-life can be calculated to be 19.4 days.

TABLE 12

Predicted PK Parameters of h10F6 in Humans

| Parameter | (Unit) | Value |
|---|---|---|
| CL | (L/day) | 0.158 |
|  | (mL/day/kg) | 2.254 |
| V1 | (L) | 2.61 |
| Q | (L/day) | 0.953 |
|  | (mL/day/kg) | 13.6 |
| V2 | (L) | 1.83 |

The predicted PK parameters of h10F6 in humans were used to estimate h10F6 PK in healthy volunteers and patients to inform the selection of the starting dose and the anticipated therapeutic dose range, respectively.

The PK of h10F6 in humans can be assumed to be linear over the dose range. However, the elimination half-life may be shorter than predicted at low doses, when target-mediated drug disposition can be a contributor to the total clearance in humans. Therefore, the AUC of h10F6 can be over-predicted in healthy volunteers and patients, particularly at low doses. As such, assuming linearity over the entire dose range results in a conservative approach to dose selection, particularly at low doses.

Doses presented in Table 13 below can be maximum doses evaluated in healthy volunteers, assuming a starting dose of 0.3 mg and a maximum dose increase of a half-log (~3-fold). These doses can be informed by a hazard identification study, such as a hazard identification study in h10F6.V1, and h10F6 ex vivo tissue cross-reactivity study, and can be modified if warranted based on review of the data. The totality of the safety, PK and PD data from prior cohorts will be carefully considered in the SRC's dose escalation decisions.

TABLE 13

Predicted Exposure of h10F6 in Healthy Volunteers

Predicted Pharmacokinetic Parameters in Healthy Volunteers

| Dose (mg) | $C_{max}$ (ug/mL) | $AUC_{inf}$ (day * ug/mL) |
|---|---|---|
| 0.3 | 0.115 | 1.94 |
| 1.0 | 0.384 | 6.77 |
| 3.0 | 1.15 | 20.3 |
| 10 | 3.84 | 67.7 |
| 30 | 11.5 | 203.0 |
| 100 | 38.4 | 676.6 |
| 300 | 115 | 2030 |
| 900 | 345 | 6089 |

The predicted human PK parameters were also used to estimate h10F6 PK in patients to inform the anticipated therapeutic dose range. The following assumptions were used to estimate h10F6 PK in patients, including linear PK, Q3W dosing, or serum to tumor partition coefficient of 10%, or any combination thereof.

The actual dose frequency to be used in patients can be informed by the safety, PK and PD data from the multiple dose study of h10F6.V1 in patients with advanced cancer. Patients can have higher levels of CD200R1 expression (e.g., TILs) than healthy volunteers, and the presence of CD200R1 can lead to faster clearance and lower exposure of h10F6, for example at low doses when target-mediated clearance is not fully saturated. While CD200R1 is a low-density surface receptor, it can be expressed at its highest level on myeloid lineage cells, for example neutrophils, whose rapid turnover can dominate the h10F6 elimination at low doses. Due to for example the expression of CD200R1 on TILs in the tumor, an equivalent or higher dose of h10F6 can be administered to achieve linear PK in patients compared to the dose of h10F6 that achieves linear PK in healthy volunteers. The concentration of an antibody in a solid tumor can be on average 10% to 30% of the serum concentration. A conservative approach of 10% can be used to inform the maximum dose being considered for each cohort.

Example 10: Binding of Anti-CD200R1 Antibodies to Primary Human Cells

To confirm that h10F6 binds to endogenous CD200R1 expressed on human cells, the binding of h10F6 to peripheral immune cell subsets was determined by flow cytometry using human PBMC from healthy donors.

Figure 13A:
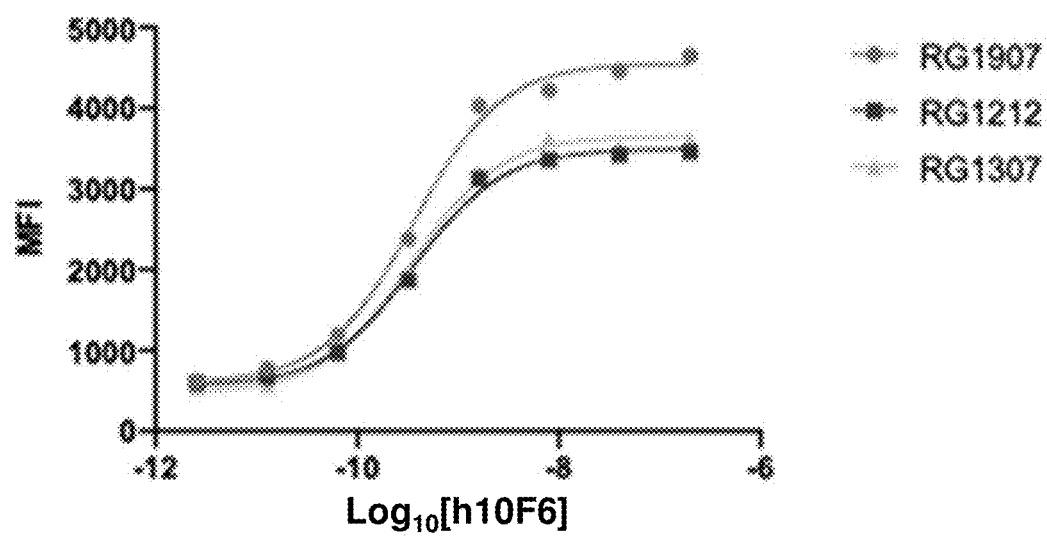
FIG. 13 depicts plots of data from flow cytometry studies of binding of h10F6 to T-cell subtypes, carried out as described in Example 10.
Figure 13B:
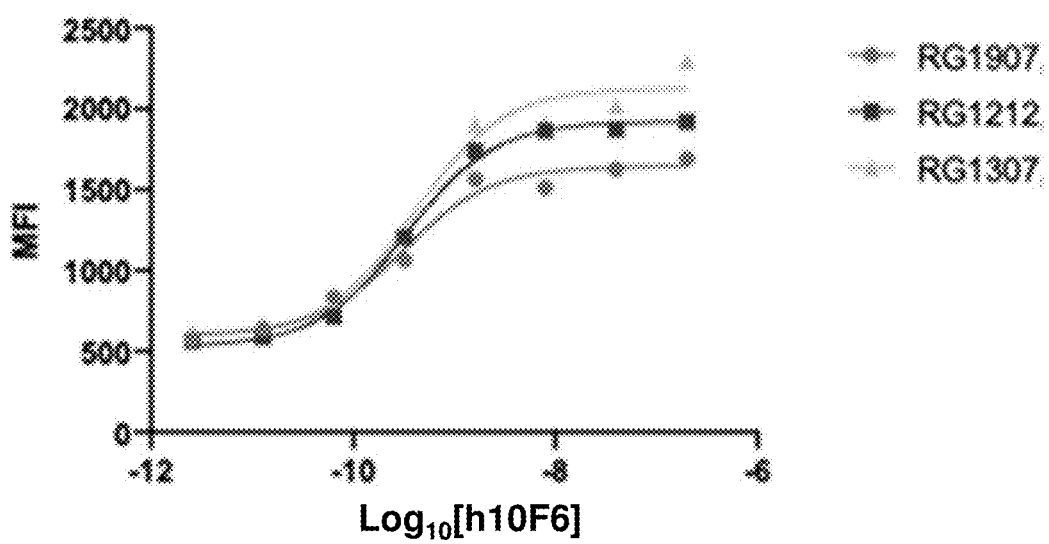

In PBMC isolated from 3 donors, h10F6 binding to immune subsets matched the expected CD200R1 expression reported in the literature (Wright, et al., 2003; Rijkers, et al., 2008; Czarnowicki, et al., 2017); CD4+ T cells expressed the highest levels of CD200R1, slightly lower expression was observed on CD8+ T cells. In comparison, a substantially lower level of CD200R1 expression was observed on B cells; the distribution of staining of B cells was bimodal, suggesting that a subset (approximately 16%) of total B cells expressed CD200R1. h10F6 shows limited binding to peripheral monocytes from 3 healthy donors. These results are consistent with studies using a commercial anti-CD200R1 antibody and freshly isolated monocytes from 3 other healthy donors (data not shown). The binding to T-cell subtypes was evaluated by testing serial dilutions of h10F6 (FIG. 13); the EC50 values for binding to these peripheral immune subsets was consistent across the 3 donors tested, ranging from 0.30 to 0.40 nM, as shown in Table 14 below.

TABLE 14

Potency of h10F6 Binding to T Cells

| Donor ID | Sample Type | Cell Type | $EC_{50}$ (MFI) |
|---|---|---|---|
| RG1307 | PBMC | CD4+ | 0.33 nM |
|  |  | CD8+ | 0.40 nM |
| RG1212 | PBMC | CD4+ | 0.35 nM |
|  |  | CD8+ | 0.33 nM |
| RG1907 | PBMC | CD4+ | 0.35 nM |
|  |  | CD8+ | 0.30 nM |

Figure 14:
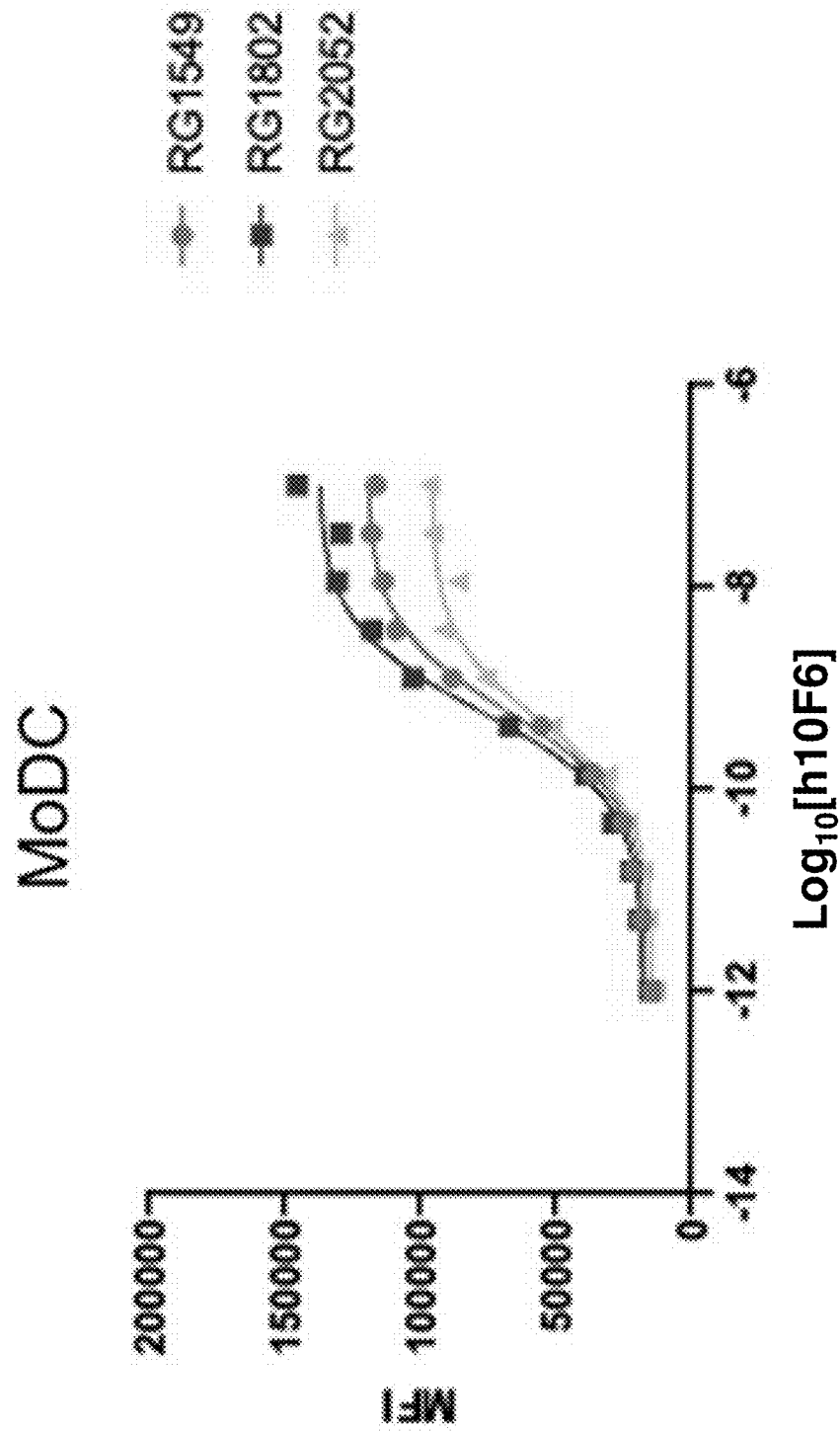
FIG. 14 depicts EC50 values for binding of MoDCs incubated with serial dilutions of biotinylated h10F6 and stained with streptavidin-PE and Live/Dead stain.

To recapitulate a tissue-resident DC phenotype, monocytes from healthy donor PBMC were isolated using a monocyte isolation kit and then differentiated in vitro with 20 ng/mL of granulocyte-macrophage colony stimulating factor (GMCSF) and 20 ng/mL of IL-4 for 1 week. h10F6 displayed binding to monocyte-derived dendritic cells (MoDC) across the 3 individual donors that were evaluated, and similar dose-response curves were obtained (FIG. 14). Binding EC50 values (0.45 to 0.60 nM) across donors are summarized in Table 15 below.

TABLE 15

Potency of Anti-CD200R1 Antibodies to Monocyte-Derived Dendritic Cells (MoDCs)

| Donor ID | Sample Type | Cell Type | $EC_{50}$ (mean fluorescence intensity, MFI) |
|---|---|---|---|
| RG2052 | Differentiated monocytes | MoDC | 0.45 nM |
| RG1802 | Differentiated monocytes | MoDC | 0.60 nM |
| RG1549 | Differentiated monocytes | MoDC | 0.60 nM |

Figure 15A:
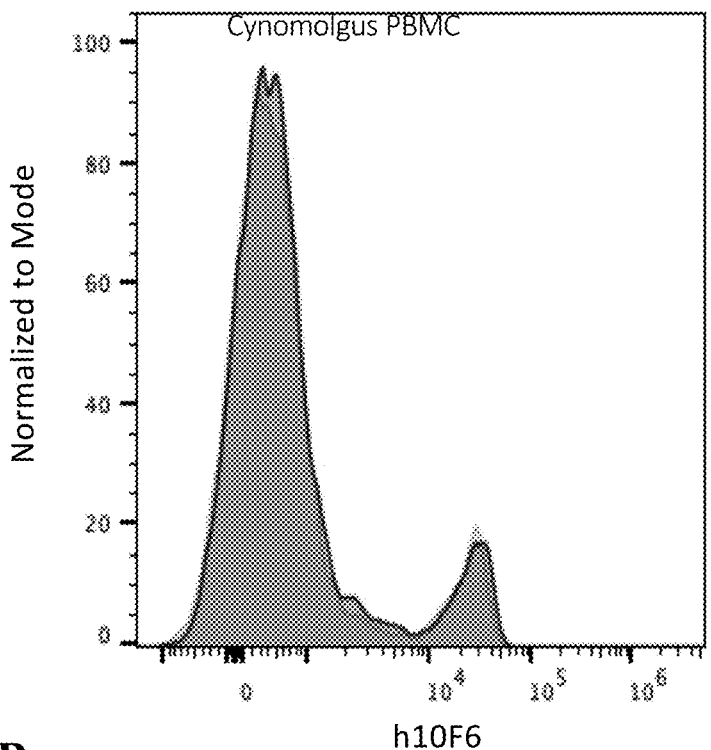
FIG. 15A, FIG. 15B, FIG. 15C, FIG. 15D, FIG. 15E, and FIG. 15F depict results from flow cytometry analyses of PBMCs of cynomolgus monkey (FIG. 15A), beagle (FIG. 15B), Rhesus monkey (FIG. 15C), rabbit (FIG. 15D), marmoset (FIG. 15E), or Sprague Dawley rat (FIG. 15F) showing no binding to h10F6 to primary immune cells in these species. PBMCs were incubated with 50 or 200 nM of biotinylated h10F6 or isotype control and stained with streptavidin-PE and Live/Dead stain.
Figure 15B:
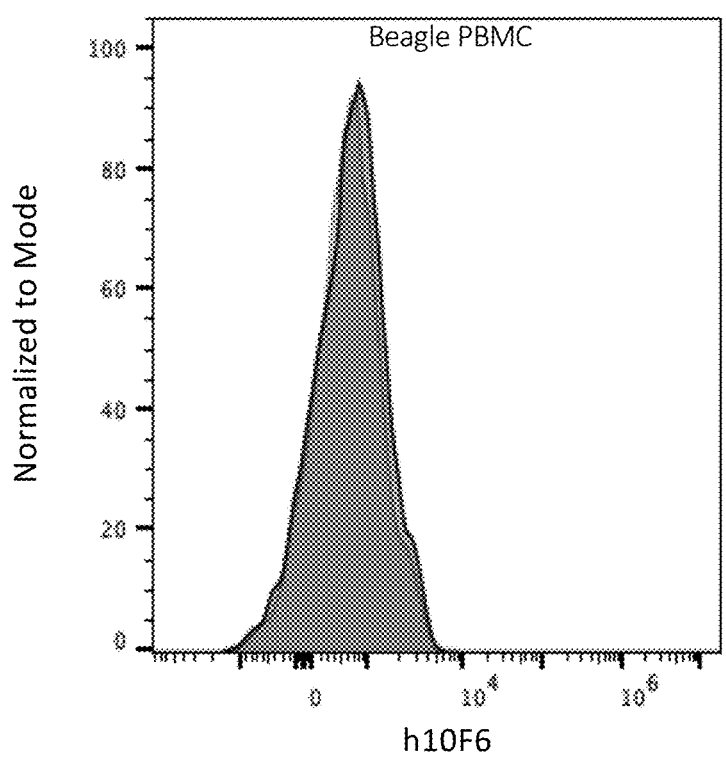
Figure 15C:
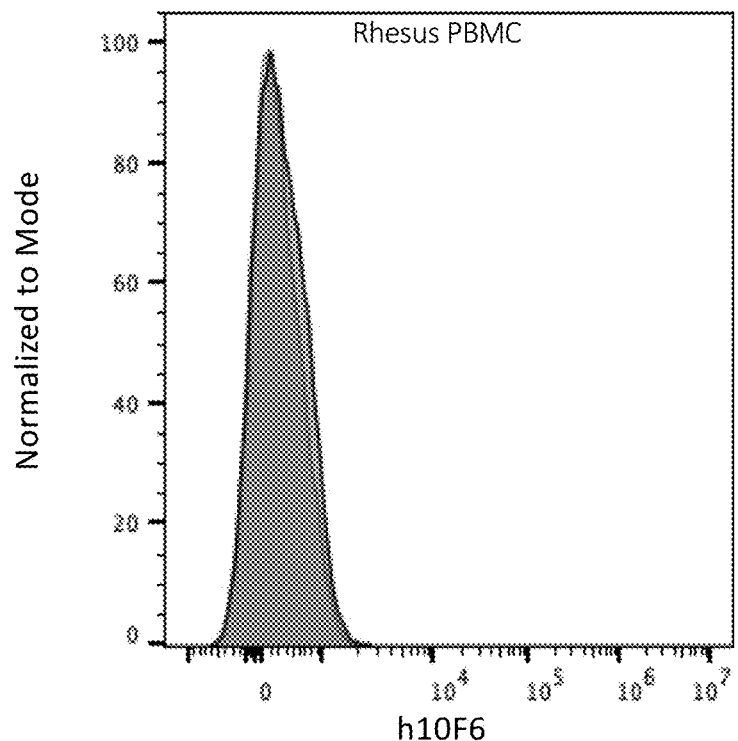
Figure 15D:
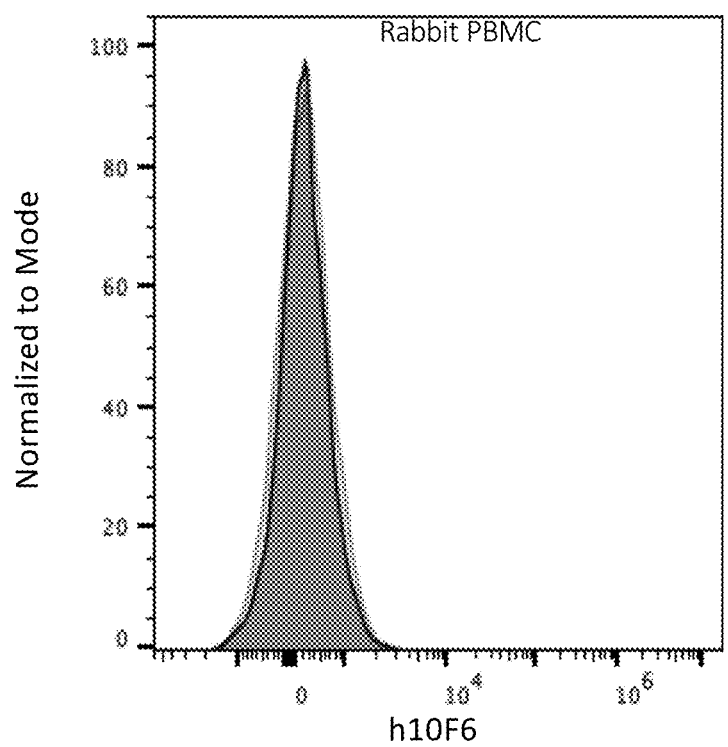
Figure 15E:
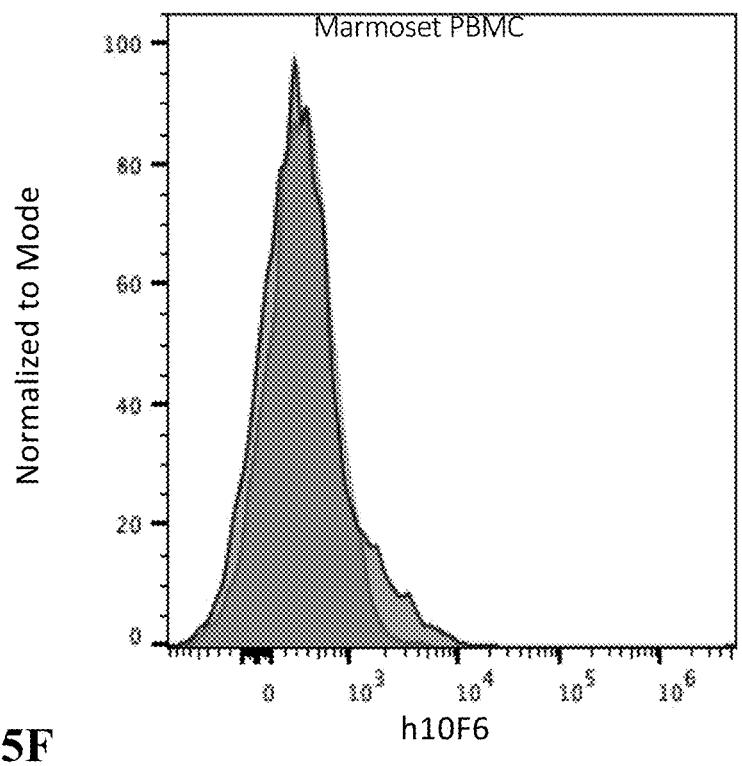
Figure 15F:
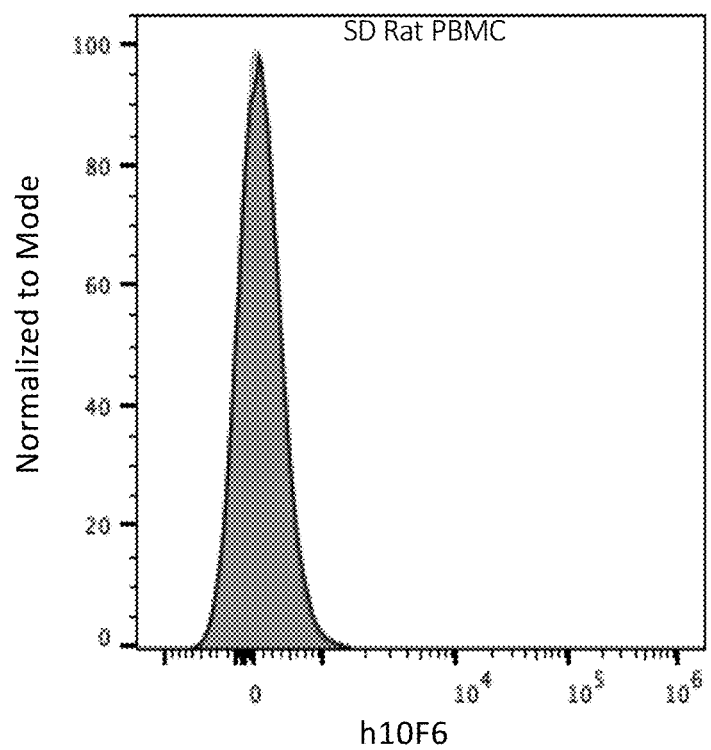

Example 11: Anti-CD200-R1 Antibodies do not Bind to Primary Rat, Rabbit, Dog, Marmoset, Rhesus, and Cynomolgus Monkey PBMCs The ability of h10F6 to bind to immune cells from other species was also evaluated. Common species that shared ≥50% sequence homology to human CD200R1 were selected for evaluation and included rat CD200R1 (54% extracellular domain, ECD, similarity), dog CD200R1 (50% ECD similarity), rabbit CD200R1 (61% ECD similarity), marmoset (82% ECD similarity), rhesus monkey (91% ECD similarity), and cynomolgus monkey (89% ECD similarity). Results of flow cytometry analyses of PBMC from each respective species demonstrated that h10F6 did not bind to rat (FIG. 15F), rabbit (FIG. 15D), or dog (FIG. 15B) primary immune cells. h10F6 also showed no binding to rhesus (FIG. 15C), marmoset (FIG. 15E), or cynomolgus monkey (FIG. 15F) cells despite high sequence homology.

Figure 16:
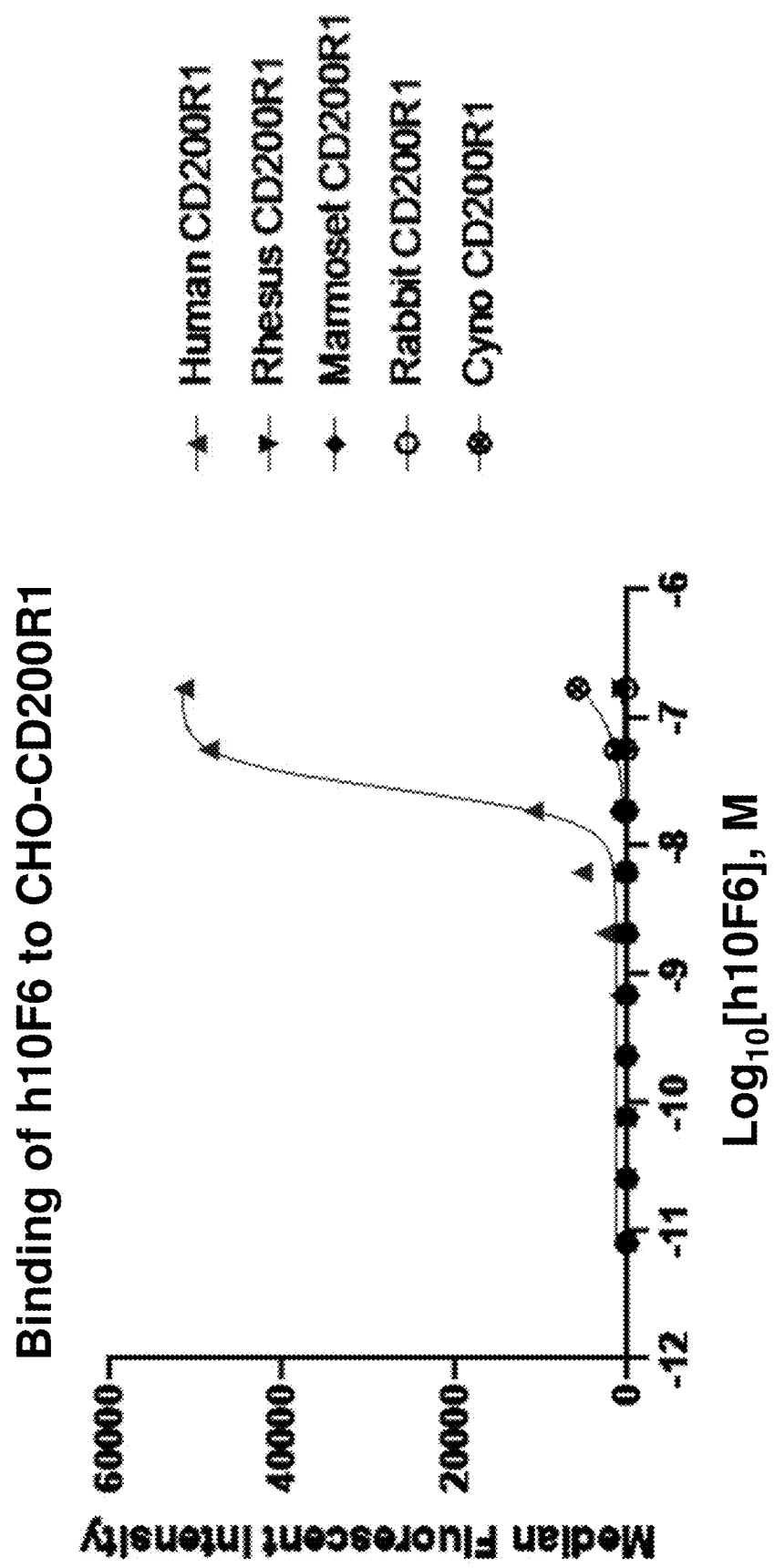
FIG. 16 depicts binding of h10F6 to CHO cells transfected with full length CD200-R1 from human, rabbit, marmoset, rhesus monkey, or cynomolgus monkey and incubated with serial dilutions of biotinylated h10F6 followed by streptavidin-PE and Live/Dead stain.

Lack of cross-reactivity to rabbit, marmoset, rhesus and cynomolgus monkey CD200R1 was confirmed by measuring binding of h10F6 to CHO cells transfected with full-length CD200R1 consensus sequences for these species, with human CD200R1 used as positive control (FIG. 16). Consistent with the results observed with primary cells, h10F6 only recognized human CD200R1.

Figure 17A:
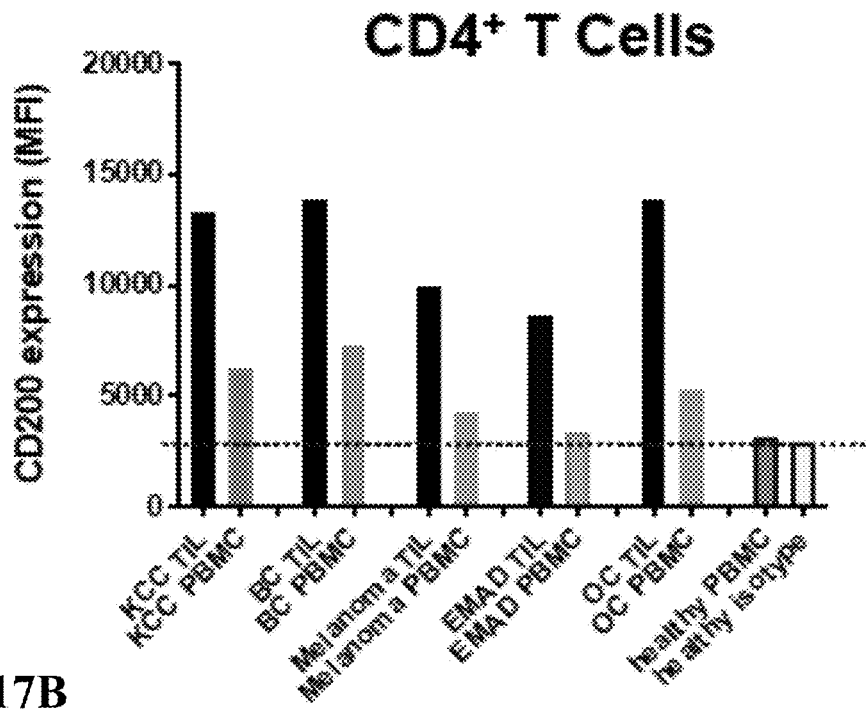
FIG. 17A, FIG. 17B, FIG. 17C, and FIG. 17D depicts expression of CD200 on TILs and PBMC in cancer patients and healthy controls. CD200 expression was evaluated in immune cell subsets derived from tumors and PBMC from cancer patients and PBMC from healthy subjects. Single-cell immune subsets were gated based on CD45+T helper cells (CD3+CD4+) (FIG. 17A), cytotoxic T cells (CD3+CD8+) (FIG. 17C), and B cells (CD3-CD19+) (FIG. 17B); myeloid cells were identified as CD11b+, (lineage negative) (FIG. 17D). CD200 expression as measured by MFI (mean fluorescence intensity) was compared on TIL subsets with matched PBMCs.
Figure 17B:
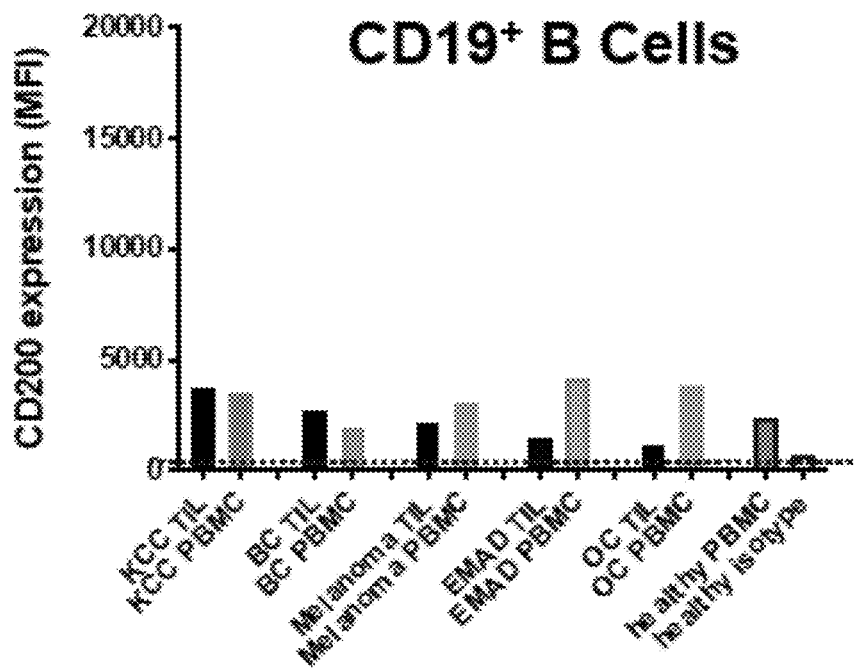
Figure 17C:
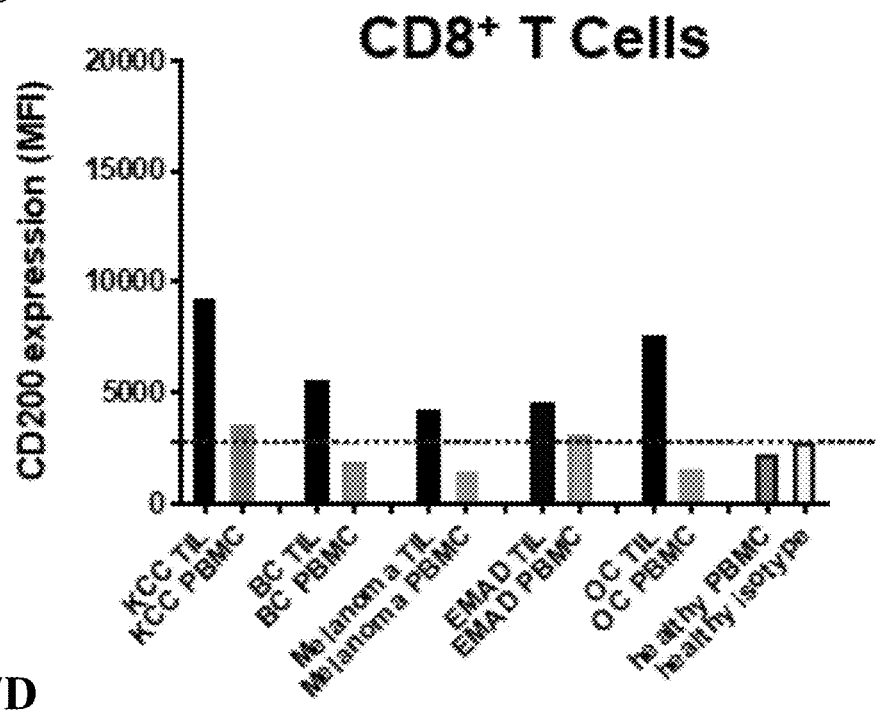
Figure 17D:
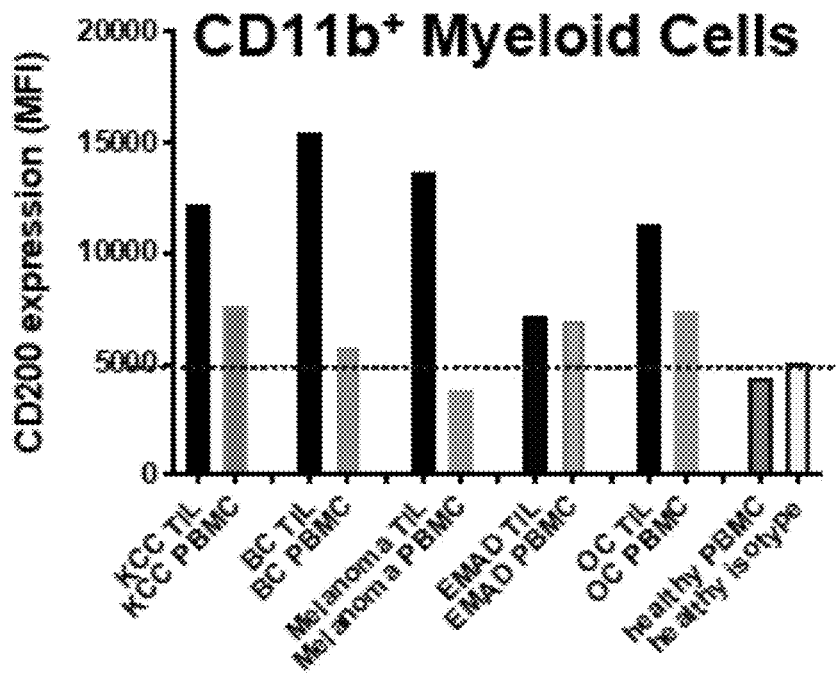
Figure 18A:
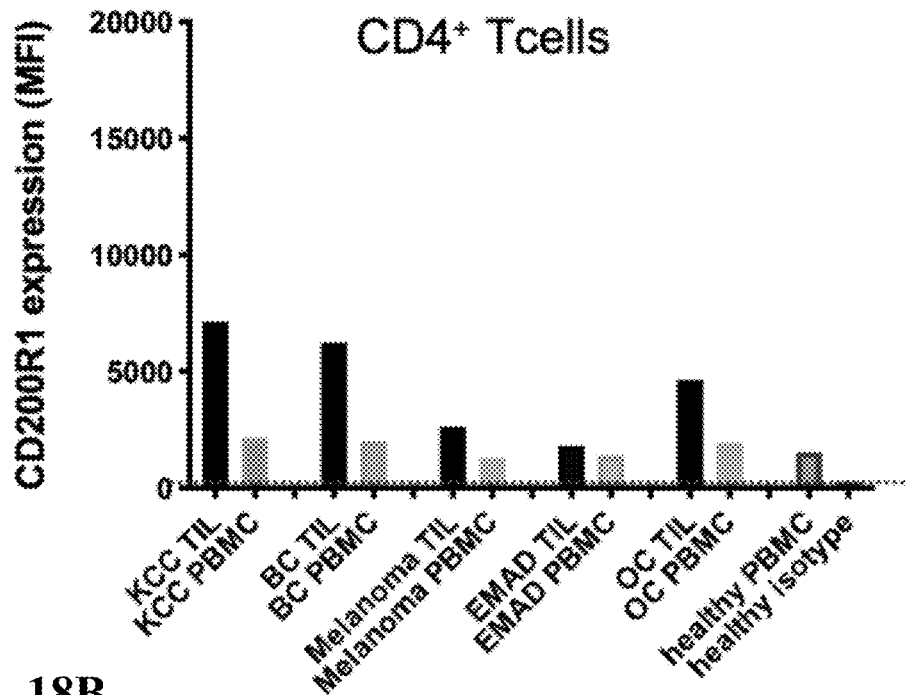
FIG. 18A, FIG. 18B, FIG. 18C, and FIG. 18D depicts CD200R1 expression evaluated in immune cell subsets derived from tumors and PBMCs from cancer patients and PBMCs from healthy subjects. Single-cell immune subsets were gated based on CD45+T helper cells (CD3+CD4+) (FIG. 18A), cytotoxic T cells (CD3+CD8+) (FIG. 18C), and B cells (CD3-CD19+) (FIG. 18B); myeloid cells were identified as CD11b+, (lineage negative) (FIG. 18D). CD200R1 expression as measured by MFI (mean fluorescence intensity) was compared on TIL subsets with matched PBMCs.
Figure 18B:
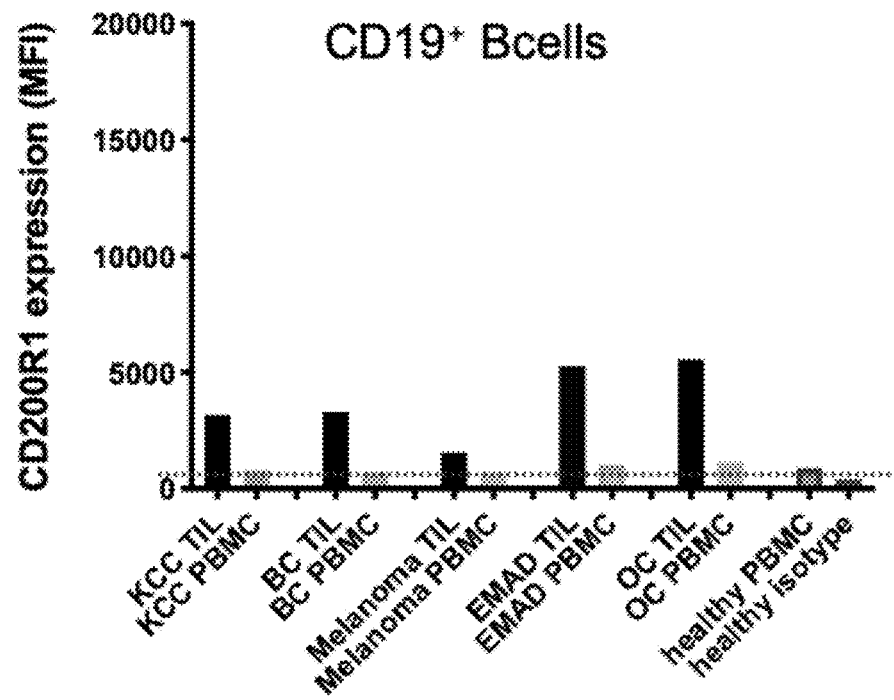
Figure 18C:
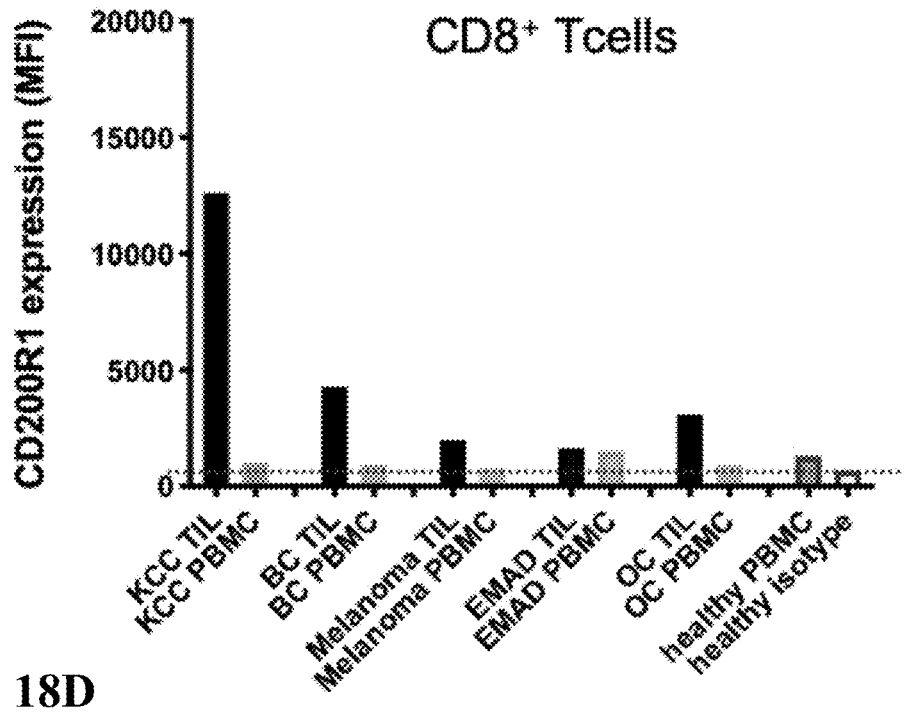
Figure 18D:
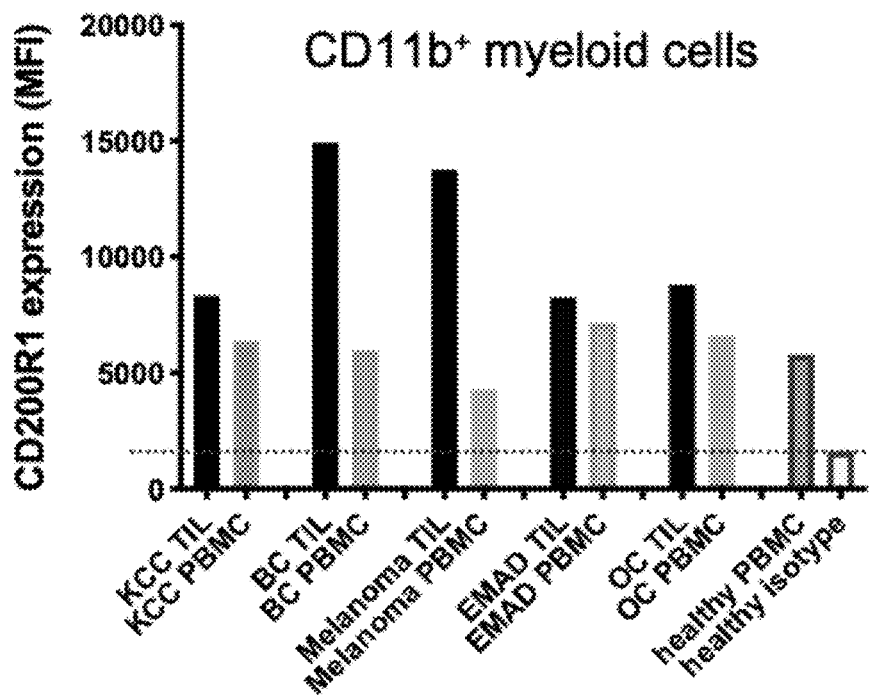

Example 12: Expression of CD200R1 on Peripheral and Tumor-Infiltrating Immune Cells The expression of CD200 and CD200R1 was assessed on tumor-infiltrating lymphocytes (TILs) from cryopreserved dissociated tumor tissue and matched PBMC from clear cell renal, breast, melanoma, endometrial adenocarcinoma and ovarian cancer patients to understand their distribution on immune cells in the periphery compared to the tumor microenvironment (CD200, FIG. 5 of IND book; CD200R1, FIG. 6 of IND book). While the CD200 levels on peripheral immune cells were similar between cancer patients and healthy donors (FIG. 17B), CD200 expression levels were upregulated in tumor-infiltrating immune cells, including CD4+ T cells (FIG. 17A), CD8+ T cells (FIG. 17C) in all 5 cancer patients tested. Tumor infiltrating CD11b+ myeloid cells in 4 out of 5 cancer patients also demonstrated elevated CD200 expression compared to matched samples from the periphery (FIG. 17D). The CD200R1 expression on patient PBMC subsets was comparable to healthy control expression levels (FIG. 18B). However, CD200R1 had higher expression on CD4+ (FIG. 18A) and CD8+ (FIG. 18C) TIL T cells compared to matched peripheral samples in 4 out of 5 cancer patients. In all 5 patient samples tested, TIL B cells and CD11b+ myeloid cells demonstrated elevated CD200R1 expression compared to matched peripheral samples (FIG. 18D). This data confirms literature reports of CD200 and CD200R1 upregulation in the tumor microenvironment (Zheng, et al., 2017; Thommen, et al., 2018; Cassetta, et al., 2019) and suggests that elevated expression of the CD200R1 inhibitory receptor and its ligand are likely contributing to the immunosuppressive tumor microenvironment.

Figure 19A:
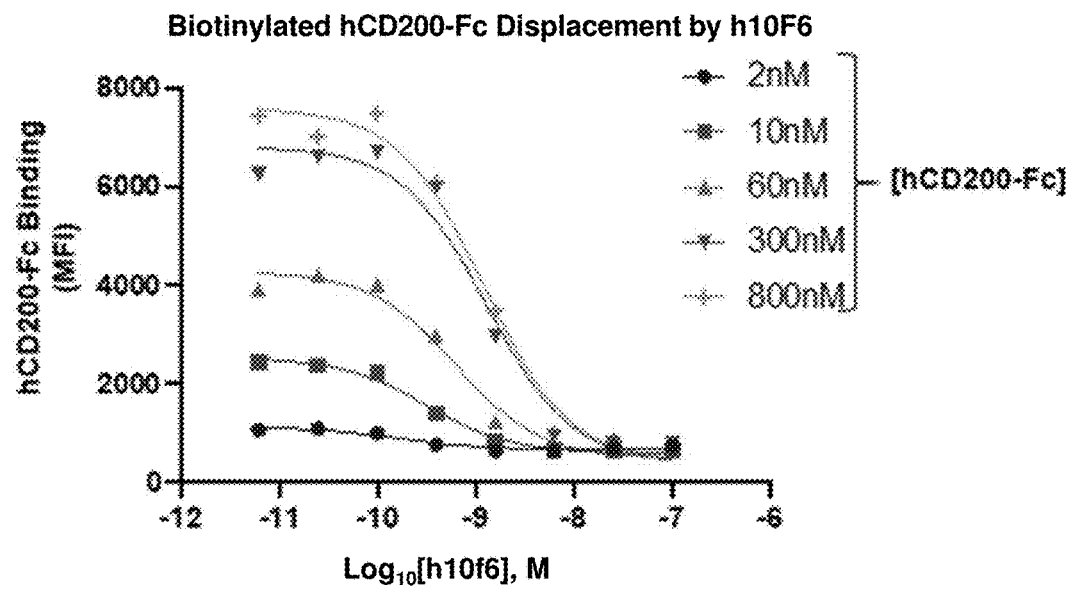
FIG. 19A and FIG. 19B depict the U937 cell line engineered to express levels hCD200R1 expected to represent a high expression population (approximately 28% of total T cells). Panel A displacement of varying concentrations of biotinylated hCD200-Fc from U937-CD
Figure 19B:
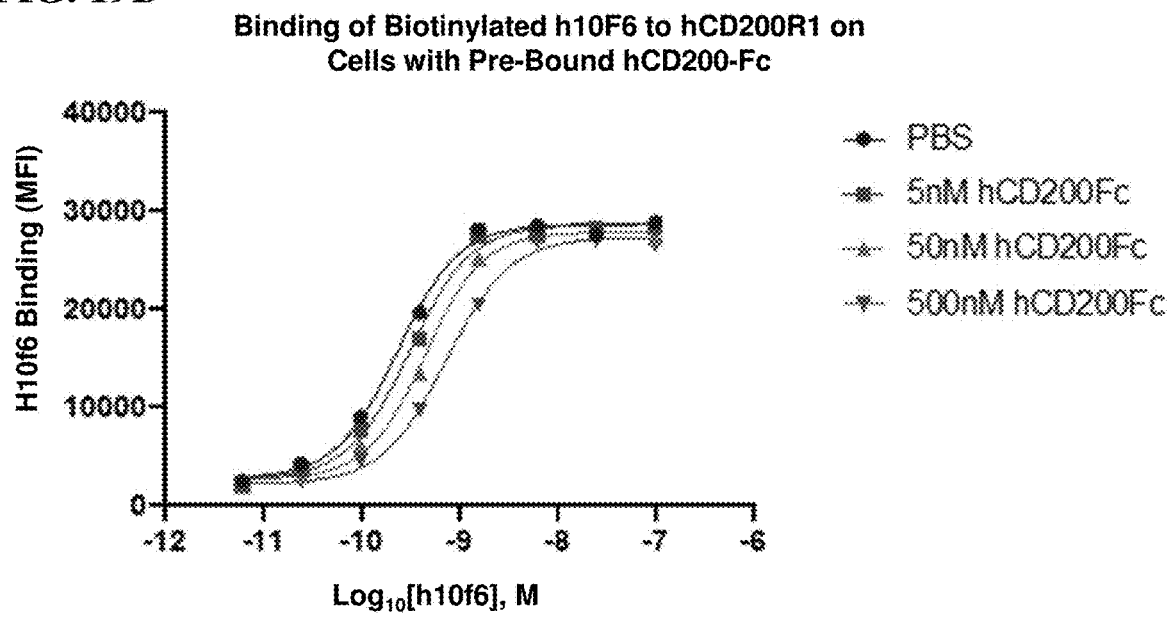

Example 13: Blocking of the CD200/CD200R1 Interaction by Anti-CD200-R1 Antibodies A. Displacement of Pre-Bound CD200 from Cells Expressing CD200R1 by Anti-CD200-R1 Antibodies In the context of a tumor and tumor-infiltrating immune cells, a proportion of CD200 expressed on tumor cells and/or endothelial cells on blood vessels is expected to be pre-bound to CD200R1 expressed on immune cells. To evaluate the capacity of h10F6 to displace pre-bound CD200 from CD200R1, a U937 cell line was engineered to express hCD200R1 (U937-CD200R1) and pre-incubated with varying concentrations of hCD200-Fc prior to incubation with h10F6. The assay was performed by monitoring displacement of biotinylated hCD200-Fc from U937-CD200R1 by h10F6 (FIG. 19, panel A) or monitoring binding of biotinylated h10F6 to U937-CD200R1 cells in the presence of different concentrations of hCD200-Fc (FIG. 19, panel B). h10F6 potently displaced hCD200-Fc from cell surface-expressed hCD200R1 in both assay formats, resulting in h10F6 blocking IC50 values that ranged from 0.16 to 1.28 nM, depending on the concentration of hCD200-Fc present. As expected, h10F6 IC50 values for displacement of pre-bound CD200 were substantially higher (less potent) than when cells expressing CD200R1 were pre-incubated with h10F6 (IC50=0.08 nM).

Figure 20:
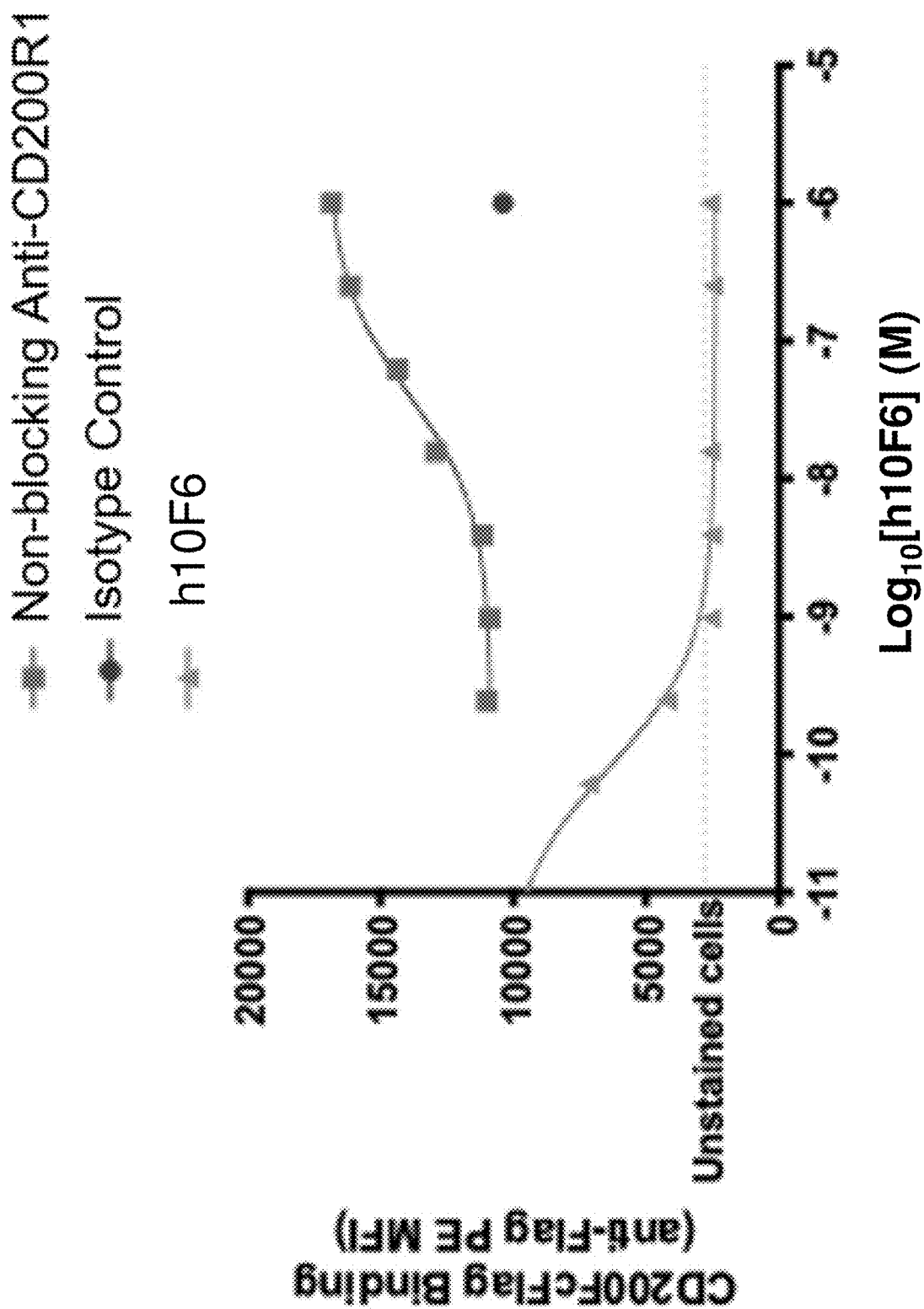
FIG. 20 depicts binding as a function of concentration of in-vitro monocyte-differentiated DCs allowed to bind to increasing concentrations of h10F6.

B. Blocking of Binding of CD200 to Primary Dendritic Cells that Endogenously Express CD200R1 by Anto-CD200-R1 Antibodies As a key attribute of h10F6's biological mechanism of action is to effectively prevent CD200 binding to CD200R1-expressing cells, we evaluated the ability of h10F6 to block soluble recombinant CD200 binding to dendritic cells that were differentiated in vitro and express high levels of endogenous CD200R1. h10F6 blocked 100% of CD200 binding to CD200R1-expressing DCs in a concentration-dependent manner with an IC50 value of 0.08 nM (FIG. 20). Here, in-vitro monocyte-differentiated DCs were allowed to bind to increasing concentrations of h10F6. Unbound antibody was removed by washing twice before adding 500 nM of CD200-Fc-FLAG fusion protein. After 20 minutes of incubation at 4° C., anti-Flag PE antibody was added for detection of CD200 binding. EC50 values for binding were determined using a 3-parameter, log 10[h10F6] vs response, nonlinear curve fit; the fitted line is extrapolated based on this model. A control antibody that binds CD200R1 but does not block CD200R1-CD200 binding (non-blocker) did not inhibit CD200 binding; in fact, it appeared to enhance binding. Together, these results demonstrate that h10F6 can prevent binding of CD200 to CD200R1 on primary immune cells.

Example 14: Inhibition of CD200R1 Signaling by Anti-CD200R1 Antibodies

The effect of h10F6 on downstream CD200R1-mediated signaling was characterized in vitro using 2 different cell-based assay systems. One evaluated the ability of h10F6 to prevent recruitment of DOK2 to the CD200R1 receptor intracellular domain. The other evaluated CD200R1-mediated downstream activation of nuclear factor kappa B (NFκB) using NFκB reporter genes.

Figure 21:
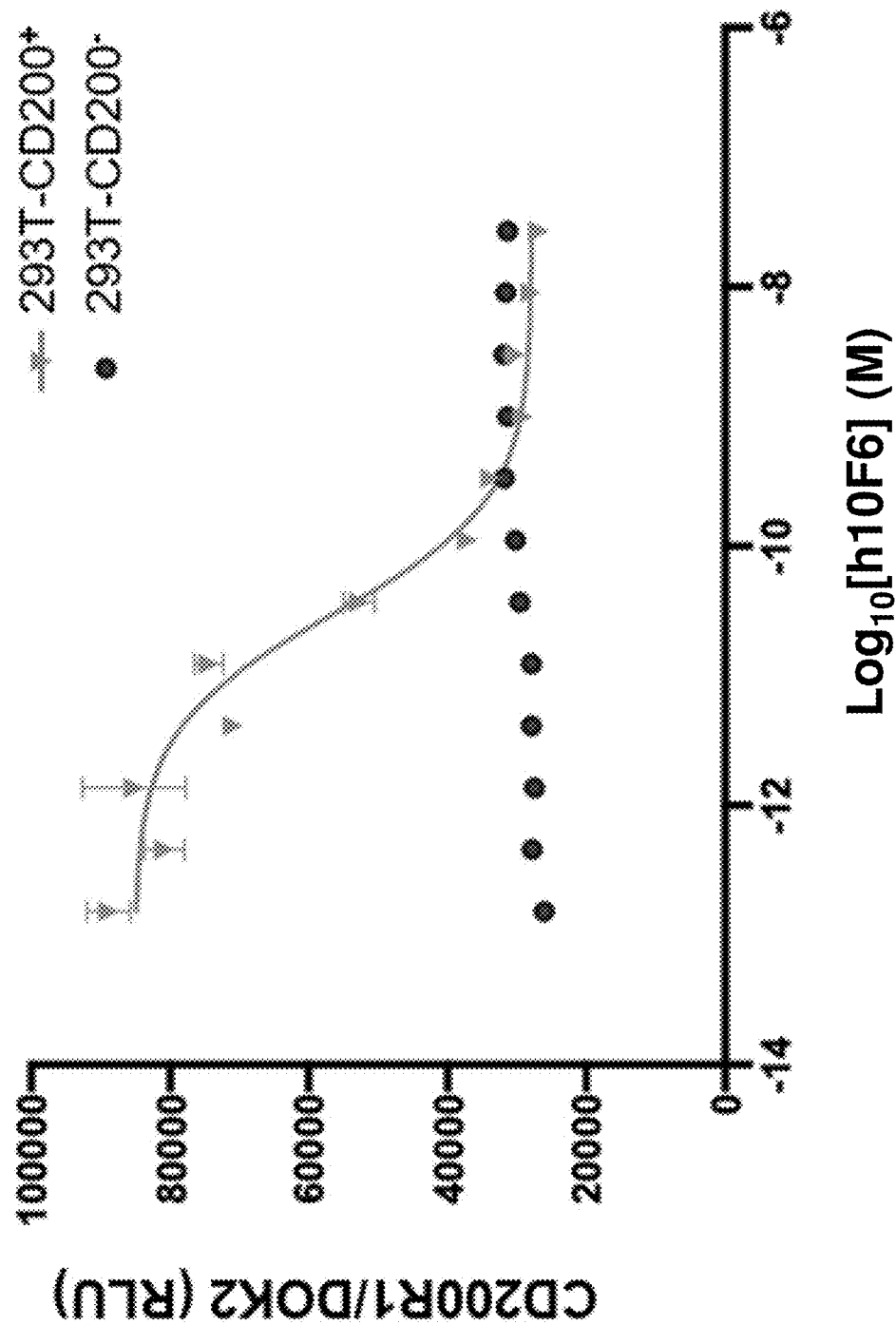
FIG. 21 depicts blocking induced recruitment of DOK2 to CD200R1 in human Jurkat cells engineered to express CD200R1 and DOK2 that were co-cultured with HEK293 cells expressing CD200.

The CD200R1 signaling pathway begins with CD200 induced phosphorylation of Y302 of CD200R1 followed by the recruitment of DOK2 (Zhang, et al., 2004; Mihrshahi, et al., 2009; Mihrshahi and Brown, 2010). As such, we evaluated the ability of h10F6 to block downstream recruitment of DOK2 using a commercially available CD200R1-specific DOK2 recruitment assay (EuroFins DiscoverX). In this in vitro cell-based assay system, the human Jurkat cell line is engineered to express CD200R1 and DOK2, each modified at the c-terminus with a separate and complementary β-galactosidase enzyme fragment. When DOK2 comes in close proximity to the intracellular domain of CD200R1, the 2 engineered enzyme fragments will complement each other to form a functional enzyme that is able to hydrolyze a proprietary substrate to produce a chemiluminescent signal. As such, co-culturing human Jurkat cells with CD200 expressing HEK293 cells induces a dose-dependent chemiluminescent signal reflective of CD200R1 signaling (FIG. 21). Adding serial dilutions of soluble h10F6 to the co-culture blocked the CD200 ligand induced recruitment of DOK2 to CD200R1 in a concentration-dependent manner (IC50=0.03 nM). HEK293T cells with no CD200 endogenous expression was used to determine the baseline level of signal. The inhibition was complete with increasing antibody concentrations as the signal returned to baseline level (indicated by HEK293T control cell stimulation).

Pre-clinical studies suggest the canonical NFκB pathway can play a tumor promoting role in ovarian, colitis-associated cancer, hepatocellular and glioblastoma mouse models. Literature reports suggest that the immunosuppressive tumor-associated macrophages (TAM) M2 phenotype and myeloid-derived suppressor cells (MDSCs) can be dependent on NFκB (Hagemann, et al., 2008; Li, et al., 2020). Moreover, disrupting the canonical NFκB pathway in myeloid cells can slow tumor growth, repolarize the anti-inflammatory M2 to a proinflammatory M1 immune infiltrate supporting an increase of CD8+ T cell and tumor cell apoptosis (Achyut, et al., 2017). A human monocytic cell line, K562, was engineered to express CD200R1 and a NFκB-luciferase reporter to explore the effect of CD200-CD200R1 signaling on NFκB pathway and the ability of h10F6 to block this effect.

Figure 22A:
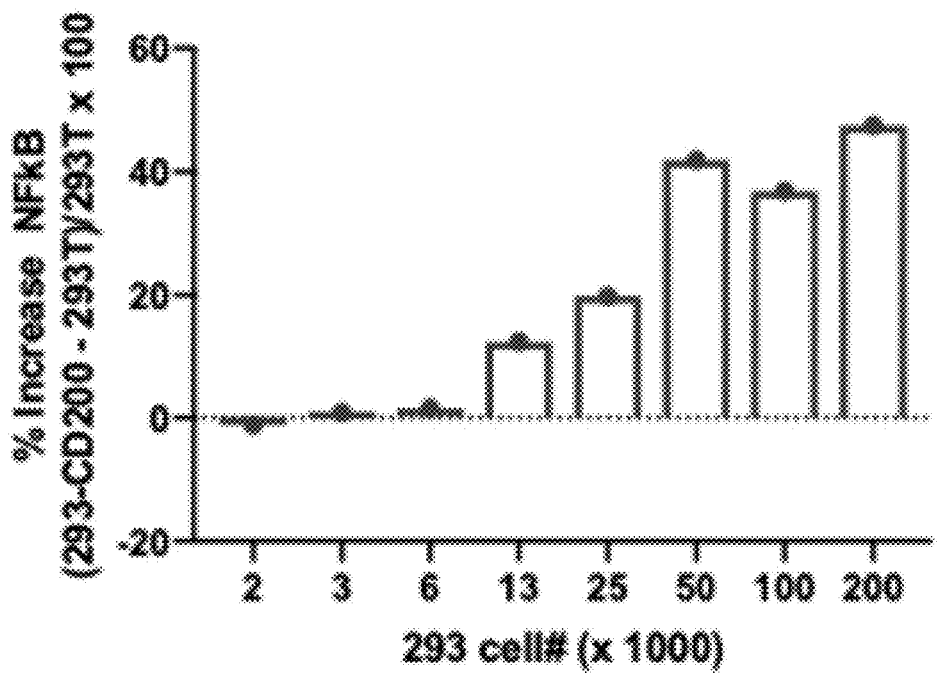
FIG. 22 depicts the effect of h10F6 on CD200-R1 induced NFκB activation of properties of the human myeloid cell line, K562, which was engineered to stably express CD200R1 and a NFκB-luciferase reporter. Panel A depicts to co-culture of K562 cells expressing CD200R1 with HEK293T cells expressing CD200 induced NFκB reporter gene activity in a cell number dependent manner. Panel B depicts the capacity of h10F6 to block NFκB signaling by applying serial dilutions of h10F6 or isotype control to co-cultured K562 cells expressing CD200R1 with HEK293T cells expressing CD200.
Figure 22B:
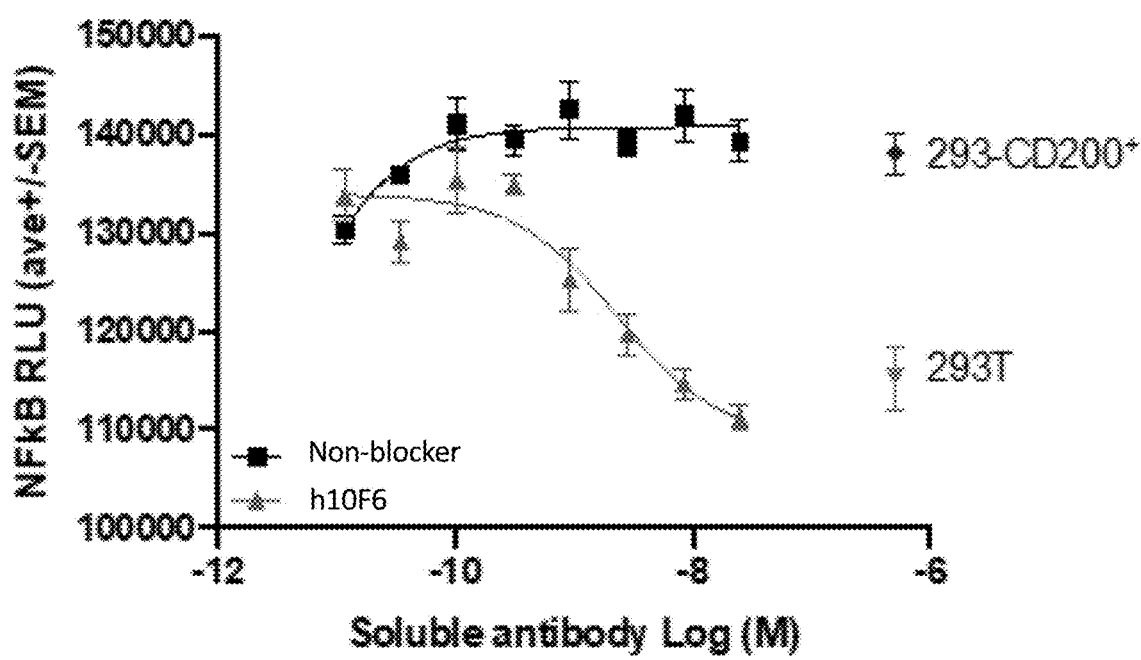

Treatment of CD200R1-expressing K562 cells with either plate-bound CD200 (data not shown) or co-culture with CD200 expressing HEK293T cells induced NFκB reporter gene activity in a cell number-dependent manner (FIG. 22, panel A). Addition of serial dilutions of soluble h10F6 to this K562 HEK293-CD200+ co-culture effectively and completely blocked the membrane bound CD200 dependent NFκB response with an IC50 value of 2.31 nM (FIG. 22, panel B) and an IC50 of 3.38 nM when CD200 was plate-bound (data not shown). These data demonstrate that h10F6 effectively blocks CD200/CD200R1 signaling in 2 independent cell-based systems.

Example 15: Enhancement of Immune Cell Activation by Anti-CD200R1 Antibodies

A. Effect of Anti-CD200R1 Antibodies in a Mixed Lymphocyte Assay

Figure 23A:
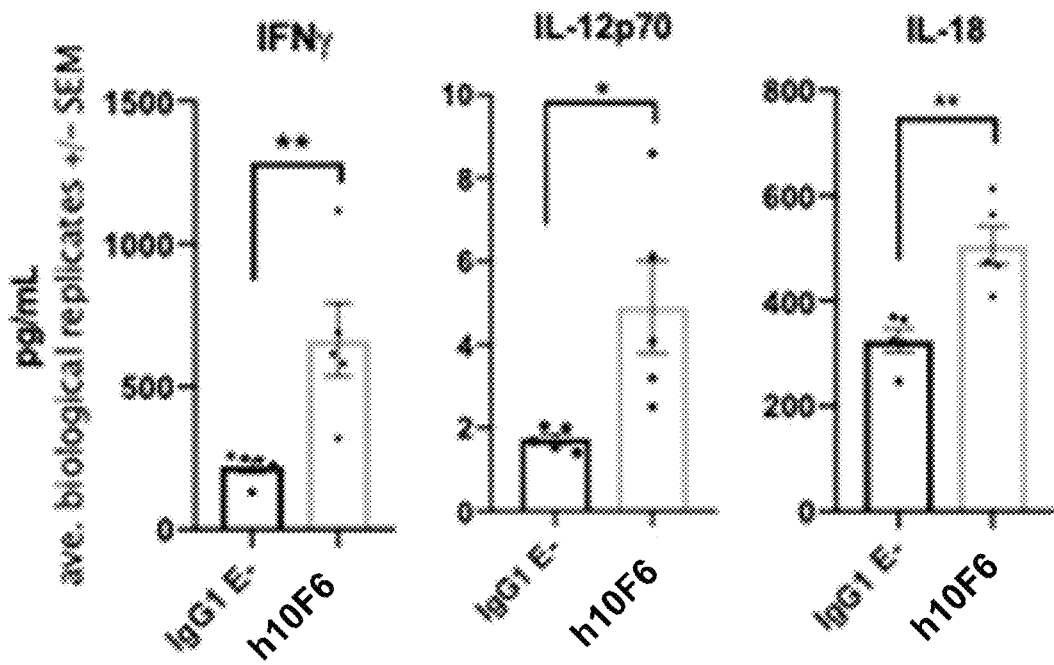
FIG. 23 depicts monocytes differentiated into dendritic cells by culturing for 7 days with 20 ng/mL GMCSF and 20 ng/mL IL-4. Dendritic cells were either polarized into tolerogenic (with 20 ng/mL IL-10 and IFNα-2b) or polarized into immunogenic DC (with 100 ng/mL LPS and 50 ng/mL TNF-α). After 3 days of polarization, pan-T cells and matured DCs were mixed together at a 20:1 (T:DC) ratio with 10 ug/mL h10F6 or isotype control. Conditioned media was harvested after 4, 5, and 6 days for cytokine measurements. T cell activation markers were measured by FACS analysis (anti-CD69, anti-CD25 and anti-Ki67). Both cytokine production (panel A; IFNγ, IL-12, and IL-18) and T cell activation markers (panel B, CD4+Ki67+ and CD8+CD69+) were measured; a time-course of IFNγ secretion at days 4, 5, and 6 (panel C) illustrates time dependence.
Figure 23B:
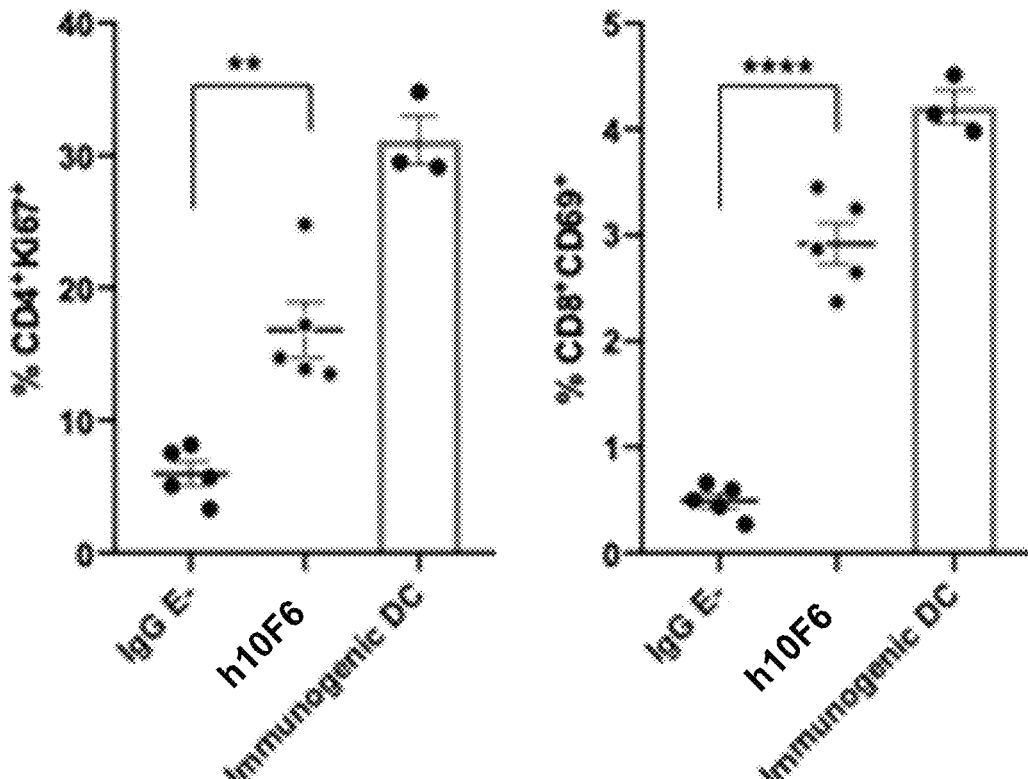
Figure 23C:
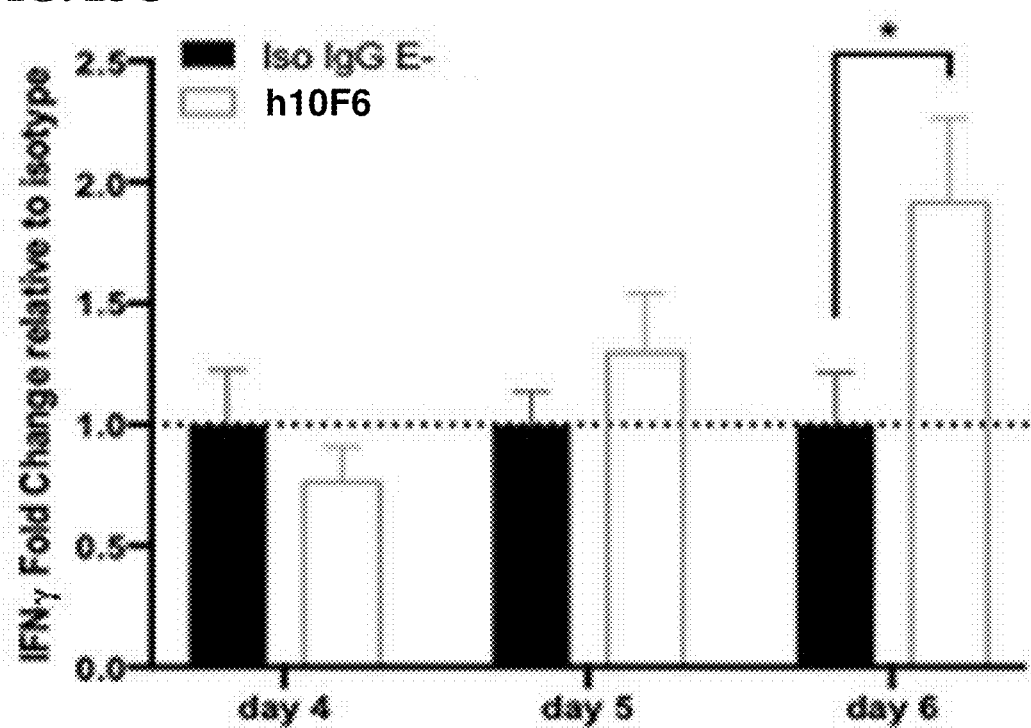

The ability of h10F6 to reverse the suppressive effects of tolerogenic DC in the context of an allogenic T cell co-culture was assessed in a mixed lymphocyte assay. Both cytokine production and T cell activation markers were measured. Briefly, monocytes were differentiated into dendritic cells by culturing for 7 days with GMCSF and IL-4. Dendritic cells were either polarized into tolerogenic or polarized into immunogenic DC to serve as an immuno-stimulatory positive control. After 3 days of polarization, pan-T cells and matured DCs were mixed together in the presence of h10F6 or isotype control antibody. Cytokine production and T cell activation markers were subsequently analyzed after 4 to 6 days of co-culture. h10F6 treatment in the tolerogenic DC mixed lymphocyte assay resulted in T cell activation as evidenced by a time-dependent, 2 to 3-fold induction of the proinflammatory cytokines including IFNγ, IL-12p70, and IL-18 (FIG. 23, panels A and C). Significant increases in the T-cell activation marker CD69 and the proliferation marker Ki67 were also observed, which reached 40-70% of maximal activation as indicated by immunogenic DC co-cultures (FIG. 23, panel B). Together, these data demonstrate the ability of h10F6 to rescue T cell function in the presence of tolerogenic DCs.

B. Effect of Anti-CD200R1 Antibodies in a Pan-T Cell Assay Evaluating Secretion of IL-2 and Production of INFγ

Figure 24A:
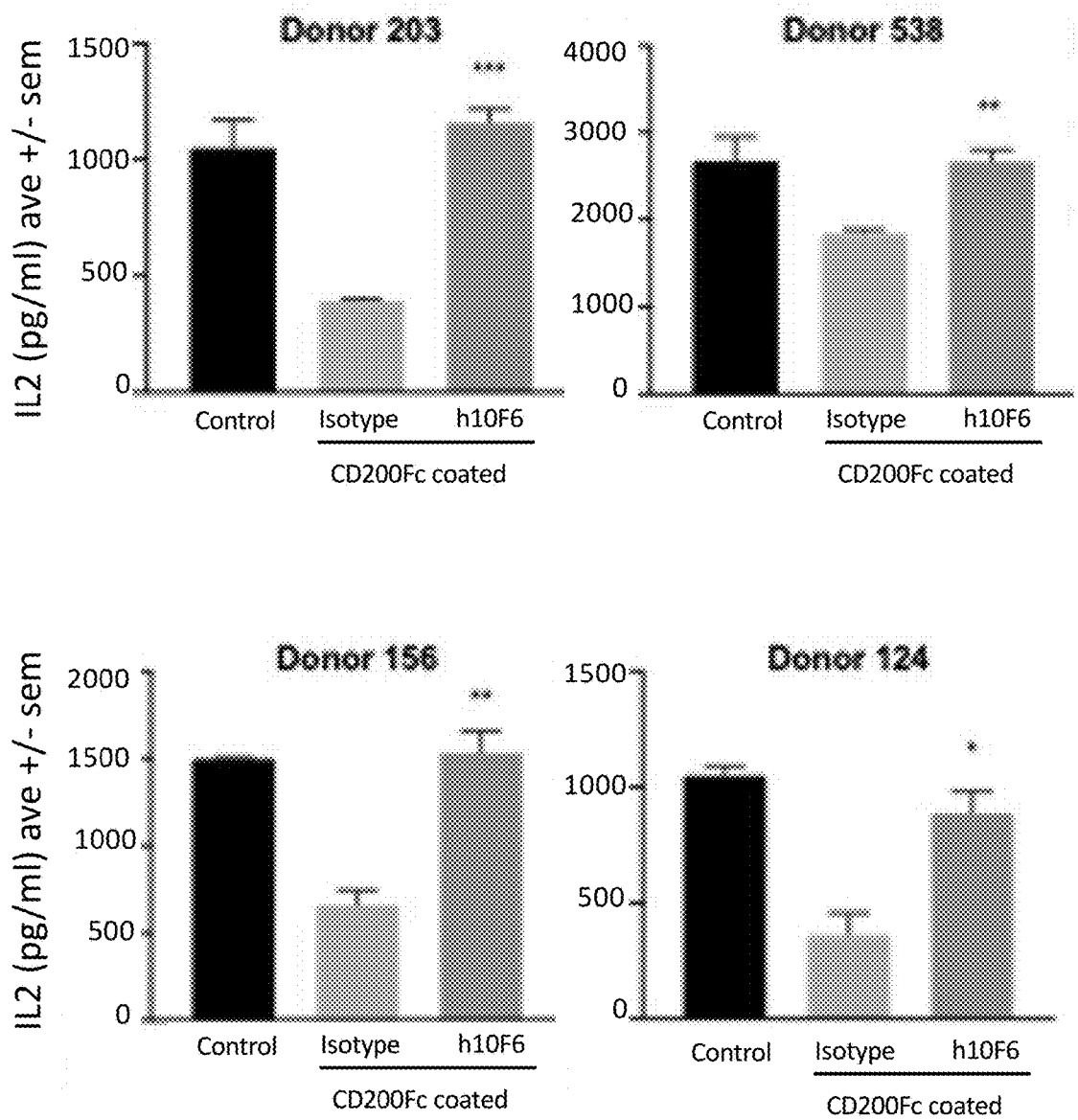
FIG. 24 depicts Human pan-T cells isolated from healthy PBMC donors and chronically stimulated with 2 µg/mL PHA and 4 ng/mL human IL-2 for 7 days in complete media. Cells were then harvested, rested of stimulants and primed with 40 ng/mL human IL-4 for 24 hours. Prior to plating cells, plates were coated overnight at 4° C. with 1 µg/mL anti-CD3 clone OKT3 and 15 µg/mL hCD200-Fc or isotype matched Fc control, referred to as Control Coat diluted in PBS. Cells were harvested, washed and plated with 50 nM antibodies for 24 hours. Cell supernatant was harvested and IL-2 secretion was measured by ELISA. In panel A, the average of IL-2 secretion levels from biological triplicates and SEM are graphed for each donor. An unpaired t-test was performed to determine significant h10F6 treatment effects compared to isotype control (*, $p<0.05$; , $p<0.01$; *, $p<0.001$). In panel B, a dose-response curve for h10F6 rescue of IFNγ secretion illustrates biological triplicates from one donor.
Figure 24B:
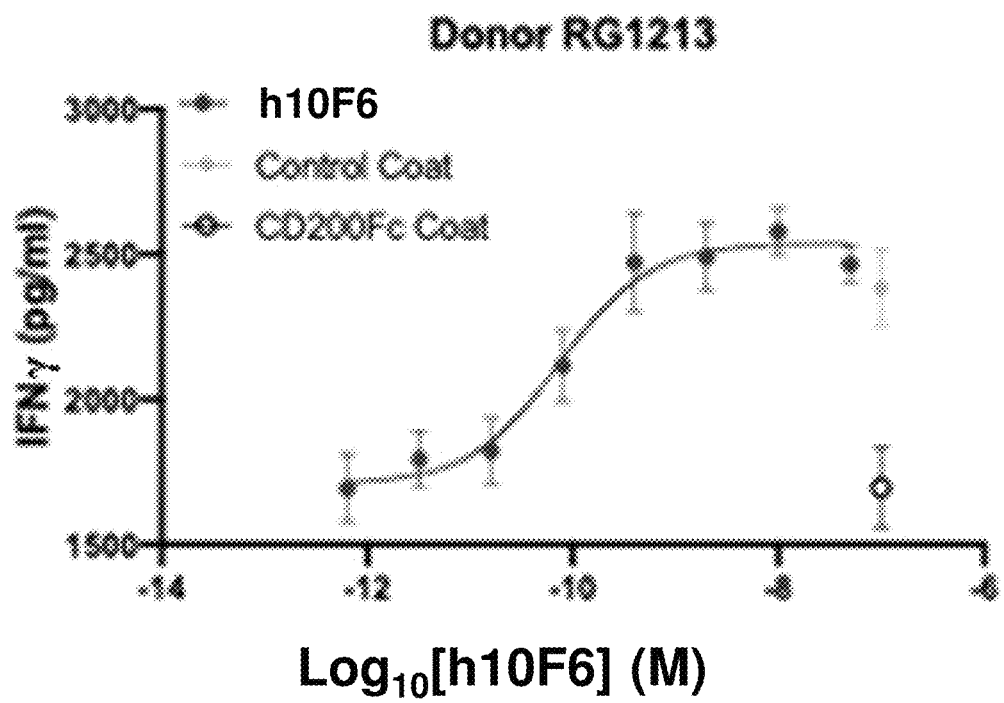

The potential of h10F6 to rescue T cell function was also evaluated in a pan-T cell assay in the presence of plate-bound CD200-Fc (FIG. 24, panel A). Human pan-T cells isolated from healthy PBMC donors were chronically stimulated with phytohemagglutinin and IL-2 for 7 days in complete media. Cells were then harvested, rested of stimulants and primed with IL-4 for 24 hours. This pre-treatment increased CD200R1 expression on pan-T cells, rendering them more sensitive to ligand (CD200). Treatment of pan-T cells with 50 nM h10F6 showed a functional rescue of IL-2 secretion in the presence of plate-bound CD200-Fc. h10F6 also rescued IFNγ production in a dose-dependent manner (EC50 of 0.07 nM, as illustrated in FIG. 24, panel B). Thus, h10F6 also directly modulates T cell function independent of myeloid cells.

Example 16: Anti-CD200R1 Antibodies Enhance PBMC-Mediated Tumor Cell Killing in Real-Time in a Dose-Dependent Manner Target tumor cells (COV644 cells that express endogenous CD200), were engineered to express green fluorescent protein (GFP). GFP-labeled COV644 tumor cells were incubated with healthy donor PBMCs. A stimulant (SEB) was also added to the media to activate the immune cells. PBMC-mediated tumor cell killing was quantified by measuring the loss of fluorescent intensity in each well over time.

The immune-mediated tumor cell killing was confirmed by visual inspection to ensure that the loss of fluorescent signal coincided with tumor cell killing. Successful priming and activation were evident by the clustering of unlabeled immune cells. Immune cell killing was confirmed by GFP-labeled cell membrane disruption and shrinkage of the target tumor cell. h10F6 was tested in the real-time IncuCyte tumor growth assay with 3 different donors. In 15 of the 24 total studies conducted, h10F6 promoted anti-tumor killing activity as quantified by a decrease in GFP signal per well compared to isotype control. h10F6 accelerated SEB-primed PBMC-mediated tumor cell death in a dose-dependent manner (FIG. 25)

Figure 25A:
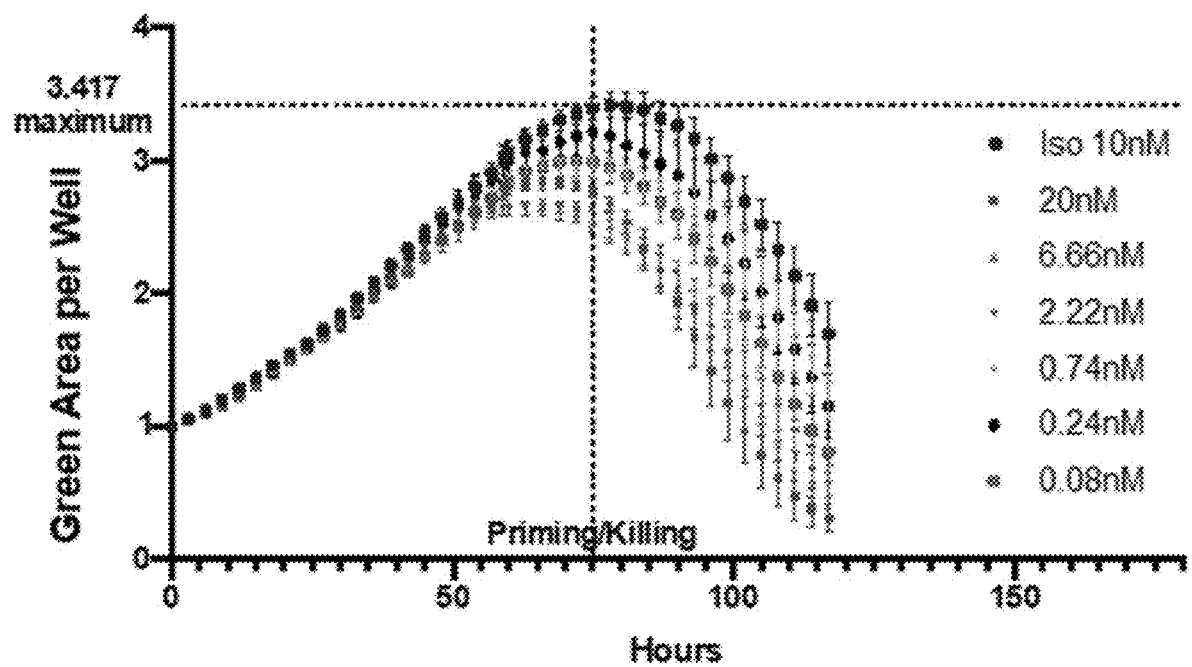
FIG. 25 depicts the acceleration of tumor cell killing by treatment of PBMCs primed with SEB with h10F6 (GFP+ COV644 tumor cells that endogenously express CD200) compared to isotype control treated PBMCs. Panel A depicts growth curves (measured by green area per well) for cells from 1 of 3 donors (RG1212) treated with the indicated concentration of h10F6 or isotype control. Panel B depicts the dose-dependent reduction of tumor cell GFP signal measured using the green area under the curve during the killing phase time frame from the same donor shown in panel A (RG1212); data are plotted as the mean±SEM of 4 to 6 individual measurements.
Figure 25B:
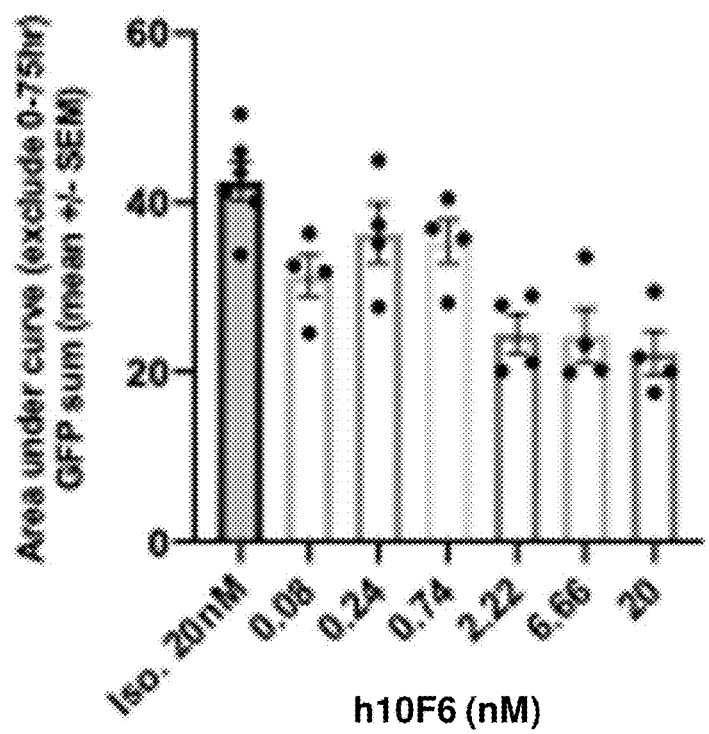
Figure 26A:
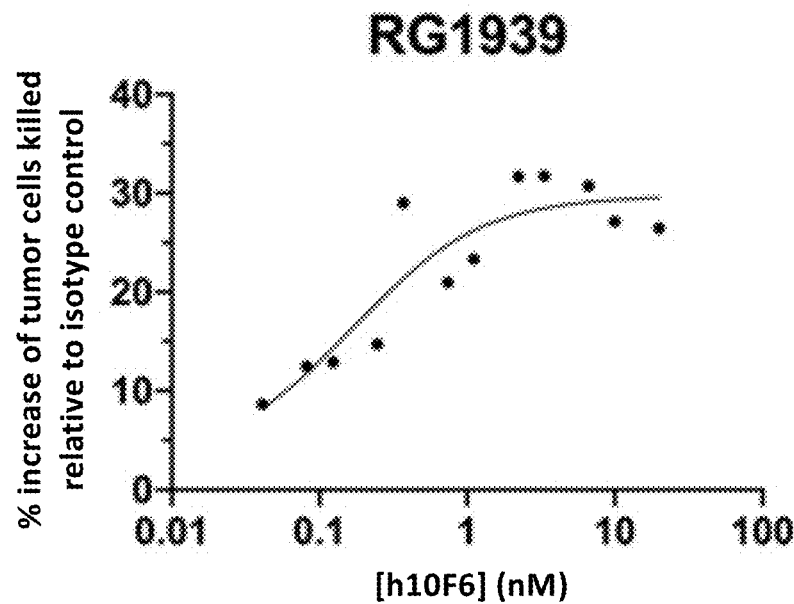
FIG. 26 depicts h10F6 enhanced PBMC-mediated tumor cell killing in a concentration-dependent manner in 3 unique donors (Panels A to C). The mean percent increase of tumor cells killed from n=4 replicates was plotted by h10F6 concentration and separated by donor (Panel D). Data from repeated experiments in RG1939 (N=2) and RG1307 (N=3) were aggregated and fit with a three-term nonlinear regression model. Individual and model fit max and min % tumor killing relative to isotype control were plotted by donor to evaluate the range and donor-to-donor variability of the h10F6 effect.
Figure 26B:
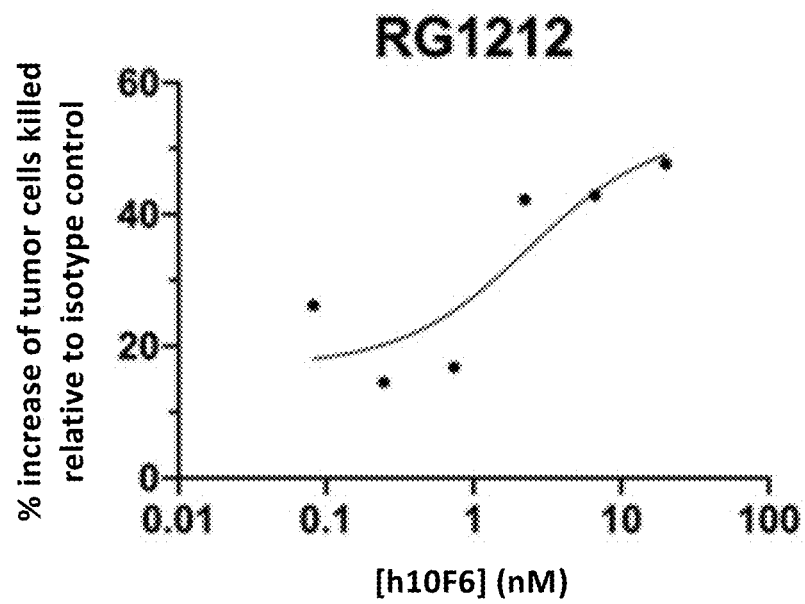
Figure 26C:
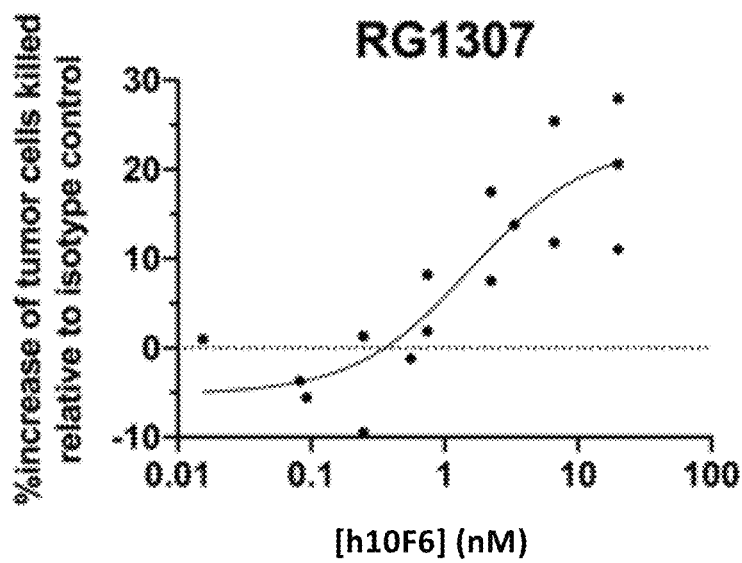
Figure 26D:
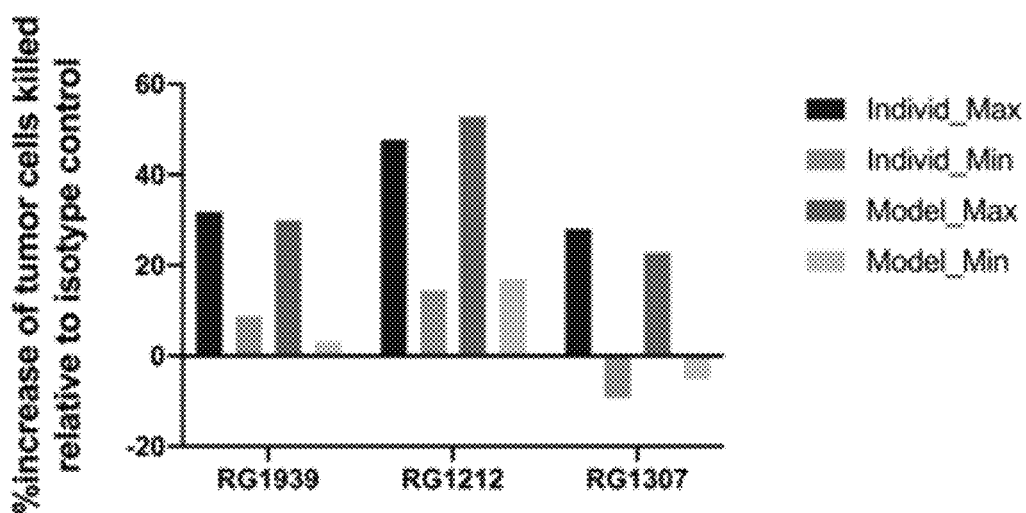

In FIG. 25, the area under the curve (AUC) of the GFP signal from the killing phase of the 15 IncuCyte PBMC-mediated tumor killing experiments that showed a h10F6 effect was fit to a nonlinear inhibitor-response regression model and the data were assessed for goodness of fit. Six experiments across 3 individual donors passed an acceptance threshold of R2≥0.40. Data from these 6 experiments was converted to % PBMC-mediated tumor killing relative to isotype control. Individual values of percent tumor killing were calculated (n=4 replicates per concentration) and converted to mean % tumor killing. The mean tumor killing percentage, which was reported as the percent increase of tumor cells killed relative to isotype control, was plotted by h10F6 concentration, and donor-specific data from repeat experiments was aggregated to report an EC50 for h10F6 in the assay by donor, as illustrated in FIG. 26.

The values for PBMC-mediated tumor cell killing across 3 donors are reported in Table 16. h10F6 increased PBMC-mediated tumor cell killing in a concentration-dependent manner, resulting in a mean EC50 of 1.37 nM (or 0.20 pg/mL, range: 0.17 to 2.38 nM). Relative to isotype control, h10F6 increased PBMC-mediated tumor cell killing by up to 52.9% (individual) and had mean maximum effect of 35.2% across the 3 donors (0% is killing achieved by isotype control, and 100% is if tumor cells emit no GFP signal throughout the killing phase).

TABLE 16

Summary of Potency and Maximal Effect of h10F6 on PBMC-Mediated Tumor Cell Killing Relative to Isotype Control

|  | RG1939 N = 2 | RG1212 N = 1 | RG1307 N = 3 | Mean NA |
|---|---|---|---|---|
| EC50 (nM) | 0.17 | 2.38 | 1.56 | 1.37 |
| % Increased Killing, Max | 29.8 | 52.9 | 22.8 | 35.2 | h10F6 potently enhanced PBMC-mediated CD200+ cancer cell death in the presence of SEB-stimulated donor PBMC.

Example 17: Toxicology Studies Using h10F6.V1

The nonclinical safety evaluation of h10F6 includes an evaluation of the in vitro pharmacology data, tolerability data from the in vivo PK studies to assess potential off-target binding, in vitro cytokine release, and tissue cross-reactivity of h10F6, and a tolerability and GLP toxicology study of the surrogate antibody h10F6.V1.

The tolerability of h10F6.V1 and potential for off-target binding and toxicity was evaluated following a single-dose IV bolus administration of h10F6 in rats and cynomolgus monkeys. The potential for h10F6.V1 to induce cytokine release by peripheral human immune cells was also assessed.

A. Tolerability in Sprague-Dawley Rats h10F6.V1 was well tolerated in rats following a single IV bolus injection (1 to 2 mL/kg) up to a dose of 10 mg/kg (2/sex/group; 1 mg/kg and 10 mg/kg. Animals were observed for significant clinical signs, moribundity, and mortality at each dosing or sample collection time point. Body weight was recorded at the time of dosing and at day 7, 14, and 21. There was no early mortality or moribundity and no test article related changes in clinical signs or body weights. In conclusion, no overt toxicity was observed that would indicate for example off-target binding of h10F6.V1 in the rat following a single IV dose up to 10 mg/kg.

B. Tolerability in Cynomolgus Monkey h10F6.V1 was well tolerated in cynomolgus monkeys (2/sex/group at 2 mg/kg and 20 mg/kg) following a single IV bolus injection (2 mL/kg) up to a dose of 20 mg/kg. Animals were screened for general health by certified veterinary staff upon arrival at the study site. Only animals in good health with clinical pathology parameters consistent with colony specific reference data were placed on study. On the dosing day, animals were observed before and after each sample collection time point for the first 6 hours post-dose and again at each subsequent time point of sample collection. After dosing, animals were observed at least twice per day for significant clinical signs, mortality, and signs of pain and distress, and at least once per day for general health and appearance. Body weight was recorded at pre-dose, at the time of dosing, and at least weekly post-dose. Blood was collected at pre-dose, 24 hours post-dose, and 35 days post-dose to assess changes in hematology and serum chemistry. There was no early mortality or moribundity and no test article related changes in clinical signs, body weights, hematology or clinical chemistry. In conclusion, no overt toxicity was observed that would indicate off-target binding of h10F6 in the cynomolgus monkeys following a single IV dose up to 20 mg/kg.

C. Cytokine Release Assay

The potential for cytokine release by PBMC following exposure to h10F6 was evaluated and was found to have no effect. The response of whole blood and PBMC samples derived from 10 healthy human donors to treatment with h10F6.V1 was compared to an anti-CD3 antibody or SEB treatment (positive controls for the PBMC and whole blood assays, respectively), humanized anti-chicken lysozyme IgG1 kappa with the N297G Fc-domain mutation isotype control treatment (isotype negative control), as well as a no treatment control. Whole blood samples were treated in a soluble format, and PBMC were treated in a plate-bound, wet-coated format. Concentration-dependent-responses for h10F6.V1 were examined at 0.002, 0.02, 0.2, 2, and 20 pg/ml in both treatment formats. Cytokine release was evaluated at a single timepoint, 24 hours after treatment for the induction of IL-2, IL-6 TNFα, and IFNγ.

h10F6.V1 treatment did not induce any notable IL-2, TNFα, and IFNγ cytokine release under any tested concentrations or conditions. h10F6.V1 treatment did not induce any notable IL-6 release in the whole blood soluble format. All donors had low to moderate levels of IL-6 in the PBMC plate-bound, wet-coated format, following h10F6 treatment. The levels of IL-6 observed in samples treated with h10F6.V1 were equivalent to the isotype IgG1 negative control antibody treatment and were lower than the anti-CD3 positive control when used at the same concentration. No correlation was observed between the concentration of h10F6.V1 and the level of IL-6 measured. h10F6 does not show evidence for in vitro cytokine release of IL-2, IL-6, TNFα, or IFNγ above negative controls when tested in whole blood (e.g., soluble treatment format) or PBMC (e.g., plate-bound, wet-coated treatment format) from 10 healthy human donors.

Example 18: Pharmacology of an Example Surrogate Antibody

A. Production of Surrogate Antibody Nonclinical Test Material in Expi-HEK293 Cells h10F6 does not cross-react with CD200R1 expressed in tested nonclinical species, including mouse, rat, rabbit, dog, and nonhuman primates (rhesus, marmoset and cynomolgus monkey). Thus, a fully humanized surrogate antibody that binds to cynomolgus CD200R1, h10F6.V1, was developed to evaluate potential hazards associated with CD200R1 inhibition. h10F6.V1 is a variant of h10F6, and shares the same primary sequence, with the exception of 3 amino acids in the heavy chain complementarity-determining region (CDR) region and 1 amino acid in the light chain CDR region.

h10F6.V1 was produced in a Expi-HEK293 expression system using the same process as described for h10F6. The characteristics of h10F6.V1 is provided in Table 17 below.

TABLE 17

Characteristics of h10F6.V1 Material

| Molecule | HPLC (% Monomer) | Mass Spec Observed Mass (Da) | Biacore $K_D$ (nM) (binding to MfCD200R1) | Endotoxin (EU/mg) |
|---|---|---|---|---|
| h10F6.V1 produced in Expi-HEK293 cells | >99 | 145,066 | 2.63 | 0.03 |

B. Binding of the Surrogate Antibody to PBMCs Isolated from Cynomolgus Monkey

To confirm that h10F6.V1 binds to endogenous CD200R1 expressed on cynomolgus monkey cells, the binding of h10F6.V1 to peripheral immune cell subsets was determined by flow cytometry using PBMC from cynomolgus monkeys.

Figure 27:
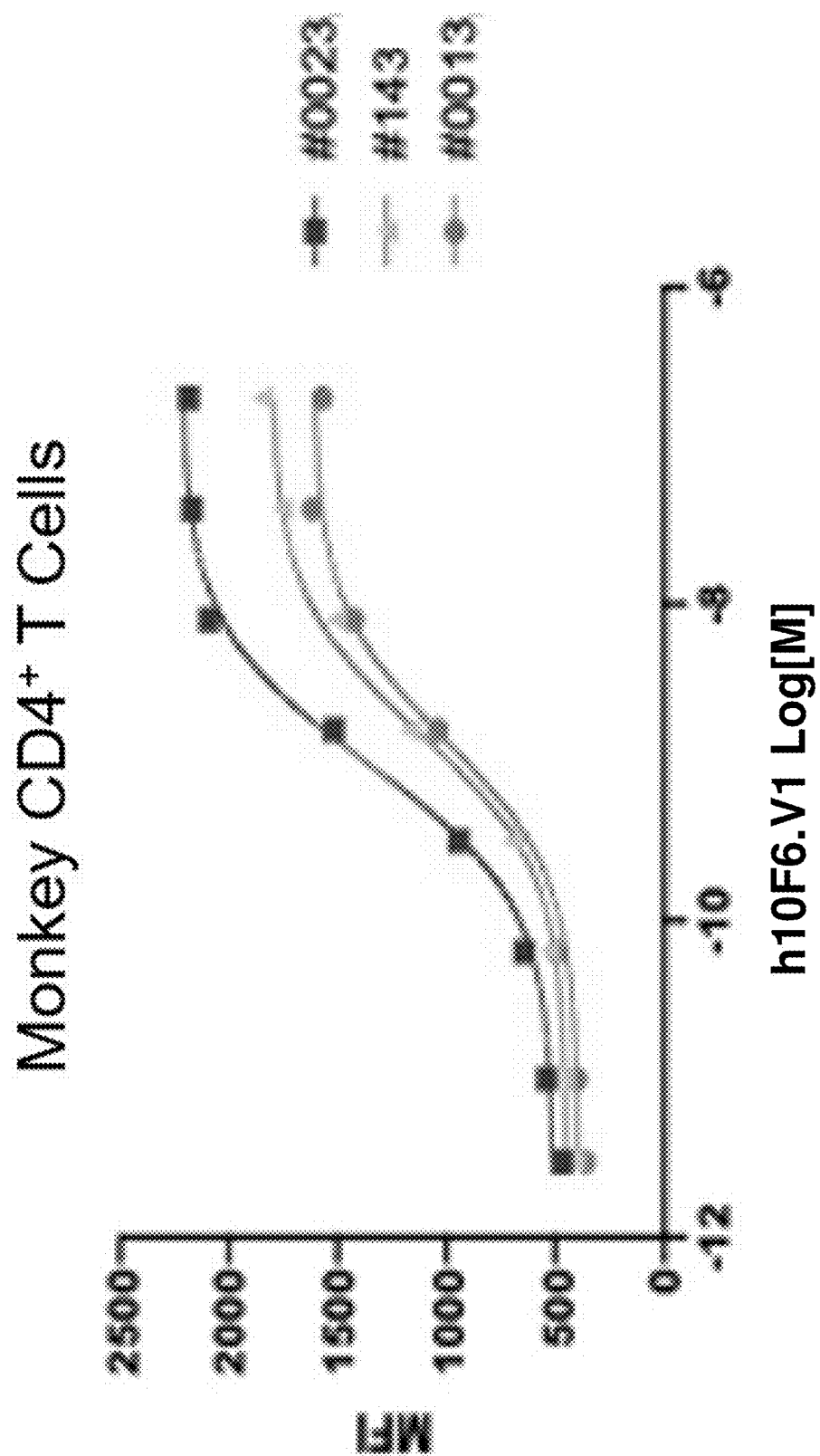
FIG. 27 depicts monkey PBMC incubated with serial dilutions of biotinylated h10F6 and stained with streptavidin-PE, Live/Dead stain, and a cocktail of fluorochrome-conjugated commercial antibodies, including anti-CD3 clone SK7, anti-CD4 clone M-T466, anti-CD8 clone BW135/80, anti-CD20 clone 2H7, anti-CD11b clone M1/70, anti-CD14 clone TUK4 and anti-HLA-DR clone REA-805 Immune cell subtypes were defined as T helper cells (CD3+ CD4+). EC50 values for binding to monkey CD4+ T cells were determined using a 3-parameter, log 10[h10F6] vs response, nonlinear curve fit.

In PBMC isolated from 3 monkeys, h10F6.V1 displayed expected binding to CD4+ T cells (FIG. 27). The binding to T cells was evaluated by testing serial dilutions of h10F6.V1. Dose-dependent binding was observed, with EC50 values ranging from 0.34 to 1.54 nM.

C. Blocking of the MfCD200/MfCD200R1 Interaction by the Surrogate Antibody

Figure 28:
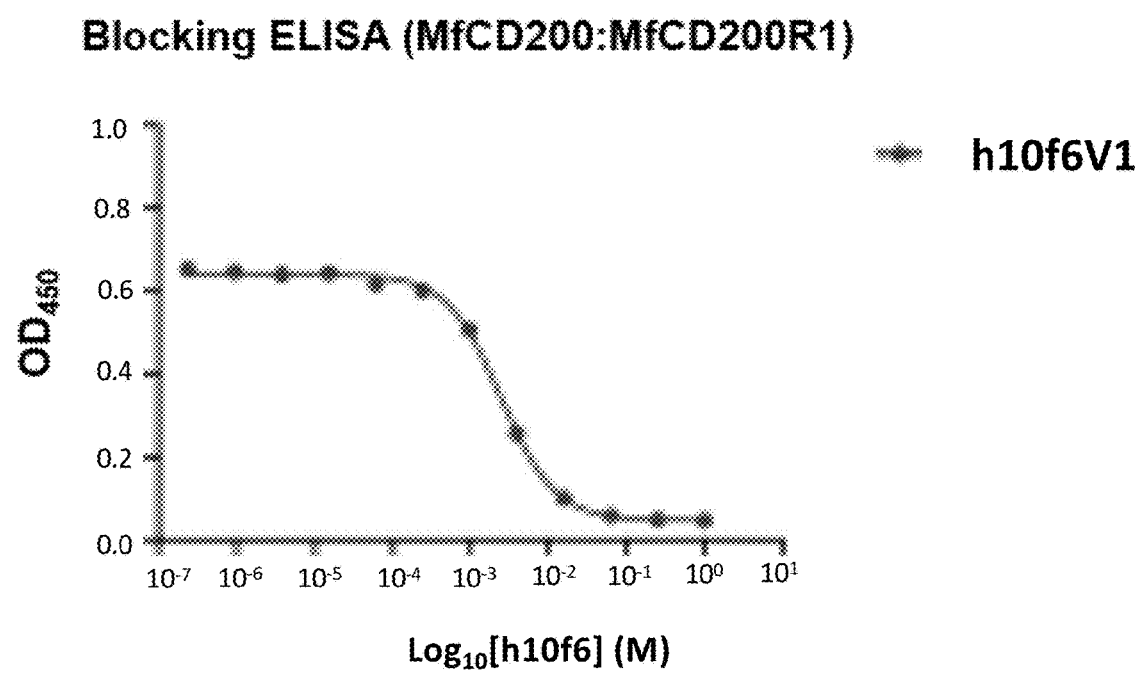
FIG. 28 depicts the capacity of h10F6 to block binding biotinylated MfCD200R1 to immobilized, Fc-tagged MfCD200, as evaluated using ELISA. Four-fold serial dilutions of h10F6 ranging from 1 µM to 2.38×10-7 µM were pre-incubated with hCD200R1 (0.04 ug/ml) or MfCD200R1 (0.12 ug/ml) prior to adding to plate-immobilized MfCD200. Binding was evaluated by incubating with HRP-streptavidin and colorimetric substrate, followed by monitoring the OD450 in each well.

The capacity of the h10F6.V1 to block binding of MfCD200R1 to immobilized MfCD200 was performed using an ELISA. The surrogate antibody blocked the MfCD200R1:MfCD200 interaction with a blocking IC50 value of 2.45 nM, as illustrated in FIG. 28.

Figure 29:
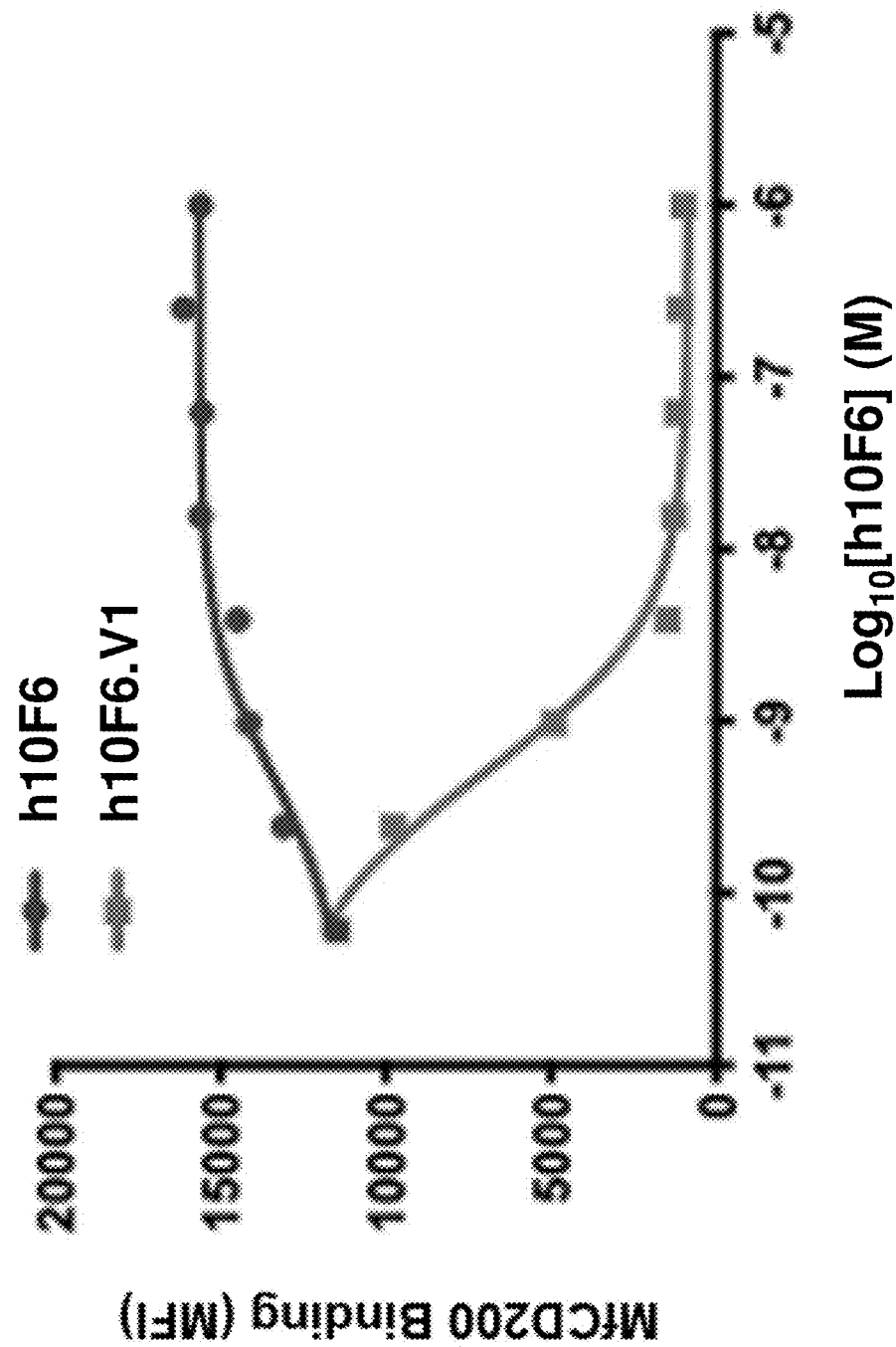
FIG. 29 depicts the human monocytic cell line, K562, engineered to stably express MfCD200R1. Binding of recombinant MfCD200 fused with a non-glycosylated hIgG1 Fc tag to the K562 cells expressing MfCD200R1 was confirmed by FACS. h10F6.V1 inhibited MfCD200-Fc binding to K562 cells expressing MfCD200R1 in a dose-dependent manner.

The human monocytic cell line, K562, was engineered to stably express MfCD200R1. The MfCD200R1 sequence was unambiguously determined by bioinformatics analysis and experimental sequence confirmation using RNA extracted from monkey esophagus from 2 donors. Binding of MfCD200 fused with a non-glycosylated hIgG1 Fc tag to the K562 cells expressing MfCD200R1 was confirmed by FACS. This binding was potently blocked by h10F6.V1 (IC50=0.50 nM), whereas the non-MfCD200R1 binder h10F6 did not block this interaction FIG. 29).

Figure 30:
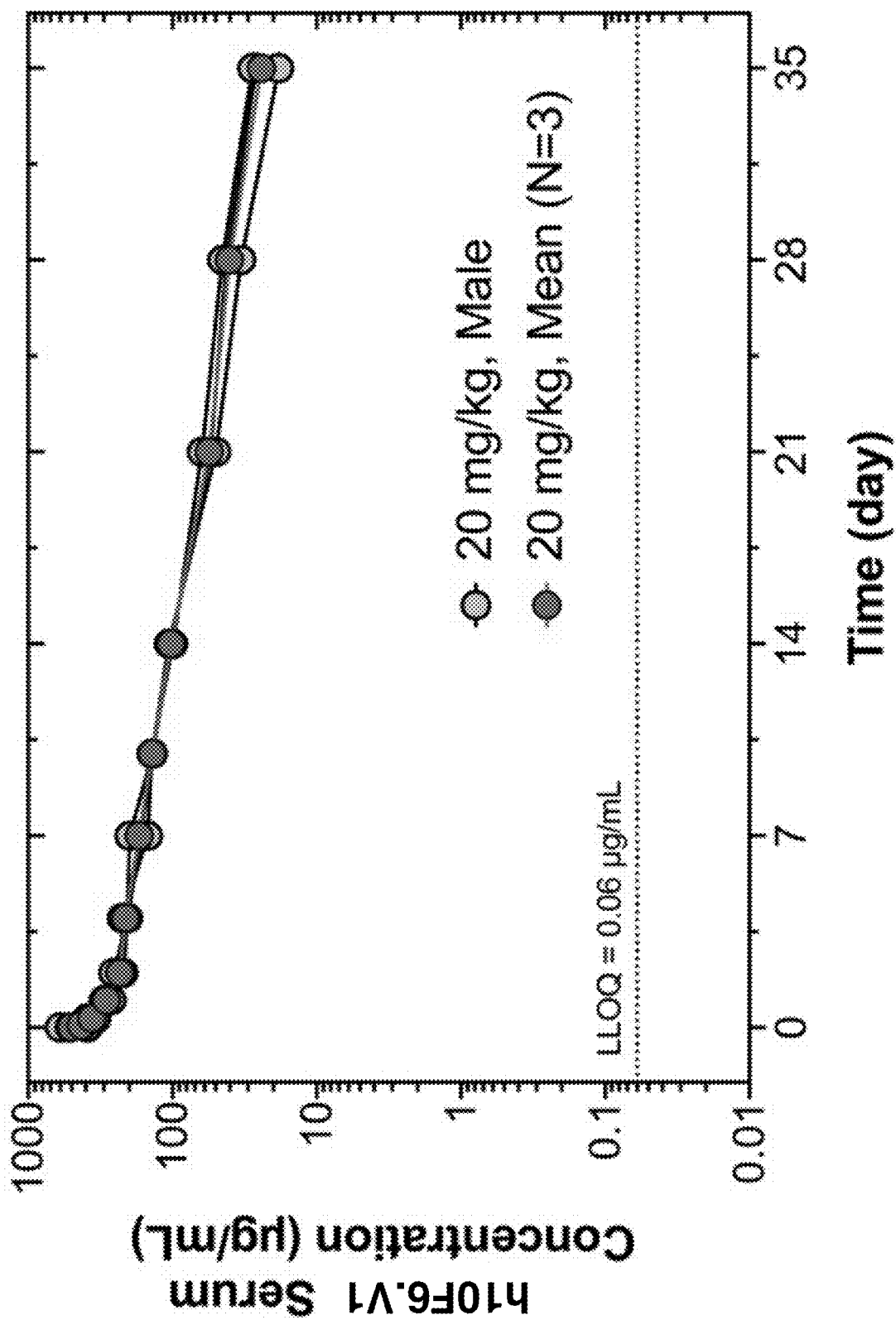
FIG. 30 depicts the mean and individual h10F6.V1 serum concentration plotted in a semi-log plot. The lower limit of quantitation (LLOQ) of the assay was 0.06 µg/mL.

D. Single-Dose Pharmacokinetics of a Surrogate Antibody in Cynomolgus Monkeys h10F6.V1 is a surrogate of h10F6 with high binding affinity to CD200R1 from cynomolgus monkey. As h10F6 does not bind CD200R1 from cynomolgus monkey, the primary toxicology species, a single dose PK study of h10F6.V1 was performed to assess its PK properties and tolerability in cynomolgus monkeys, and determine its suitability for use in the GLP hazard identification study. The concentration-time PK profiles of h10F6.V1 in monkeys are illustrated in FIG. 30.

Mean PK parameters of h10F6.V1 in monkeys are summarized in Table 18 below. Following a single IV bolus injection of 20 mg/kg to cynomolgus monkeys, h10F6.V1 serum concentrations declined in a biphasic manner. The elimination of h10F6.V1 was linear with time, suggesting no evidence of ADA or other nonlinear elimination behavior (e.g., target-mediated drug disposition; TMDD) for up to 35 days. The mean terminal half-life was 10.2 days, and the mean values for clearance and estimated volume of distribution at steady-state were consistent with values that can be typical for humanized IgG with linear PK in monkeys

TABLE 18

PK Parameters of Surrogate Antibody Following Single-dose IV Administration to Cynomolgus Monkeys

| | Mean PK Parameters (N = 3M) | | | | |
|---|---|---|---|---|---|
| Dose | Cmax (ug/mL) | AUClast (day*ug/mL) | T1/2 (day) | CL (mL/kg/day) | VSS (mL/kg) |
| 20 mg/kg | 515 | 3670 | 10.2 | 4.97 | 69.9 |
| CV % | 17.9 | 2.7 | 14.8 | 5.4 | 6.8 | h10F6.V1 had linear PK in monkeys, suggesting that linear, non-saturable, non-specific clearance mechanisms are the dominant contributors to h10F6.V1 elimination in monkeys at the 20 mg/kg dose studied. h10F6.V1 was well tolerated through Day 35 based on clinical observations and an assessment of serum chemistry and hematology parameters (See Section 14.2.3.1). Thus, the PK and tolerability of h10F6.V1 in monkeys supports its suitability as a surrogate for h10F6 and its use in the GLP toxicology study.

Example 19: Toxicology Studies Using Surrogate Antibody

Evaluation of h10F6 binding to CD200R1 expressed in other species revealed that it does not cross-react with CD200R1 expressed in species used to evaluate nonclinical safety. Consequently, evaluation of potential toxicities of h10F6 in a pharmacologically relevant animal species was not possible and a surrogate antibody that binds to CD200R1 from cynomolgus monkey, h10F6.V1, was developed to evaluate nonclinical safety for the purposes of hazard identification.

A. Tolerability in Single-Dose Studies in Cynomolgus Monkey h10F6.V1 was well tolerated in cynomolgus monkeys (3 males) following a single IV bolus injection (2 mL/kg, 20 mg/kg). Animals were screened for general health by certified veterinary staff upon arrival at the study site. Only animals in good health with clinical pathology parameters consistent with colony-specific reference data were placed on study. On the dosing day, animals were observed before and after each sample collection time point for the first 6 hours post-dose and again at each subsequent time point of sample collection. After dosing, animals were observed at least twice per day for significant clinical signs, mortality, and signs of pain and distress, and at least once per day for general health and appearance. Body weight was recorded at pre-dose, at the time of dosing, and at least weekly post-dose. Blood was collected at pre-dose, 24 hours post-dose, and 35 days post-dose to assess changes in hematology and serum chemistry. There was no early mortality or moribundity and no test article related changes in clinical signs, body weights, hematology or clinical chemistry. No overt toxicity was observed that can indicate that the inhibition of the CD200/CD200R1 interaction in the cynomolgus monkeys following a single IV dose at 20 mg/kg is hazardous.

B. Toxicology and Safety Pharmacology in a Repeat-Dose Study in Cynomolgus Monkey A repeat-dose GLP study can determine the potential toxicity of h10F6.V1 when administered once a week by slow bolus IV injection, for example for 4-weeks, to male and female cynomolgus monkeys for the purposes of hazard identification of toxicity potentially associated with the disruption of the CD200/CD200R1 interaction. This study can also evaluate the potential reversibility of any findings following a 6-week recovery period. In addition, the TK characteristics and exploratory biomarkers can be evaluated. Doses can be selected based on a non-GLP single-dose PD study, such as that described above. Based on RO predictions, the 100 mg/kg/dose can provide an extended period of target saturation. The 10 mg/kg/dose level can produce no observable indications and can provide about 99% RO over the once weekly dosing interval. A study design is provided in Table 19 below.

TABLE 19

Study design for 4-week GLP Toxicology Study of Surrogate Antibody by Intravenous Infusion to Cynomolgus Monkeys

| Group # | Treatment | Dosage (mg/kg/dose) | Concentration (mg/mL) | Dose Volume (mL/kg) | # of Male Animals | # of Female Animals |
|---|---|---|---|---|---|---|
| 1 | Vehicle | 0 | 0 | 2 | 5 | 5 |
| 2 | Surrogate Antibody | 10 | 5 | 2 | 3 | 3 |
| 3 | Surrogate Antibody | 100 | 50 | 2 | 5 | 5 |

Test article related effects on standard toxicological endpoints including clinical observations, body weights, body weight changes, food consumption, ophthalmology, hematology, clinical chemistry, coagulation, urinalysis, organ weights, macroscopic and microscopic histopathology can be evaluated. In addition, effects on safety pharmacology parameters (neurobehavior, electrocardiography, heart rate, blood pressure, or respiratory rate) can be monitored. In addition to the standard parameters, effects on peripheral blood immunophenotyping parameters (CD3, FoxP3, CD25, CD159a, CD20, CD4, Ki67, and CD8) and cytokine (IL-2, IL-6, IL-8, MCP-1, IFNγ, and TNFα) levels can be monitored, for example using validated assays. Samples for TK, and exploratory biomarker analysis are can be collected for evaluation. Local tolerance can also be evaluated.

The following parameters and end points were evaluated in this study: mortality, clinical observations, body weights, qualitative food consumption, ophthalmology, qualitative electrocardiology, body temperature, neurologicals exams, respirations rates, clinical pathology parameters (hematology, coagulation, clinical chemistry, and urinalysis), bioanalysis and toxicokinetic parameters, anti-drug antibody parameters, immunophenotyping, receptor occupancy analysis, cytokine analysis, exploratory plasma processing, exploratory whole blood for RNA, organ weights, and macroscopic and microscopic examinations.

Administration of h10F6.V1 at 10 or 100 mg/kg to cynomolgus monkeys by intravenous bolus injection once weekly for 4 weeks was not associated with changes in clinical observations, food consumption, body weights, ophthalmology exams, electrocardiology, body temperature, neurological exams, respiration rates, hematology, coagulation, clinical chemistry, urinalysis parameters, or bone marrow cytology.

For immunophenotyping, h10F6.V1-related changes were limited to increases in Ki67 expression on T-lymphocytes, CD25+T-lymphocytes, and NK cells that were observed on Day 15 predose and Day 29 in the 10 and 100 mg/kg groups. Administration of h10F6.V1 resulted in reductions in % Free Receptor and increases in percent of receptor occupancy (% RO) on neutrophils at 10 mg/kg on Day 1: 48 hours postdose and Day 8 predose; and at 100 mg/kg on Day 1: 48 hours postdose through the end of recovery period on Day 63. There were also increases in % Total Receptor on T-helper lymphocytes for both dose groups on Day 22: 48 hours postdose and increased % RO on T-lymphocytes for both dose groups on Day 1: 48 hours postdose through Day 29. These increases returned to near baseline by Day 50. There were no h10F6.V1-related changes in any other tested cell populations or activation markers for both dose groups.

Cytokine evaluation showed no changes in plasma IL-2, IL-6, IL-8, MCP-1, IFN-γ, and TNF-α concentrations compared to prestudy and control ranges that could be attributed to h10F6.V1 administration at any time points for all dosed animals.

For microscopic evaluation, at terminal euthanasia, a higher incidence and/or severity of mononuclear cell infiltration was observed in the brain (mild) and eye (mild) of one female administered 100 mg/kg, adrenal gland (minimal) of animals administered ≥10 mg/kg, and pituitary gland (minimal) of males administered 100 mg/kg. At recovery euthanasia, a higher incidence and/or severity of mononuclear cell infiltration was observed in the brain (mild) of one male administered 100 mg/kg, adrenal gland (minimal) of one female administered 100 mg/kg, and pituitary gland (minimal) of males administered 100 mg/kg. Mononuclear cell infiltrates can be observed as background findings or in association with the administration of biologics. The higher incidence and/or severity observed in dosed animals, inconsistency in incidence across sexes, and the low magnitude of severity difference suggests that these infiltrates most likely represent a nonspecific class effect associated with the administration of biologics rather than a direct h10F6.V1-related effect; however, a contributory and/or direct h10F6.V1-related effect cannot be completely ruled out. At terminal and recovery euthanasia, no h10F6.V1-related organ weight differences or macroscopic findings were observed.

In conclusion, administration of h10F6.V1 by intravenous (slow bolus) injection once weekly on Days 1, 8, 15, and 22 was well tolerated in cynomolgus monkeys at levels of ≤100 mg/kg. Histopathologic changes consisted of mononuclear cell infiltrates in the brain, eye (terminal euthanasia only), and pituitary gland at 100 mg/kg, and adrenal gland at ≥10 mg/kg. These changes may have been related to immune complexes from anti-drug antibodies and were considered non-adverse. Based on these results, the no-observed-adverse-effect level was considered to be 100 mg/kg.

Example 20: Comparative Pharmacology Summary for h10F6 and the Surrogate Antibody Preliminary data generated using material produced in Expi-293HEK cells indicates that h10F6.V1 binds to recombinant MfCD200R1 with a KD of 2.63 nM, demonstrating that its binding affinity for MfCD200R1 can be comparable (within ~20-fold) to the binding affinity of h10F6 for hCD200R1, as shown in Table 20 below. Consistent with the results of recombinant protein binding studies, the tested surrogate antibody can bind to primary cynomolgus monkey CD4+ T cells that express CD200R1 with comparable affinity (within ~4-fold; Table 20) to h10F6 binding to human T cells. Furthermore, results of in vitro blocking studies demonstrated that h10F6.V1 can block the interaction between MfCD200R1 and MfCD200 with comparable potency to h10F6 for human hCD200R1 and hCD200 in both an ELISA and in a MfCD200R1 over-expressing cell-based system, within ~6 to 7 fold; Table 20).

TABLE 20

Comparative Pharmacology for h10F6 and a Surrogate Antibody

| | SPR Binding Affinity ($K_D$; nM) | Cell-Surface Binding (EC50; nM) | Blocking ELISA (IC50; nM) | Cell-Surface Blocking (IC50; nM) |
| --- | --- | --- | --- | --- |
| h10F6-hCD200R1:hCD200 | 0.12 | 0.40 | 0.36 | 0.08 |
| Surrogate Antibody-hCD200R1:hCD200 | 2.63 | 1.30 | 2.45 | 0.50 |

Taken together, these results indicate that the surrogate antibody h10F6.V1 can inhibit binding of MfCD200R1:MfCD200 in a comparable manner to h10F6's inhibition of binding of hCD200R1:hCD200.

Comparative Pharmacokinetics for h10F6 and a h10F6.V1

The PK properties of h10F6.V1 and h10F6 were similar when evaluated in cynomolgus monkey at a single dose of 20 mg/kg administered by IV bolus injection. The mean terminal half-life of h10F6.V1 and h10F6 was 10.2 days and 11.5 to 13.3 days, respectively, and their exposures were comparable (within 1.5-fold as measured by Cmax and AUClast). The PK of h10F6.V1 produced in CHO-K1 cells will be evaluated in the GLP hazard identification study. h10F6 is a hCD200R1-specific, non-glycosylated, and neutral charged IgG antibody and thus is expected to have similar PK properties when h10F6 is produced in CHO-K1 cells or in Expi-HEK293 cells.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

BIBLIOGRAPHY

1. Mihrshahi et al., (2009) "Essential Roles for Dok2 and RasGAP in CD200 Receptor-Mediated Regulation of Human Myeloid Cells." J. Immunology. 183:4879-4886.
2. Mihrshahi et al., (2010) "Downstream of Tyrosine Kinase 1 and 2 Plays Opposing Roles in CD200 Receptor Signaling." J. Immunology. 185:7216-7222
3. Wang et al., (2019) "Siglec-15 as an immune suppressor and potential target for normalization cancer immunotherapy." Nat. Med. Vol 25:656-666.
4. Woodle, E. Steve et al., (1999), "Phase 1 Trial of a Humanized, Fc Receptor Nonbinding OKT3 Antibody, huOKT3Yγ1 (Ala-Ala) in the Treatment of Acute Renal Allograft Rejection", Transplantation, 68(5): 608-616 (1999)).
5. Linsley P. S., et al., "Copy Number Loss of the Interferon Gene Cluster in Melanomas Is Linked to Reduced T Cell Infiltrate and Poor Patient Prognosis", PLoS One, 9(10): e109760 (2014).

---

What is claimed is:

1. An anti-CD200R1 antibody comprising (i) a first light chain hypervariable region (HVR-L1), a second light chain hypervariable region (HVR-L2), and a third light chain hypervariable region (HVR-L3); and (ii) a first heavy chain hypervariable region (HVR-H1), a second heavy chain hypervariable region (HVR-H2), and a third heavy chain hypervariable region (HVR-H3), comprising:

(a) HVR-L1 of SEQ ID NO: 11, HVR-L2 of SEQ ID NO: 12, and HVR-L3 of SEQ ID NO: 13; and HVR-H1 of SEQ ID NO: 15, HVR-H2 of SEQ ID NO: 16, and HVR-H3 of SEQ ID NO: 17;

(b) HVR-L1 of SEQ ID NO: 19, HVR-L2 of SEQ ID NO: 20, and HVR-L3 of SEQ ID NO: 21; and HVR-H1 of SEQ ID NO: 23, HVR-H2 of SEQ ID NO: 24, and HVR-H3 of SEQ ID NO: 25;

(c) HVR-L1 of SEQ ID NO: 27, HVR-L2 of SEQ ID NO: 28, and HVR-L3 of SEQ ID NO: 29; and HVR-H1 of SEQ ID NO: 31, HVR-H2 of SEQ ID NO: 32, and HVR-H3 of SEQ ID NO: 33;

(d) HVR-L1 of SEQ ID NO: 35, HVR-L2 of SEQ ID NO: 36, and HVR-L3 of SEQ ID NO: 37; and HVR-H1 of SEQ ID NO: 39, HVR-H2 of SEQ ID NO: 40, and HVR-H3 of SEQ ID NO: 41;

(e) HVR-L1 of SEQ ID NO: 43, HVR-L2 of SEQ ID NO: 44, and HVR-L3 of SEQ ID NO: 45; and HVR-H1 of SEQ ID NO: 47, HVR-H2 of SEQ ID NO: 48, and HVR-H3 of SEQ ID NO: 49;

(f) HVR-L1 of SEQ ID NO: 51, HVR-L2 of SEQ ID NO: 52, and HVR-L3 of SEQ ID NO: 53; and HVR-H1 of SEQ ID NO: 55, HVR-H2 of SEQ ID NO: 56, and HVR-H3 of SEQ ID NO: 57;

(g) HVR-L1 of SEQ ID NO: 59, HVR-L2 of SEQ ID NO: 60, and HVR-L3 of SEQ ID NO: 61; and HVR-H1 of SEQ ID NO: 63, HVR-H2 of SEQ ID NO: 64, and HVR-H3 of SEQ ID NO: 65;
(h) HVR-L1 of SEQ ID NO: 77, HVR-L2 of SEQ ID NO: 78, and HVR-L3 of SEQ ID NO: 79; and HVR-H1 of SEQ ID NO: 81, HVR-H2 of SEQ ID NO: 82, and HVR-H3 of SEQ ID NO: 83;
(i) HVR-L1 of SEQ ID NO: 11, HVR-L2 of SEQ ID NO: 12, and HVR-L3 of SEQ ID NO: 13; and HVR-H1 of SEQ ID NO: 85, HVR-H2 of SEQ ID NO: 86, and HVR-H3 of SEQ ID NO: 87;
(j) HVR-L1 of SEQ ID NO: 11, HVR-L2 of SEQ ID NO: 12, and HVR-L3 of SEQ ID NO: 13; and HVR-H1 of SEQ ID NO: 81, HVR-H2 of SEQ ID NO: 82, and HVR-H3 of SEQ ID NO: 83; or
(k) HVR-L1 of SEQ ID NO: 77, HVR-L2 of SEQ ID NO: 78, and HVR-L3 of SEQ ID NO: 79; and HVR-H1 of SEQ ID NO: 85, HVR-H2 of SEQ ID NO: 86, and HVR-H3 of SEQ ID NO: 87.

2. The antibody of claim 1, wherein the antibody comprises a light chain variable domain ($V_L$) amino acid sequence having at least 90% identity to a sequence selected from SEQ ID NO: 10, 18, 26, 34, 42, 50, 58, 66, or 76.

3. The antibody of claim 1, wherein
(a) the antibody comprises a light chain variable domain (VL) amino acid sequence having at least 90% identity to SEQ ID NO: 10, and a heavy chain variable domain (VH) amino acid sequence having at least 90% identity to SEQ ID NO: 14;
(b) the antibody comprises a light chain variable domain (VL) amino acid sequence having at least 90% identity to SEQ ID NO: 18, and a heavy chain variable domain (VH) amino acid sequence having at least 90% identity to SEQ ID NO: 22;
(c) the antibody comprises a light chain variable domain (VL) amino acid sequence having at least 90% identity to SEQ ID NO: 26, and a heavy chain variable domain (VH) amino acid sequence having at least 90% identity to SEQ ID NO: 30;
(d) the antibody comprises a light chain variable domain (VL) amino acid sequence having at least 90% identity to SEQ ID NO: 34, and a heavy chain variable domain (VH) amino acid sequence having at least 90% identity to SEQ ID NO: 38;
(e) the antibody comprises a light chain variable domain (VL) amino acid sequence having at least 90% identity to SEQ ID NO: 42, and a heavy chain variable domain (VH) amino acid sequence having at least 90% identity to SEQ ID NO: 46;
(f) the antibody comprises a light chain variable domain (VL) amino acid sequence having at least 90% identity to SEQ ID NO: 50, and a heavy chain variable domain (VH) amino acid sequence having at least 90% identity to SEQ ID NO: 54;
(g) the antibody comprises a light chain variable domain (VL) amino acid sequence having at least 90% identity to SEQ ID NO: 58, and a heavy chain variable domain (VH) amino acid sequence having at least 90% identity to SEQ ID NO: 62;
(h) the antibody comprises a light chain variable domain (VL) amino acid sequence having at least 90% identity to SEQ ID NO: 66, and a heavy chain variable domain (VH) amino acid sequence having at least 90% identity to SEQ ID NO: 67;
(i) the antibody comprises a light chain variable domain (VL) amino acid sequence having at least 90% identity to SEQ ID NO: 76, and a heavy chain variable domain (VH) amino acid sequence having at least 90% identity to SEQ ID NO: 80;
(j) the antibody comprises a light chain variable domain (VL) amino acid sequence having at least 90% identity to SEQ ID NO: 66, and a heavy chain variable domain (VH) amino acid sequence having at least 90% identity to SEQ ID NO: 84;
(k) the antibody comprises a light chain variable domain (VL) amino acid sequence having at least 90% identity to SEQ ID NO: 66, and a heavy chain variable domain (VH) amino acid sequence having at least 90% identity to SEQ ID NO: 80; or
(l) the antibody comprises a light chain variable domain (VL) amino acid sequence having at least 90% identity to SEQ ID NO: 76, and a heavy chain variable domain (VH) amino acid sequence having at least 90% identity to SEQ ID NO: 84.

4. The antibody of claim 1, wherein the antibody comprises a light chain (LC) amino acid sequence having at least 90% identity to a sequence selected from SEQ ID NO: 68, 71, and 74.

5. The antibody of claim 1, wherein the antibody comprises:
(a) a light chain (LC) amino acid sequence having at least 90% identity to SEQ ID NO: 68; and a heavy chain (HC) amino acid sequence having at least 90% identity to SEQ ID NO: 69;
(b) a light chain (LC) amino acid sequence having at least 90% identity to SEQ ID NO: 68; and a heavy chain (HC) amino acid sequence having at least 90% identity to SEQ ID NO: 70;
(c) a light chain (LC) amino acid sequence having at least 90% identity to SEQ ID NO: 71; and a heavy chain (HC) amino acid sequence having at least 90% identity to SEQ ID NO: 88;
(d) a light chain (LC) amino acid sequence having at least 90% identity to SEQ ID NO: 71; and a heavy chain (HC) amino acid sequence having at least 90% identity to SEQ ID NO: 72;
(e) a light chain (LC) amino acid sequence having at least 90% identity to SEQ ID NO: 68; and a heavy chain (HC) amino acid sequence having at least 90% identity to SEQ ID NO: 89;
(f) a light chain (LC) amino acid sequence having at least 90% identity to SEQ ID NO: 68; and a heavy chain (HC) amino acid sequence having at least 90% identity to SEQ ID NO: 73;
(g) a light chain (LC) amino acid sequence having at least 90% identity to SEQ ID NO: 68; and a heavy chain (HC) amino acid sequence having at least 90% identity to SEQ ID NO: 88;
(h) a light chain (LC) amino acid sequence having at least 90% identity to SEQ ID NO: 71; and a heavy chain (HC) amino acid sequence having at least 90% identity to SEQ ID NO: 89; or
(i) a light chain (LC) amino acid sequence having at least 90% identity to SEQ ID NO: 74; and a heavy chain (HC) amino acid sequence having at least 90% identity to SEQ ID NO: 75.

6. The antibody of claim 1, wherein the antibody is characterized by:
(a) binds to hu-CD200R1 with a binding affinity of $1 \times 10^{-8}$ M or less;
(b) binds to hu-CD200R1-iso4-Alt or hu-CD200R1-iso4-Ref, and hu-CD200R1-iso1-Alt or hu-CD200R1-iso1-Ref with a binding affinity of $1 \times 10^{-8}$ M or less;

(c) binds to hu-CD200R1-iso4-Alt and hu-CD200R1-iso4-Ref with a binding affinity of $1\times10^{-8}$ M or less;

(d) binds to hu-CD200R1-iso4-Alt, hu-CD200R1-iso4-Ref, hu-CD200R1-iso1-Alt, and hu-CD200R1-iso1-Ref with a binding affinity of $1\times10^{-8}$ M or less;

(e) binds to cyno-CD200R1 with a binding affinity of $1\times10^{-8}$ M or less;

(f) binds to hu-CD200R1 and to cyno-CD200R1 with a binding affinity of $1\times10^{-8}$ M or less;

(g) blocks hu-CD200-Fc binding to hu-CD200R1-iso4-Alt (SEQ ID NO: 1), hu-CD200R1-iso4-Ref (SEQ ID NO: 2), hu-CD200R1-iso1-Alt (SEQ ID NO: 3), and hu-CD200R1-iso1-Ref (SEQ ID NO: 4) measured by ELISA with an $IC_{50}$ of 10 nM or less;

(h) blocks hu-CD200-Fc binding to hu-CD200R1 expressed on a cell with an $IC_{50}$ of 2.5 nM or less;

(i) binds to human T-cells with an $EC_{50}$ of 2.5 nM or less;

(j) increases IFNγ production from human tumor cells by at least 1.2-fold with an antibody concentration of 100 nM or less;

(k) increases IFNγ or IL-2 production from hu-CD200-Fc coated human T cells relative to IgG control by at least 1.2-fold;

(l) increases activation of human CD4+ T-cells or human Cd8+ T-cells by at least 1.5-fold;

(m) does not agonize CD200R1 signaling;

(n) blocks induction of pDok2 activity in U937 monocytic cell lines treated with soluble hu-CD200-Fc; or (o) blocks NFkβ transcription induced by hu-CD200 binding hu-CD200R1 expressing cell-lines.

7. A pharmaceutical composition comprising an anti-CD200R1 antibody of claim 1 and a pharmaceutically acceptable carrier.

8. The antibody of claim 1, wherein the antibody comprises a heavy chain variable domain (VH) amino acid sequence having at least 90% identity to a sequence selected from SEQ ID NO: 14, 22, 30, 38, 46, 54, 62, 67, 80, or 84.

9. The antibody of claim 1, wherein the antibody comprises a heavy chain (HC) amino acid sequence having at least 90% identity to a sequence selected from SEQ ID NO: 69, 70, 72, 73, 75, 88, and 89.

10. The pharmaceutical composition of claim 7, wherein the composition further comprises a chemotherapeutic agent or an antibody comprising a specificity for an immune checkpoint molecule.

11. The pharmaceutical composition of claim 7, wherein the anti-CD200R1 antibody is the sole active agent of the composition.

12. An anti-CD200R1 antibody comprising (i) the heavy chain (HC) amino acid sequence of SEQ ID NO: 69, and (ii) the light chain (LC) amino acid sequence of SEQ ID NO: 68.

13. An anti-CD200R1 antibody comprising (i) the heavy chain variable domain (VH) amino acid sequence of SEQ ID NO: 67, and (ii) the light chain variable domain (VL) amino acid sequence of SEQ ID NO: 66.

14. The antibody of claim 1, wherein the antibody binds to hu-CD200R1 with a binding affinity of $1\times10^{-8}$ M or less, wherein the binding affinity is measured by equilibrium dissociation constant ($K_D$) to a hu-CD200R1 polypeptide of SEQ ID NO: 1, SEQ ID NO: 2, SEQ ID NO: 3, or SEQ ID NO: 4.

15. The antibody of claim 1, wherein the antibody binds to hu-CD200R1-iso4-Alt or hu-CD200R1-iso4-Ref, and hu-CD200R1-iso1-Alt, with a binding affinity of $1\times10^{-8}$ M or less, wherein the binding affinity is measured by equilibrium dissociation constant ($K_D$) to a hu-CD200R1-iso4-Alt polypeptide of SEQ ID NO: 1 or a hu-CD200R1-iso4-Ref polypeptide of SEQ ID NO: 2, and a hu-CD200R1-iso1-Alt polypeptide of SEQ ID NO: 3.

16. The antibody of claim 1, wherein the antibody binds to hu-CD200R1-iso4-Alt or hu-CD200R1-iso4-Ref, and hu-CD200R1-iso1-Ref with a binding affinity of $1\times10^{-8}$ M or less, wherein the binding affinity is measured by equilibrium dissociation constant ($K_D$) to a hu-CD200R1-iso4-Alt polypeptide of SEQ ID NO: 1 or a hu-CD200R1-iso4-Ref polypeptide of SEQ ID NO: 2, and a hu-CD200R1-iso1-Ref polypeptide of SEQ ID NO: 4.

17. The antibody of claim 1, wherein the antibody binds to hu-CD200R1-iso4-Alt and hu-CD200R1-iso4-Ref with a binding affinity of $1\times10^{-8}$ M or less wherein the binding affinity is measured by equilibrium dissociation constant ($K_D$) to a hu-CD200R1-iso4-Alt polypeptide of SEQ ID NO: 1, and a hu-CD200R1-iso4-Ref polypeptide of SEQ ID NO: 2.

18. The antibody of claim 1, wherein the antibody binds to hu-CD200R1-iso4-Alt, hu-CD200R1-iso4-Ref, hu-CD200R1-iso1-Alt, and hu-CD200R1-iso1-Ref with a binding affinity of $1\times10^{-8}$ M or less, wherein the binding affinity is measured by equilibrium dissociation constant ($K_D$) to a hu-CD200R1-iso4-Alt polypeptide of SEQ ID NO: 1, or a hu-CD200R1-iso4-Ref polypeptide of SEQ ID NO: 2, and a huCD200R1-iso1-Alt polypeptide of of SEQ: 4 or a huCD200R1-iso1-Ref polypeptide of SEQ: 3.

19. The antibody of claim 1, wherein the antibody binds to cyno-CD200R1 with a binding affinity of $1\times10^{-8}$ M or less, wherein the binding affinity is measured by equilibrium dissociation constant ($K_D$) to a cyno-CD200R1 polypeptide of SEQ ID NO: 5.

20. The antibody of claim 1, wherein the antibody binds to a hu-CD200R1 isoform and to cyno-CD200R1 with a binding affinity of $1\times10^{-8}$ M or less, wherein the binding affinity is measured by equilibrium dissociation constant ($K_D$) to a hu-CD200R1 polypeptide of SEQ ID NO: 1, SEQ ID NO: 2, SEQ ID NO: 3, or SEQ ID NO: 4, and a cyno-CD200R1 polypeptide of SEQ ID NO: 5.

21. The antibody of claim 1, wherein the antibody blocks hu-CD200-Fc binding to hu-CD200R1 expressed on a cell with an IC50 of 2.5 nM or less, wherein the cell is a U937 cell stably expressing hu-CD200R1.

22. The antibody of claim 1, wherein the antibody binds to human T-cells with an EC50 of 2.5 nM or less, wherein the human T cells are CD4+ T cells or CD8+ T cells.

23. The antibody of claim 1, wherein the antibody increases IFNγ production from human tumor cells by at least 1.2-fold, with an antibody concentration of 100 nM or less, wherein the tumor cell is of a type is selected from colorectal, endometrial, lung, melanoma, ovarian, pancreatic, or prostate.

24. The antibody of claim 1, wherein the antibody blocks NFkβ transcription induced by a hu-CD200 of a hu-CD200-expressing K562 cell binding to a hu-CD200R1 of a hu-CD200R1.

25. An anti-CD200R1 antibody comprising:

(a) the light chain variable domain (VL) amino acid sequence of SEQ ID NO: 10, and the heavy chain variable domain (VH) amino acid sequence of SEQ ID NO: 14;

(b) the light chain variable domain (VL) amino acid sequence of SEQ ID NO: 18, and the heavy chain variable domain (VH) amino acid sequence of SEQ ID NO: 22;

(c) the light chain variable domain (VL) amino acid sequence of SEQ ID NO: 26, and the heavy chain variable domain (VH) amino acid sequence of SEQ ID NO: 30;
(d) the light chain variable domain (VL) amino acid sequence of SEQ ID NO: 34, and the heavy chain variable domain (VH) amino acid sequence of SEQ ID NO: 38;
(e) the light chain variable domain (VL) amino acid sequence of SEQ ID NO: 42, and the heavy chain variable domain (VH) amino acid sequence of SEQ ID NO: 46;
(f) the light chain variable domain (VL) amino acid sequence of SEQ ID NO: 50, and the heavy chain variable domain (VH) amino acid sequence of SEQ ID NO: 54;
(g) the light chain variable domain (VL) amino acid sequence of SEQ ID NO: 58, and the heavy chain variable domain (VH) amino acid sequence of SEQ ID NO: 62;
(h) the light chain variable domain (VL) amino acid sequence of SEQ ID NO: 66, and the heavy chain variable domain (VH) amino acid sequence of SEQ ID NO: 67;
(i) the light chain variable domain (VL) amino acid sequence of SEQ ID NO: 76, and the heavy chain variable domain (VH) amino acid sequence of SEQ ID NO: 80;
(j) the light chain variable domain (VL) amino acid sequence of SEQ ID NO: 66, and the heavy chain variable domain (VH) amino acid sequence of SEQ ID NO: 84;
(k) the light chain variable domain (VL) amino acid sequence of SEQ ID NO: 66, and the heavy chain variable domain (VH) amino acid sequence of SEQ ID NO: 80; or
(l) the light chain variable domain (VL) amino acid sequence of SEQ ID NO: 76, and the heavy chain variable domain (VH) amino acid sequence of SEQ ID NO: 84.

26. An anti-CD200R1 antibody comprising:
(a) the light chain (LC) amino acid sequence of SEQ ID NO: 68; and the heavy chain (HC) amino acid sequence of SEQ ID NO: 69;
(b) the light chain (LC) amino acid sequence of SEQ ID NO: 68; and the heavy chain (HC) amino acid sequence of SEQ ID NO: 70;
(c) the light chain (LC) amino acid sequence of SEQ ID NO: 71; and the heavy chain (HC) amino acid sequence of SEQ ID NO: 88;
(d) the light chain (LC) amino acid sequence of SEQ ID NO: 71; and the heavy chain (HC) amino acid sequence of SEQ ID NO: 72;
(e) the light chain (LC) amino acid sequence of SEQ ID NO: 68; and the heavy chain (HC) amino acid sequence of SEQ ID NO: 89;
(f) the light chain (LC) amino acid sequence of SEQ ID NO: 68; and the heavy chain (HC) amino acid sequence of SEQ ID NO: 73;
(g) the light chain (LC) amino acid sequence of SEQ ID NO: 68; and the heavy chain (HC) amino acid sequence of SEQ ID NO: 88;
(h) the light chain (LC) amino acid sequence of SEQ ID NO: 71; and the heavy chain (HC) amino acid sequence of SEQ ID NO: 89; or
(i) the light chain (LC) amino acid sequence of SEQ ID NO: 74; and the heavy chain (HC) amino acid sequence of SEQ ID NO: 75.

27. An anti-CD200R1 antibody comprising (i) a first light chain hypervariable region (HVR-L1), a second light chain hypervariable region (HVR-L2), and a third light chain hypervariable region (HVR-L3); and (ii) a first heavy chain hypervariable region (HVR-H1), a second heavy chain hypervariable region (HVR-H2), and a third heavy chain hypervariable region (HVR-H3), comprising HVR-L1 of SEQ ID NO: 11, HVR-L2 of SEQ ID NO: 12, and HVR-L3 of SEQ ID NO: 13; and HVR-H1 of SEQ ID NO: 15, HVR-H2 of SEQ ID NO: 16, and HVR-H3 of SEQ ID NO: 17.

28. An anti-CD200R1 antibody comprising (i) a first light chain hypervariable region (HVR-L1), a second light chain hypervariable region (HVR-L2), and a third light chain hypervariable region (HVR-L3); and (ii) a first heavy chain hypervariable region (HVR-H1), a second heavy chain hypervariable region (HVR-H2), and a third heavy chain hypervariable region (HVR-H3), comprising HVR-L1 of SEQ ID NO: 77, HVR-L2 of SEQ ID NO: 78, and HVR-L3 of SEQ ID NO: 79; and HVR-H1 of SEQ ID NO: 81, HVR-H2 of SEQ ID NO: 82, and HVR-H3 of SEQ ID NO: 83.

29. An anti-CD200R1 antibody comprising (i) the heavy chain (HC) amino acid sequence of SEQ ID NO: 88, and (ii) the light chain (LC) amino acid sequence of SEQ ID NO: 71.

30. An anti-CD200R1 antibody comprising (i) the heavy chain variable domain (VH) amino acid sequence of SEQ ID NO: 80, and (ii) the light chain variable domain (VL) amino acid sequence of SEQ ID NO: 76.

* * * * *

UNITED STATES PATENT AND TRADEMARK OFFICE
CERTIFICATE OF CORRECTION

PATENT NO. : 11,787,861 B2
APPLICATION NO. : 17/333963
DATED : October 17, 2023
INVENTOR(S) : Yu Chen et al.

It is certified that error appears in the above-identified patent and that said Letters Patent is hereby corrected as shown below:

In the Specification

Column 24, Line 54:
"IIQSNEDFFT"
Should be changed to:
--HQSNEDPPT--

Column 29, Line 56:
"MGWSCIILFLVATATGVHSDIVLTQSPDSLAVSLGERATINCRASESVDY"
Should be changed to:
--DIVLTQSPDSLAVSLGERATINCRASESVDY--

Column 29, Line 61:
"MGWSCIILFLVATATGVHSEVQLQESGPGLVKPSETLSLTCTVSGFSLTN"
Should be changed to:
--EVQLQESGPGLVKPSETLSLTCTVSGFSLTN--

Column 29, Line 64:
"SSKSTSGGTAAGCLVKDYFPEPVTVSWNSGALTSGVHTFPAVLQSSGLY"
Should be changed to:
--SSKSTSGGTAALGCLVKDYFPEPVTVSWNSGALTSGVHTFPAVLQSSGLY--

Column 31, Line 11:
"MGWSCIILFLVATATGVHSEVQLQESGPGLVKPSETLSLTCTVSGFSLTN"
Should be changed to:
--EVQLQESGPGLVKPSETLSLTCTVSGFSLTN--

Column 31, Line 14:
"SSKSTSGGTAAGCLVKDYFPEPVTVSWNSGALTSGVHTFPAVLQSSGLY"

Signed and Sealed this
Ninth Day of January, 2024

Katherine Kelly Vidal
*Director of the United States Patent and Trademark Office*

CERTIFICATE OF CORRECTION (continued)
U.S. Pat. No. 11,787,861 B2

Should be changed to:
--SSKSTSGGTAALGCLVKDYFPEPVTVSWNSGALTSGVHTFPAVLQSSGLY--

Column 31, Line 19:
"MGWSCIILFLVATATGVHSDIVLTQSPDSLAVSLGERATINCRASESVDY"
Should be changed to:
--DIVLTQSPDSLAVSLGERATINCRASESVDY--

Column 31, Line 24:
"MGWSCIILFLVATATGVHSEVQLQESGPGLVKPSETLSLTCTVSGFSLTN"
Should be changed to:
--EVQLQESGPGLVKPSETLSLTCTVSGFSLTN--

Column 31, Line 27:
"SSKSTSGGTAAGCLVKDYFPEPVTVSWNSGALTSGVHTFPAVLQSSGLY"
Should be changed to:
--SSKSTSGGTAALGCLVKDYFPEPVTVSWNSGALTSGVHTFPAVLQSSGLY--

Column 31, Line 33:
"MGWSCIILFLVATATGVHSEVQLQESGPGLVKPSETLSLTCTVSGFSLTN"
Should be changed to:
--EVQLQESGPGLVKPSETLSLTCTVSGFSLTN--

Column 31, Line 36:
"SSKSTSGGTAAGCLVKDYFPEPVTVSWNSGALTSGVHTFPAVLQSSGLY"
Should be changed to:
--SSKSTSGGTAALGCLVKDYFPEPVTVSWNSGALTSGVHTFPAVLQSSGLY--

Column 31, Line 41: "MGWSCIILFLVATATGVHSDIQLTQSPSSLSASVGDRVTITCRASKSVST"
Should be changed to:
--DIQLTQSPSSLSASVGDRVTITCRASKSVST--

Column 31, Line 46:
"MGWSCIILFLVATATGVHSEVQLVQSGAEVKKPGASVKVSCKASGYTFTS"
Should be changed to:
--EVQLVQSGAEVKKPGASVKVSCKASGYTFTS--

Column 33, Line 41:
"MGWSCIILFLVATATGVHSEVQLQESGPGLVKPSETLSLTCTVSGFSL"
Should be changed to:
--EVQLQESGPGLVKPSETLSLTCTVSGFSL--

Column 33, Line 44:
"VFPLAPSSKSTSGGTAAGCLVKDYFPEPVTVSWNSGALTSGVHTFPA"

Should be changed to:

CERTIFICATE OF CORRECTION (continued)
U.S. Pat. No. 11,787,861 B2

--VFPLAPSSKSTSGGTAALGCLVKDYFPEPVTVSWNSGALTSGVHTFPA--

Column 33, Line 51:
"MGWSCIILFLVATATGVHSEVQLQESGPGLVKPSETLSLTCTVSGFSL"
Should be changed to:
--EVQLQESGPGLVKPSETLSLTCTVSGFSL--

Column 33, Line 54:
"VFPLAPSSKSTSGGTAAGCLVKDYFPEPVTVSWNSGALTSGVHTFPA"
Should be changed to:
--VFPLAPSSKSTSGGTAALGCLVKDYFPEPVTVSWNSGALTSGVHTFPA--

SEQUENCE LISTING

```
<160> NUMBER OF SEQ ID NOS: 97

<210> SEQ ID NO 1
<211> LENGTH: 240
<212> TYPE: PRT
<213> ORGANISM: Homo sapiens

<400> SEQUENCE: 1

Ala Ala Gln Pro Asn Asn Ser Leu Met Leu Gln Thr Ser Lys Glu Asn
1               5                   10                  15

His Ala Leu Ala Ser Ser Ser Leu Cys Met Asp Glu Lys Gln Ile Thr
            20                  25                  30

Gln Asn Tyr Ser Lys Val Leu Ala Glu Val Asn Thr Ser Trp Pro Val
        35                  40                  45

Lys Met Ala Thr Asn Ala Val Leu Cys Cys Pro Pro Ile Ala Leu Arg
    50                  55                  60

Asn Leu Ile Ile Ile Thr Trp Glu Ile Ile Leu Arg Gly Gln Pro Ser
65                  70                  75                  80

Cys Thr Lys Ala Tyr Arg Lys Glu Thr Asn Glu Thr Lys Glu Thr Asn
                85                  90                  95

Cys Thr Asp Glu Arg Ile Thr Trp Val Ser Arg Pro Asp Gln Asn Ser
            100                 105                 110
```

```
Asp Leu Gln Ile Arg Pro Val Ala Ile Thr His Asp Gly Tyr Tyr Arg
            115                 120                 125

Cys Ile Met Val Thr Pro Asp Gly Asn Phe His Arg Gly Tyr His Leu
        130                 135                 140

Gln Val Leu Val Thr Pro Glu Val Thr Leu Phe Gln Asn Arg Asn Arg
145                 150                 155                 160

Thr Ala Val Cys Lys Ala Val Ala Gly Lys Pro Ala Gln Ile Ser
                165                 170                 175

Trp Ile Pro Glu Gly Asp Cys Ala Thr Lys Gln Glu Tyr Trp Ser Asn
            180                 185                 190

Gly Thr Val Thr Val Lys Ser Thr Cys His Trp Glu Val His Asn Val
            195                 200                 205

Ser Thr Val Thr Cys His Val Ser His Leu Thr Gly Asn Lys Ser Leu
            210                 215                 220

Tyr Ile Glu Leu Leu Pro Val Pro Gly Ala Lys Lys Ser Ala Lys Leu
225                 230                 235                 240

<210> SEQ ID NO 2
<211> LENGTH: 240
<212> TYPE: PRT
<213> ORGANISM: Homo sapiens

<400> SEQUENCE: 2

Ala Ala Gln Pro Asn Asn Ser Leu Met Leu Gln Thr Ser Lys Glu Asn
1               5                   10                  15

His Ala Leu Ala Ser Ser Ser Leu Cys Met Asp Glu Lys Gln Ile Thr
            20                  25                  30

Gln Asn Tyr Ser Lys Val Leu Ala Glu Val Asn Thr Ser Trp Pro Val
        35                  40                  45

Lys Met Ala Thr Asn Ala Val Leu Cys Cys Pro Pro Ile Ala Leu Arg
    50                  55                  60

Asn Leu Ile Ile Ile Thr Trp Glu Ile Ile Leu Arg Gly Gln Pro Ser
65                  70                  75                  80

Cys Thr Lys Ala Tyr Lys Lys Glu Thr Asn Glu Thr Lys Glu Thr Asn
            85                  90                  95

Cys Thr Asp Glu Arg Ile Thr Trp Val Ser Arg Pro Asp Gln Asn Ser
        100                 105                 110

Asp Leu Gln Ile Arg Thr Val Ala Ile Thr His Asp Gly Tyr Tyr Arg
    115                 120                 125

Cys Ile Met Val Thr Pro Asp Gly Asn Phe His Arg Gly Tyr His Leu
        130                 135                 140

Gln Val Leu Val Thr Pro Glu Val Thr Leu Phe Gln Asn Arg Asn Arg
145                 150                 155                 160

Thr Ala Val Cys Lys Ala Val Ala Gly Lys Pro Ala Ala His Ile Ser
                165                 170                 175

Trp Ile Pro Glu Gly Asp Cys Ala Thr Lys Gln Glu Tyr Trp Ser Asn
            180                 185                 190

Gly Thr Val Thr Val Lys Ser Thr Cys His Trp Glu Val His Asn Val
            195                 200                 205

Ser Thr Val Thr Cys His Val Ser His Leu Thr Gly Asn Lys Ser Leu
            210                 215                 220

Tyr Ile Glu Leu Leu Pro Val Pro Gly Ala Lys Lys Ser Ala Lys Leu
225                 230                 235                 240
```

```
<210> SEQ ID NO 3
<211> LENGTH: 215
<212> TYPE: PRT
<213> ORGANISM: Homo sapiens

<400> SEQUENCE: 3

Met Asp Glu Lys Gln Ile Thr Gln Asn Tyr Ser Lys Val Leu Ala Glu
1               5                   10                  15

Val Asn Thr Ser Trp Pro Val Lys Met Ala Thr Asn Ala Val Leu Cys
            20                  25                  30

Cys Pro Pro Ile Ala Leu Arg Asn Leu Ile Ile Ile Thr Trp Glu Ile
        35                  40                  45

Ile Leu Arg Gly Gln Pro Ser Cys Thr Lys Ala Tyr Arg Lys Glu Thr
    50                  55                  60

Asn Glu Thr Lys Glu Thr Asn Cys Thr Asp Glu Arg Ile Thr Trp Val
65                  70                  75                  80

Ser Arg Pro Asp Gln Asn Ser Asp Leu Gln Ile Arg Pro Val Ala Ile
                85                  90                  95

Thr His Asp Gly Tyr Tyr Arg Cys Ile Met Val Thr Pro Asp Gly Asn
            100                 105                 110

Phe His Arg Gly Tyr His Leu Gln Val Leu Val Thr Pro Glu Val Thr
        115                 120                 125

Leu Phe Gln Asn Arg Asn Arg Thr Ala Val Cys Lys Ala Val Ala Gly
    130                 135                 140

Lys Pro Ala Ala Gln Ile Ser Trp Ile Pro Glu Gly Asp Cys Ala Thr
145                 150                 155                 160

Lys Gln Glu Tyr Trp Ser Asn Gly Thr Val Thr Val Lys Ser Thr Cys
                165                 170                 175

His Trp Glu Val His Asn Val Ser Thr Val Thr Cys His Val Ser His
            180                 185                 190

Leu Thr Gly Asn Lys Ser Leu Tyr Ile Glu Leu Leu Pro Val Pro Gly
        195                 200                 205

Ala Lys Lys Ser Ala Lys Leu
    210                 215

<210> SEQ ID NO 4
<211> LENGTH: 215
<212> TYPE: PRT
<213> ORGANISM: Homo sapiens

<400> SEQUENCE: 4

Met Asp Glu Lys Gln Ile Thr Gln Asn Tyr Ser Lys Val Leu Ala Glu
1               5                   10                  15

Val Asn Thr Ser Trp Pro Val Lys Met Ala Thr Asn Ala Val Leu Cys
            20                  25                  30

Cys Pro Pro Ile Ala Leu Arg Asn Leu Ile Ile Ile Thr Trp Glu Ile
        35                  40                  45

Ile Leu Arg Gly Gln Pro Ser Cys Thr Lys Ala Tyr Lys Lys Glu Thr
    50                  55                  60

Asn Glu Thr Lys Glu Thr Asn Cys Thr Asp Glu Arg Ile Thr Trp Val
65                  70                  75                  80

Ser Arg Pro Asp Gln Asn Ser Asp Leu Gln Ile Arg Thr Val Ala Ile
                85                  90                  95

Thr His Asp Gly Tyr Tyr Arg Cys Ile Met Val Thr Pro Asp Gly Asn
            100                 105                 110
```

```
Phe His Arg Gly Tyr His Leu Gln Val Leu Val Thr Pro Glu Val Thr
            115                 120                 125

Leu Phe Gln Asn Arg Asn Arg Thr Ala Val Cys Lys Ala Val Ala Gly
130                 135                 140

Lys Pro Ala Ala His Ile Ser Trp Ile Pro Glu Gly Asp Cys Ala Thr
145                 150                 155                 160

Lys Gln Glu Tyr Trp Ser Asn Gly Thr Val Thr Val Lys Ser Thr Cys
                165                 170                 175

His Trp Glu Val His Asn Val Ser Thr Val Thr Cys His Val Ser His
            180                 185                 190

Leu Thr Gly Asn Lys Ser Leu Tyr Ile Glu Leu Leu Pro Val Pro Gly
        195                 200                 205

Ala Lys Lys Ser Ala Lys Leu
    210                 215

<210> SEQ ID NO 5
<211> LENGTH: 241
<212> TYPE: PRT
<213> ORGANISM: Macaca fascicularis

<400> SEQUENCE: 5

Ala Ala Gln Ser Asn Asn Ser Leu Met Leu Gln Thr Ser Lys Glu Asn
1               5                   10                  15

His Thr Leu Ala Ser Asn Ser Leu Cys Met Asp Glu Lys Gln Ile Thr
            20                  25                  30

Gln Asn His Ser Lys Val Leu Ala Glu Val Asn Ile Ser Trp Pro Val
        35                  40                  45

Gln Met Ala Arg Asn Ala Val Leu Cys Cys Pro Pro Ile Glu Phe Arg
    50                  55                  60

Asn Leu Ile Val Ile Thr Trp Glu Ile Ile Leu Arg Gly Gln Pro Ser
65                  70                  75                  80

Cys Thr Lys Thr Tyr Arg Lys Asp Thr Asn Glu Thr Lys Glu Thr Asn
                85                  90                  95

Cys Thr Asp Glu Arg Ile Thr Trp Val Ser Thr Pro Asp Gln Asn Ser
            100                 105                 110

Asp Leu Gln Ile His Pro Val Ala Ile Thr His Asp Gly Tyr Tyr Arg
        115                 120                 125

Cys Ile Met Ala Thr Pro Asp Gly Asn Phe His Arg Gly Tyr His Leu
    130                 135                 140

Gln Val Leu Val Thr Pro Glu Val Thr Leu Phe Glu Ser Arg Asn Arg
145                 150                 155                 160

Thr Ala Val Cys Lys Ala Val Ala Gly Lys Pro Ala Ala Gln Ile Ser
                165                 170                 175

Trp Ile Pro Ala Gly Asp Cys Ala Pro Thr Glu Gln Glu Tyr Trp Gly
            180                 185                 190

Asn Gly Thr Val Thr Val Lys Ser Thr Cys His Trp Glu Gly His Asn
        195                 200                 205

Val Ser Thr Val Thr Cys His Val Ser His Leu Thr Gly Asn Lys Ser
    210                 215                 220

Leu Tyr Ile Glu Leu Leu Pro Val Pro Gly Ala Lys Lys Ser Ala Lys
225                 230                 235                 240

Leu
```

<210> SEQ ID NO 6
<211> LENGTH: 241
<212> TYPE: PRT
<213> ORGANISM: Macaca mulatta

<400> SEQUENCE: 6

```
Ala Ala Gln Ser Asn Asn Ser Leu Met Leu Gln Thr Ser Lys Glu Asn
1               5                   10                  15

His Thr Leu Ala Ser Asn Ser Leu Cys Met Asp Glu Lys Gln Ile Thr
            20                  25                  30

Gln Asn His Ser Lys Val Leu Ala Glu Val Asn Ile Ser Trp Pro Val
        35                  40                  45

Gln Met Ala Arg Asn Ala Val Leu Cys Cys Pro Pro Ile Glu Phe Arg
50                  55                  60

Asn Leu Ile Val Ile Thr Trp Glu Ile Ile Leu Arg Gly Gln Pro Ser
65                  70                  75                  80

Cys Thr Lys Ser Tyr Arg Lys Glu Thr Asn Glu Thr Lys Glu Thr Asn
                85                  90                  95

Cys Thr Asp Glu Arg Ile Thr Trp Val Ser Thr Pro Asp Gln Asn Ser
            100                 105                 110

Asp Leu Gln Ile Tyr Pro Val Ala Ile Thr His Asp Gly Tyr Tyr Arg
        115                 120                 125

Cys Ile Met Ala Thr Pro Asp Gly Asn Phe His Arg Gly Tyr His Leu
130                 135                 140

Gln Val Leu Val Thr Pro Glu Val Thr Leu Phe Glu Ser Arg Asn Arg
145                 150                 155                 160

Thr Ala Val Cys Lys Ala Val Ala Gly Lys Pro Ala Ala Gln Ile Ser
                165                 170                 175

Trp Ile Pro Ala Gly Asp Cys Ala Pro Thr Glu Gln Glu Tyr Trp Gly
            180                 185                 190

Asn Gly Thr Val Thr Val Lys Ser Thr Cys His Trp Glu Gly His Asn
        195                 200                 205

Val Ser Thr Val Thr Cys His Val Ser His Leu Thr Gly Asn Lys Ser
210                 215                 220

Leu Tyr Ile Glu Leu Leu Pro Val Pro Gly Ala Lys Lys Ser Ala Lys
225                 230                 235                 240

Leu
```

<210> SEQ ID NO 7
<211> LENGTH: 232
<212> TYPE: PRT
<213> ORGANISM: Homo sapiens

<400> SEQUENCE: 7

```
Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95
```

```
Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
            115                 120                 125

Gly Lys Ile Ser Gly Thr Ala Cys Leu Thr Val Tyr Val Gln Pro Ile
            130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
            195                 200                 205

Gly Lys Glu Val Ile Cys Gln Val Leu His Leu Gly Thr Val Thr Asp
            210                 215                 220

Phe Lys Gln Thr Val Asn Lys Gly
225                 230

<210> SEQ ID NO 8
<211> LENGTH: 232
<212> TYPE: PRT
<213> ORGANISM: Macaca fascicularis

<400> SEQUENCE: 8

Met Glu Arg Leu Val Ile Arg Met Pro Phe Cys His Leu Ser Thr Tyr
1               5                   10                  15

Ser Leu Val Trp Gly Met Ala Ala Val Leu Cys Ala Ala Gln Val
            20                  25                  30

Gln Val Val Thr Gln Asp Glu Arg Glu Gln Leu Tyr Thr Pro Ala Ser
            35                  40                  45

Leu Arg Cys Ser Leu Gln Asn Ala Gln Glu Val Leu Ile Val Thr Trp
50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Thr Thr Ile Thr Phe Trp Asn Ile Thr
            100                 105                 110

Leu Glu Asp Glu Gly Cys Tyr Met Cys Leu Phe Asn Thr Phe Gly Ser
            115                 120                 125

Gly Lys Ile Ser Gly Thr Ala Cys Leu Thr Val Tyr Val Gln Pro Ile
            130                 135                 140

Val Ser Leu His Tyr Lys Tyr Ser Glu Asp His Leu Asn Ile Thr Cys
145                 150                 155                 160

Ser Ala Thr Ala Arg Pro Ala Pro Met Ile Phe Trp Lys Val Pro Arg
                165                 170                 175

Ser Gly Phe Glu Asn Ser Thr Val Thr Gln Ser His Pro Asn Gly Thr
            180                 185                 190

Thr Ser Val Thr Ser Ile Leu His Val Lys Asp Pro Lys Asn Gln Val
            195                 200                 205

Gly Lys Glu Val Ile Cys Gln Val Leu His Leu Gly Thr Val Thr Asp
            210                 215                 220

Phe Lys Gln Thr Phe Asp Lys Gly
225                 230
```

```
<210> SEQ ID NO 9
<211> LENGTH: 228
<212> TYPE: PRT
<213> ORGANISM: Artificial
<220> FEATURE:
<223> OTHER INFORMATION: Synthetic polypeptide

<400> SEQUENCE: 9

Gly Gly Ser Gly Ser Gly Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Gly Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly
225

<210> SEQ ID NO 10
<211> LENGTH: 111
<212> TYPE: PRT
<213> ORGANISM: Artificial
<220> FEATURE:
<223> OTHER INFORMATION: Synthetic polypeptide

<400> SEQUENCE: 10

Asp Ile Val Leu Thr Gln Ser Pro Pro Ser Leu Ala Val Ser Leu Gly
1               5                   10                  15

Gln Arg Ala Thr Met Ser Cys Arg Ala Ser Glu Ser Val Asp Tyr Ser
            20                  25                  30

Gly Asn Ser Phe Met His Trp Phe Gln Gln Lys Ala Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80
```

Pro Leu Glu Ala Asp Asp Val Ala Thr Tyr Tyr Cys His Gln Ser Asn
            85                  90                  95

Glu Asp Pro Pro Thr Phe Gly Gly Gly Thr Lys Leu Glu Met Lys
            100                 105                 110

<210> SEQ ID NO 11
<211> LENGTH: 15
<212> TYPE: PRT
<213> ORGANISM: Artificial
<220> FEATURE:
<223> OTHER INFORMATION: Synthetic polypeptide

<400> SEQUENCE: 11

Arg Ala Ser Glu Ser Val Asp Tyr Ser Gly Asn Ser Phe Met His
1               5                   10                  15

<210> SEQ ID NO 12
<211> LENGTH: 7
<212> TYPE: PRT
<213> ORGANISM: Artificial
<220> FEATURE:
<223> OTHER INFORMATION: Synthetic polypeptide

<400> SEQUENCE: 12

Arg Ala Ser Asn Leu Glu Ser
1               5

<210> SEQ ID NO 13
<211> LENGTH: 9
<212> TYPE: PRT
<213> ORGANISM: Artificial
<220> FEATURE:
<223> OTHER INFORMATION: Synthetic polypeptide

<400> SEQUENCE: 13

His Gln Ser Asn Glu Asp Pro Pro Thr
1               5

<210> SEQ ID NO 14
<211> LENGTH: 118
<212> TYPE: PRT
<213> ORGANISM: Artificial
<220> FEATURE:
<223> OTHER INFORMATION: Synthetic polypeptide

<400> SEQUENCE: 14

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asn Tyr
            20                  25                  30

Ala Val Ser Trp Val Arg Gln Pro Pro Gly Lys Gly Leu Glu Trp Leu
            35                  40                  45

Gly Val Met Trp Ala Gly Gly Thr Asn Tyr Asn Ser Val Phe Lys
        50                  55                  60

Ser Arg Leu Thr Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
            85                  90                  95

Arg Glu Arg Pro Leu Thr Gly Val Met Asp Tyr Trp Gly Gln Gly Thr
            100                 105                 110

Ser Val Thr Val Ser Ser
            115

```
<210> SEQ ID NO 15
<211> LENGTH: 6
<212> TYPE: PRT
<213> ORGANISM: Artificial
<220> FEATURE:
<223> OTHER INFORMATION: Synthetic polypeptide

<400> SEQUENCE: 15

Thr Asn Tyr Ala Val Ser
1               5

<210> SEQ ID NO 16
<211> LENGTH: 12
<212> TYPE: PRT
<213> ORGANISM: Artificial
<220> FEATURE:
<223> OTHER INFORMATION: Synthetic polypeptide

<400> SEQUENCE: 16

Val Met Trp Ala Gly Gly Gly Thr Asn Tyr Asn Ser
1               5                   10

<210> SEQ ID NO 17
<211> LENGTH: 12
<212> TYPE: PRT
<213> ORGANISM: Artificial
<220> FEATURE:
<223> OTHER INFORMATION: Synthetic polypeptide

<400> SEQUENCE: 17

Ala Arg Glu Arg Pro Leu Thr Gly Val Met Asp Tyr
1               5                   10

<210> SEQ ID NO 18
<211> LENGTH: 106
<212> TYPE: PRT
<213> ORGANISM: Artificial
<220> FEATURE:
<223> OTHER INFORMATION: Synthetic polypeptide

<400> SEQUENCE: 18

Gln Ile Val Leu Thr Gln Ser Pro Ala Leu Thr Ser Ala Ser Pro Gly
1               5                   10                  15

Glu Lys Val Thr Met Thr Cys Ser Ala Ser Ser Ser Val Ser Tyr Met
            20                  25                  30

Tyr Trp Phe Gln Gln Lys Pro Arg Ser Ser Pro Lys Pro Trp Ile Tyr
        35                  40                  45

Leu Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Tyr Pro Leu Thr
                85                  90                  95

Phe Gly Ala Gly Thr Lys Leu Glu Leu Lys
            100                 105

<210> SEQ ID NO 19
<211> LENGTH: 10
<212> TYPE: PRT
<213> ORGANISM: Artificial
<220> FEATURE:
<223> OTHER INFORMATION: Synthetic polypeptide
```

```
<400> SEQUENCE: 19

Ser Ala Ser Ser Val Ser Tyr Met Tyr
1               5                   10

<210> SEQ ID NO 20
<211> LENGTH: 7
<212> TYPE: PRT
<213> ORGANISM: Artificial
<220> FEATURE:
<223> OTHER INFORMATION: Synthetic polypeptide

<400> SEQUENCE: 20

Leu Thr Ser Lys Leu Ala Ser
1               5

<210> SEQ ID NO 21
<211> LENGTH: 9
<212> TYPE: PRT
<213> ORGANISM: Artificial
<220> FEATURE:
<223> OTHER INFORMATION: Synthetic polypeptide

<400> SEQUENCE: 21

Gln Gln Trp Ser Ser Tyr Pro Leu Thr
1               5

<210> SEQ ID NO 22
<211> LENGTH: 120
<212> TYPE: PRT
<213> ORGANISM: Artificial
<220> FEATURE:
<223> OTHER INFORMATION: Synthetic polypeptide

<400> SEQUENCE: 22

Glu Val Gln Leu Gln Gln Ser Gly Thr Val Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Arg Ile Asp Pro Ala Asn Asp Asn Thr Lys Tyr Ala Pro Lys Phe
    50                  55                  60

Gln Asp Arg Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Arg Val Glu Gly Arg Thr Gly Thr Tyr Phe Asp Tyr Trp Gly Gln
            100                 105                 110

Gly Thr Thr Leu Thr Val Ser Ser
        115                 120

<210> SEQ ID NO 23
<211> LENGTH: 6
<212> TYPE: PRT
<213> ORGANISM: Artificial
<220> FEATURE:
<223> OTHER INFORMATION: Synthetic polypeptide

<400> SEQUENCE: 23

Lys Asp Asp Tyr Met His
1               5
```

```
<210> SEQ ID NO 24
<211> LENGTH: 13
<212> TYPE: PRT
<213> ORGANISM: Artificial
<220> FEATURE:
<223> OTHER INFORMATION: Synthetic polypeptide

<400> SEQUENCE: 24

Arg Ile Asp Pro Ala Asn Asp Asn Thr Lys Tyr Ala Pro
1               5                   10

<210> SEQ ID NO 25
<211> LENGTH: 13
<212> TYPE: PRT
<213> ORGANISM: Artificial
<220> FEATURE:
<223> OTHER INFORMATION: Synthetic polypeptide

<400> SEQUENCE: 25

Thr Arg Val Glu Gly Arg Thr Gly Thr Tyr Phe Asp Tyr
1               5                   10

<210> SEQ ID NO 26
<211> LENGTH: 107
<212> TYPE: PRT
<213> ORGANISM: Artificial
<220> FEATURE:
<223> OTHER INFORMATION: Synthetic polypeptide

<400> SEQUENCE: 26

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Phe Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln Tyr Asn Glu Tyr Pro Trp
                85                  90                  95

Thr Phe Gly Gly Gly Thr Lys Leu Glu Ile Lys
            100                 105

<210> SEQ ID NO 27
<211> LENGTH: 11
<212> TYPE: PRT
<213> ORGANISM: Artificial
<220> FEATURE:
<223> OTHER INFORMATION: Synthetic polypeptide

<400> SEQUENCE: 27

Arg Ala Ser Lys Ser Ile Ser Lys Tyr Leu Ala
1               5                   10

<210> SEQ ID NO 28
<211> LENGTH: 7
<212> TYPE: PRT
<213> ORGANISM: Artificial
<220> FEATURE:
<223> OTHER INFORMATION: Synthetic polypeptide
```

```
<400> SEQUENCE: 28

Ser Gly Ser Thr Leu Gln Ser
1               5

<210> SEQ ID NO 29
<211> LENGTH: 9
<212> TYPE: PRT
<213> ORGANISM: Artificial
<220> FEATURE:
<223> OTHER INFORMATION: Synthetic polypeptide

<400> SEQUENCE: 29

Gln Gln Tyr Asn Glu Tyr Pro Trp Thr
1               5

<210> SEQ ID NO 30
<211> LENGTH: 122
<212> TYPE: PRT
<213> ORGANISM: Artificial
<220> FEATURE:
<223> OTHER INFORMATION: Synthetic polypeptide

<400> SEQUENCE: 30

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Arg Ile Asp Pro Glu Asn Gly Asn Thr Lys Tyr Gly Pro Lys Phe
    50                  55                  60

Gln Asp Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Thr Arg Gln Leu Gly Leu Arg Arg Val Trp Tyr Ala Leu Asp Tyr Trp
            100                 105                 110

Gly Gln Gly Thr Ser Val Thr Val Ser Ser
        115                 120

<210> SEQ ID NO 31
<211> LENGTH: 6
<212> TYPE: PRT
<213> ORGANISM: Artificial
<220> FEATURE:
<223> OTHER INFORMATION: Synthetic polypeptide

<400> SEQUENCE: 31

Lys Asp Asp Tyr Met His
1               5

<210> SEQ ID NO 32
<211> LENGTH: 13
<212> TYPE: PRT
<213> ORGANISM: Artificial
<220> FEATURE:
<223> OTHER INFORMATION: Synthetic polypeptide

<400> SEQUENCE: 32

Arg Ile Asp Pro Glu Asn Gly Asn Thr Lys Tyr Gly Pro
1               5                   10
```

```
<210> SEQ ID NO 33
<211> LENGTH: 15
<212> TYPE: PRT
<213> ORGANISM: Artificial
<220> FEATURE:
<223> OTHER INFORMATION: Synthetic polypeptide

<400> SEQUENCE: 33

Thr Arg Gln Leu Gly Leu Arg Arg Val Trp Tyr Ala Leu Asp Tyr
1               5                   10                  15

<210> SEQ ID NO 34
<211> LENGTH: 107
<212> TYPE: PRT
<213> ORGANISM: Artificial
<220> FEATURE:
<223> OTHER INFORMATION: Synthetic polypeptide

<400> SEQUENCE: 34

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
        50                  55                  60

Ser Gly Ser Val Thr Asp Phe Thr Leu Thr Ile Ser Ser Leu Glu Pro
65                  70                  75                  80

Glu Asp Phe Ala Met Tyr Tyr Cys Gln Gln Tyr Asn Glu Tyr Pro Trp
                85                  90                  95

Thr Phe Gly Gly Gly Thr Lys Leu Glu Ile Lys
            100                 105

<210> SEQ ID NO 35
<211> LENGTH: 11
<212> TYPE: PRT
<213> ORGANISM: Artificial
<220> FEATURE:
<223> OTHER INFORMATION: Synthetic polypeptide

<400> SEQUENCE: 35

Arg Ala Ser Lys Ser Ile Ser Lys Tyr Leu Ala
1               5                   10

<210> SEQ ID NO 36
<211> LENGTH: 7
<212> TYPE: PRT
<213> ORGANISM: Artificial
<220> FEATURE:
<223> OTHER INFORMATION: Synthetic polypeptide

<400> SEQUENCE: 36

Ser Gly Ser Thr Leu Gln Ser
1               5

<210> SEQ ID NO 37
<211> LENGTH: 9
<212> TYPE: PRT
<213> ORGANISM: Artificial
<220> FEATURE:
<223> OTHER INFORMATION: Synthetic polypeptide
```

```
<400> SEQUENCE: 37

Gln Gln Tyr Asn Glu Tyr Pro Trp Thr
1               5

<210> SEQ ID NO 38
<211> LENGTH: 122
<212> TYPE: PRT
<213> ORGANISM: Artificial
<220> FEATURE:
<223> OTHER INFORMATION: Synthetic polypeptide

<400> SEQUENCE: 38

Glu Val Gln Leu Gln Gln Ser Gly Ala Glu Phe Val Arg Pro Gly Ala
1               5                   10                  15

Ser Val Lys Leu Ser Cys Thr Thr Ser Gly Phe Tyr Ile Lys Asp Asp
                20                  25                  30

Tyr Ile His Trp Val Lys Gln Arg Pro Glu Gln Gly Leu Glu Trp Ile
            35                  40                  45

Gly Arg Ile Asp Pro Ala Asn Gly Asn Thr Lys Tyr Ala Pro Lys Phe
        50                  55                  60

Gln Asp Lys Ala Thr Ile Thr Ala Asp Thr Ser Ser Asn Thr Ala Tyr
65                  70                  75                  80

Leu Gln Leu Ser Arg Leu Thr Ser Glu Asp Thr Ala Val Tyr Tyr Cys
                85                  90                  95

Ala Arg Gln Leu Gly Leu Arg Arg Thr Trp Tyr Ser Leu Asp Tyr Trp
            100                 105                 110

Gly Gln Gly Thr Ser Val Thr Val Ser Ser
        115                 120

<210> SEQ ID NO 39
<211> LENGTH: 6
<212> TYPE: PRT
<213> ORGANISM: Artificial
<220> FEATURE:
<223> OTHER INFORMATION: Synthetic polypeptide

<400> SEQUENCE: 39

Lys Asp Asp Tyr Ile His
1               5

<210> SEQ ID NO 40
<211> LENGTH: 13
<212> TYPE: PRT
<213> ORGANISM: Artificial
<220> FEATURE:
<223> OTHER INFORMATION: Synthetic polypeptide

<400> SEQUENCE: 40

Arg Ile Asp Pro Ala Asn Gly Asn Thr Lys Tyr Ala Pro
1               5                   10

<210> SEQ ID NO 41
<211> LENGTH: 15
<212> TYPE: PRT
<213> ORGANISM: Artificial
<220> FEATURE:
<223> OTHER INFORMATION: Synthetic polypeptide

<400> SEQUENCE: 41

Ala Arg Gln Leu Gly Leu Arg Arg Thr Trp Tyr Ser Leu Asp Tyr
1               5                   10                  15
```

```
<210> SEQ ID NO 42
<211> LENGTH: 105
<212> TYPE: PRT
<213> ORGANISM: Artificial
<220> FEATURE:
<223> OTHER INFORMATION: Synthetic polypeptide

<400> SEQUENCE: 42

Asp Val Gln Met Ile Gln Ser Pro Ser Ser Leu Ser Ala Ser Leu Gly
1               5                   10                  15

Asp Lys Val Thr Met Thr Cys Gln Ala Ser His Thr Ile Asn Leu Asn
            20                  25                  30

Trp Phe Gln Gln Lys Pro Gly Lys Ala Pro Lys Leu Leu Ile Tyr Gly
        35                  40                  45

Thr Ser Asn Leu Glu Asp Gly Val Pro Pro Arg Phe Ser Gly Ser Gly
    50                  55                  60

Tyr Gly Thr Asp Phe Thr Leu Thr Ile Ser Ser Leu Glu Asp Glu Asp
65                  70                  75                  80

Met Ala Thr Tyr Phe Cys Leu Gln His Thr Tyr Leu Pro Trp Thr Phe
                85                  90                  95

Gly Gly Gly Thr Lys Leu Glu Ile Lys
            100                 105

<210> SEQ ID NO 43
<211> LENGTH: 9
<212> TYPE: PRT
<213> ORGANISM: Artificial
<220> FEATURE:
<223> OTHER INFORMATION: Synthetic polypeptide

<400> SEQUENCE: 43

Gln Ala Ser His Thr Ile Asn Leu Asn
1               5

<210> SEQ ID NO 44
<211> LENGTH: 7
<212> TYPE: PRT
<213> ORGANISM: Artificial
<220> FEATURE:
<223> OTHER INFORMATION: Synthetic polypeptide

<400> SEQUENCE: 44

Gly Thr Ser Asn Leu Glu Asp
1               5

<210> SEQ ID NO 45
<211> LENGTH: 9
<212> TYPE: PRT
<213> ORGANISM: Artificial
<220> FEATURE:
<223> OTHER INFORMATION: Synthetic polypeptide

<400> SEQUENCE: 45

Leu Gln His Thr Tyr Leu Pro Trp Thr
1               5

<210> SEQ ID NO 46
<211> LENGTH: 122
<212> TYPE: PRT
<213> ORGANISM: Artificial
<220> FEATURE:
<223> OTHER INFORMATION: Synthetic polypeptide
```

<400> SEQUENCE: 46

Glu Val Gln Leu Gln Gln Ser Gly Ala Glu Phe Val Arg Pro Gly Ala
1               5                   10                  15

Ser Val Arg Leu Ser Cys Thr Thr Ser Gly Phe Tyr Ile Lys Asp Asp
                20                  25                  30

Tyr Ile His Trp Val Lys Gln Arg Pro Glu Gln Gly Leu Glu Trp Ile
            35                  40                  45

Gly Arg Ile Asp Pro Ala Asn Gly Asn Thr Lys Tyr Ala Pro Lys Phe
50                  55                  60

Gln Asp Lys Ala Thr Ile Thr Ala Asp Thr Ser Ser Asn Thr Ala Tyr
65                  70                  75                  80

Leu Gln Leu Asn Ser Leu Thr Ser Glu Asp Thr Ala Val Tyr Tyr Cys
                85                  90                  95

Thr Arg Gln Leu Gly Leu Arg Arg Thr Trp Tyr Ala Met Asp Tyr Trp
                100                 105                 110

Gly Gln Gly Thr Ser Val Thr Val Ser Ser
            115                 120

<210> SEQ ID NO 47
<211> LENGTH: 6
<212> TYPE: PRT
<213> ORGANISM: Artificial
<220> FEATURE:
<223> OTHER INFORMATION: Synthetic polypeptide

<400> SEQUENCE: 47

Lys Asp Asp Tyr Ile His
1               5

<210> SEQ ID NO 48
<211> LENGTH: 13
<212> TYPE: PRT
<213> ORGANISM: Artificial
<220> FEATURE:
<223> OTHER INFORMATION: Synthetic polypeptide

<400> SEQUENCE: 48

Arg Ile Asp Pro Ala Asn Gly Asn Thr Lys Tyr Ala Pro
1               5                   10

<210> SEQ ID NO 49
<211> LENGTH: 15
<212> TYPE: PRT
<213> ORGANISM: Artificial
<220> FEATURE:
<223> OTHER INFORMATION: Synthetic polypeptide

<400> SEQUENCE: 49

Thr Arg Gln Leu Gly Leu Arg Arg Thr Trp Tyr Ala Met Asp Tyr
1               5                   10                  15

<210> SEQ ID NO 50
<211> LENGTH: 105
<212> TYPE: PRT
<213> ORGANISM: Artificial
<220> FEATURE:
<223> OTHER INFORMATION: Synthetic polypeptide

<400> SEQUENCE: 50

Asp Val Gln Met Ile Gln Ser Pro Ser Leu Ser Ala Ser Leu Gly
1               5                   10                  15

Asp Lys Val Thr Met Thr Cys Gln Ala Ser His Thr Ile Asn Leu Asn
            20                  25                  30

Trp Phe Gln Gln Lys Pro Gly Lys Ala Pro Lys Leu Leu Ile Tyr Gly
        35                  40                  45

Thr Ser Asn Leu Glu Asp Gly Val Pro Pro Arg Phe Ser Gly Ser Gly
    50                  55                  60

Tyr Gly Thr Asp Phe Thr Leu Thr Ile Ser Ser Leu Glu Asp Glu Asp
65                  70                  75                  80

Met Ala Thr Tyr Phe Cys Leu Gln His Thr Tyr Leu Pro Trp Thr Phe
                85                  90                  95

Gly Gly Gly Thr Lys Leu Glu Ile Lys
            100                 105

<210> SEQ ID NO 51
<211> LENGTH: 9
<212> TYPE: PRT
<213> ORGANISM: Artificial
<220> FEATURE:
<223> OTHER INFORMATION: Synthetic polypeptide

<400> SEQUENCE: 51

Gln Ala Ser His Thr Ile Asn Leu Asn
1               5

<210> SEQ ID NO 52
<211> LENGTH: 7
<212> TYPE: PRT
<213> ORGANISM: Artificial
<220> FEATURE:
<223> OTHER INFORMATION: Synthetic polypeptide

<400> SEQUENCE: 52

Gly Thr Ser Asn Leu Glu Asp
1               5

<210> SEQ ID NO 53
<211> LENGTH: 9
<212> TYPE: PRT
<213> ORGANISM: Artificial
<220> FEATURE:
<223> OTHER INFORMATION: Synthetic polypeptide

<400> SEQUENCE: 53

Leu Gln His Thr Tyr Leu Pro Trp Thr
1               5

<210> SEQ ID NO 54
<211> LENGTH: 114
<212> TYPE: PRT
<213> ORGANISM: Artificial
<220> FEATURE:
<223> OTHER INFORMATION: Synthetic polypeptide

<400> SEQUENCE: 54

Glu Val Gln Leu Gln Gln Ser Gly Thr Val Leu Ala Arg Pro Gly Ala
1               5                   10                  15

Ser Val Lys Met Ser Cys Glu Ala Ser Gly Tyr Thr Phe Thr Ser Tyr
            20                  25                  30

```
Trp Met His Trp Val Lys Gln Ser Pro Gly Gln Gly Leu Glu Trp Val
             35                  40                  45
Gly Ala Ile Tyr Pro Gly Asn Ser Asp Thr Asn Tyr Asn Gln Lys Phe
 50                      55                  60
Lys Gly Lys Ala Lys Leu Thr Ala Val Thr Ser Ala Ser Thr Ala Tyr
 65                  70                  75                  80
Met Glu Leu Ser Ser Leu Thr Asn Glu Asp Ser Ala Val Tyr Tyr Cys
                 85                  90                  95
Thr Thr Ala Val Gly Ser Tyr Trp Gly Gln Gly Thr Leu Val Thr Val
                100                 105                 110
Ser Ala

<210> SEQ ID NO 55
<211> LENGTH: 6
<212> TYPE: PRT
<213> ORGANISM: Artificial
<220> FEATURE:
<223> OTHER INFORMATION: Synthetic polypeptide

<400> SEQUENCE: 55

Thr Ser Tyr Trp Met His
1               5

<210> SEQ ID NO 56
<211> LENGTH: 13
<212> TYPE: PRT
<213> ORGANISM: Artificial
<220> FEATURE:
<223> OTHER INFORMATION: Synthetic polypeptide

<400> SEQUENCE: 56

Ala Ile Tyr Pro Gly Asn Ser Asp Thr Asn Tyr Asn Gln
1               5                  10

<210> SEQ ID NO 57
<211> LENGTH: 7
<212> TYPE: PRT
<213> ORGANISM: Artificial
<220> FEATURE:
<223> OTHER INFORMATION: Synthetic polypeptide

<400> SEQUENCE: 57

Thr Thr Ala Val Gly Ser Tyr
1               5

<210> SEQ ID NO 58
<211> LENGTH: 110
<212> TYPE: PRT
<213> ORGANISM: Artificial
<220> FEATURE:
<223> OTHER INFORMATION: Synthetic polypeptide

<400> SEQUENCE: 58

Asp Ile Val Leu Thr Gln Ser Pro Ala Ser Leu Ala Val Ser Leu Gly
1               5                   10                  15
Gln Arg Ala Thr Ile Ser Cys Arg Ala Ser Lys Ser Val Ser Thr Ser
             20                  25                  30
Gly Tyr Ser Tyr Met His Trp Tyr Gln Gln Lys Pro Gly Gln Pro Pro
             35                  40                  45
Lys Leu Leu Ile Tyr Leu Ala Ser Asn Leu Glu Ser Gly Val Pro Val
 50                  55                  60
```

```
Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Asn Arg
                 85                  90                  95

Glu Leu Leu Thr Phe Gly Ala Gly Thr Lys Leu Glu Leu Lys
            100                 105                 110
```

<210> SEQ ID NO 59
<211> LENGTH: 15
<212> TYPE: PRT
<213> ORGANISM: Artificial
<220> FEATURE:
<223> OTHER INFORMATION: Synthetic polypeptide

<400> SEQUENCE: 59

```
Arg Ala Ser Lys Ser Val Ser Thr Ser Gly Tyr Ser Tyr Met His
 1               5                  10                  15
```

<210> SEQ ID NO 60
<211> LENGTH: 7
<212> TYPE: PRT
<213> ORGANISM: Artificial
<220> FEATURE:
<223> OTHER INFORMATION: Synthetic polypeptide

<400> SEQUENCE: 60

```
Leu Ala Ser Asn Leu Glu Ser
 1               5
```

<210> SEQ ID NO 61
<211> LENGTH: 8
<212> TYPE: PRT
<213> ORGANISM: Artificial
<220> FEATURE:
<223> OTHER INFORMATION: Synthetic polypeptide

<400> SEQUENCE: 61

```
Gln His Asn Arg Glu Leu Leu Thr
 1               5
```

<210> SEQ ID NO 62
<211> LENGTH: 119
<212> TYPE: PRT
<213> ORGANISM: Artificial
<220> FEATURE:
<223> OTHER INFORMATION: Synthetic polypeptide

<400> SEQUENCE: 62

```
Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Thr Ser Tyr
             20                  25                  30

Val Met Phe Trp Val Lys Gln Lys Pro Gly Gln Gly Leu Glu Trp Ile
         35                  40                  45

Gly Tyr Ile Asn Pro Tyr Asn Asp Asp Thr Lys Tyr Asn Glu Lys Phe
     50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
                 85                  90                  95
```

```
Ala Arg Glu Asp Tyr Tyr Gly Ser Arg Phe Val Tyr Trp Gly Gln Gly
            100                 105                 110

Thr Leu Val Thr Val Ser Ser
        115

<210> SEQ ID NO 63
<211> LENGTH: 6
<212> TYPE: PRT
<213> ORGANISM: Artificial
<220> FEATURE:
<223> OTHER INFORMATION: Synthetic polypeptide

<400> SEQUENCE: 63

Thr Ser Tyr Val Met Phe
1               5

<210> SEQ ID NO 64
<211> LENGTH: 13
<212> TYPE: PRT
<213> ORGANISM: Artificial
<220> FEATURE:
<223> OTHER INFORMATION: Synthetic polypeptide

<400> SEQUENCE: 64

Tyr Ile Asn Pro Tyr Asn Asp Asp Thr Lys Tyr Asn Glu
1               5                   10

<210> SEQ ID NO 65
<211> LENGTH: 13
<212> TYPE: PRT
<213> ORGANISM: Artificial
<220> FEATURE:
<223> OTHER INFORMATION: Synthetic polypeptide

<400> SEQUENCE: 65

Ala Arg Glu Asp Tyr Tyr Gly Ser Arg Phe Val Tyr Trp
1               5                   10

<210> SEQ ID NO 66
<211> LENGTH: 111
<212> TYPE: PRT
<213> ORGANISM: Artificial
<220> FEATURE:
<223> OTHER INFORMATION: Synthetic polypeptide

<400> SEQUENCE: 66

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Tyr Ser
            20                  25                  30

Gly Asn Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys His Gln Ser Asn
                85                  90                  95

Glu Asp Pro Pro Thr Phe Gly Gly Gly Thr Lys Val Glu Ile Lys
            100                 105                 110
```

<210> SEQ ID NO 67
<211> LENGTH: 118
<212> TYPE: PRT
<213> ORGANISM: Artificial
<220> FEATURE:
<223> OTHER INFORMATION: Synthetic polypeptide

<400> SEQUENCE: 67

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Ala Val Ser Trp Val Arg Gln Pro Pro Gly Lys Gly Leu Glu Trp Leu
        35                  40                  45

Gly Val Met Trp Ala Gly Gly Thr Asn Tyr Asn Ser Val Phe Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Pro Leu Thr Gly Val Met Asp Tyr Trp Gly Gln Gly Thr
            100                 105                 110

Leu Val Thr Val Ser Ser
        115
```

<210> SEQ ID NO 68
<211> LENGTH: 218
<212> TYPE: PRT
<213> ORGANISM: Artificial
<220> FEATURE:
<223> OTHER INFORMATION: Synthetic polypeptide

<400> SEQUENCE: 68

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Tyr Ser
            20                  25                  30

Gly Asn Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys His Gln Ser Asn
                85                  90                  95

Glu Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

```
His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 69
<211> LENGTH: 447
<212> TYPE: PRT
<213> ORGANISM: Artificial
<220> FEATURE:
<223> OTHER INFORMATION: Synthetic polypeptide

<400> SEQUENCE: 69

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Ala Val Ser Trp Val Arg Gln Pro Pro Gly Lys Gly Leu Glu Trp Leu
        35                  40                  45

Gly Val Met Trp Ala Gly Gly Thr Asn Tyr Asn Ser Val Phe Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Pro Leu Thr Gly Val Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 70
<211> LENGTH: 448
<212> TYPE: PRT
<213> ORGANISM: Artificial
<220> FEATURE:
<223> OTHER INFORMATION: Synthetic polypeptide

<400> SEQUENCE: 70

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Ala Val Ser Trp Val Arg Gln Pro Pro Gly Lys Gly Leu Glu Trp Leu
            35                  40                  45

Gly Val Met Trp Ala Gly Gly Thr Asn Tyr Asn Ser Val Phe Lys
        50                  55                  60

Ser Arg Leu Thr Ile Ser Lys Asp Asn Ser Lys Asn Gln Val Ser Leu
65              70                  75                  80

Lys Leu Ser Ser Val Thr Ala Ala Asp Thr Ala Val Tyr Tyr Cys Ala
                85                  90                  95

Arg Glu Arg Pro Leu Thr Gly Val Met Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 71
<211> LENGTH: 218
<212> TYPE: PRT
<213> ORGANISM: Artificial
<220> FEATURE:
<223> OTHER INFORMATION: Synthetic polypeptide

<400> SEQUENCE: 71

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Tyr Ser
            20                  25                  30

Gly Asn Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys His Gln Ser Asn
                85                  90                  95

Trp Asp Pro Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 72
<211> LENGTH: 448
<212> TYPE: PRT
<213> ORGANISM: Artificial
<220> FEATURE:
<223> OTHER INFORMATION: Synthetic polypeptide

<400> SEQUENCE: 72

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Arg Val Ser Trp Val Arg Gln Pro Gly Lys Gly Leu Glu Trp Leu
        35                  40                  45

Gly Val Met Tyr Ala Gly Gly Thr Asn Tyr Asn Ser Val Phe Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Pro Leu Thr Gly Val Met Asp Asn Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
            435                 440                 445
```

<210> SEQ ID NO 73
<211> LENGTH: 448
<212> TYPE: PRT
<213> ORGANISM: Artificial
<220> FEATURE:
<223> OTHER INFORMATION: Synthetic polypeptide

<400> SEQUENCE: 73

```
Glu Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Asn Tyr
                20                  25                  30
Trp Val Ser Trp Val Arg Gln Pro Pro Gly Lys Gly Leu Glu Trp Leu
                35                  40                  45
Gly Thr Met Trp Ala Gly Gly Thr Asn Tyr Asn Ser Val Phe Lys
            50                  55                  60
Ser Arg Leu Thr Ile Ser Lys Asp Asn Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Glu Arg Pro Leu Thr Gly Pro Met Asp Tyr Trp Gly Gln Gly Thr
                100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 74
<211> LENGTH: 217
<212> TYPE: PRT
<213> ORGANISM: Artificial
<220> FEATURE:
<223> OTHER INFORMATION: Synthetic polypeptide

<400> SEQUENCE: 74

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Asn Arg
                85                  90                  95

Glu Leu Leu Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160
```

```
Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 75
<211> LENGTH: 448
<212> TYPE: PRT
<213> ORGANISM: Artificial
<220> FEATURE:
<223> OTHER INFORMATION: Synthetic polypeptide

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met Phe Trp Val Arg Gln Ala Pro Gly Gln Arg Leu Glu Trp Ile
        35                  40                  45

Gly Tyr Ile Asn Pro Tyr Asn Asp Asp Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Tyr Tyr Gly Ser Arg Phe Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Gly Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 76
<211> LENGTH: 111
<212> TYPE: PRT
<213> ORGANISM: Artificial
<220> FEATURE:
<223> OTHER INFORMATION: Synthetic polypeptide

<400> SEQUENCE: 76

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Tyr Ser
            20                  25                  30

Gly Asn Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys His Gln Ser Asn
                85                  90                  95

Trp Asp Pro Pro Thr Phe Gly Gly Gly Thr Lys Val Glu Ile Lys
            100                 105                 110

<210> SEQ ID NO 77
<211> LENGTH: 15
<212> TYPE: PRT
<213> ORGANISM: Artificial
<220> FEATURE:
<223> OTHER INFORMATION: Synthetic polypeptide

<400> SEQUENCE: 77

Arg Ala Ser Glu Ser Val Asp Tyr Ser Gly Asn Ser Phe Met His
1               5                   10                  15

<210> SEQ ID NO 78
<211> LENGTH: 7
<212> TYPE: PRT
<213> ORGANISM: Artificial
<220> FEATURE:
<223> OTHER INFORMATION: Synthetic polypeptide

<400> SEQUENCE: 78

Arg Ala Ser Asn Leu Glu Ser
1               5

<210> SEQ ID NO 79
<211> LENGTH: 9
<212> TYPE: PRT
<213> ORGANISM: Artificial
<220> FEATURE:
<223> OTHER INFORMATION: Synthetic polypeptide

<400> SEQUENCE: 79

His Gln Ser Asn Trp Asp Pro Pro Thr
1               5

<210> SEQ ID NO 80
<211> LENGTH: 118
<212> TYPE: PRT
<213> ORGANISM: Artificial
<220> FEATURE:
<223> OTHER INFORMATION: Synthetic polypeptide

<400> SEQUENCE: 80

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Arg Val Ser Trp Val Arg Gln Pro Pro Gly Lys Gly Leu Glu Trp Leu
        35                  40                  45

Gly Val Met Tyr Ala Gly Gly Thr Asn Tyr Asn Ser Val Phe Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Pro Leu Thr Gly Val Met Asp Asn Trp Gly Gln Gly Thr
            100                 105                 110

Leu Val Thr Val Ser Ser
        115

<210> SEQ ID NO 81
<211> LENGTH: 6
<212> TYPE: PRT
<213> ORGANISM: Artificial
<220> FEATURE:
<223> OTHER INFORMATION: Synthetic polypeptide

<400> SEQUENCE: 81

Thr Asn Tyr Arg Val Ser
1               5

<210> SEQ ID NO 82
<211> LENGTH: 12
<212> TYPE: PRT
<213> ORGANISM: Artificial
<220> FEATURE:
<223> OTHER INFORMATION: Synthetic polypeptide

<400> SEQUENCE: 82

Val Met Tyr Ala Gly Gly Thr Asn Tyr Asn Ser
1               5                   10

```
<210> SEQ ID NO 83
<211> LENGTH: 12
<212> TYPE: PRT
<213> ORGANISM: Artificial
<220> FEATURE:
<223> OTHER INFORMATION: Synthetic polypeptide

<400> SEQUENCE: 83

Ala Arg Glu Arg Pro Leu Thr Gly Val Met Asp Asn
1               5                   10

<210> SEQ ID NO 84
<211> LENGTH: 118
<212> TYPE: PRT
<213> ORGANISM: Artificial
<220> FEATURE:
<223> OTHER INFORMATION: Synthetic polypeptide

<400> SEQUENCE: 84

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Trp Val Ser Trp Val Arg Gln Pro Pro Gly Lys Gly Leu Glu Trp Leu
        35                  40                  45

Gly Thr Met Trp Ala Gly Gly Thr Asn Tyr Asn Ser Val Phe Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Pro Leu Thr Gly Pro Met Asp Tyr Trp Gly Gln Gly Thr
            100                 105                 110

Leu Val Thr Val Ser Ser
        115

<210> SEQ ID NO 85
<211> LENGTH: 6
<212> TYPE: PRT
<213> ORGANISM: Artificial
<220> FEATURE:
<223> OTHER INFORMATION: Synthetic polypeptide

<400> SEQUENCE: 85

Thr Asn Tyr Trp Val Ser
1               5

<210> SEQ ID NO 86
<211> LENGTH: 12
<212> TYPE: PRT
<213> ORGANISM: Artificial
<220> FEATURE:
<223> OTHER INFORMATION: Synthetic polypeptide

<400> SEQUENCE: 86

Thr Met Trp Ala Gly Gly Gly Thr Asn Tyr Asn Ser
1               5                   10

<210> SEQ ID NO 87
<211> LENGTH: 12
<212> TYPE: PRT
<213> ORGANISM: Artificial
<220> FEATURE:
<223> OTHER INFORMATION: Synthetic polypeptide
```

```
<400> SEQUENCE: 87

Ala Arg Glu Arg Pro Leu Thr Gly Pro Met Asp Tyr
1               5                   10

<210> SEQ ID NO 88
<211> LENGTH: 447
<212> TYPE: PRT
<213> ORGANISM: Artificial
<220> FEATURE:
<223> OTHER INFORMATION: Synthetic polypeptide

<400> SEQUENCE: 88

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Arg Val Ser Trp Val Arg Gln Pro Pro Gly Lys Gly Leu Glu Trp Leu
        35                  40                  45

Gly Val Met Tyr Ala Gly Gly Thr Asn Tyr Asn Ser Val Phe Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Pro Leu Thr Gly Val Met Asp Asn Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 89
<211> LENGTH: 447
<212> TYPE: PRT
<213> ORGANISM: Artificial
<220> FEATURE:
<223> OTHER INFORMATION: Synthetic polypeptide

<400> SEQUENCE: 89

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Trp Val Ser Trp Val Arg Gln Pro Pro Gly Lys Gly Leu Glu Trp Leu
        35                  40                  45

Gly Thr Met Trp Ala Gly Gly Thr Asn Tyr Asn Ser Val Phe Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Pro Leu Thr Gly Pro Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gly Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 90
<211> LENGTH: 31
<212> TYPE: PRT
<213> ORGANISM: Artificial
<220> FEATURE:
<223> OTHER INFORMATION: Synthetic polypeptide

<400> SEQUENCE: 90

Gly Gly Gly Ser Gly Leu Asn Asp Ile Phe Glu Ala Gln Lys Ile Glu
1               5                   10                  15

Trp His Glu Gly Ser Gly Gly His His His His His His His
            20                  25                  30

<210> SEQ ID NO 91
<211> LENGTH: 19
<212> TYPE: PRT
<213> ORGANISM: Artificial
<220> FEATURE:
<223> OTHER INFORMATION: Synthetic polypeptide

<400> SEQUENCE: 91

Met Gly Trp Ser Cys Ile Ile Leu Phe Leu Val Ala Thr Ala Thr Gly
1               5                   10                  15

Val His Ser

<210> SEQ ID NO 92
<211> LENGTH: 28
<212> TYPE: DNA
<213> ORGANISM: Artificial
<220> FEATURE:
<223> OTHER INFORMATION: Synthetic polynucleotide

<400> SEQUENCE: 92
tcttgtccac cttggtgctg ctggccgg                                    28
```

```
<210> SEQ ID NO 93
<211> LENGTH: 28
<212> TYPE: DNA
<213> ORGANISM: Artificial
<220> FEATURE:
<223> OTHER INFORMATION: Synthetic polynucleotide

<400> SEQUENCE: 93
tttgtccacc gtggtgctgc tggctggt                                          28

<210> SEQ ID NO 94
<211> LENGTH: 25
<212> TYPE: DNA
<213> ORGANISM: Artificial
<220> FEATURE:
<223> OTHER INFORMATION: Synthetic polynucleotide

<400> SEQUENCE: 94
gatcagtcca actgttcagg acgcc                                             25

<210> SEQ ID NO 95
<211> LENGTH: 33
<212> TYPE: DNA
<213> ORGANISM: Artificial
<220> FEATURE:
<223> OTHER INFORMATION: Synthetic polynucleotide

<400> SEQUENCE: 95
acactcagca cgggacaaac tcttctccac agt                                    33

<210> SEQ ID NO 96
<211> LENGTH: 33
<212> TYPE: DNA
<213> ORGANISM: Artificial
<220> FEATURE:
<223> OTHER INFORMATION: Synthetic polynucleotide

<400> SEQUENCE: 96
acactctgca ggagacagac tcttttccac agt                                    33

<210> SEQ ID NO 97
<211> LENGTH: 33
<212> TYPE: DNA
<213> ORGANISM: Artificial
<220> FEATURE:
<223> OTHER INFORMATION: Synthetic polynucleotide

<400> SEQUENCE: 97
acactcagca cgggacaaac tcttctccac atg                                    33
```